(12) United States Patent
Woloszko et al.

(10) Patent No.: US 7,270,658 B2
(45) Date of Patent: Sep. 18, 2007

(54) SYSTEMS AND METHODS FOR ELECTROSURGERY

(75) Inventors: Jean Woloszko, Mountain View, CA (US); David C. Hovda, Mountain View, CA (US); Hira V. Thapliyal, Los Altos, CA (US); Philip E. Eggers, Dublin, OH (US)

(73) Assignee: ArthroCare Corporation, Austin, TX (US)

( * ) Notice: Subject to any disclaimer, the term of this patent is extended or adjusted under 35 U.S.C. 154(b) by 129 days.

(21) Appl. No.: 10/384,050

(22) Filed: Mar. 10, 2003

(65) Prior Publication Data

US 2003/0212395 A1  Nov. 13, 2003

Related U.S. Application Data

(60) Division of application No. 09/708,962, filed on Nov. 8, 2000, now Pat. No. 6,726,684, and a continuation-in-part of application No. 09/676,194, filed on Sep. 28, 2000, now Pat. No. 6,602,248.

(60) Provisional application No. 60/204,206, filed on May 12, 2000.

(51) Int. Cl.
*A61B 18/14* (2006.01)
(52) U.S. Cl. .............................. 606/32; 606/41; 606/49; 607/99
(58) Field of Classification Search .................. 607/99; 606/41
See application file for complete search history.

(56) References Cited

U.S. PATENT DOCUMENTS 2,050,904 A   8/1936  Trice (Continued)

FOREIGN PATENT DOCUMENTS

DE   3930451   3/1991

(Continued)

OTHER PUBLICATIONS

Pearce, John A. (1986) *Electrosurgery*, pp. 17, 69-75, 87, John Wiley & Sons, New York.

(Continued)

*Primary Examiner*—Lee S. Cohen
(74) *Attorney, Agent, or Firm*—Brian E. Szymczak

(57) ABSTRACT

Methods and apparatus for selectively applying electrical energy to a target location within a patient's body, particularly including tissue in the spine. In a method of the invention high frequency (RF) electrical energy is applied to one or more active electrodes on an electrosurgical probe in the presence of an electrically conductive fluid to remove, contract or otherwise modify the structure of tissue targeted for treatment. In one aspect, a dura mater and spinal cord are insulated from the electrical energy by an insulator positioned on a non-active side of the probe. In another aspect, a plasma is aggressively formed in the electrically conductive fluid by delivering a conductive fluid to a distal end portion of the probe and aspirating the fluid from a location proximal of the return electrode. In another aspect, a distal end of an electrosurgical probe having at least one electrode on a biased, curved, bent, or steerable shaft is guided or steered to a target site within an intervertebral disc having a disc defect for treatment of tissue to be treated at the target site by the selective application of electrical energy thereto.

19 Claims, 64 Drawing Sheets

U.S. PATENT DOCUMENTS

| | | | |
|---|---|---|---|
| 2,056,377 A | 10/1936 | Wappler | 125/303 |
| 3,633,425 A | 1/1972 | Sanford | 73/356 |
| 3,815,604 A | 6/1974 | O'Malley et al. | 128/305 |
| 3,828,780 A | 8/1974 | Morrison, Jr. | 128/275 |
| 3,901,242 A | 8/1975 | Storz | 128/303 |
| 3,920,021 A | 11/1975 | Hiltebrandt | 128/303 |
| 3,939,839 A | 2/1976 | Curtiss | 128/303 |
| 3,970,088 A | 7/1976 | Morrison | 128/303 |
| 4,033,351 A | 7/1977 | Hetzel | 128/303 |
| 4,040,426 A | 8/1977 | Morrison, Jr. | 128/303 |
| 4,043,342 A | 8/1977 | Morrison, Jr. | 128/303 |
| 4,074,718 A | 2/1978 | Morrison, Jr. | 128/303 |
| 4,092,986 A | 6/1978 | Schneiderman | 128/303 |
| 4,116,198 A | 9/1978 | Roos | 128/303 |
| 4,181,131 A | 1/1980 | Ogiu | 128/303 |
| 4,184,492 A | 1/1980 | Meinke et al. | 128/303 |
| 4,202,337 A | 5/1980 | Hren et al. | 128/303 |
| 4,228,800 A | 10/1980 | Degler, Jr. et al. | 128/303 |
| 4,232,676 A | 11/1980 | Herczog | 128/303 |
| 4,240,441 A | 12/1980 | Khalil | 128/692 |
| 4,248,231 A | 2/1981 | Herczog et al. | 128/303 |
| 4,269,174 A | 5/1981 | Adair | |
| 4,326,529 A | 4/1982 | Doss et al. | 128/303 |
| 4,381,007 A | 4/1983 | Doss | 128/303 |
| 4,474,179 A | 10/1984 | Koch | 606/40 |
| 4,476,862 A | 10/1984 | Pao | 128/303 |
| 4,483,338 A | 11/1984 | Bloom et al. | |
| 4,532,924 A | 8/1985 | Auth et al. | 128/303 |
| 4,548,207 A | 10/1985 | Reimels | 128/303 |
| 4,567,890 A | 2/1986 | Ohta et al. | 128/303 |
| 4,573,448 A | 3/1986 | Kambin | 606/170 |
| 4,582,057 A | 4/1986 | Auth et al. | |
| 4,590,934 A | 5/1986 | Malis et al. | 128/303 |
| 4,593,691 A | 6/1986 | Lindstrom et al. | 128/303 |
| 4,658,817 A | 4/1987 | Hardy | |
| 4,660,571 A | 4/1987 | Hess et al. | 128/784 |
| 4,674,499 A | 6/1987 | Pao | 128/303 |
| 4,682,596 A | 7/1987 | Bales et al. | 128/303 |
| 4,706,667 A | 11/1987 | Roos | 128/303 |
| 4,709,698 A | 12/1987 | Johnston et al. | 128/303 |
| 4,727,874 A | 3/1988 | Bowers et al. | 128/303 |
| 4,765,331 A | 8/1988 | Petruzzi et al. | 128/303 |
| 4,785,823 A | 11/1988 | Eggers et al. | 128/692 |
| 4,805,616 A | 2/1989 | Pao | 128/303 |
| 4,823,791 A | 4/1989 | D'Amelio et al. | 123/303 |
| 4,832,048 A | 5/1989 | Cohen | 128/786 |
| 4,860,752 A | 8/1989 | Turner | 128/422 |
| 4,896,671 A | 1/1990 | Cunningham et al. | |
| 4,907,589 A | 3/1990 | Cosman | 606/34 |
| 4,920,978 A | 5/1990 | Colvin | 128/784 |
| 4,931,047 A | 6/1990 | Broadwin et al. | 604/22 |
| 4,936,281 A | 6/1990 | Stasz | 128/660 |
| 4,936,301 A | 6/1990 | Rexroth et al. | 606/45 |
| 4,943,290 A | 7/1990 | Rexroth et al. | 606/45 |
| 4,955,377 A | 9/1990 | Lennox et al. | 128/401 |
| 4,958,539 A | 9/1990 | Stasz et al. | |
| 4,966,597 A | 10/1990 | Cosman | 606/50 |
| 4,967,765 A | 11/1990 | Turner et al. | 128/785 |
| 4,976,709 A | 12/1990 | Sand | |
| 4,976,711 A | 12/1990 | Parins et al. | 606/48 |
| 4,979,948 A | 12/1990 | Geddes et al. | 606/33 |
| 4,998,933 A | 3/1991 | Eggers et al. | 606/41 |
| 5,007,908 A | 4/1991 | Rydell | 606/47 |
| 5,009,656 A | 4/1991 | Reimels | 606/48 |
| 5,035,696 A | 7/1991 | Rydell | 606/47 |
| 5,047,026 A | 9/1991 | Rydell | 606/48 |
| 5,047,027 A | 9/1991 | Rydell | 606/48 |
| 5,057,105 A | 10/1991 | Malone et al. | 606/28 |
| 5,057,106 A | 10/1991 | Kasevich et al. | 606/33 |
| 5,078,717 A | 1/1992 | Parins et al. | 606/48 |
| 5,080,660 A | 1/1992 | Buelna | 606/45 |
| 5,083,565 A | 1/1992 | Parins | 128/642 |
| 5,084,044 A | 1/1992 | Quint | 606/27 |
| 5,085,659 A | 2/1992 | Rydell | 606/47 |
| 5,088,997 A | 2/1992 | Delahuerga et al. | 606/42 |
| 5,092,339 A | 3/1992 | Geddes et al. | 128/692 |
| 5,098,431 A | 3/1992 | Rydell | 606/48 |
| 5,099,840 A | 3/1992 | Goble | 128/422 |
| 5,102,410 A | 4/1992 | Dressel | 606/15 |
| 5,108,391 A | 4/1992 | Flachenecker et al. | 606/38 |
| 5,112,330 A | 5/1992 | Nishigaki et al. | 606/46 |
| 5,122,138 A | 6/1992 | Manwaring | 606/46 |
| 5,125,928 A | 6/1992 | Parins et al. | 606/48 |
| 5,137,530 A | 8/1992 | Sand | |
| 5,156,151 A | 10/1992 | Imran | 600/375 |
| 5,167,659 A | 12/1992 | Ohtomo et al. | 606/40 |
| 5,171,311 A | 12/1992 | Rydell et al. | 606/48 |
| 5,178,620 A | 1/1993 | Eggers et al. | 606/41 |
| 5,190,517 A | 3/1993 | Zieve et al. | 604/22 |
| 5,192,280 A | 3/1993 | Parins | 606/48 |
| 5,195,959 A | 3/1993 | Smith | 604/34 |
| 5,197,466 A | 3/1993 | Marchosky et al. | 128/399 |
| 5,197,963 A | 3/1993 | Parins | 606/46 |
| 5,201,729 A | 4/1993 | Hertzmann et al. | 606/2 |
| 5,207,675 A | 5/1993 | Canady | 606/40 |
| 5,207,684 A | 5/1993 | Nobles | 606/108 |
| 5,217,457 A | 6/1993 | Delahuerga et al. | 606/42 |
| 5,217,459 A | 6/1993 | Kamerling | 606/48 |
| 5,230,334 A | 7/1993 | Klopotek | |
| 5,249,585 A | 10/1993 | Turner et al. | 607/99 |
| 5,261,410 A | 11/1993 | Alfano et al. | 600/475 |
| 5,267,994 A | 12/1993 | Gentelia et al. | 606/15 |
| 5,267,997 A | 12/1993 | Farin et al. | 606/38 |
| 5,273,524 A | 12/1993 | Fox et al. | 604/21 |
| 5,277,201 A | 1/1994 | Stern | 607/98 |
| 5,281,216 A | 1/1994 | Klicek | 606/42 |
| 5,281,218 A | 1/1994 | Imran | 606/41 |
| 5,290,282 A | 3/1994 | Casscells | 606/29 |
| 5,300,069 A | 4/1994 | Hunsberger et al. | 606/37 |
| 5,306,238 A | 4/1994 | Fleenor | 606/42 |
| 5,312,400 A | 5/1994 | Bales et al. | 606/41 |
| 5,314,406 A | 5/1994 | Arias et al. | 604/21 |
| 5,318,563 A | 6/1994 | Malis et al. | 606/38 |
| 5,318,564 A | 6/1994 | Eggers | |
| 5,324,254 A | 6/1994 | Phillips | 604/21 |
| 5,330,470 A | 7/1994 | Hagen | 606/42 |
| 5,334,140 A | 8/1994 | Philips | 604/35 |
| 5,334,183 A | 8/1994 | Wuchinich | 606/46 |
| 5,336,220 A | 8/1994 | Ryan et al. | 604/22 |
| 5,342,357 A | 8/1994 | Nardella | 606/40 |
| 5,347,662 A | 9/1994 | Carper-White | 606/40 |
| 5,366,443 A | 11/1994 | Eggers et al. | 604/114 |
| 5,370,675 A | 12/1994 | Edwards et al. | 607/101 |
| 5,374,261 A | 12/1994 | Yoon | 604/385.01 |
| 5,374,265 A | 12/1994 | Sand | |
| 5,375,588 A | 12/1994 | Yoon | 128/4 |
| 5,380,277 A | 1/1995 | Phillips | 604/33 |
| 5,380,316 A | 1/1995 | Aita et al. | 606/7 |
| 5,383,876 A | 1/1995 | Nardella | 606/49 |
| 5,383,917 A | 1/1995 | Desai et al. | 607/702 |
| 5,389,096 A | 2/1995 | Aita et al. | 606/15 |
| 5,395,312 A | 3/1995 | Desai | 604/22 |
| 5,400,267 A | 3/1995 | Denen et al. | 702/59 |
| 5,401,272 A | 3/1995 | Perkins | 606/15 |
| 5,403,311 A | 4/1995 | Abele et al. | |
| 5,417,687 A | 5/1995 | Nardella et al. | 606/32 |
| 5,419,767 A | 5/1995 | Eggers et al. | 604/114 |
| 5,423,810 A | 6/1995 | Goble et al. | 606/40 |
| 5,423,882 A | 6/1995 | Jackman et al. | 607/122 |
| 5,433,739 A | 7/1995 | Sluijter et al. | 607/99 |
| 5,436,566 A | 7/1995 | Thompson et al. | 324/713 |
| 5,438,302 A | 8/1995 | Goble | 331/167 |
| 5,439,446 A | 8/1995 | Barry | 604/104 |
| 5,441,499 A | 8/1995 | Fritzsch | 606/45 |

| Patent No. | Date | Inventor | Class |
|---|---|---|---|
| 5,451,224 A | 9/1995 | Goble et al. | 606/48 |
| 5,454,809 A | 10/1995 | Janssen | 606/41 |
| 5,458,596 A | 10/1995 | Lax et al. | |
| 5,496,312 A | 3/1996 | Klicek | 606/34 |
| 5,496,314 A | 3/1996 | Eggers | 606/41 |
| 5,496,317 A | 3/1996 | Goble et al. | 606/48 |
| 5,514,130 A | 5/1996 | Baker | 606/41 |
| 5,542,945 A | 8/1996 | Fritzsch | |
| 5,554,152 A | 9/1996 | Aita et al. | 606/7 |
| 5,556,397 A | 9/1996 | Long et al. | 606/48 |
| 5,562,703 A | 10/1996 | Desai | |
| 5,569,242 A | 10/1996 | Lax et al. | 606/42 |
| 5,571,100 A | 11/1996 | Goble et al. | 606/41 |
| 5,571,189 A | 11/1996 | Kuslich | 623/17.12 |
| 5,584,872 A | 12/1996 | LaFontaine et al. | 607/117 |
| 5,609,151 A | 3/1997 | Mulier et al. | 128/642 |
| 5,626,576 A | 5/1997 | Janssen | |
| 5,633,578 A | 5/1997 | Eggers et al. | 323/301 |
| 5,647,869 A | 7/1997 | Goble et al. | 606/37 |
| 5,660,836 A | 8/1997 | Knowlton | |
| 5,662,680 A | 9/1997 | Desai | 606/210 |
| 5,676,693 A | 10/1997 | LaFontaine et al. | 607/116 |
| 5,681,282 A | 10/1997 | Eggers et al. | 604/114 |
| 5,683,366 A | 11/1997 | Eggers et al. | 604/114 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | 604/114 |
| 5,697,909 A | 12/1997 | Eggers et al. | 604/114 |
| 5,700,262 A | 12/1997 | Acosta et al. | 606/48 |
| 5,720,744 A | 2/1998 | Eggleston et al. | 606/40 |
| 5,725,524 A | 3/1998 | Mulier et al. | 606/41 |
| 5,749,869 A | 5/1998 | Lindenmeier et al. | 606/34 |
| 5,766,153 A | 6/1998 | Eggers et al. | 604/114 |
| 5,785,705 A | 7/1998 | Baker | |
| 5,800,431 A | 9/1998 | Brown | 606/42 |
| 5,807,395 A | 9/1998 | Mulier et al. | 606/41 |
| 5,810,764 A | 9/1998 | Eggers et al. | 604/23 |
| 5,810,809 A | 9/1998 | Rydell | 606/49 |
| 5,823,955 A | 10/1998 | Kuck et al. | |
| 5,836,875 A | 11/1998 | Webster, Jr. | 600/374 |
| 5,843,019 A | 12/1998 | Eggers et al. | 604/22 |
| 5,846,196 A | 12/1998 | Siekmeyer et al. | |
| 5,860,874 A | 1/1999 | Wateska et al. | 606/41 |
| 5,860,951 A | 1/1999 | Eggers et al. | |
| 5,860,975 A | 1/1999 | Goble et al. | 606/45 |
| 5,871,469 A | 2/1999 | Eggers et al. | 604/114 |
| 5,873,855 A | 2/1999 | Eggers et al. | 604/114 |
| 5,877,289 A | 3/1999 | Thorpe et al. | 530/387.7 |
| 5,885,277 A | 3/1999 | Korth | 606/35 |
| 5,888,198 A | 3/1999 | Eggers et al. | 604/114 |
| 5,891,095 A | 4/1999 | Eggers et al. | 604/114 |
| 5,891,134 A | 4/1999 | Goble et al. | 606/27 |
| 5,897,553 A | 4/1999 | Mulier | 606/41 |
| 5,902,272 A | 5/1999 | Eggers et al. | 604/114 |
| 5,916,214 A | 6/1999 | Cosio et al. | |
| 5,944,715 A | 8/1999 | Goble et al. | 606/41 |
| 5,954,716 A | 9/1999 | Sharkey et al. | 606/32 |
| 5,980,504 A | 11/1999 | Sharkey et al. | 604/510 |
| 6,004,319 A | 12/1999 | Goble et al. | 606/48 |
| 6,007,570 A | 12/1999 | Sharkey et al. | 607/96 |
| 6,013,076 A | 1/2000 | Goble et al. | 606/41 |
| 6,015,406 A | 1/2000 | Goble et al. | 606/41 |
| 6,024,733 A | 2/2000 | Eggers et al. | 604/500 |
| 6,027,501 A | 2/2000 | Goble et al. | 606/41 |
| 6,039,734 A | 3/2000 | Goble et al. | 606/41 |
| 6,047,700 A | 4/2000 | Eggers et al. | 128/898 |
| 6,056,746 A | 5/2000 | Goble et al. | 606/48 |
| 6,063,079 A | 5/2000 | Hovda et al. | 606/41 |
| 6,066,134 A | 5/2000 | Eggers et al. | 606/32 |
| 6,068,628 A | 5/2000 | Fanton et al. | 606/41 |
| 6,073,051 A | 6/2000 | Sharkey et al. | |
| 6,074,386 A | 6/2000 | Goble et al. | 606/34 |
| 6,090,106 A | 7/2000 | Goble et al. | 606/41 |
| 6,093,186 A | 7/2000 | Goble et al. | 606/34 |
| 6,093,187 A | 7/2000 | Lecuyer | 606/45 |
| 6,095,149 A | 8/2000 | Sharkey et al. | |
| 6,096,036 A | 8/2000 | Bowe et al. | |
| 6,102,046 A | 8/2000 | Weinstein et al. | 128/898 |
| 6,105,581 A | 8/2000 | Eggers et al. | |
| 6,109,268 A | 8/2000 | Thapliyal et al. | 128/898 |
| 6,117,109 A | 9/2000 | Eggers et al. | 604/114 |
| 6,122,549 A | 9/2000 | Sharkey et al. | |
| 6,126,682 A | 10/2000 | Sharkey et al. | 607/96 |
| 6,142,992 A | 11/2000 | Cheng et al. | 606/34 |
| 6,146,380 A | 11/2000 | Racz et al. | 606/41 |
| 6,149,620 A | 11/2000 | Baker et al. | 604/22 |
| 6,159,194 A | 12/2000 | Eggers et al. | 604/500 |
| 6,159,208 A | 12/2000 | Hovda et al. | 606/41 |
| 6,168,593 B1 | 1/2001 | Sharkey et al. | 606/34 |
| 6,174,309 B1 | 1/2001 | Wrublewski et al. | 606/45 |
| 6,176,857 B1 | 1/2001 | Ashley | 606/32 |
| 6,179,824 B1 | 1/2001 | Eggers et al. | 604/500 |
| 6,179,836 B1 | 1/2001 | Eggers et al. | 606/45 |
| 6,183,469 B1 | 2/2001 | Thapliyal et al. | 606/41 |
| 6,190,381 B1 | 2/2001 | Olsen et al. | 606/32 |
| 6,203,542 B1 | 3/2001 | Ellsberry et al. | 606/41 |
| 6,210,402 B1 | 4/2001 | Olsen et al. | 606/32 |
| 6,224,592 B1 | 5/2001 | Eggers et al. | 606/32 |
| 6,228,081 B1 | 5/2001 | Goble | 606/34 |
| 6,234,178 B1 | 5/2001 | Goble et al. | 606/32 |
| 6,235,020 B1 | 5/2001 | Cheng et al. | 606/34 |
| 6,237,604 B1 | 5/2001 | Burnside et al. | 128/897 |
| 6,238,391 B1 | 5/2001 | Olsen et al. | 606/41 |
| 6,254,600 B1 | 7/2001 | Willink et al. | 606/41 |
| 6,258,086 B1 | 7/2001 | Ashley et al. | |
| 6,261,286 B1 | 7/2001 | Goble et al. | 606/34 |
| 6,261,311 B1 | 7/2001 | Sharkey et al. | |
| 6,264,652 B1 | 7/2001 | Eggers et al. | 606/41 |
| 6,270,460 B1 | 8/2001 | McCartan et al. | 600/459 |
| 6,277,112 B1 | 8/2001 | Underwood et al. | 606/32 |
| 6,280,441 B1 | 8/2001 | Ryan | 606/45 |
| 6,283,961 B1 | 9/2001 | Underwood et al. | |
| 6,293,942 B1 | 9/2001 | Goble et al. | 606/38 |
| 6,296,636 B1 | 10/2001 | Cheng et al. | 606/32 |
| 6,296,638 B1 | 10/2001 | Davison et al. | 606/41 |
| 6,306,134 B1 | 10/2001 | Goble et al. | 606/42 |
| 6,308,089 B1 | 10/2001 | von der Ruhr et al. | 600/338 |
| 6,309,387 B1 | 10/2001 | Eggers et al. | 606/41 |
| 6,312,408 B1 | 11/2001 | Eggers et al. | 604/114 |
| 6,319,250 B1 | 11/2001 | Falwell et al. | |
| 6,322,549 B1 | 11/2001 | Eggers et al. | 604/500 |
| 6,355,032 B1 | 3/2002 | Hovda et al. | 606/32 |
| 6,363,937 B1 | 4/2002 | Hovda et al. | 128/898 |
| 6,364,877 B1 | 4/2002 | Goble et al. | 606/34 |
| 6,379,351 B1 | 4/2002 | Thapliyal et al. | 606/41 |
| 6,391,025 B1 | 5/2002 | Weinstein et al. | 606/41 |
| 6,416,507 B1 | 7/2002 | Eggers et al. | 606/32 |
| 6,416,508 B1 | 7/2002 | Eggers et al. | 606/32 |
| 6,416,509 B1 | 7/2002 | Goble et al. | 606/37 |
| 6,432,103 B1 | 8/2002 | Ellsberry et al. | 606/41 |
| 6,468,274 B1 | 10/2002 | Alleyne et al. | 606/32 |
| 6,468,275 B1 | 10/2002 | Wampler et al. | 606/48 |
| 6,482,201 B1 | 11/2002 | Olsen et al. | 606/41 |
| 6,500,173 B2 | 12/2002 | Underwood et al. | |
| 6,517,498 B1 | 2/2003 | Burbank et al. | 600/564 |
| 6,530,922 B2 | 3/2003 | Cosman et al. | 606/34 |
| 6,575,968 B1 | 6/2003 | Eggers et al. | |
| 6,578,579 B2 | 6/2003 | Burnside et al. | 128/897 |
| 6,589,237 B2 | 7/2003 | Woloszko et al. | 606/41 |
| 6,602,248 B1 | 8/2003 | Sharps et al. | 606/32 |
| 6,620,156 B1 | 9/2003 | Garito et al. | 606/50 |
| 6,632,193 B1 | 10/2003 | Davison et al. | 604/22 |
| 6,632,220 B1 | 10/2003 | Eggers et al. | 606/41 |
| 6,679,886 B2 | 1/2004 | Weikel et al. | 606/79 |
| 6,746,451 B2 | 6/2004 | Middleton et al. | 606/79 |
| 6,749,604 B1 | 6/2004 | Eggers et al. | 606/41 |

| | | | |
|---|---|---|---|
| 6,749,608 B2 | 6/2004 | Garito et al. ............... 606/45 |
| 6,761,718 B2 | 7/2004 | Madsen ..................... 606/50 |
| 6,770,071 B2 | 8/2004 | Woloszko et al. ........... 606/41 |
| 6,780,178 B2 | 8/2004 | Palanker et al. ............. 600/41 |
| 6,780,180 B1 | 8/2004 | Goble et al. ................. 606/41 |
| 6,802,842 B2 | 10/2004 | Ellman et al. ............... 606/45 |
| 6,837,887 B2 | 1/2005 | Woloszko et al. ........... 606/41 |
| 6,837,888 B2 | 1/2005 | Ciarrocca et al. ............ 606/41 |
| 6,878,155 B2 * | 4/2005 | Sharkey et al. .............. 607/96 |
| 6,920,883 B2 | 7/2005 | Bessette et al. ............ 128/898 |
| 6,929,640 B1 | 8/2005 | Underwood et al. ......... 606/32 |
| 6,949,096 B2 | 9/2005 | Davison et al. .............. 606/32 |
| 6,974,453 B2 | 12/2005 | Woloszko et al. ........... 606/41 |
| 6,991,631 B2 | 1/2006 | Woloszko et al. ........... 606/41 |
| 7,004,941 B2 | 2/2006 | Tvinnereim et al. ......... 606/41 |
| 7,014,633 B2 | 3/2006 | Cragg ....................... 604/500 |
| 7,041,102 B2 | 5/2006 | Truckai et al. ............... 606/51 |
| 7,070,596 B1 | 7/2006 | Woloszko et al. ........... 606/41 |
| 7,090,672 B2 | 8/2006 | Underwood et al. ......... 606/41 |
| 7,094,215 B2 | 8/2006 | Davison et al. .............. 604/22 |
| 7,104,986 B2 | 9/2006 | Hovda et al. ................ 606/32 |
| 7,108,696 B2 | 9/2006 | Daniel et al. ................ 606/41 |
| 2002/0016583 A1 | 2/2002 | Cragg |
| 2002/0029036 A1 | 3/2002 | Goble et al. ................. 606/38 |
| 2002/0095151 A1 | 7/2002 | Dahia et al. ................. 606/41 |
| 2003/0013986 A1 | 1/2003 | Saadat ....................... 600/549 |
| 2003/0028189 A1 | 2/2003 | Woloszko et al. ........... 604/45 |
| 2003/0088245 A1 | 5/2003 | Woloszko et al. ........... 606/41 |
| 2003/0158545 A1 | 8/2003 | Hovda et al. ................ 606/32 |
| 2003/0171743 A1 | 9/2003 | Tasti et al. ................... 606/32 |
| 2003/0208194 A1 | 11/2003 | Hovda et al. ................ 606/41 |
| 2003/0208196 A1 | 11/2003 | Stone .......................... 606/41 |
| 2003/0212395 A1 | 11/2003 | Woloszko et al. ........... 606/32 |
| 2003/0212396 A1 | 11/2003 | Eggers et al. ................ 606/41 |
| 2004/0024399 A1 | 2/2004 | Sharps et al. ................ 606/32 |
| 2004/0049180 A1 | 3/2004 | Sharps et al. ................ 606/32 |
| 2004/0054366 A1 | 3/2004 | Davison et al. .............. 606/45 |
| 2004/0127893 A1 | 7/2004 | Hovda ........................ 606/41 |
| 2004/0153057 A1 | 8/2004 | Davison ..................... 600/410 |
| 2004/0186469 A1 | 9/2004 | Woloszko et al. ........... 606/41 |
| 2004/0230190 A1 | 11/2004 | Dahia et al. ................. 604/41 |
| 2005/0004634 A1 | 1/2005 | Hovda et al. ................ 606/41 |
| 2005/0010205 A1 | 1/2005 | Hovda et al. ................ 606/32 |
| 2005/0119650 A1 | 6/2005 | Sanders et al. .............. 424/426 |
| 2005/0131402 A1 | 6/2005 | Ciarrocca et al. ........... 600/450 |
| 2005/0187543 A1 | 8/2005 | Underwood et al. ......... 606/41 |
| 2005/0234439 A1 | 10/2005 | Underwood et al. ......... 606/32 |
| 2005/0251134 A1 | 11/2005 | Woloszko et al. ........... 606/32 |
| 2005/0261754 A1 | 11/2005 | Woloaszko et al. .......... 606/32 |
| 2005/0288665 A1 | 12/2005 | Woloszko et al. ........... 606/32 |
| 2006/0036237 A1 | 2/2006 | Davison et al. .............. 606/41 |
| 2006/0095031 A1 | 5/2006 | Ormsby ...................... 606/34 |
| 2006/0129145 A1 | 6/2006 | Ormsby et al. .............. 606/41 |
| 2006/0178670 A1 | 8/2006 | Woloszko et al. ........... 606/48 |
| 2006/0189971 A1 | 8/2006 | Egers et al. ................. 606/32 |
| 2006/0253117 A1 | 11/2006 | Hovda et al. .............. 128/898 |
| 2006/0259025 A1 | 11/2006 | Dahia ........................ 607/108 |
| 2007/0001088 A1 | 1/2007 | Dahia ........................ 606/41 |

FOREIGN PATENT DOCUMENTS

| | | |
|---|---|---|
| EP | 0 703 461 | 3/1996 |
| EP | 0 740 926 A2 | 11/1996 |
| EP | 0 754 437 | 1/1997 |
| EP | 0 694290 | 11/2000 |
| FR | 2313949 | 1/1977 |
| GB | 2 308 979 | 7/1997 |
| GB | 2 308 980 | 7/1997 |
| GB | 2 308 981 | 7/1997 |
| GB | 2 327 350 | 1/1999 |
| GB | 2 327 351 | 1/1999 |
| GB | 2 327 352 | 1/1999 |
| JP | 57-57802 | 4/1982 |
| JP | 57-117843 | 7/1982 |
| NL | 05/000434 | 12/2006 |
| WO | 90/03152 | 4/1990 |
| WO | WO90/07303 | 7/1990 |
| WO | 92/21278 | 12/1992 |
| WO | WO93/13816 | 7/1993 |
| WO | 93/20747 | 10/1993 |
| WO | WO94/04220 | 3/1994 |
| WO | 94/08654 | 4/1994 |
| WO | 94/14383 | 7/1994 |
| WO | WO95/34259 | 12/1995 |
| WO | 96/00042 | 1/1996 |
| WO | 97/00646 | 1/1997 |
| WO | 97/00647 | 1/1997 |
| WO | 97/24073 | 7/1997 |
| WO | 97/24993 | 7/1997 |
| WO | 97/24994 | 7/1997 |
| WO | 97/34992 | 7/1997 |
| WO | WO97/24074 | 7/1997 |
| WO | 97/48345 | 12/1997 |
| WO | 97/48346 | 12/1997 |
| WO | 98/01087 | 1/1998 |
| WO | 98/07468 | 2/1998 |
| WO | 98/11944 | 3/1998 |
| WO | 98/17190 | 4/1998 |
| WO | 98/27879 | 7/1998 |
| WO | 98/27880 | 7/1998 |
| WO | 99/47058 | 9/1999 |
| WO | 99/51155 | 10/1999 |
| WO | 99/51158 | 10/1999 |
| WO | 01/87154 | 5/2001 |
| WO | 02/36028 | 5/2002 |
| WO | 05/125287 | 12/2005 |

OTHER PUBLICATIONS

Costello, A. J. et al. "Nd:YAG Laser Ablation of the Prostate as a Treatment of Benign Prostatic Hypertrophy," (1992) Lasers in Surger and Medicine 12:121-124.
J.W. Ramsey et al. *Urological Research* vol. 13, pp. 99-102 (1985).
V.E. Elsasser et al. *Acta Medicotechnica* vol. 24, No. 4, pp. 129-134 (1976).
P.C. Nardella (1989) *SPIE* 1068:42-49 Radio Frequency Energy and Impedance Feedback.
Rand et al. (1985) *J. Arthro. Surg.* 1:242-246 Effect of Electrocautery on Fresh Human Articular Cartilage.
Buchelt, M. et al. "Excimer Laser Ablation of Fibrocartilage: An In Vitro and In Vivo Study," (1991) Lasers in Surgery and Medicine 11:271-279.
R. Tucker et al., Abstract P14-11, p. 248, "A Bipolar Electrosurgical Turp Loop".
R. Tucker et al. *J. of Urology* vol. 141, pp. 662-665, (1989).
R. Tucker et al. *Urological Research* vol. 18, pp. 291-294 (1990).
Kramolowsky et al. *J. of Urology* vol. 143, pp. 275-277 (1990).
Kramolowsky et al. *J. of Urology* vol. 146, pp. 669-674 (1991).
J. Saal et al. *NASS-APS First Joint Meeting*, Charleston SC, Apr. 1998.
Slager et al. *Z. Kardiol.* 76:Suppl. 6, 67-71 (1987).
Slager et al. *JACC* 5(6) :1382-6 (1985).
A.K. Dobbie *Bio-Medical Engineering*. vol. 4, pp. 206-216 (1969).
W. Honig *IEEE* pp. 58-65 (1975).
M.B. Dennis et al. *Digestive Diseases and Sciences* vol. 24(11), pp. 845-848 (1979).
K. Barry et al. *American Heart Journal* vol. 117, pp. 332-341 (1982).
C.P. Swain *Gut* vol. 25, pp. 1424-1431 (1984).
B. Lee et al. *JACC* vol. 13(5), pp. 1167-1175 (1989).
Piercey et al. *Gastroenterology* vol. 74(3), pp. 527-534 (1978).
Olsen MD, Bipolar Laparoscopic Cholecstecomy Lecture (marked confidential), Oct. 7, 1991.
Codman & Shurtleff, Inc. "The Malis Bipolar Coagulating and Bipolar Cutting System CMC-II" brochure, early, 2 pgs.

Codman & Shurtleff, Inc. "The Malis Bipolar Electrosurgical System CMC--III Instruction Manual", 15 pgs.

Cook et al., "Therapeutic Medical Devices: Application and Design", Prentice Hall, Inc., 3 pgs.

Geddes, "Medical Device Accidents: With Illustrative Cases" CRC Press, 3 pgs.

Letter from Department of Health to Jerry Malis dated Jan. 24, 1991, 3 pgs.

Letter from Department of Health to Jerry Malis dated Jul. 25, 1985, 1 pg.

Letter form Jerry Malis to FDA dated Jul. 25, 1985, 2 pgs.

Lu, et al., "Electrical Thermal Angioplasty: Catheter Design Features, In Vitro Tissue Ablation Studies and in Vitro Experimental Findings," *Am j. Cardiol* vol. 60, pp. 1117-1122.

Malis, L., "Electrosurgery, Technical Note," *J. Neursurg.*, vol. 85, pp. 970-975, Nov. 1996.

Malis, L., "Excerpted from a seminar by Leonard I. Malis, M.D. at the 1995 American Association of Neurological Surgeons Meeting," 1pg.

Malis, L., "Instrumentation for Microvascular Neurosurgery" *Cerebrovascular surgery*, vol. 1, pp. 245-260.

Malis, L., "New Trends in Microsurgery and Applied Technology," *Advanced Technology in Neurosurgery*, pp. 1-16.

Malis, L., "The Value of Irrigation During Bipolar Coagulation" See ARTC 21602, 1 pg.

O'Malley, Schaum's Outline of Theory and Problems of Basic Circuit Analysis, McGraw-Hill, 2$^{nd}$ Ed., pp. 3-5.

Pearce, John A., "Electrosurgery", Handbook of Biomedical Engineering, chapter 3, Academic Press Inc., N.Y., pp. 98-113.

Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455.

Selikowitz et al., "Electric Current and Voltage Recordings on the Myocardium During electrosurgical Procedures in Canines," *Surgery, Gynecology & Obstetrics*, vol. 164, pp. 219-224.

Shuman, "Bipolar Versus Monopolar Electrosurgery: Clinical Applications," *Dentistry Today*, vol. 20, No. 12, 7 pgs.

Stoffels, E. et al., "Investigation on the Interaction Plasma-Bone Tissue", E-MRS Spring Meeting, 1 pg.

Stoffels, E. et al., "Biomedical APplications of Plasmas", Tutorial presented prior to the 55$^{th}$ Gaseous Electronics Conference in Minneapolis, MN, 41 pgs.

Stoffels, E. et al., "Plasma Interactions with Liing Cells", Eindhoven University of Technology, 1 pg.

Stoffels, E. et al., "Superficial Treatment of Mammalian Cells using Plasma Needle", J. Phys. D: Appl. Phys. 26, pp. 2908-2913.

Stoffels, E. et al., "Plasma Needle", Eindhoven University of Technology, 1 pg.

Stoffels, E. et al., "Plasma Physicists Move into Medicine", Physicsweb, 1 pg.

Stoffels, E. et al., "Plasma Treated Tissue Engineered Skin to Study Skin Damage", Biomechanincs and Tissue Engineering, Materials Technology, 1 pg.

Stoffels, E. et al., "Plasma Treatment of Dental Cavities: A Feasibility Study", IEEE Transaction on Plasma Science, vol. 32, No. 4, pp. 1540-1542.

Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550.

Stoffels, E. et al., "Electrical and Optical Characterization of the Plasma Needle", New Journal of Physics 6, pp. 1-14.

Stoffels, E. et al., "Where Plasma Meets Plasma", Eindhoven University of Technology, 23 pgs.

Stoffels, E. et al., "Gas Plasma effects on Living Cells", Physica Scripta, T107, pp. 79-82.

Stoffels, E. et al., "Plasma Treatment of Mammalian Vascular Cells: A Quantitative Description", IEEE Transaction on Plasma Science, vol. 33, No. 2, pp. 771-775.

Stoffels, E. et al., "Deactivation of Escherichia Coli by the Plasma Needle", J. Phys. D: Appl. Phys. 38, pp. 1716-1721.

Stoffels, E. et al., "Development of a Gas Plasma Catheter for Gas Plasma Surgery", XXVIIth ICPIG, Endoven University of Technology, pp. 18-22.

Stoffels, E. et al., "Development of a Smart Positioning Sensor for the Plasma Needle", Plasma Sources Sci. Technol. 15, pp. 582-589.

Stoffels, E. et al., Killing of S. Mutans Bacteria Using a Plasma Needle at Atmospheric Pressure, IEEE Transaction on Plasma Science, vol. 34, No. 4, pp. 1317-1324.

Stoffels, E. et al., "Plasma-Needle Treatment of Substrates with Respect to Wettability and Growth of Excherichia Coli and Streptococcus Mutans", IEEE Transaction on Plasma Science, vol. 34, No. 4, pp. 1325-1330.

Stoffels, E. et al., "Reattachment and Apoptosis sfter Plasma-Needle Treatment of Cultured Cells", IEEE Transaction on Plasma Science, vol. 34, No. 4, pp. 1331-1336.

Stoffels, E. et al., "UV excimer Lamp Irradiation of Fibroblasts: The Influence on Antioxidant Homostasis", IEEE Transaction on Plasma Science, vol. 34, No. 4, pp. 1359-1364.

Stoffels, E. et al., "Plasma Needle for In Vivo Medical Treatment: Recent Developments and Perspectives", Plasma Sources Sci. technol. 25, pp. S169-S180.

Tucker, R. et al., "Demodulated Low Frequency Currents from Electrosurgical Procedures," *Surgery Gynecology and Obstetrics*, 159:39-43.

Valley Forge Scientific Corp., "Summary of Safety and Effective Information from 510K", 2pgs.

Valley Forge's New Products, Clinica, 475, 5.

Valleylab SSE2L Instruction Manual, 11 pgs.

Valleylab, Inc. "Valleylab Part No. 945 100 102 A" Surgistat Service Manual, pp. 1-46.

Wattiez, Arnaud et al., "Electrosurgery in Operative Endoscopy," electrosurgical Effects, Blackwell Science, pp. 85-93.

Wyeth, "Electrosurgical Unit" pp. 1181-1202.

Aesculap, "Flexible endoscope", Micro, Neuro and Spine surgery, 3 pgs.

\* cited by examiner

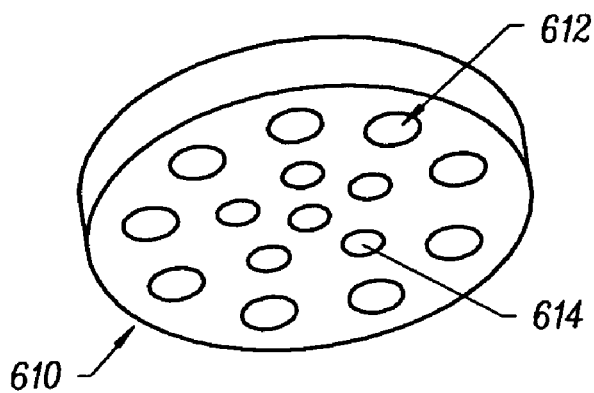
FIG. 11A
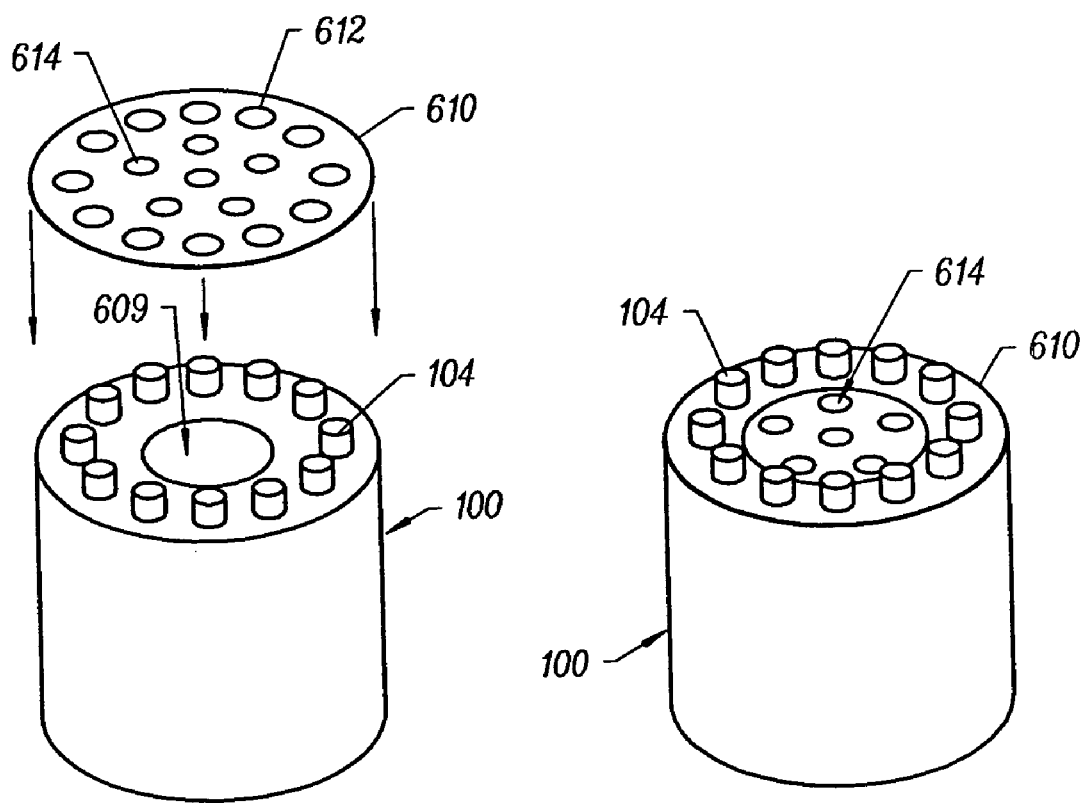
FIG. 11B
FIG. 11C

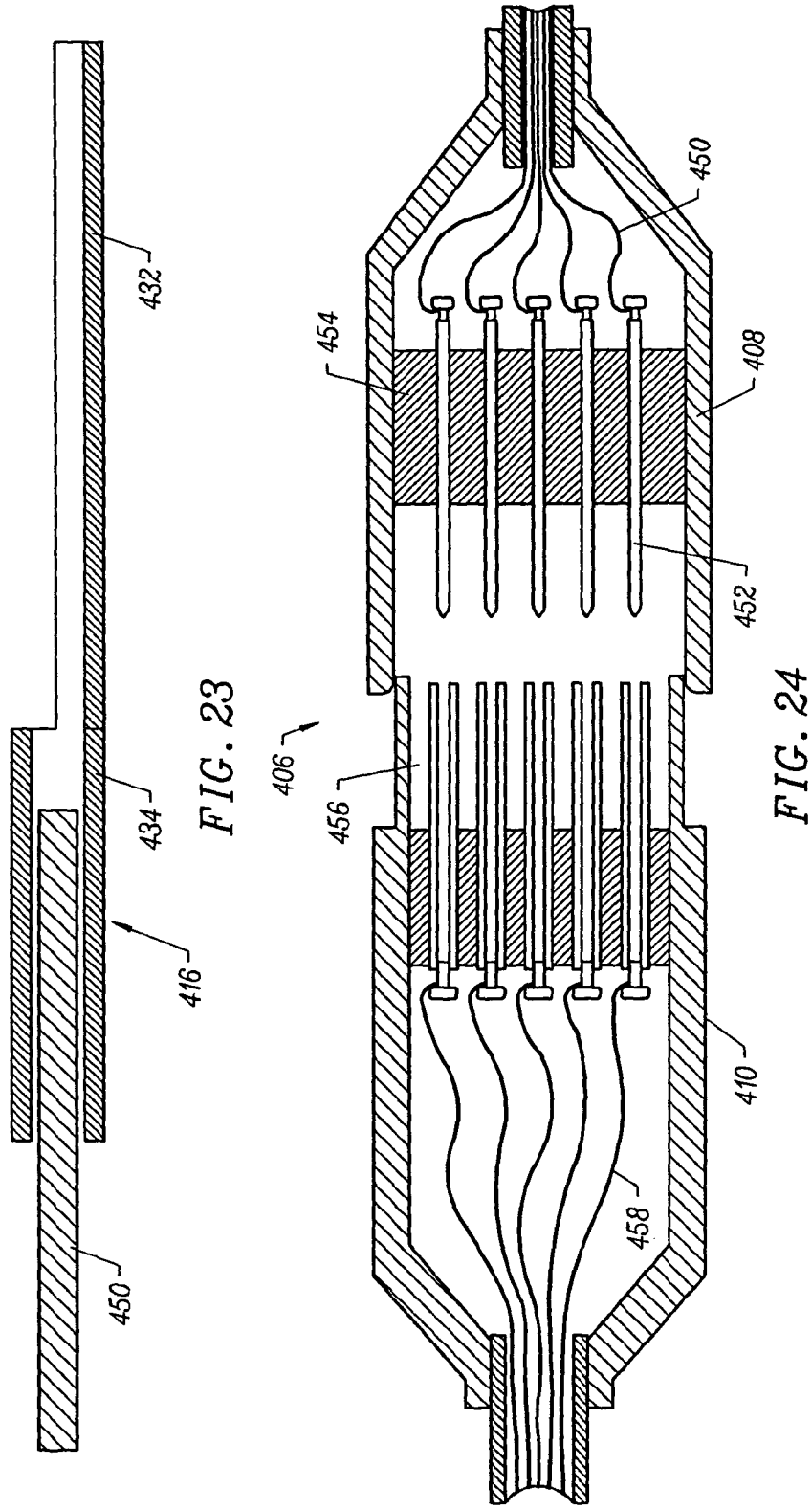

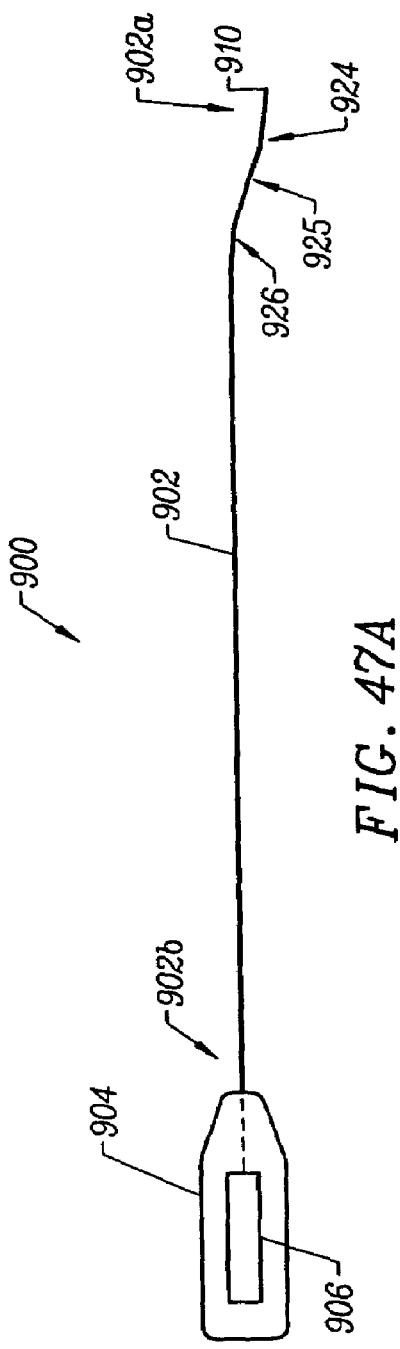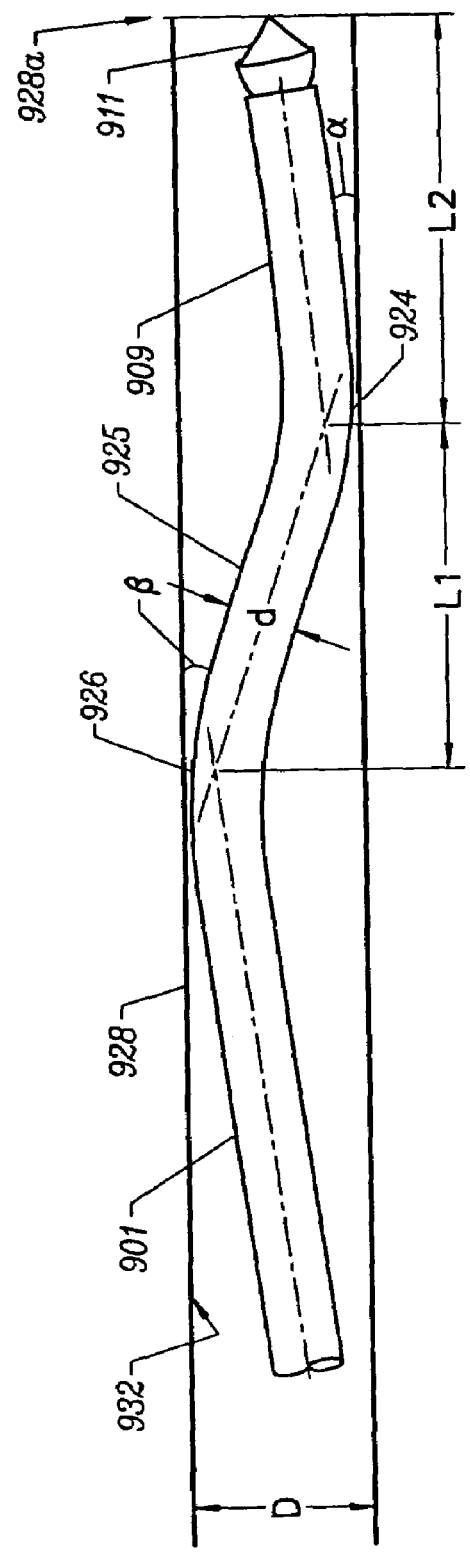
FIG. 47A
FIG. 47B

SYSTEMS AND METHODS FOR ELECTROSURGERY

RELATED APPLICATIONS

This application is a divisional of U.S. patent application Ser. No. 09/708,962 filed Nov. 8, 2000, now U.S. Pat. No. 6,726,684, which claims the benefit of Provisional Patent Application No. 60/204,206 filed May 12, 2000, and is a continuation-in-part of U.S. patent application Ser. No. 09/676,194, entitled "Methods for Repairing Damaged Intervertebral Discs", filed Sep. 28, 2000, now U.S. Pat. No. 6,602,248.

The present invention is related to commonly assigned co-pending Provisional Patent Application Nos. 60/062,996 and 60/062,997, non-provisional U.S. patent application Ser. No. 08/970,239 entitled "Electrosurgical Systems and Methods for Treating the Spine," filed Nov. 14, 1997, and Ser. No. 08/977,845 entitled "Systems and Methods for Electrosurgical Dermatological Treatment," filed on Nov. 25, 1997, U.S. application Ser. No. 08/753,227, filed on Nov. 22, 1996, and PCT International Application, U.S. National Phase Serial No. PCT/US94/05168, filed on May 10, 1994, now U.S. Pat. No. 5,697,281, which was a continuation-in-part of application Ser. No. 08/059,681, filed on May 10, 1993, which was a continuation-in-part of application Ser. No. 07/958,977, filed on Oct. 9, 1992 which was a continuation-in-part of application Ser. No. 07/817,575, filed on Jan. 7, 1992, the complete disclosures of which are incorporated herein by reference for all purposes. The present invention is also related to commonly assigned U.S. Pat. No. 5,683,366, filed Nov. 22, 1995, and U.S. Pat. No. 5,697,536, filed on Jun. 2, 1995, the complete disclosures of which are incorporated herein by reference for all purposes.

BACKGROUND OF THE INVENTION

The present invention relates generally to the field of electrosurgery, and more particularly to surgical devices and methods which employ high frequency electrical energy to treat tissue in regions of the spine. The present invention is particularly suited for the treatment of herniated discs and other disorders of intervertebral discs. This invention also relates to treatment of an intervertebral disc by guiding an electrosurgical probe to a target site within an intervertebral disc.

The major causes of persistent, often disabling, back pain are disruption of the disc annulus, chronic inflammation of the disc (e.g., herniation), or relative instability of the vertebral bodies surrounding a given disc, such as the instability that often occurs due to a degenerative disease. Spinal discs mainly function to cushion and tether the vertebrae, providing flexibility and stability to the patient's spine. Spinal discs comprise a central hydrophilic cushion, the nucleus pulposus, surrounded by a multi-layered ligament, the annulus fibrosus. As discs degenerate, they lose their water content and height, bringing vertebrae closer together. This results in a weakening of the shock absorption properties of the disc and a narrowing of the nerve openings in the sides of the spine which may lead to pinching of the nerve root. This disc degeneration can cause back and leg pain. Weakness in the annulus fibrosus of degenerative discs, or disc injury, can allow fragments of the nucleus pulposus to migrate from within the disc into the annulus fibrosus or the spinal canal. Displaced annulus fibrosus, or protrusion of the nucleus pulposus, e.g., herniation, may impinge on spinal nerves or nerve roots. The mere proximity of the nucleus pulposus or a damaged annulus to a nerve can cause direct pressure against the nerve, resulting in pain and sensory and motor deficit.

Often, inflammation from disc herniation can be treated successfully by non-surgical means, such as rest, therapeutic exercise, oral anti-inflammatory medications or epidural injection of corticosteroids. In some cases, the disc tissue is irreparably damaged, thereby necessitating removal of a portion of the disc or the entire disc to eliminate the source of inflammation and pressure. In more severe cases, the adjacent vertebral bodies must be stabilized following excision of the disc material to avoid recurrence of the disabling back pain. One approach to stabilizing the vertebrae, termed spinal fusion, is to insert an interbody graft or implant into the space vacated by the degenerative disc. In this procedure, a small amount of bone may be grafted and packed into the implants. This allows the bone to grow through and around the implant, fusing the vertebral bodies and preventing reoccurrence of the symptoms.

Until recently, spinal discectomy and fusion procedures resulted in major operations and traumatic dissection of muscle and bone removal or bone fusion. To overcome the disadvantages of traditional traumatic spine surgery, minimally invasive spine surgery was developed. In endoscopic spinal procedures, the spinal canal is not violated and therefore epidural bleeding with ensuring scarring is minimized or completely avoided. In addition, the risk of instability from ligament and bone removal is generally lower in endoscopic procedures than with open discectomy. Further, more rapid rehabilitation facilitates faster recovery and return to work.

Minimally invasive techniques for the treatment of spinal diseases or disorders include chemonucleolysis, laser techniques and mechanical techniques. These procedures generally require the surgeon to form a passage or operating corridor from the external surface of the patient to the spinal disc(s) for passage of surgical instruments, implants and the like. Typically, the formation of this operating corridor requires the removal of soft tissue, muscle or other types of tissue depending on the procedure (i.e., laparascopic, thoracoscopic, arthroscopic, back, etc.). This tissue is usually removed with mechanical instruments, such as pituitary rongeurs, curettes, graspers, cutters, drills, microdebriders and the like. Unfortunately, these mechanical instruments greatly lengthen and increase the complexity of the procedure. In addition, these instruments might sever blood vessels within this tissue, usually causing profuse bleeding that obstructs the surgeon's view of the target site.

Once the operating corridor is established, the nerve root is retracted and a portion or all of the disc is removed with mechanical instruments, such as a pituitary rongeur. In addition to the above problems with mechanical instruments, there are serious concerns because these instruments are not precise, and it is often difficult, during the procedure, to differentiate between the target disc tissue, and other structures within the spine, such as bone, cartilage, ligaments, nerves and non-target tissue. Thus, the surgeon must be extremely careful to minimize damage to the cartilage and bone within the spine, and to avoid damaging nerves, such as the spinal nerves and the dura mater surrounding the spinal cord.

Lasers were initially considered ideal for spine surgery because lasers ablate or vaporize tissue with heat, which also acts to cauterize and seal the small blood vessels in the tissue. Unfortunately, lasers are both expensive and somewhat tedious to use in these procedures. Another disadvantage with lasers is the difficulty in judging the depth of tissue ablation. Since the surgeon generally points and shoots the laser without contacting the tissue, he or she does not receive any tactile feedback to judge how deeply the laser is cutting. Because healthy tissue, bones, ligaments and spinal nerves often lie within close proximity of the spinal disc, it is essential to maintain a minimum depth of tissue damage, which cannot always be ensured with a laser.

Monopolar and bipolar radiofrequency devices have been used in limited roles in spine surgery, such as to cauterize severed vessels to improve visualization.

Monopolar devices, however, suffer from the disadvantage that the electric current will flow through undefined paths in the patient's body, thereby increasing the risk of unwanted electrical stimulation to portions of the patient's body. In addition, since the defined path through the patient's body has a relatively high impedance (because of the large resistance or resistivity of the patient's body), large voltage differences must typically be applied between the return and active electrodes in order to generate a current suitable for ablation or cutting of the target tissue. This current, however, may inadvertently flow along body paths having less impedance than the defined electrical path, which will substantially increase the current flowing through these paths, possibly causing damage to or destroying surrounding tissue or neighboring peripheral nerves.

There is a need for an apparatus or system including an electrosurgical instrument, such as a catheter or probe, wherein the instrument can be introduced into an intervertebral disc during an endoscopic procedure, and the distal portion of the instrument can be guided to a target site within the disc, wherein the target site can be treated with minimal or no damage to surrounding, non-target tissue. The instant invention provides such an electrosurgical system and methods for treating tissue by a cool ablation mechanism involving generation of a plasma in the presence of an electrically conductive fluid and molecular dissociation of tissue components, as is described in enabling detail hereinbelow.

SUMMARY OF THE INVENTION

The present invention provides systems, apparatus and methods for selectively applying electrical energy to structures within a patient's body, such as tissue within or around the spine. The systems and methods of the present invention are particularly useful for ablation, resection, aspiration, collagen shrinkage and/or hemostasis of tissue and other body structures in open and endoscopic spine surgery.

In one aspect of the invention, a method is provided for treating discs within a patient's spine. Specifically, a method of the present invention comprises positioning at least one active electrode within close proximity of a disc in the spine (either endoscopically, or through an open procedure). The dura mater tissue that surrounds the spinal cord is insulated from the active electrode(s) and a high frequency voltage is applied between the active electrode(s) and one or more return electrodes to apply sufficient energy to the disc tissue to reduce the volume of the disc.

In one embodiment, the high frequency voltage is sufficient to ablate at least a portion of the nucleus pulposus, either the extruded portion outside the annulus or a portion or all of the nucleus pulposus within the annulus. In another embodiment, the active electrode is advanced into the annulus and sufficient high frequency voltage is applied to contract or shrink the collagen fibers within the nucleus pulposus. This causes the pulposus to shrink and withdraw from its impingement on the spinal nerve. In other embodiments, the present invention may be used to both ablate the extruded portion of the nucleus pulposus, and then to contract or shrink the inner disc material to allow repair of the annulus.

In a specific configuration, electrically conducting fluid, such as isotonic saline, is directed to the target site between the target disc tissue and the active electrode. In monopolar embodiments, the conductive fluid need only be sufficient to surround the active electrode, and to provide a layer of fluid between the electrode and the tissue. In bipolar embodiments, the conductive fluid preferably generates a current flow path between the active electrode(s) and one or more return electrodes.

In procedures requiring contraction of tissue, high frequency voltage is applied to the active electrode(s) to elevate the temperature of collagen fibers within the tissue at the target site from body temperature (about 37° C.) to a tissue temperature in the range of about 45° C. to 90° C., usually about 60° C. to 70° C., to substantially irreversibly contract these collagen fibers. In a preferred embodiment, an electrically conductive fluid is provided between the active electrode(s) and one or more return electrodes positioned on an electrosurgical probe proximal to the active electrode(s) to provide a current flow path from the active electrode(s) away from the tissue to the return electrode(s). The current flow path may be generated by directing an electrically conductive fluid along a fluid path past the return electrode and to the target site, or by locating a viscous electrically conducting fluid, such as a gel, at the target site, and submersing the active electrode(s) and the return electrode(s) within the conductive gel. The collagen fibers may be heated either by passing the electric current through the tissue to a selected depth before the current returns to the return electrode(s) and/or by heating the electrically conductive fluid and generating a jet or plume of heated fluid which is directed towards the target tissue. In the latter embodiment, the electric current may not pass into the tissue at all. In both embodiments, the heated fluid and/or the electric current elevates the temperature of the collagen sufficiently to cause hydrothermal shrinkage of the collagen fibers.

In procedures requiring ablation of tissue, the tissue is removed by molecular dissociation or disintegration processes. In these embodiments, the high frequency voltage applied to the active electrode(s) is sufficient to vaporize an electrically conductive fluid (e.g., gel or saline) between the active electrode(s) and the tissue. Within the vaporized fluid an ionized plasma is formed, and charged particles (e.g., electrons) cause the molecular breakdown or disintegration of several cell layers of the tissue. This molecular dissociation is accompanied by the volumetric removal of the tissue. This process can be precisely controlled to effect the volumetric removal of tissue as thin as 10 microns to 150 microns with minimal heating of, or damage to, surrounding or underlying tissue structures. A more complete description of this phenomenon is described in commonly assigned U.S. Pat. No. 5,683,366, the complete disclosure of which is incorporated herein by reference.

In another aspect of the invention, the present invention is useful for performing spinal surgery. The method comprises positioning an electrosurgical instrument in close proximity to an intervertebral disc. An electrically conductive fluid is delivered toward a distal tip of the electrosurgical instrument. A high frequency electrical energy is applied to the active electrode such that the conductive fluid completes a current flow path between the active electrode and a return electrode. The conductive fluid is aspirated through an aspiration lumen positioned proximal of the return electrode.

Because the aspiration lumen is positioned away from the fluid delivery lumen and proximal of the return electrode, a plasma can be aggressively created and the tissue can be ablated or contracted more efficiently.

The tissue may be completely ablated in situ with the mechanisms described above, or the tissue may be partially ablated and partially resected and aspirated from this operating corridor. In a preferred configuration, the probe will include one or more aspiration electrode(s) at or near the distal opening of an aspiration lumen. In this embodiment, high frequency voltage is applied between the aspiration electrode(s) and one or more return electrodes (which can be the same or different electrodes from the ones used to ablate tissue) to partially or completely ablate the tissue fragments as they are aspirated into the lumen, thereby preventing clogging of the lumen and expediting the tissue removal process. In other configurations, the aspiration electrodes can be disposed within the aspiration lumen.

The present invention offers a number of advantages over current mechanical and laser techniques for spine surgery. The ability to precisely control the volumetric removal of tissue results in a field of tissue ablation or removal that is very defined, consistent and predictable. The shallow depth of tissue heating also helps to minimize or completely eliminate damage to healthy tissue structures, cartilage, bone and/or spinal nerves that are often adjacent the target tissue. In addition, small blood vessels within the tissue are simultaneously cauterized and sealed as the tissue is removed to continuously maintain hemostasis during the procedure. This increases the surgeon's field of view, and shortens the length of the procedure. Moreover, since the present invention allows for the use of electrically conductive fluid (contrary to prior art bipolar and monopolar electrosurgery techniques), isotonic saline may be used during the procedure. Saline is the preferred medium for irrigation because it has the same concentration as the body's fluids and, therefore, is not absorbed into the body as much as certain other fluids.

Apparatus according to the present invention generally include an electrosurgical probe or catheter having a shaft with proximal and distal ends, one or more active electrode(s) at the distal end and one or more connectors coupling the active electrode(s) to a source of high frequency electrical energy. For endoscopic spine surgery, the shaft will typically have a distal end portion sized to fit between adjacent vertebrae in the patient's spine. In some embodiments, the distal end portion can have an active side which has the active electrodes and an insulated non-active side. In a specific use, the insulator can be used to protect the dura mater (and spinal column) from iatrogenic injury.

Some embodiments of the electrosurgical probe can include a fluid delivery element for delivering electrically conductive fluid to the active electrode(s). The fluid delivery element may be located on the probe, e.g., a fluid lumen or tube, or it may be part of a separate instrument. In an exemplary embodiment, the lumen will extend through a fluid tube exterior to the probe shaft that ends adjacent the distal tip of the shaft.

Alternatively, an electrically conducting gel or spray, such as a saline electrolyte or other conductive gel, may be applied to the target site. The electrically conductive fluid will preferably generate a current flow path between the active electrode(s) and one or more return electrodes. In an exemplary embodiment, the return electrode is located on the probe and spaced a sufficient distance from the active electrode(s) to substantially avoid or minimize current shorting therebetween and to shield the return electrode from tissue at the target site.

In a specific configuration, the electrosurgical probe will include an electrically insulating electrode support member having a tissue treatment surface at the distal end of the probe. One or more active electrode(s) are coupled to, or integral with, the electrode support member such that the active electrode(s) are spaced from the return electrode. In one embodiment, the probe includes an electrode array having a plurality of electrically isolated active electrodes embedded in the electrode support member such that the active electrodes extend about 0.2 mm to about 10 mm from the tissue treatment surface of the electrode support member.

In other embodiments, the probe can include one or more lumens for aspirating the electrically conductive fluid from the target area. In an exemplary embodiment, the lumen will extend along the exterior of the probe shaft and end proximal of the return electrode. In a specific configuration, the aspiration lumen and fluid delivery lumen both extend along the exterior of the probe shaft in an annular configuration. The fluid delivery lumen will extend to the distal tip of the shaft while the aspiration lumen will extend only to a point proximal of the return electrode.

In yet another aspect, the present invention provides a method of treating an intervertebral disc having a nucleus pulposus and an annulus fibrosus. The method comprises advancing a distal end of an electrosurgical instrument into the annulus fibrosus. The distal end of the electrosurgical instrument is moved, typically biased or steered, to a curved configuration that approximates a curvature of an inner surface of the annulus fibrosus. A high frequency voltage is delivered between an active electrode and a return electrode that are positioned on the distal end of the electrosurgical instrument to treat the inner surface of the annulus fibrosus.

In yet another aspect, the present invention provides a method of treating an intervertebral disc. The method comprises positioning a distal end of an electrosurgical probe within close proximity of an outer surface of the intervertebral disc. A high frequency voltage is delivered between an active electrode and a return electrode. The high frequency voltage is sufficient to create a channel in the disc tissue. The active electrode is then advanced through the channel created in the intervertebral disc. The distal end of the electrosurgical instrument is moved to a curved configuration that approximates a curvature of an inner surface of the annulus fibrosus. A high frequency voltage is delivered between the active electrode and the return electrode to treat the inner surface of the annulus fibrosus.

In a further aspect, the present invention provides an apparatus for treating an intervertebral disc. The apparatus comprises a steerable distal end portion that is moveable to a curved configuration that approximates the curvature of the inner surface of an annulus fibrosus. At least one active electrode and a return electrode are positioned on the distal end of the apparatus. A high frequency energy source is configured to create a voltage difference between the active electrode and the return electrode. Preferably, the return electrode is positioned proximal of the active electrode so as to draw the electric current away from the target tissue.

In another aspect, the present invention provides a method of using an electrosurgical system for treating a disorder of an intervertebral disc of a patient, wherein the electrosurgical system includes a power supply coupled to at least one active electrode disposed on a shaft distal end of an electrosurgical probe. Such disc disorders include fragmentation and migration of the nucleus pulposus into the annulus fibrosus, discogenic or axial pain, one or more fissures in the annulus fibrosus, or contained herniation (a protrusion of the nucleus pulposus which is contained within the annulus fibrosus) of the disc. The method includes inserting the shaft distal end within the intervertebral disc such that the active electrode is in the vicinity of the tissue targeted for treatment (fissure, contained herniation, etc.), and thereafter applying a high frequency voltage between the active electrode and a return electrode sufficient to ablate target tissue. In preferred embodiments, the voltage generates a plasma in the vicinity of the target site and tissue at the target site is ablated by the molecular dissociation of disc tissue components to form low molecular weight ablation by-products, the latter being readily aspirated from the target site or tissue being treated.

In one embodiment, the shaft may be guided by a combination of axial translation of the shaft and rotation of the shaft about its longitudinal axis. In one aspect of the invention, the shaft has a pre-defined curvature, both before and after the shaft has been guided to the vicinity of the contained herniation. The pre-defined curvature may include a first and a second curve in the shaft, the second curve being proximal to the first curve.

In another aspect of the invention, the shaft may lack a pre-defined curvature, and may be bent to a suitable conformation prior to a particular surgical procedure. In yet another aspect of the invention, the shaft may lack a pre-defined curvature, and the shaft distal end may be steered during a surgical procedure so as to adopt a suitable conformation, thereby allowing the shaft distal end to be guided to a target site within an intervertebral disc.

By applying a high frequency voltage between the active electrode and the return electrode, disc tissue at the target site undergoes molecular dissociation. In one embodiment, the active electrode includes an electrode head having an apical spike and a cusp, wherein the electrode head is adapted for providing a high current density in the vicinity of the electrode head when a high frequency voltage is applied between the active electrode and the return electrode. The method may be conveniently performed percutaneously, and one or more stages in the treatment or procedure may be performed under fluoroscopy to allow visualization of the shaft within the disc to be treated.

Further aspects, features, and advantages of the present invention will appear from the following description in which the preferred embodiments have been set forth in detail in conjunction with the accompanying drawings.

BRIEF DESCRIPTION OF THE DRAWINGS

FIGS. 11A–11C illustrate an alternative embodiment incorporating a mesh electrode for ablating aspirated tissue fragments;

FIG. 23 is a side cross-sectional view of the working end of the planar ablation probe, illustrating the electrical connection with one of the active electrodes of FIG. 22;

FIG. 24 is a side cross-sectional view of the proximal end of the planar ablation probe, illustrating the electrical connection with a power source connector;

FIG. 47A is a side view of an electrosurgical probe having a curved shaft;

FIG. 47B is a side view of the distal end portion of the curved shaft of FIG. 47A, with the shaft distal end portion within an introducer device;

DESCRIPTION OF SPECIFIC EMBODIMENTS

Figure 1:
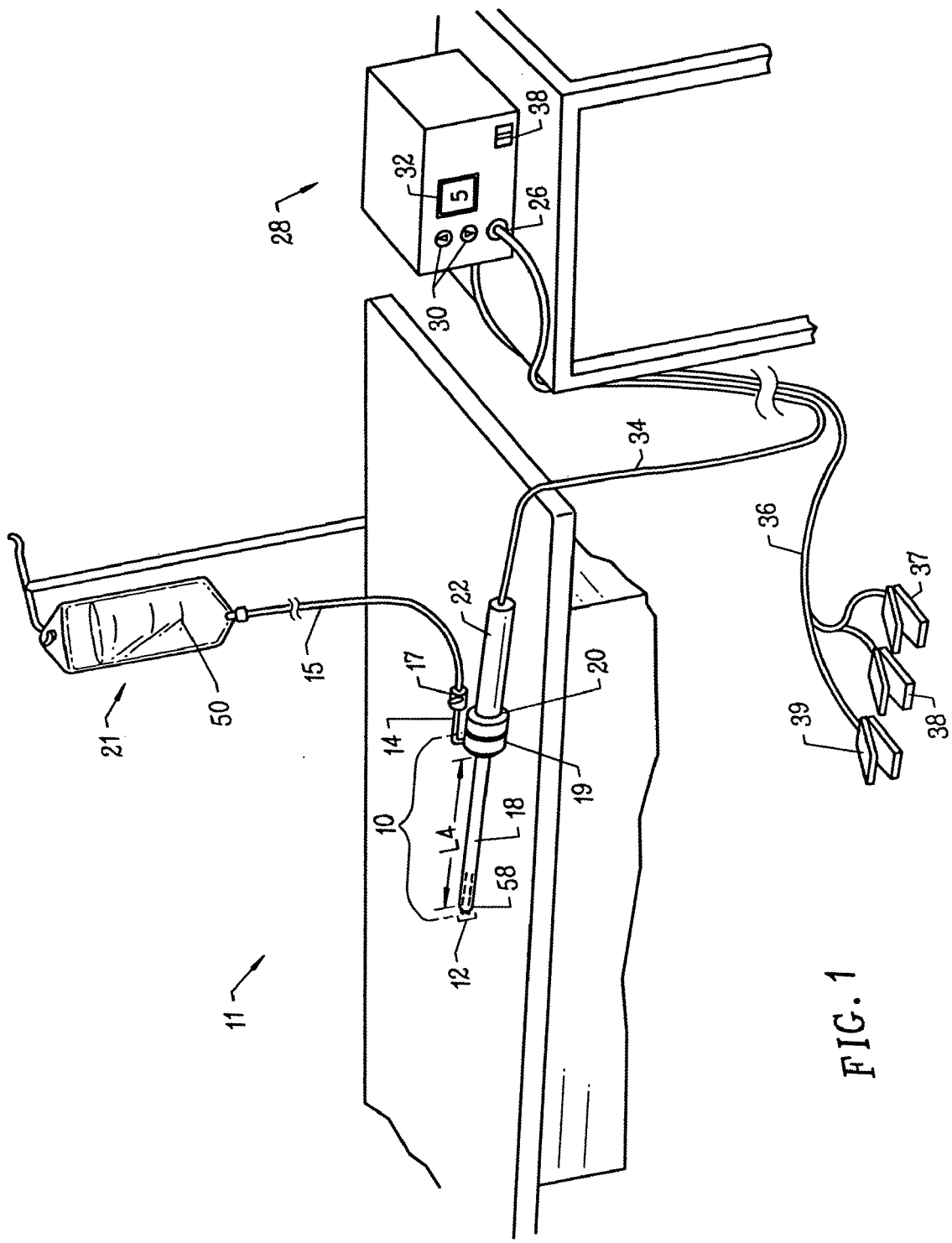
FIG. 1 is a perspective view of an electrosurgical system incorporating a power supply and an electrosurgical probe for tissue ablation, resection, incision, contraction and for vessel hemostasis according to the present invention.

The present invention provides systems and methods for selectively applying electrical energy to a target location within or on a patient's body, particularly including tissue or other body structures in the spine. These procedures include laminectomy/disketomy procedures for treating herniated disks, decompressive laminectomy for stenosis in the lumbosacral and cervical spine, medial facetectomy, posterior lumbosacral and cervical spine fusions, treatment of scoliosis associated with vertebral disease, foraminotomies to remove the roof of the intervertebral foramina to relieve nerve root compression and cervical and lumbar diskectomies, shrinkage of vertebral support tissue, and the like. These procedures may be performed through open procedures, or using minimally invasive techniques, such as thoracoscopy, arthroscopy, laparascopy or the like.

In the present invention, high frequency (RF) electrical energy is applied to one or more active electrodes in the presence of electrically conductive fluid to remove and/or modify the structure of tissue structures. Depending on the specific procedure, the present invention may be used to: (1) volumetrically remove tissue, bone, ligament or cartilage (i.e., ablate or effect molecular dissociation of the body structure); (2) cut or resect tissue or other body structures;

(3) shrink or contract collagen connective tissue; and/or (4) coagulate severed blood vessels.

In some procedures, e.g., shrinkage of nucleus pulposus in herniated discs, it is desired to shrink or contract collagen connective tissue at the target site. In these procedures, the RF energy heats the tissue directly by virtue of the electrical current flow therethrough, and/or indirectly through the exposure of the tissue to fluid heated by RF energy, to elevate the tissue temperature from normal body temperatures (e.g., 37° C.) to temperatures in the range of 45° C. to 90° C., preferably in the range from about 60° C. to 70° C. Thermal shrinkage of collagen fibers occurs within a small temperature range which, for mammalian collagen is in the range from 60° C. to 70° C. (Deak, G., et al., "The Thermal Shrinkage Process of Collagen Fibres as Revealed by Polarization Optical Analysis of Topooptical Staining Reactions," Acta Morphologica Acad. Sci. of Hungary, Vol. 15(2), pp 195–208, 1967). Collagen fibers typically undergo thermal shrinkage in the range of 60° C. to about 70° C. Previously reported research has attributed thermal shrinkage of collagen to the cleaving of the internal stabilizing cross-linkages within the collagen matrix (Deak, ibid). It has also been reported that when the collagen temperature is increased above 70° C., the collagen matrix begins to relax again and the shrinkage effect is reversed resulting in no net shrinkage (Allain, J. C., et al., "Isometric Tensions Developed During the Hydrothermal Swelling of Rat Skin," Connective Tissue Research, Vol. 7, pp. 127–133, 1980). Consequently, the controlled heating of tissue to a precise depth is critical to the achievement of therapeutic collagen shrinkage. A more detailed description of collagen shrinkage can be found in U.S. patent application Ser. No. 08/942,580, filed Oct. 2, 1997, entitled "Systems and Methods for Electrosurgical Tissue Contraction," previously incorporated herein by reference.

The preferred depth of heating to effect the shrinkage of collagen in the heated region (i.e., the depth to which the tissue is elevated to temperatures between 60° C. to 70° C.) generally depends on (1) the thickness of the tissue, (2) the location of nearby structures (e.g., nerves) that should not be exposed to damaging temperatures, and/or (3) the volume of contraction desired to relieve pressure on the spinal nerve. The depth of heating is usually in the range from 0 to 3.5 mm. In the case of collagen within the nucleus pulposus, the depth of heating is preferably in the range from about 0 to about 2.0 mm.

In another method of the present invention, the tissue structures are volumetrically removed or ablated. In this procedure, a high frequency voltage difference is applied between one or more active electrode(s) and one or more return electrodes to develop high electric field intensities in the vicinity of the target tissue site. The high electric field intensities lead to electric field induced molecular breakdown of target tissue through molecular dissociation (rather than thermal evaporation or carbonization). Applicant believes that the tissue structure is volumetrically removed through molecular disintegration of larger organic molecules into smaller molecules and/or atoms, such as hydrogen, oxides of carbon, hydrocarbons and nitrogen compounds. This molecular disintegration completely removes the tissue structure, as opposed to dehydrating the tissue material by the removal of liquid within the cells of the tissue and extracellular fluids, as is typically the case with electrosurgical desiccation and vaporization.

The high electric field intensities may be generated by applying a high frequency voltage that is sufficient to vaporize an electrically conductive fluid over at least a portion of the active electrode(s) in the region between the distal tip of the active electrode(s) and the target tissue. The electrically conductive fluid may be a gas or liquid, such as isotonic saline, delivered to the target site, or a viscous fluid, such as a gel, that is located at the target site. In the latter embodiment, the active electrode(s) are submersed in the electrically conductive gel during the surgical procedure. Since the vapor layer or vaporized region has a relatively high electrical impedance, it minimizes the current flow into the electrically conducting fluid. This ionization, under optimal conditions, induces the discharge of energetic electrons and photons from the vapor layer and to the surface of the target tissue. A more detailed description of this cold ablation phenomenon, termed Coblation®, can be found in commonly assigned U.S. Pat. No. 5,683,366 the complete disclosure of which is incorporated herein by reference.

The present invention applies high frequency (RF) electrical energy in an electrically conductive fluid environment to remove (i.e., resect, cut or ablate) or contract a tissue structure, and to seal transected vessels within the region of the target tissue. The present invention is particularly useful for sealing larger arterial vessels, e.g., having a diameter on the order of 1 mm or greater. In some embodiments, a high frequency power supply is provided having an ablation mode, wherein a first voltage is applied to an active electrode sufficient to effect molecular dissociation or disintegration of the tissue, and a coagulation mode, wherein a second, lower voltage is applied to an active electrode (either the same or a different electrode) sufficient to achieve hemostasis of severed vessels within the tissue. In other embodiments, an electrosurgical probe is provided having one or more coagulation electrode(s) configured for sealing a severed vessel, such as an arterial vessel, and one or more active electrodes configured for either contracting the collagen fibers within the tissue or removing (ablating) the tissue, e.g., by applying sufficient energy to the tissue to effect molecular dissociation. In the latter embodiments, the coagulation electrode(s) may be configured such that a single voltage can be applied to coagulate with the coagulation electrode(s), and to ablate or contract with the active electrode(s). In other embodiments, the power supply and electrosurgical probe are configured such that the coagulation electrode is used when the power supply is in the coagulation mode (low voltage), and the active electrode(s) are used when the power supply is in the ablation mode (higher voltage).

In the method of the present invention, one or more active electrodes are brought into close proximity to tissue at a target site, and the power supply is activated in the ablation mode such that sufficient voltage is applied between the active electrodes and the return electrode to volumetrically remove the tissue through molecular dissociation, as described below. During this process, some vessels within the tissue may be severed. Smaller vessels will be automatically sealed with the system and method of the present invention. Larger vessels, and those with a higher flow rate, such as arterial vessels, may not be automatically sealed in the ablation mode. In these cases, the severed vessels may be sealed by activating a control (e.g., a foot pedal) to reduce the voltage of the power supply into the coagulation mode. In this mode, the active electrodes may be pressed against the severed vessel to provide sealing and/or coagulation of the vessel. Alternatively, a coagulation electrode located on the same or a different probe may be pressed against the severed vessel. Once the vessel is adequately sealed, the surgeon activates a control (e.g., another foot pedal) to increase the voltage of the power supply back into the ablation mode.

The present invention is particularly useful for removing or ablating tissue around nerves, such as spinal or cranial nerves, e.g., the spinal cord and the surrounding dura mater. One of the significant drawbacks with the prior art cutters, graspers, and lasers is that these devices do not differentiate between the target tissue and the surrounding nerves or bone. Therefore, the surgeon must be extremely careful during these procedures to avoid damage to the bone or nerves within and around the spinal cord. In the present invention, the Coblation® process for removing tissue results in extremely small depths of collateral tissue damage as discussed above. This allows the surgeon to remove tissue close to a nerve without causing collateral damage to the nerve fibers.

In addition to the generally precise nature of the novel mechanisms of the present invention, applicant has discovered an additional method of ensuring that adjacent nerves are not damaged during tissue removal. According to the present invention, systems and methods are provided for distinguishing between the fatty tissue immediately surrounding nerve fibers and the normal tissue that is to be removed during the procedure. Peripheral nerves usually comprise a connective tissue sheath, or epineurium, enclosing the bundles of nerve fibers to protect these nerve fibers. The outer protective tissue sheath or epineurium typically comprises a fatty tissue (e.g., adipose tissue) having substantially different electrical properties than the normal target tissue, such as the disc and other surrounding tissue that are, for example, removed from the spine during spinal procedures. The system of the present invention measures the electrical properties of the tissue at the tip of the probe with one or more active electrode(s). These electrical properties may include electrical conductivity at one, several or a range of frequencies (e.g., in the range from 1 kHz to 100 MHz), dielectric constant, capacitance or combinations of these. In this embodiment, an audible signal may be produced when the sensing electrode(s) at the tip of the probe detects the fatty tissue surrounding a nerve, or direct feedback control can be provided to only supply power to the active electrode(s) either individually or to the complete array of electrodes, if and when the tissue encountered at the tip or working end of the probe is normal (e.g., non-fatty) tissue based on the measured electrical properties.

In one embodiment, the current limiting elements (discussed in detail below) are configured such that the active electrodes, will shut down or turn off when the electrical impedance reaches a threshold level. When this threshold level is set to the impedance of the fatty tissue surrounding nerves, the active electrodes will shut off whenever they come in contact with, or in close proximity to, nerves. Meanwhile, the other active electrodes, which are in contact with or in close proximity to target tissue, will continue to conduct electric current to the return electrode. This selective ablation or removal of lower impedance tissue in combination with the Coblation® mechanism of the present invention allows the surgeon to precisely remove tissue around nerves or bone.

In addition to the above, applicant has discovered that the Coblation® mechanism of the present invention can be manipulated to ablate or remove certain tissue structures, while having little effect on other tissue structures. As discussed above, the present invention uses a technique of vaporizing electrically conductive fluid to form a plasma layer or pocket around the active electrode(s), and then inducing the discharge of energy from this plasma or vapor layer to break the molecular bonds of the tissue structure. Based on initial experiments, applicants believe that the free electrons within the ionized vapor layer are accelerated in the high electric fields near the electrode tip(s). When the density of the vapor layer (or within a bubble formed in the electrically conductive liquid) becomes sufficiently low (i.e., less than approximately $10^{20}$ atoms/cm$^3$ for aqueous solutions), the electron mean free path increases to enable subsequently injected electrons to cause impact ionization within these regions of low density (i.e., vapor layers or bubbles). Energy evolved by the energetic electrons (e.g., 4 eV to 5 eV) can subsequently bombard a molecule and break its bonds, dissociating a molecule into free radicals, which then combine into final gaseous or liquid species.

The energy evolved by the energetic electrons may be varied by adjusting a variety of factors, such as: the number of active electrodes; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the present invention can be configured to break the molecular bonds of certain tissue, while having too low an energy to break the molecular bonds of other tissue. For example, fatty tissue, (e.g., adipose tissue) has double bonds that require a substantially higher energy level than 4 eV to 5 eV to break (typically on the order of about 8 eV). Accordingly, the present invention in its current configuration generally does not ablate or remove such fatty tissue. However, the present invention may be used to effectively ablate cells to release the inner fat content in a liquid form. Of course, factors may be changed such that these double bonds can be broken (e.g., increasing the voltage or changing the electrode configuration to increase the current density at the electrode tips).

The electrosurgical probe or catheter will comprise a shaft or a handpiece having a proximal end and a distal end which supports one or more active electrode(s). The shaft or handpiece may assume a wide variety of configurations, with the primary purpose being to mechanically support the active electrode and permit the treating physician to manipulate the electrode from a proximal end of the shaft. The shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode(s) or electrode array. The shaft will usually include a plurality of wires or other conductive elements running axially therethrough to permit connection of the electrode array to a connector at the proximal end of the shaft.

For endoscopic procedures within the spine, the shaft will have a suitable diameter and length to allow the surgeon to reach the target site (e.g., a disc) by delivering the shaft through the thoracic cavity, the abdomen or the like. Thus, the shaft will usually have a length in the range of about 5.0 cm to 30.0 cm, and a diameter in the range of about 0.2 mm to about 20 mm. Alternatively, the shaft may be delivered directly through the patient's back in a posterior approach, which would considerably reduce the required length of the shaft. In any of these embodiments, the shaft may also be introduced through rigid or flexible endoscopes. Specific shaft designs will be described in detail in connection with the drawings hereinafter.

Figure 34:
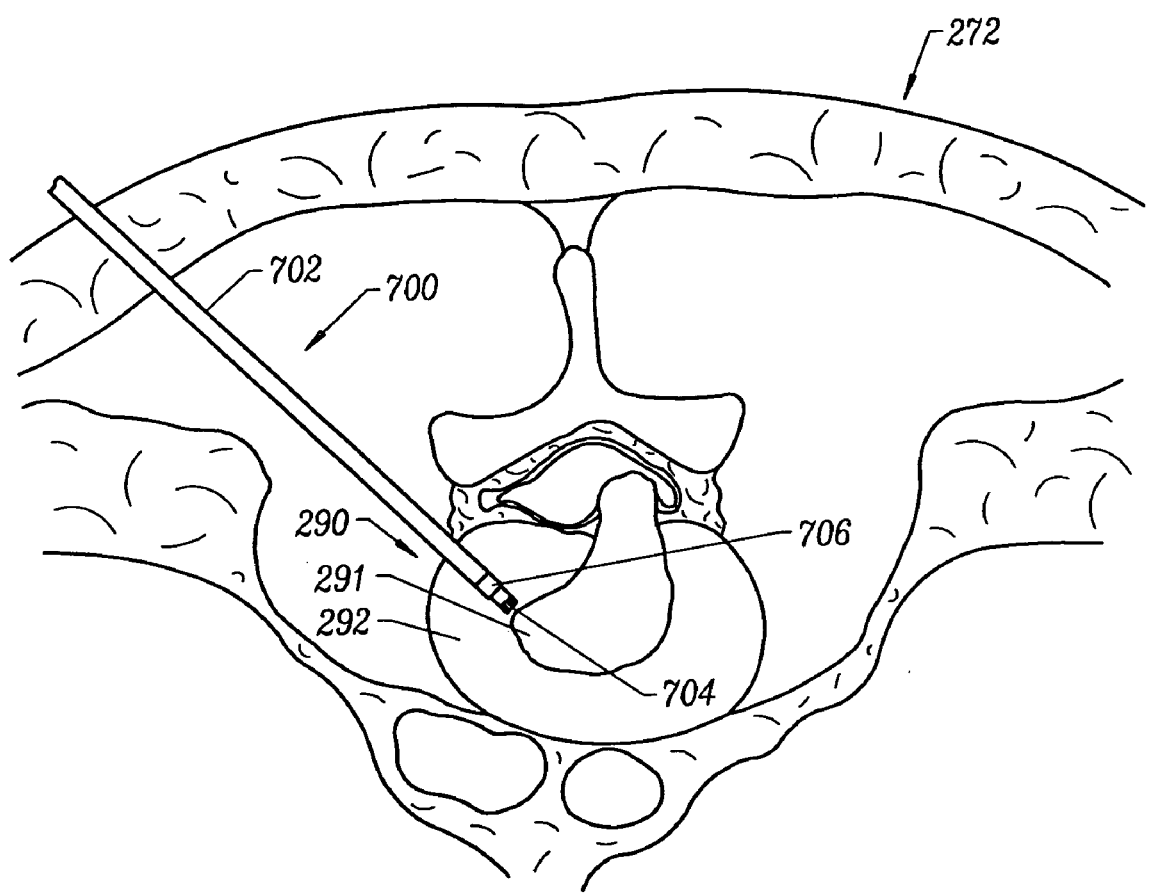
FIGS. 34–36 illustrates another system and method of the present invention for percutaneously contracting collagen fibers within an intervertebral disc with a small, needle-sized instrument.
Figure 35:
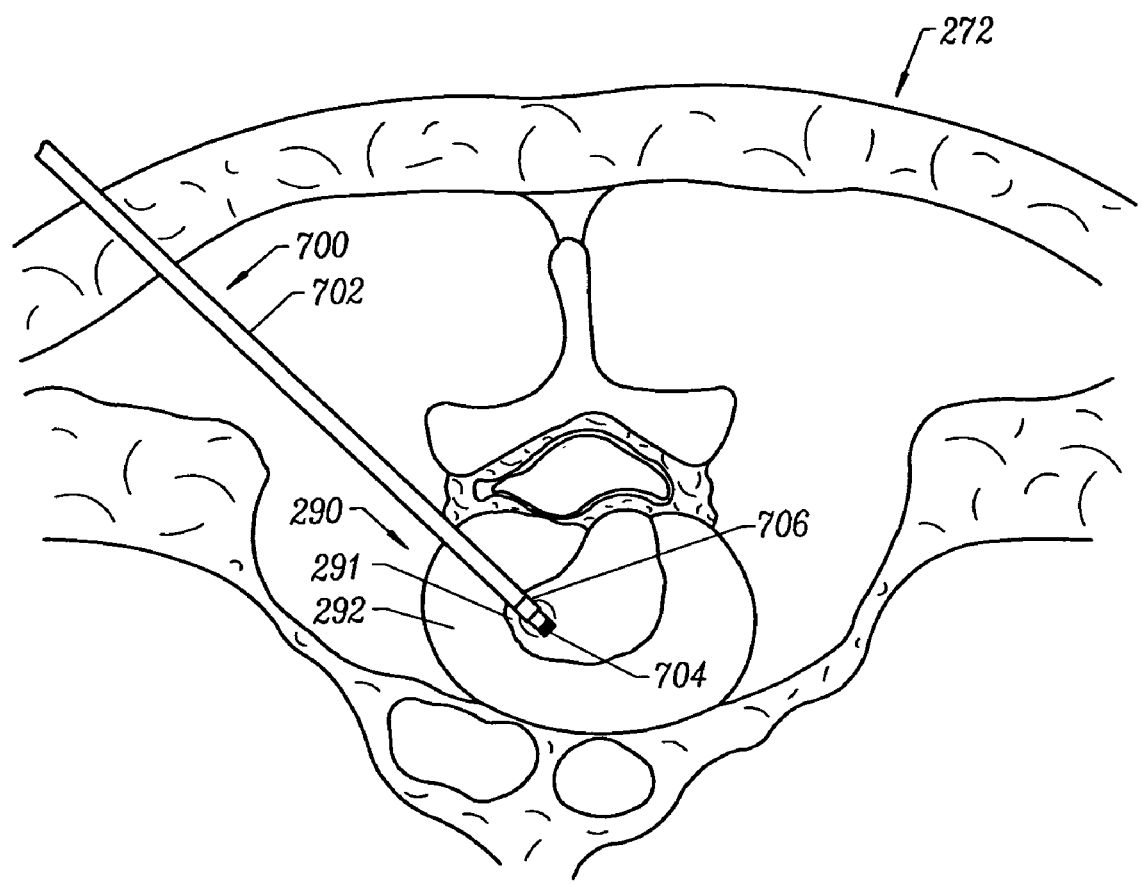
Figure 36:
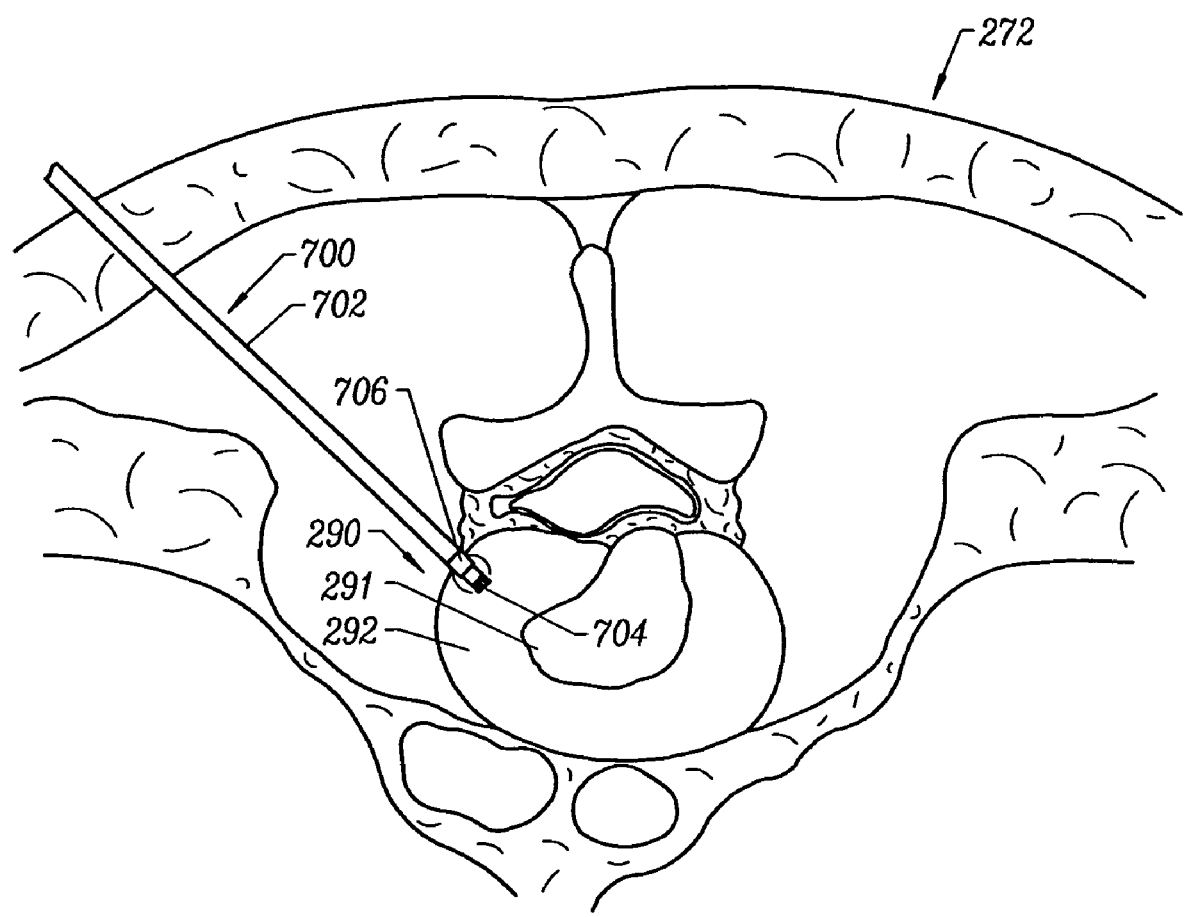

In one embodiment, the probe may comprise a long, thin needle (e.g., on the order of about 1 mm in diameter or less) that can be percutaneously introduced through the patient's back directly into the spine (see FIGS. 34–36). The needle will include one or more active electrode(s) for applying electrical energy to tissues within the spine. The needle may include one or more return electrodes, or the return electrode may be positioned on the patient's back, as a dispersive pad. In either embodiment, sufficient electrical energy is applied through the needle to the active electrode(s) to either shrink the collagen fibers within the intervertebral disk, or to ablate tissue within the disk.

The current flow path between the active electrode(s) and the return electrode(s) may be generated by submerging the tissue site in an electrically conductive fluid (e.g., within a liquid or a viscous fluid, such as an electrically conductive gel) or by directing an electrically conductive fluid along a fluid path to the target site (i.e., a liquid, such as isotonic saline, or a gas, such as argon). This latter method is particularly effective in a dry environment (i.e., the tissue is not submerged in fluid) because the electrically conductive fluid provides a suitable current flow path from the active electrode to the return electrode. A more complete description of an exemplary method of directing electrically conductive fluid between the active and return electrodes is described in U.S. Pat. No. 5,697,536, previously incorporated herein by reference.

The electrically conductive fluid should have a threshold conductivity to provide a suitable conductive path between the return electrode(s) and the active electrode(s). The electrical conductivity of the fluid (in units of millisiemens per centimeter or mS/cm) will usually be greater than 0.2 mS/cm, preferably will be greater than 2 mS/cm, and more preferably greater than 10 mS/cm. In an exemplary embodiment, the electrically conductive fluid is isotonic saline, which has a conductivity of about 17 mS/cm. Alternatively, the fluid may be an electrically conductive gel or spray, such as a saline electrolyte gel, a conductive ECG spray, an electrode conductivity gel, an ultrasound transmission or scanning gel, or the like. Suitable gels or sprays are commercially available from Graham-Field, Inc of Hauppauge, N.Y.

In some procedures it may also be necessary to retrieve or aspirate the electrically conductive fluid after it has been directed to the target site. In addition, it may be desirable to aspirate small pieces of tissue that are not completely disintegrated by the high frequency energy, or other fluids at the target site, such as blood, mucus, the gaseous products of ablation, etc. Accordingly, the system of the present invention will usually include a suction lumen in the probe, or on another instrument, for aspirating fluids from the target site. In addition, the invention may include one or more aspiration electrode(s) coupled to the distal end of the suction lumen for ablating, or at least reducing the volume of, non-ablated tissue fragments that are aspirated into the lumen. The aspiration electrode(s) function mainly to inhibit clogging of the lumen that may otherwise occur as larger tissue fragments are drawn therein. The aspiration electrode(s) may be different from the ablation active electrode(s), or the same electrode(s) may serve both functions. A more complete description of probes incorporating aspiration electrode(s) can be found in commonly assigned, co-pending patent application Ser. No. 09/010,382 filed Jan. 21, 1998, the complete disclosure of which is incorporated herein by reference.

The present invention may use a single active electrode or an electrode array distributed over a contact surface of a probe. In the latter embodiment, the electrode array usually includes a plurality of independently current-limited and/or power-controlled active electrodes to apply electrical energy selectively to the target tissue while limiting the unwanted application of electrical energy to the surrounding tissue and environment resulting from power dissipation into surrounding electrically conductive liquids, such as blood, normal saline, electrically conductive gel and the like. The active electrodes may be independently current-limited by isolating the electrodes from each other and connecting each electrode to a separate power source that is isolated from the other active electrodes. Alternatively, the active electrodes may be connected to each other at either the proximal or distal ends of the probe to form a single wire that couples to a power source.

In some embodiments, the active electrode(s) have an active portion or surface with surface geometries shaped to promote the electric field intensity and associated current density along the leading edges of the electrodes. Suitable surface geometries may be obtained by creating electrode shapes that include preferential sharp edges, or by creating asperities or other surface roughness on the active surface(s) of the electrodes. Electrode shapes according to the present invention can include the use of formed wire (e.g., by drawing round wire through a shaping die) to form electrodes with a variety of cross-sectional shapes, such as square, rectangular, L or V shaped, or the like. Electrode edges may also be created by removing a portion of the elongate metal electrode to reshape the cross-section. For example, material can be ground along the length of a round or hollow wire electrode to form D or C shaped wires, respectively, with edges facing in the cutting direction. Alternatively, material can be removed at closely spaced intervals along the electrode length to form transverse grooves, slots, threads or the like along the electrodes.

Additionally or alternatively, the active electrode surface(s) may be modified through chemical, electrochemical or abrasive methods to create a multiplicity of surface asperities on the electrode surface. These surface asperities will promote high electric field intensities between the active electrode surface(s) and the target tissue to facilitate ablation or cutting of the tissue. For example, surface asperities may be created by etching the active electrodes with etchants having a pH less than 7.0 or by using a high velocity stream of abrasive particles (e.g., grit blasting) to create asperities on the surface of an elongated electrode.

The active electrode(s) are typically mounted in or on an electrically insulating electrode support that extends from the electrosurgical probe. In some embodiments, the electrode support comprises a plurality of wafer layers bonded together, e.g., by a glass adhesive or the like, or a single wafer. The wafer layer(s) have conductive strips printed thereon to form the active electrode(s) and the return electrode(s). In one embodiment, the proximal end of the wafer layer(s) will have a number of holes extending from the conductor strips to an exposed surface of the wafer layers for connection to electrical conductor lead traces in the electrosurgical probe or handpiece. The wafer layers preferably comprise a ceramic material, such as alumina, and the electrode will preferably comprise a metallic material, such as gold, copper, platinum, palladium, tungsten, silver or the like. Suitable multilayer ceramic electrodes are commercially available from e.g., VisPro Corporation of Beaverton, Oreg.

In one configuration, each individual active electrode in the electrode array is electrically insulated from all other active electrodes in the array within the probe and is connected to a power source which is isolated from each of the other active electrodes in the array or to circuitry which limits or interrupts current flow to the active electrode when low resistivity material (e.g., blood, electrically conductive saline irrigant or electrically conductive gel) causes a lower impedance path between the return electrode and the individual active electrode. The isolated power sources for each individual active electrode may be separate power supply circuits having internal impedance characteristics which limit power to the associated active electrode when a low impedance return path is encountered. By way of example, the isolated power source may be a user-selectable constant current source. In this embodiment, lower impedance paths will automatically result in lower resistive heating levels since the heating is proportional to the square of the operating current times the impedance. Alternatively, a single power source may be connected to each of the active electrodes through independently actuatable switches, or by independent current limiting elements, such as inductors, capacitors, resistors and/or combinations thereof. The current limiting elements may be provided in the probe, connectors, cable, controller or along the conductive path from the controller to the distal tip of the probe. Alternatively, the resistance and/or capacitance may occur on the surface of the active electrode(s) due to oxide layers which form selected active electrodes (e.g., titanium or a resistive coating on the surface of metal, such as platinum).

The tip region of the probe may comprise many independent active electrodes designed to deliver electrical energy in the vicinity of the tip. The selective application of electrical energy to the conductive fluid is achieved by connecting each individual active electrode and the return electrode to a power source having independently controlled or current limited channels. The return electrode(s) may comprise a single tubular member of conductive material proximal to the electrode array at the tip which also serves as a conduit for the supply of the electrically conductive fluid between the active and return electrodes. Alternatively, the probe may comprise an array of return electrodes at the distal tip of the probe (together with the active electrodes) to maintain the electric current at the tip. The application of high frequency voltage between the return electrode(s) and the electrode array results in the generation of high electric field intensities at the distal tips of the active electrodes with conduction of high frequency current from each individual active electrode to the return electrode. The current flow from each individual active electrode to the return electrode(s) is controlled by either active or passive means, or a combination thereof, to deliver electrical energy to the surrounding conductive fluid while minimizing energy delivery to surrounding (non-target) tissue.

The application of a high frequency voltage between the return electrode(s) and the active electrode(s) for appropriate time intervals effects cutting, removing, ablating, shaping, contracting or otherwise modifying the target tissue. The tissue volume over which energy is dissipated (i.e., a high current density exists) may be precisely controlled, for example, by the use of a multiplicity of small active electrodes whose effective diameters or principal dimensions range from about 5 mm to 0.01 mm, preferably from about 2 mm to 0.05 mm, and more preferably from about 1 mm to 0.1 mm. Electrode areas for both circular and non-circular electrodes will have a contact area (per active electrode) below 25 $mm^2$, preferably being in the range from 0.0001 $mm^2$ to 1 $mm^2$, and more preferably from 0.005 $mm^2$ to 0.5 $mm^2$. The circumscribed area of the electrode array is in the range from 0.25 $mm^2$ to 200 $mm^2$, preferably from 0.5 $mm^2$ to 100 $m^2$, and will usually include at least two isolated active electrodes, preferably at least five active electrodes, often greater than ten active electrodes and even fifty or more active electrodes, disposed over the distal contact surfaces on the shaft. The use of small diameter active electrodes increases the electric field intensity and reduces the extent or depth of tissue heating as a consequence of the divergence of current flux lines which emanate from the exposed surface of each active electrode.

The area of the tissue treatment surface can vary widely, and the tissue treatment surface can assume a variety of geometries, with particular areas and geometries being selected for specific applications. Active electrode surfaces can have areas in the range from 0.25 $mm^2$ to 75 $mm^2$, usually being from about 0.5 $mm^2$ to 40 $mm^2$. The geometries can be planar, concave, convex, hemispherical, conical, linear "in-line" array or virtually any other regular or irregular shape. Most commonly, the active electrode(s) or active electrode(s) will be formed at the distal tip of the electrosurgical probe shaft, frequently being planar, disk-shaped, or hemispherical surfaces for use in reshaping procedures or being linear arrays for use in cutting. Alternatively or additionally, the active electrode(s) may be formed on lateral surfaces of the electrosurgical probe shaft (e.g., in the manner of a spatula), facilitating access to certain body structures in endoscopic procedures.

It should be clearly understood that the invention is not limited to electrically isolated active electrodes, or even to a plurality of active electrodes. For example, the array of active electrodes may be connected to a single lead that extends through the probe shaft to a power source of high frequency current. Alternatively, the probe may incorporate a single electrode that extends directly through the probe shaft or is connected to a single lead that extends to the power source. The active electrode may have a ball shape (e.g., for tissue vaporization and desiccation), a twizzle shape (for vaporization and needle-like cutting), a spring shape (for rapid tissue debulking and desiccation), a twisted metal shape, an annular or solid tube shape or the like. Alternatively, the electrode may comprise a plurality of filaments, a rigid or flexible brush electrode (for debulking a tumor, such as a fibroid, bladder tumor or a prostate adenoma), a side-effect brush electrode on a lateral surface of the shaft, a coiled electrode or the like. In one embodiment, the probe comprises a single active electrode that extends from an insulating member, e.g., ceramic, at the distal end of the probe. The insulating member is preferably a tubular structure that separates the active electrode from a tubular or annular return electrode positioned proximal to the insulating member and the active electrode.

In some embodiments, the electrode support and the fluid outlet may be recessed from an outer surface of the probe or handpiece to confine the electrically conductive fluid to the region immediately surrounding the electrode support. In addition, the shaft may be shaped so as to form a cavity around the electrode support and the fluid outlet. This helps to assure that the electrically conductive fluid will remain in contact with the active electrode(s) and the return electrode(s) to maintain the conductive path therebetween. In addition, this will help to maintain a vapor or plasma layer between the active electrode(s) and the tissue at the treatment site throughout the procedure, which reduces the thermal damage that might otherwise occur if the vapor layer were extinguished due to a lack of conductive fluid. Provision of the electrically conductive fluid around the target site also helps to maintain the tissue temperature at desired levels.

The voltage applied between the return electrode(s) and the electrode array will be at high or radio frequency, typically between about 5 kHz and 20 MHz, usually being between about 30 kHz and 2.5 MHz, preferably being between about 50 kHz and 500 kHz, more preferably less than 350 kHz, and most preferably between about 100 kHz and 200 kHz. The RMS (root mean square) voltage applied will usually be in the range from about 5 volts to 1000 volts, preferably being in the range from about 10 volts to 500 volts depending on the active electrode size, the operating frequency and the operation mode of the particular procedure or desired effect on the tissue (i.e., contraction, coagulation or ablation). Typically, the peak-to-peak voltage will be in the range of 10 volts to 2000 volts, preferably in the range of 20 volts to 1200 volts and more preferably in the range of about 40 volts to 800 volts (again, depending on the electrode size, the operating frequency and the operation mode).

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed about 10 Hz to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being heated, and/or the maximum allowed temperature selected for the probe tip. The power source allows the user to select the voltage level according to the specific requirements of a particular spine procedure, arthroscopic surgery, dermatological procedure, ophthalmic procedures, FESS procedure, open surgery or other endoscopic surgery procedure. A description of a suitable power source can be found in U.S. Provisional Patent Application No. 60/062,997 entitled "Systems and Methods for Electrosurgical Tissue and Fluid Coagulation," filed Oct. 23, 1997, the complete disclosure of which is incorporated herein by reference.

The power source may be current limited or otherwise controlled so that undesired heating of the target tissue or surrounding (non-target) tissue does not occur. In a presently preferred embodiment of the present invention, current limiting inductors are placed in series with each independent active electrode, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in copending PCT application No. PCT/US94/05168, the complete disclosure of which is incorporated herein by reference. Additionally, current limiting resistors may be selected. Preferably, these resistors will have a large positive temperature coefficient of resistance so that, as the current level begins to rise for any individual active electrode in contact with a low resistance medium (e.g., saline irrigant or conductive gel), the resistance of the current limiting resistor increases significantly, thereby minimizing the power delivery from the active electrode into the low resistance medium (e.g., saline irrigant, a conductive gel, or natural body fluids such as blood).

Referring to FIG. 1, an exemplary electrosurgical system 11 for treatment of tissue in the spine will now be described in detail. Electrosurgical system 11 generally comprises an electrosurgical handpiece or probe 10 connected to a power supply 28 for providing high frequency voltage to a target site, and a fluid source 21 for supplying electrically conductive fluid 50 to probe 10. In addition, electrosurgical system 11 may include an endoscope (not shown) with a fiber optic head light for viewing the surgical site, particularly in endoscopic spine procedures. The endoscope may be integral with probe 10, or it may be part of a separate instrument. The system 11 may also include a vacuum source (not shown) for coupling to a suction lumen or tube 211 (see FIG. 2) in the probe 10 for aspirating the target site.

As shown, probe 10 generally includes a proximal handle 19 and an elongate shaft 18 having an array 12 of active electrodes 58 at its distal end. A connecting cable 34 has a connector 26 for electrically coupling the active electrodes 58 to power supply 28. The active electrodes 58 are electrically isolated from each other and each of the electrodes 58 is connected to an active or passive control network within power supply 28 by means of a plurality of individually insulated conductors (not shown). A fluid supply tube 15 is connected to a fluid tube 14 of probe 10 for supplying electrically conductive fluid 50 to the target site.

Power supply 28 has an operator controllable voltage level adjustment 30 to change the applied voltage level, which is observable at a voltage level display 32. Power supply 28 also includes first, second and third foot pedals 37, 38, 39 and a cable 36 which is removably coupled to power supply 28. The foot pedals 37, 38, 39 allow the surgeon to remotely adjust the energy level applied to active electrodes 58. In an exemplary embodiment, first foot pedal 37 is used to place the power supply into the "ablation" mode and second foot pedal 38 places power supply 28 into the "coagulation" mode. The third foot pedal 39 allows the user to adjust the voltage level within the "ablation" mode. In the ablation mode, a sufficient voltage is applied to the active electrodes to establish the requisite conditions for molecular dissociation of the tissue, as described elsewhere herein. As discussed above, the requisite voltage level for ablation will vary depending on the number, size, shape and spacing of the electrodes, the distance to which the electrodes extend from the support member, etc. Once the surgeon places the power supply in the "ablation" mode, voltage level adjustment 30 or third foot pedal 39 may be used to adjust the voltage level to adjust the degree or aggressiveness of the ablation.

Of course, it will be recognized that the voltage and modality of the power supply may be controlled by other input devices. However, applicant has found that foot pedals are convenient methods of controlling the power supply while manipulating the probe during a surgical procedure.

In the coagulation mode, the power supply 28 applies a low enough voltage to the active electrodes (or the coagulation electrode) to avoid vaporization of the electrically conductive fluid and subsequent molecular dissociation of the tissue. The surgeon may automatically toggle the power supply between the ablation and coagulation modes by alternatively stepping on foot pedals 37, 38, respectively. This allows the surgeon to quickly move between coagulation and ablation in situ, without having to remove his/her concentration from the surgical field or without having to request an assistant to switch the power supply. By way of example, as the surgeon is sculpting or ablating soft tissue in the ablation mode, the probe typically will simultaneously seal and/or coagulate any small severed vessels within the tissue. However, larger vessels, or vessels with high fluid pressures (e.g., arterial vessels) may not be sealed in the ablation mode. Accordingly, the surgeon can simply step on foot pedal 38, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by stepping on foot pedal 37. A specific design of a suitable power supply for use with the present invention can be found in U.S. Provisional Patent Application No. 60/062, 997, entitled "Systems and Methods for Electrosurgical Tissue and Fluid Coagulation," filed Oct. 23, 1997, which is incorporated herein by reference.

Figure 2:
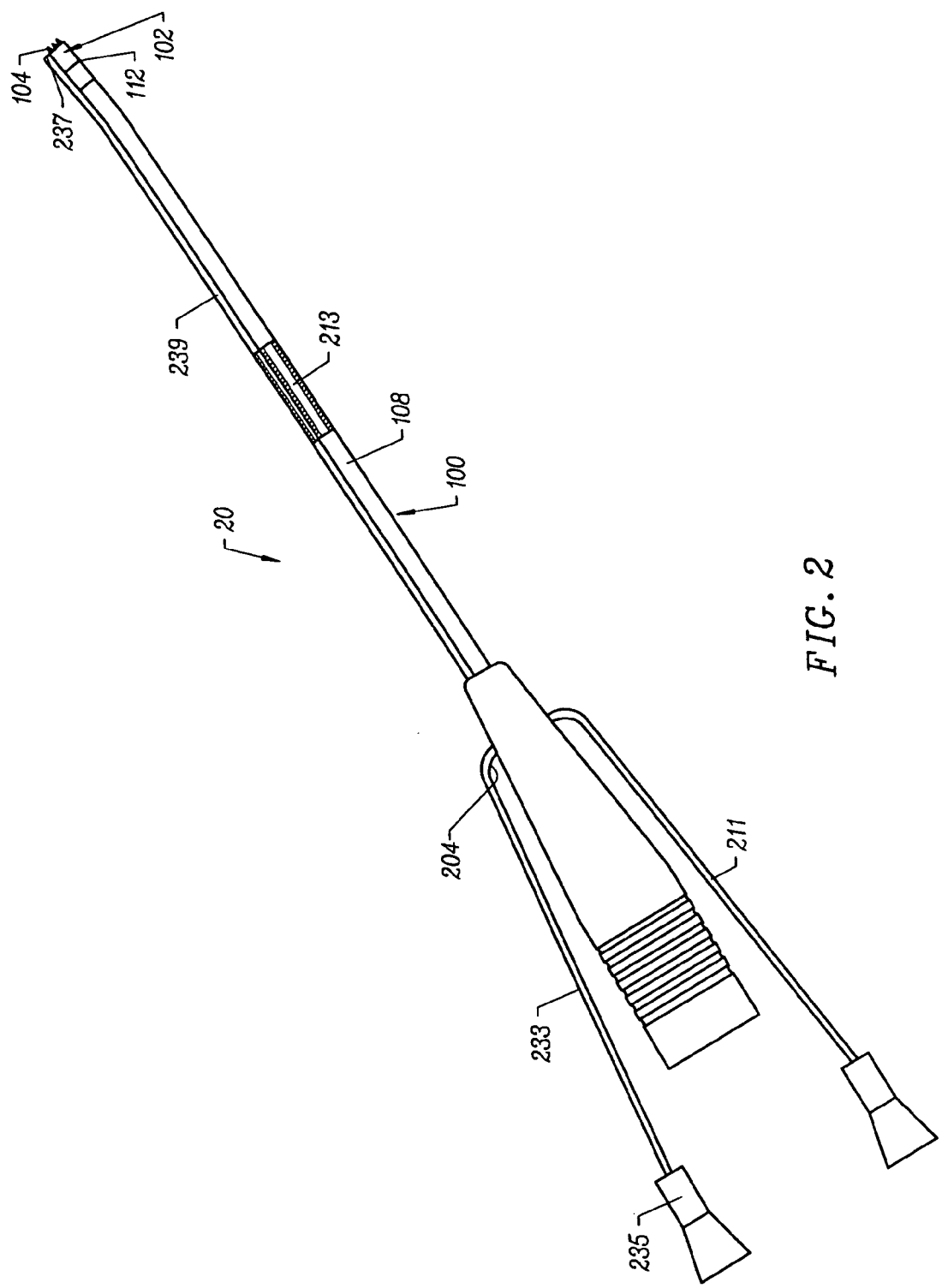
FIG. 2 is a side view of an electrosurgical probe according to the present invention.

FIGS. 2–5 illustrate an exemplary electrosurgical probe 20 constructed according to the principles of the present invention. As shown in FIG. 2, probe 20 generally includes an elongated shaft 100 which may be flexible or rigid, a handle 204 coupled to the proximal end of shaft 100 and an electrode support member 102 coupled to the distal end of shaft 100. Shaft 100 preferably comprises a plastic material that is easily molded into the shape shown in FIG. 2. In an alternative embodiment (not shown), shaft 100 comprises an electrically conducting material, usually metal, which is selected from the group comprising tungsten, stainless steel alloys, platinum or its alloys, titanium or its alloys, molybdenum or its alloys, and nickel or its alloys. In this embodiment, shaft 100 includes an electrically insulating jacket 108, which is typically formed as one or more electrically insulating sheaths or coatings, such as polytetrafluoroethylene, polyimide, and the like. The provision of electrically insulating jacket 108 over the shaft prevents direct electrical contact between these metal elements and any adjacent body structure or the surgeon. Such direct electrical contact between a body structure (e.g., tendon) and an exposed electrode could result in unwanted heating of the structure at the point of contact causing necrosis.

Handle 204 typically comprises a plastic material that is easily molded into a suitable shape for handling by the surgeon. Handle 204 defines an inner cavity (not shown) that houses the electrical connections 250 (FIG. 5), and provides a suitable interface for connection to an electrical connecting cable 22 (see FIG. 1). Electrode support member 102 extends from the distal end of shaft 100 (usually about 1 mm to 20 mm), and provides support for a plurality of electrically isolated active electrodes 104 (see FIG. 4). As shown in FIG. 2, a fluid tube 233 extends through an opening in handle 204, and includes a connector 235 for connection to a fluid supply source, for supplying electrically conductive fluid to the target site. Fluid tube 233 is coupled to a distal fluid tube 239 that extends along the outer surface of shaft 100 to an opening 237 at the distal end of the probe 20, as discussed in detail below. Of course, the invention is not limited to this configuration. For example, fluid tube 233 may extend through a single lumen (not shown) in shaft 100, or it may be coupled to a plurality of lumens (also not shown) that extend through shaft 100 to a plurality of openings at its distal end. Probe 20 may also include a valve 17 (FIG. 1) or equivalent structure for controlling the flow rate of the electrically conductive fluid to the target site.

Figure 3:
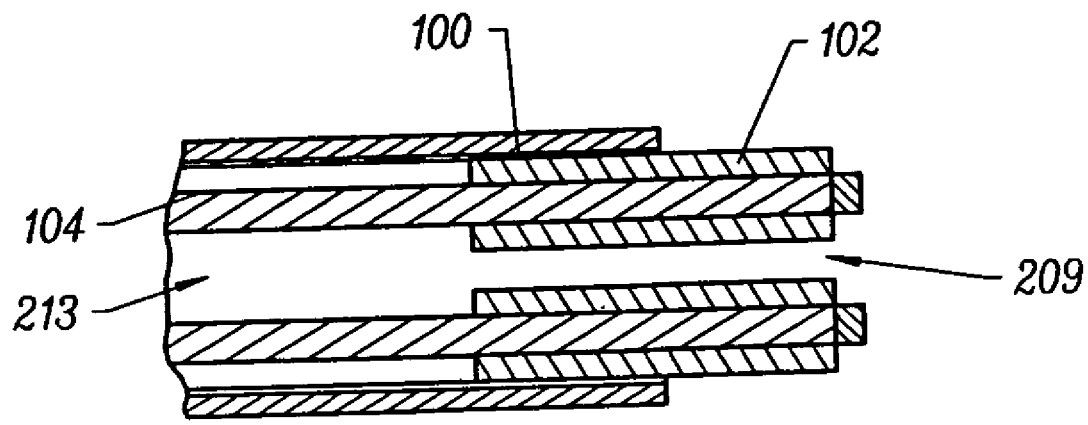
FIG. 3 is a cross-sectional view of a distal portion of the probe of FIG. 2.
Figure 4:
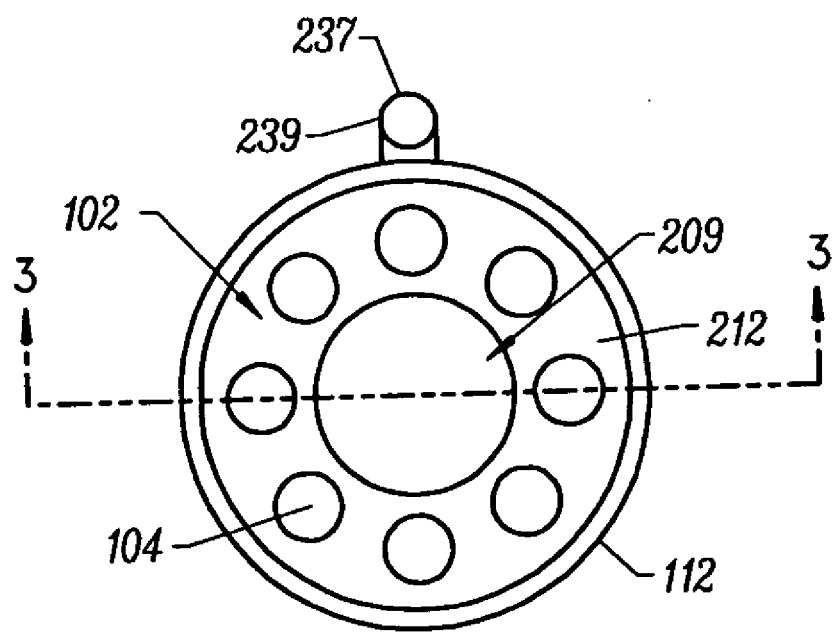
FIG. 4 is an end view of the probe of FIG. 2, illustrating an array of active electrodes.

As shown in FIGS. 3 and 4, electrode support member 102 has a substantially planar tissue treatment surface 212 and comprises a suitable insulating material (e.g., ceramic or glass material, such as alumina, zirconia and the like) which could be formed at the time of manufacture in a flat, hemispherical or other shape according to the requirements of a particular procedure. The preferred support member material is alumina, available from Kyocera Industrial Ceramics Corporation, Elkgrove, Ill., because of its high thermal conductivity, good electrically insulative properties, high flexural modulus, resistance to carbon tracking, biocompatibility, and high melting point. The support member 102 is adhesively joined to a tubular support member (not shown) that extends most or all of the distance between support member 102 and the proximal end of probe 20. The tubular member preferably comprises an electrically insulating material, such as an epoxy or silicone-based material.

In a preferred construction technique, active electrodes 104 extend through pre-formed openings in the support member 102 so that they protrude above tissue treatment surface 212 by the desired distance. The electrodes 104 are then bonded to the tissue treatment surface 212 of support member 102, typically by an inorganic sealing material. The sealing material is selected to provide effective electrical insulation, and good adhesion to both the alumina member 102 and the platinum or titanium active electrodes 104. The sealing material additionally should have a compatible thermal expansion coefficient and a melting point well below that of platinum or titanium and alumina or zirconia, typically being a glass or glass ceramic.

In the embodiment shown in FIGS. 2–5, probe 20 includes a return electrode 112 for completing the current path between active electrodes 104 and a high frequency power supply 28 (see FIG. 1). As shown, return electrode 112 preferably comprises an annular conductive band coupled to the distal end of shaft 100 slightly proximal to tissue treatment surface 212 of electrode support member 102, typically about 0.5 mm to 10 mm and more preferably about 1 mm to 10 mm proximal to surface 212. Return electrode 112 is coupled to a connector 258 (FIG. 5) that extends to the proximal end of probe 10, where it is suitably connected to power supply 28 (FIG. 1).

As shown in FIG. 2, return electrode 112 is not directly connected to active electrodes 104. To complete a current path so that active electrodes 104 are electrically connected to return electrode 112, electrically conductive fluid (e.g., isotonic saline) is caused to flow therebetween. In the representative embodiment, the electrically conductive fluid is delivered through an external fluid tube 239 to opening 237, as described above. Alternatively, the fluid may be delivered by a fluid delivery element (not shown) that is separate from probe 20. In some microendoscopic discectomy procedures, for example, the trocar cannula may be flooded with isotonic saline and the probe 20 will be introduced into this flooded cavity. Electrically conductive fluid will be continually resupplied with a separate instrument to maintain the conduction path between return electrode 112 and active electrodes 104.

In alternative embodiments, the fluid path may be formed in probe 20 by, for example, an inner lumen or an annular gap between the return electrode and a tubular support member within shaft 100 (not shown). This annular gap may be formed near the perimeter of the shaft 100 such that the electrically conductive fluid tends to flow radially inward towards the target site, or it may be formed towards the center of shaft 100 so that the fluid flows radially outward. In both of these embodiments, a fluid source (e.g., a bag of fluid elevated above the surgical site or having a pumping device), is coupled to probe 20 via a fluid supply tube (not shown) that may or may not have a controllable valve. A more complete description of an electrosurgical probe incorporating one or more fluid lumen(s) can be found in parent application U.S. Pat. No. 5,697,281, filed on Jun. 7, 1995, the complete disclosure of which is incorporated herein by reference.

Referring to FIG. 4, the electrically isolated active electrodes 104 are spaced apart over tissue treatment surface 212 of electrode support member 102. The tissue treatment surface and individual active electrodes 104 will usually have dimensions within the ranges set forth above. In the representative embodiment, the tissue treatment surface 212 has a circular cross-sectional shape with a diameter in the range of about 1 mm to 30 mm, usually about 2 mm to 20 mm. The individual active electrodes 104 preferably extend outward from tissue treatment surface 212 by a distance of about 0.1 mm to 8 mm, usually about 0.2 mm to 4 mm. Applicant has found that this configuration increases the high electric field intensities and associated current densities around active electrodes 104 to facilitate the ablation of tissue as described in detail above.

In the embodiment of FIGS. 2–5, the probe includes a single, larger opening 209 in the center of tissue treatment surface 212, and a plurality of active electrodes (e.g., about 3–15 electrodes) around the perimeter of surface 212 (see FIG. 3). Alternatively, the probe may include a single, annular, or partially annular, active electrode at the perimeter of the tissue treatment surface. The central opening 209 is coupled to a suction or aspiration lumen 213 (see FIG. 2) within shaft 100 and a suction tube 211 (FIG. 2) for aspirating tissue, fluids and/or gases from the target site. In this embodiment, the electrically conductive fluid generally flows from opening 237 of fluid tube 239 radially inward past active electrodes 104 and then back through the central opening 209 of support member 102. Aspirating the electrically conductive fluid during surgery allows the surgeon to see the target site, and it prevents the fluid from flowing into the patient's body, e.g., into the spine, the abdomen or the thoracic cavity. This aspiration should be controlled, however, so that the conductive fluid maintains a conductive path between the active electrode(s) and the return electrode.

Of course, it will be recognized that the distal tip of probe may have a variety of different configurations. For example, the probe may include a plurality of openings 209 around the outer perimeter of tissue treatment surface 212 (this embodiment not shown in the drawings). In this embodiment, the active electrodes 104 extend from the center of tissue treatment surface 212 radially inward from openings 209. The openings are suitably coupled to fluid tube 233 for delivering electrically conductive fluid to the target site, and aspiration lumen 213 for aspirating the fluid after it has completed the conductive path between the return electrode 112 and the active electrodes 104.

Figure 6:
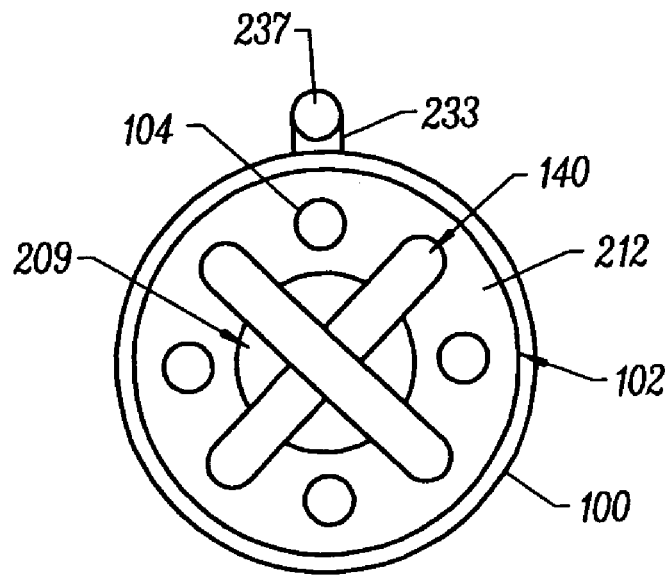
FIGS. 6–9 are end views of alternative embodiments of the probe of FIG. 2, incorporating aspiration electrode(s)

In some embodiments, the probe 20 will also include one or more aspiration electrode(s) coupled to the aspiration lumen for inhibiting clogging during aspiration of tissue fragments from the surgical site. As shown in FIG. 6, one or more of the active electrodes 104 may comprise loop electrodes 140 that extend across distal opening 209 of the suction lumen within shaft 100. In the representative embodiment, two of the active electrodes 104 comprise loop electrodes 140 that cross over the distal opening 209. Of course, it will be recognized that a variety of different configurations are possible, such as a single loop electrode, or multiple loop electrodes having different configurations than shown. In addition, the electrodes may have shapes other than loops, such as the coiled configurations shown in FIGS. 6 and 7. Alternatively, the electrodes may be formed within suction lumen proximal to the distal opening 209, as shown in FIG. 8. The main function of loop electrodes 140 is to ablate portions of tissue that are drawn into the suction lumen to prevent clogging of the lumen.

Loop electrodes 140 are electrically isolated from the other active electrodes 104, which can be referred to hereinafter as the ablation electrodes 104. Loop electrodes 140 may or may not be electrically isolated from each other. Loop electrodes 140 will usually extend only about 0.05 mm to 4 mm, preferably about 0.1 mm to 1 mm from the tissue treatment surface of electrode support member 104.

Figure 7:
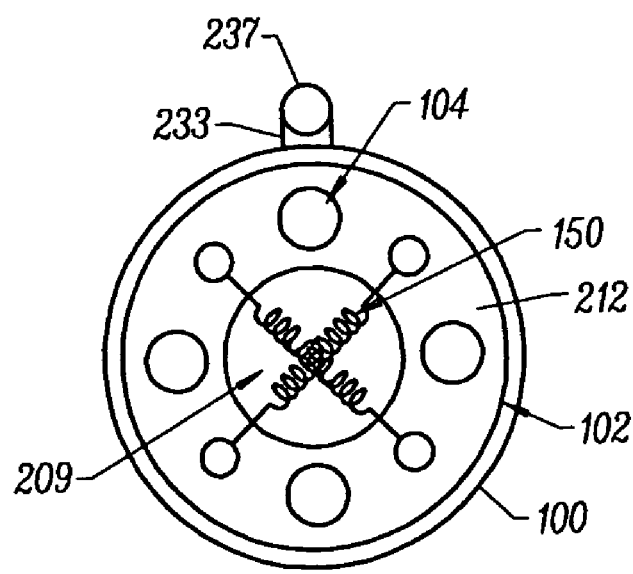
Figure 8:
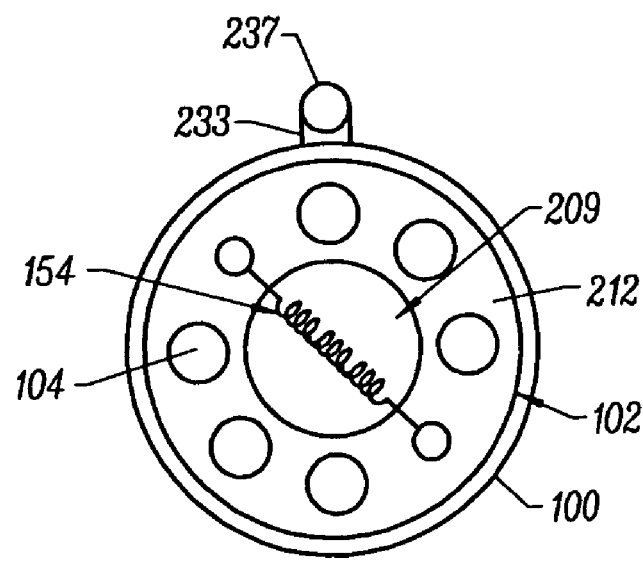

Referring now to FIGS. 7 and 8, alternative embodiments for aspiration electrodes will now be described. As shown in FIG. 7, the aspiration electrodes may comprise a pair of coiled electrodes 150 that extend across distal opening 209 of the suction lumen. The larger surface area of the coiled electrodes 150 usually increases the effectiveness of the electrodes 150 on tissue fragments passing through opening 209. In FIG. 8, the aspiration electrode comprises a single coiled electrode 154 passing across the distal opening 209 of suction lumen. This single electrode 154 may be sufficient to inhibit clogging of the suction lumen. Alternatively, the aspiration electrodes may be positioned within the suction lumen proximal to the distal opening 209. Preferably, these electrodes are close to opening 209 so that tissue does not clog the opening 209 before it reaches electrode 154. In this embodiment, a separate return electrode 156 may be provided within the suction lumen to confine the electric currents therein.

Figure 10:
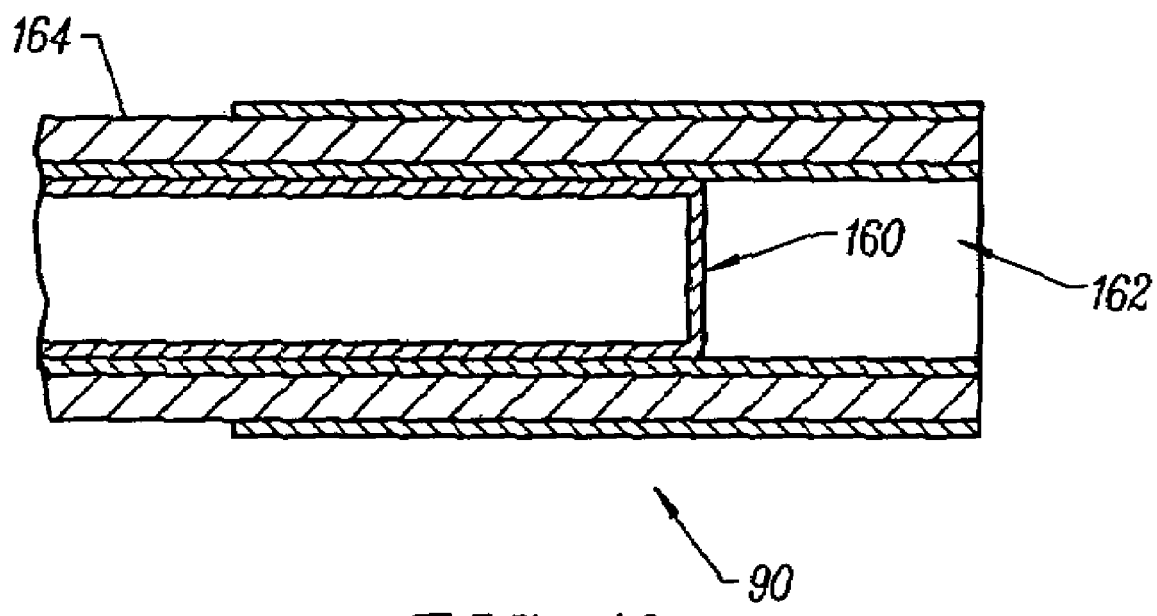
FIG. 10 is a longitudinal sectional view of the distal portion of an electrosurgical probe.
Figure 12:
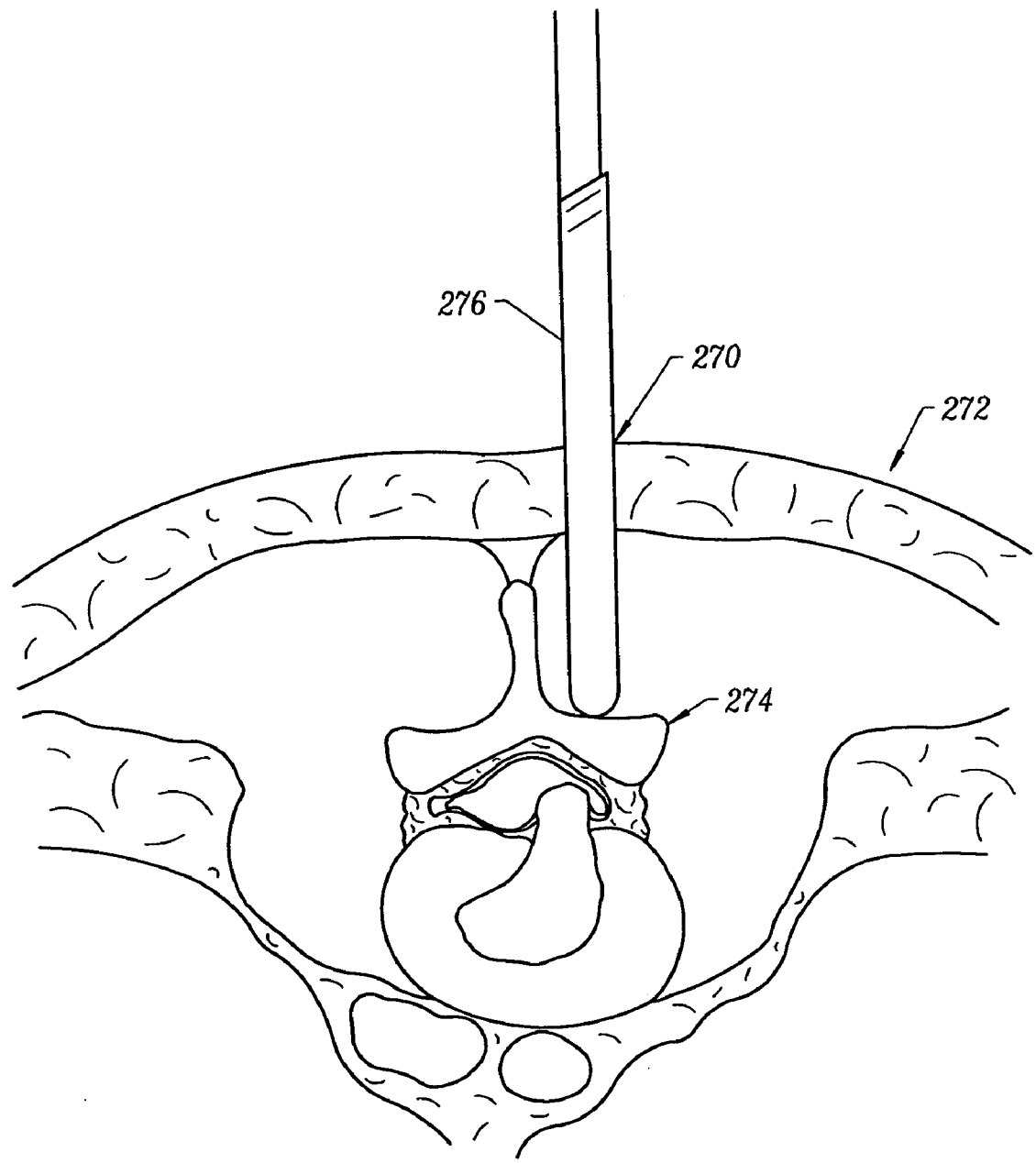
FIGS. 12–15 illustrate a method of performing a microendoscopic discectomy according to the principles of the present invention.

Referring to FIG. 10, another embodiment of the present invention incorporates an aspiration electrode 160 within the aspiration lumen 162 of the probe. As shown, the electrode 160 is positioned just proximal of distal opening 209 so that the tissue fragments are ablated as they enter lumen 162. In the representative embodiment, the aspiration electrode 160 comprises a loop electrode that stretches across the aspiration lumen 162. However, it will be recognized that many other configurations are possible.

In this embodiment, the return electrode 164 is located outside of the probe as in the previously described embodiments. Alternatively, the return electrode(s) may be located within the aspiration lumen 162 with the aspiration electrode 160. For example, the inner insulating coating 163 may be exposed at portions within the lumen 162 to provide a conductive path between this exposed portion of return electrode 164 and the aspiration electrode 160. The latter embodiment has the advantage of confining the electric currents to within the aspiration lumen. In addition, in dry fields in which the conductive fluid is delivered to the target site, it is usually easier to maintain a conductive fluid path between the active and return electrodes in the latter embodiment because the conductive fluid is aspirated through the aspiration lumen 162 along with the tissue fragments.

Figure 9:
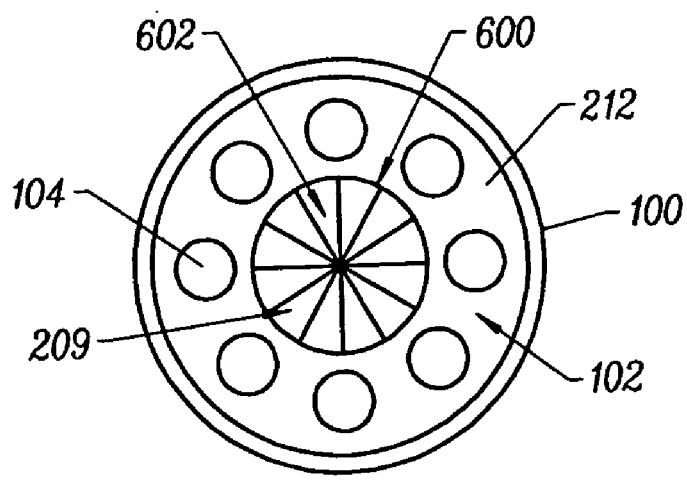

Referring to FIG. 9, another embodiment of the present invention incorporates a wire mesh electrode 600 extending across the distal portion of aspiration lumen 162. As shown, mesh electrode 600 includes a plurality of openings 602 to allow fluids and tissue fragments to flow through into aspiration lumen 162. The size of the openings 602 will vary depending on a variety of factors. The mesh electrode may be coupled to the distal or proximal surfaces of ceramic support member 102. Wire mesh electrode 600 comprises a conductive material, such as platinum, titanium, tantalum, steel, stainless steel, tungsten, copper, gold or the like. In the representative embodiment, wire mesh electrode 600 comprises a different material having a different electric potential than the active electrode(s) 104. Preferably, mesh electrode 600 comprises steel and active electrode(s) 104 comprises tungsten. Applicant has found that a slight variance in the electrochemical potential of mesh electrode 600 and active electrode(s) 104 improves the performance of the device. Of course, it will be recognized that the mesh electrode may be electrically insulated from active electrode(s) as in previous embodiments Referring now to FIGS. 11A–11C, an alternative embodiment incorporating a metal screen 610 is illustrated. As shown, metal screen 610 has a plurality of peripheral openings 612 for receiving active electrodes 104, and a plurality of inner openings 614 for allowing aspiration of fluid and tissue through opening 609 of the aspiration lumen. As shown, screen 610 is press fitted over active electrodes 104 and then adhered to shaft 100 of probe 20. Similar to the mesh electrode embodiment, metal screen 610 may comprise a variety of conductive metals, such as platinum, titanium, tantalum, steel, stainless steel, tungsten, copper, gold, or the like. In the representative embodiment, metal screen 610 is coupled directly to, or integral with, active electrode(s) 104. In this embodiment, the active electrode(s) 104 and the metal screen 610 are electrically coupled to each other.

Figure 32A:
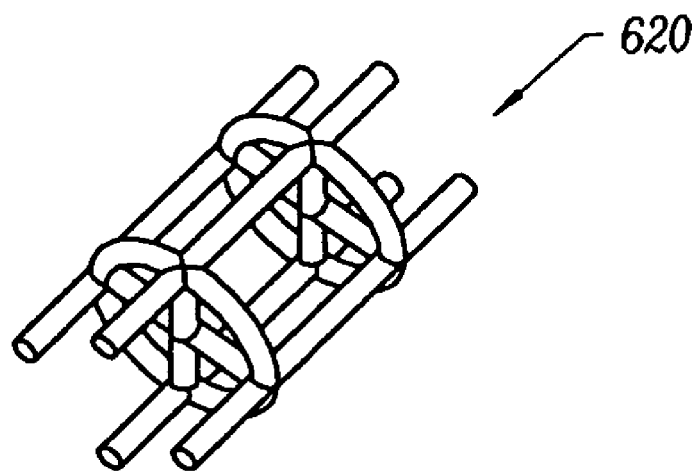
FIGS. 32A and 32B illustrate an alternative cage aspiration electrode for use with the electrosurgical probes shown in FIGS. 2–11.
Figure 32B:
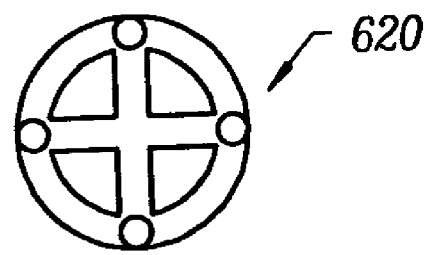
Figure 33A:
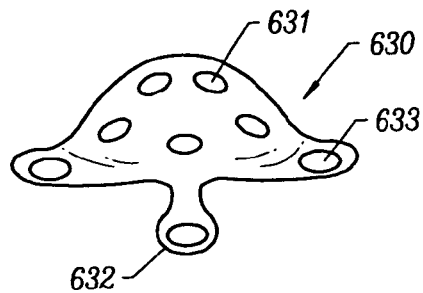
FIGS. 33A–33C illustrate an alternative dome shaped aspiration electrode for use with the electrosurgical probes of FIGS. 2–11.
Figure 33B:
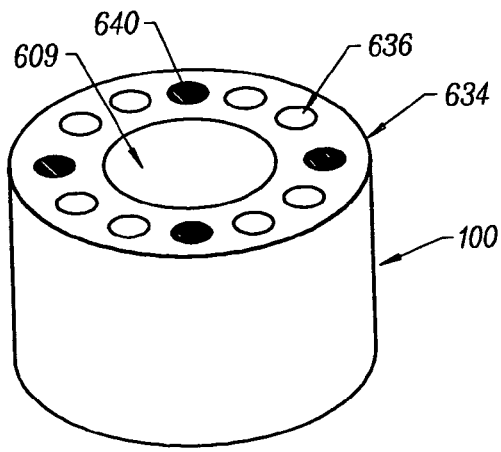
Figure 33C:
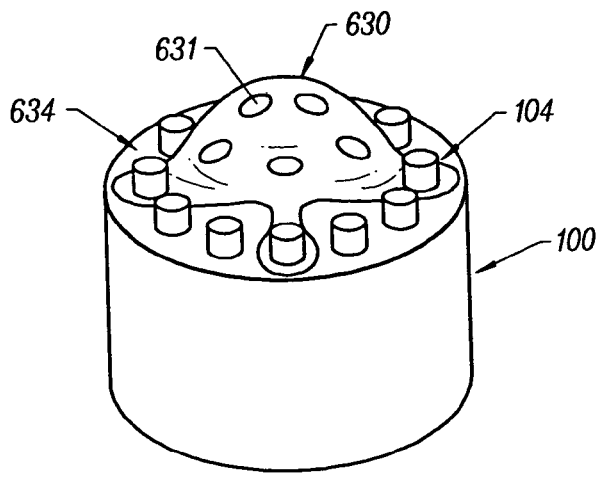

FIGS. 32A–B and 33A–C illustrate alternative embodiments of the mesh and screen aspiration electrodes. As shown in FIGS. 32A and 32B, the probe may include a conductive cage electrode 620 that extends into the aspiration lumen 162 (not shown) to increase the effect of the electrode on aspirated tissue. FIGS. 33A–33C illustrate a dome-shaped screen electrode 630 that includes one or more anchors 632 (four in the representative embodiment) for attaching the screen electrode 630 to a conductive spacer 634. Screen electrode 630 includes a plurality of holes 631 for allowing fluid and tissue fragments to pass therethrough to aspiration lumen 162. Screen electrode 630 is sized to fit within opening 609 of aspiration lumen 162 except for the anchors 632 which include holes 633 for receiving active electrodes 104. Spacer 634 includes peripheral holes 636 for receiving active electrodes 104 and a central hole 638 aligned with suction lumen 162. Spacer 634 may further include insulated holes 640 for electrically isolating screen electrode 630 from active electrodes 104. As shown in FIG. 33C, dome-shaped screen electrode 630 preferably extends distally from the probe shaft 100 about the same distance as the active electrodes 104. Applicant has found that this configuration enhances the ablation rate for tissue adjacent to active electrodes 104, while still maintaining the ability to ablate aspirated tissue fragments passing through screen 630.

Figure 5:
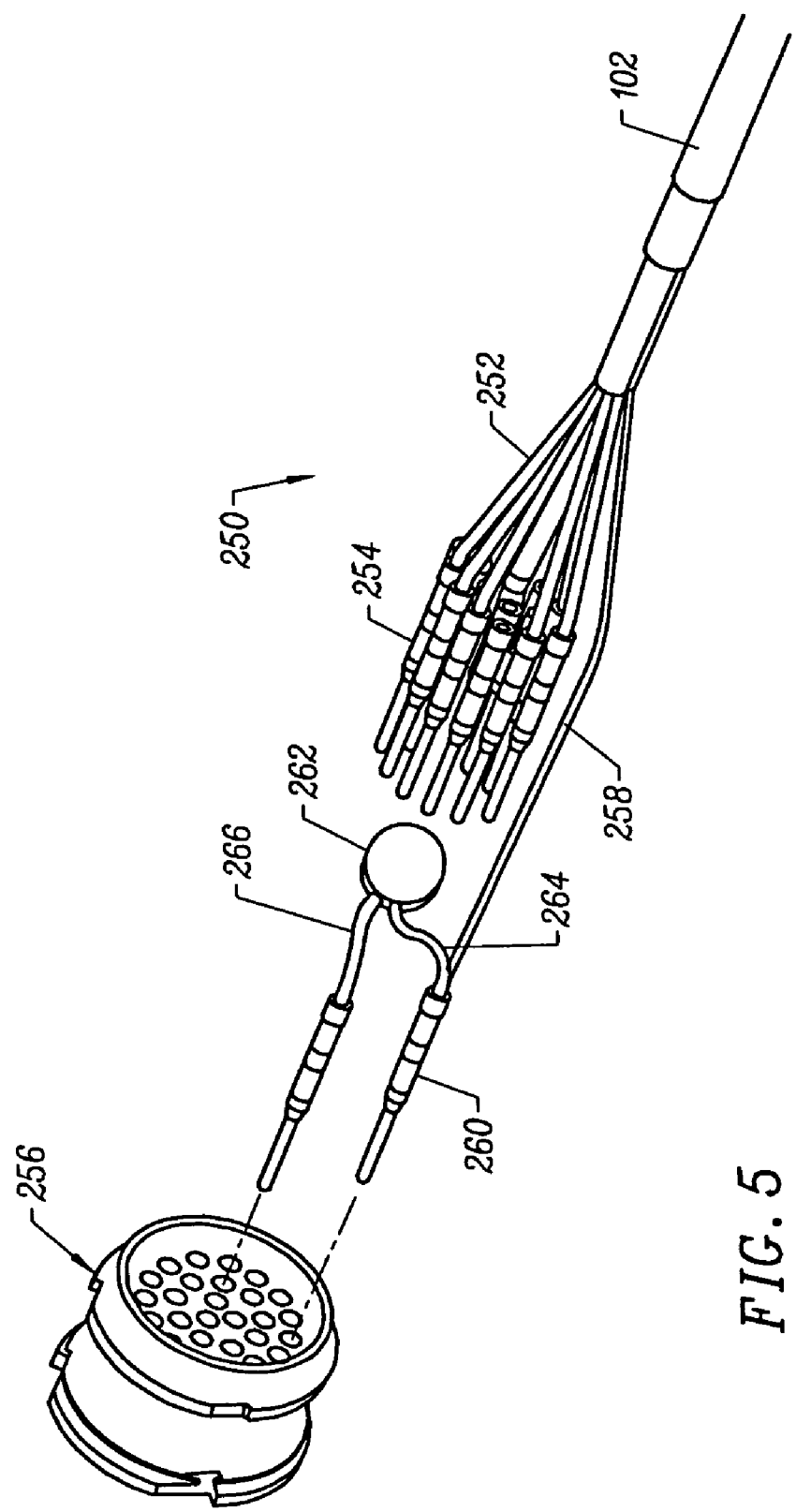
FIG. 5 is an exploded view of the electrical connections within the probe of FIG. 2.

FIG. 5 illustrates the electrical connections 250 within handle 204 for coupling active electrodes 104 and return electrode 112 to the power supply 28. As shown, a plurality of wires 252 extend through shaft 100 to couple electrodes 104 to a plurality of pins 254, which are plugged into a connector block 256 for coupling to a connecting cable 22 (FIG. 1). Similarly, return electrode 112 is coupled to connector block 256 via a wire 258 and a plug 260.

In some embodiments of the present invention, the probe 20 further includes an identification element that is characteristic of the particular electrode assembly so that the same power supply 28 can be used for different electrosurgical operations. In one embodiment, for example, the probe 20 includes a voltage reduction element or a voltage reduction circuit for reducing the voltage applied between the active electrodes 104 and the return electrode 112. The voltage reduction element serves to reduce the voltage applied by the power supply so that the voltage between the active electrodes and the return electrode is low enough to avoid excessive power dissipation into the electrically conducting medium and/or ablation of the soft tissue at the target site. The voltage reduction element primarily allows the electrosurgical probe 20 to be compatible with various generator or power supply models that are adapted to apply higher voltages for ablation, molecular dissociation, or vaporization of tissue (e.g., generators supplied by ArthroCare Corporation, Sunnyvale, Calif.). For contraction of tissue, for example, the voltage reduction element will serve to reduce a voltage of about 100 to 135 volts rms (which is a setting of 1 on the ArthroCare Model 970 and 980 (i.e., 2000) Generators) to about 45 to 60 volts rms, which is a suitable voltage for contraction of tissue without ablation (e.g., without molecular dissociation) of the tissue.

Of course for some procedures in endoscopic spine surgery, the probe will typically not require a voltage reduction element. Alternatively, the probe may include a voltage increasing element or circuit, if desired.

In the representative embodiment, the voltage reduction element comprises a pair of capacitors forming a bridge divider (not shown) coupled to the power supply and coagulation electrode 380. The capacitors usually have a capacitance of about 200 pF to 500 pF (at 500 volts) and preferably about 300 pF to 350 pF (at 500 volts). Of course, the capacitors may be located in other places within the system, such as in, or distributed along the length of, the cable, the generator, the connector, etc. In addition, it will be recognized that other voltage reduction elements, such as diodes, transistors, inductors, resistors, capacitors or combinations thereof, may be used in conjunction with the present invention. For example, the probe 350 may include a coded resistor (not shown) that is constructed to lower the voltage applied between the return and coagulation electrodes 360, 380, respectively. In addition, electrical circuits may be employed for this purpose.

Alternatively or additionally, the cable 22 that couples the power supply 28 to probe 20/90 may be used as a voltage reduction element. The cable has an inherent capacitance that can be used to reduce the power supply voltage if the cable is placed into the electrical circuit between the power supply, the active electrodes and the return electrode. In this embodiment, the cable 22 may be used alone, or in combination with one of the voltage reduction elements discussed above, e.g., a capacitor.

In some embodiments, probe 20/90 will further include a switch (not shown) or other input that allows the surgeon to couple and decouple the identification element to the rest of the electronics in probe 20/90. For example, if the surgeon would like to use the same probe for ablation of tissue and contraction of tissue in the same procedure, this can be accomplished by manipulating the switch. Thus, for ablation of tissue, the surgeon will decouple the voltage reduction element from the electronics so that the full voltage applied by the power source is applied to the electrodes on the probe. When the surgeon desires to reduce the voltage to a suitable level for contraction of tissue, he/she couples the voltage reduction element to the electronics to reduce the voltage applied by the power supply to the active electrodes.

Further, it should be noted that the present invention can be used with a power supply that is adapted to apply a voltage within the selected range for treatment of tissue. In this embodiment, a voltage reduction element or circuitry may not be desired.

Figure 13:
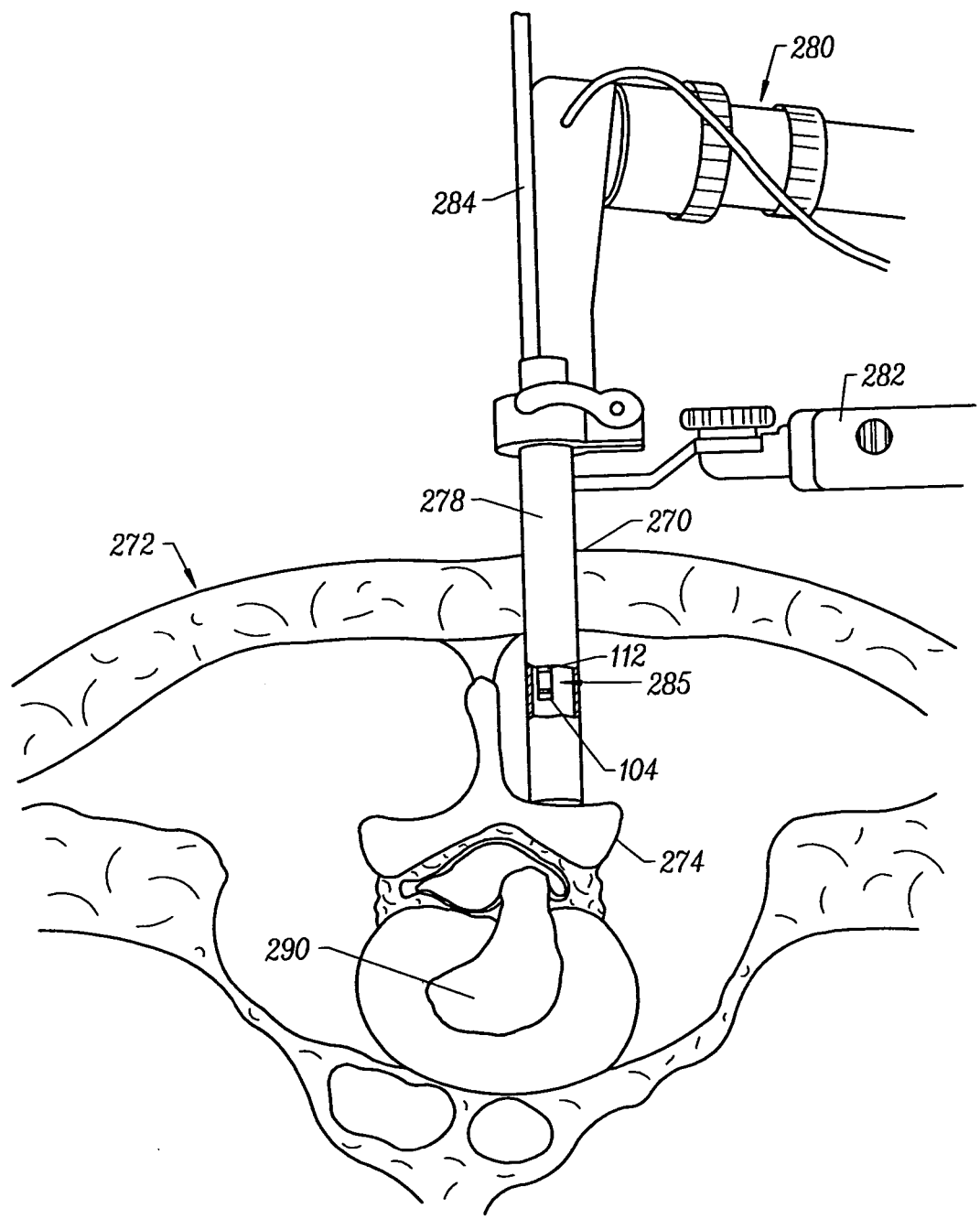

The present invention is particularly useful in microendoscopic discectomy procedures, e.g., for decompressing a nerve root with a lumbar discectomy. As shown in FIGS. 12–15, a percutaneous penetration 270 is made in the patients' back 272 so that the superior lamina 274 can be accessed. Typically, a small needle (not shown) is used initially to localize the disc space level, and a guidewire (not shown) is inserted and advanced under lateral fluoroscopy to the inferior edge of the lamina 274. Sequential cannulated dilators 276 are inserted over the guide wire and each other to provide a hole from percutaneous penetration 270 to the lamina 274. The first dilator may be used to "palpate" the lamina 274, assuring proper location of its tip between the spinous process and facet complex just above the inferior edge of the lamina 274. As shown in FIG. 13, a tubular retractor 278 is then passed over the largest dilator down to the lamina 274. The dilators 276 are removed, establishing an operating corridor within the tubular retractor 278.

As shown in FIG. 13, an endoscope 280 is then inserted into the tubular retractor 278 and a ring clamp 282 is used to secure the endoscope 280. Typically, the formation of the operating corridor within retractor 278 requires the removal of soft tissue, muscle or other types of tissue that were forced into this corridor as the dilators 276 and retractor 278 were advanced down to the lamina 274. In procedures of the prior art, this tissue has usually been removed with mechanical instruments, such as pituitary rongeurs, curettes, graspers, cutters, drills, microdebriders and the like. Unfortunately, these mechanical instruments greatly lengthen and increase the complexity of the procedure. In addition, these instruments sever blood vessels within this tissue, usually causing profuse bleeding that obstructs the surgeon's view of the target site.

According to the present invention, an electrosurgical probe or catheter 284 as described above is introduced into the operating corridor within the retractor 278 to remove the soft tissue, muscle and other obstructions from this corridor so that the surgeon can easily access and visualize the lamina 274. Once the surgeon has introduced the probe 284, electrically conductive fluid 285 is delivered through tube 233 and opening 237 to the tissue (see FIG. 2). The fluid flows past the return electrode 112 to the active electrodes 104 at the distal end of the shaft. The rate of fluid flow is controlled with valve 17 (FIG. 1) such that the zone between the tissue and electrode support 102 is constantly immersed in the fluid. The power supply 28 is then turned on and adjusted such that a high frequency voltage difference is applied between active electrodes 104 and return electrode 112. The electrically conductive fluid provides the conduction path (see current flux lines) between active electrodes 104 and the return electrode 112.

The high frequency voltage is sufficient to convert the electrically conductive fluid (not shown) between the target tissue and active electrode(s) 104 into an ionized vapor layer or plasma (not shown). As a result of the applied voltage difference between active electrode(s) 104 and the target tissue (i.e., the voltage gradient across the plasma layer), charged particles in the plasma (e.g., electrons) cause dissociation of the molecular bonds within tissue structures. This molecular dissociation is accompanied by the volumetric removal (i.e., ablative sublimation) of tissue and the production of low molecular weight gases, such as oxygen, nitrogen, carbon dioxide, hydrogen and methane. This process can be precisely controlled to effect the volumetric removal of tissue as thin as 10 microns to 150 microns with minimal heating of, or damage to, underlying tissue structures. A more detailed description of this phenomenon is presented in commonly assigned U.S. Pat. No. 5,697,882, the complete disclosure of which is incorporated herein by reference.

During the process, the gases will be aspirated through opening 209 and suction tube 211 to a vacuum source. In addition, excess electrically conductive fluid, and other fluids (e.g., blood) will be aspirated from the operating corridor to facilitate the surgeon's view. During ablation of the tissue, the residual heat generated by the current flux lines (typically less than 150° C.), will usually be sufficient to coagulate any severed blood vessels at the site. If not, the surgeon may switch the power supply 28 into the coagulation mode by lowering the voltage to a level below the threshold for fluid vaporization, as discussed above. This simultaneous hemostasis results in less bleeding and facilitates the surgeon's ability to perform the procedure.

Another advantage of the present invention is the ability to precisely ablate soft tissue without causing necrosis or thermal damage to the underlying and surrounding tissues, nerves or bone. In addition, the voltage can be controlled so that the energy directed to the target site is insufficient to ablate the lamina 274 so that the surgeon can literally clean the tissue off the lamina 274, without ablating or otherwise effecting significant damage to the lamina.

Figure 14:
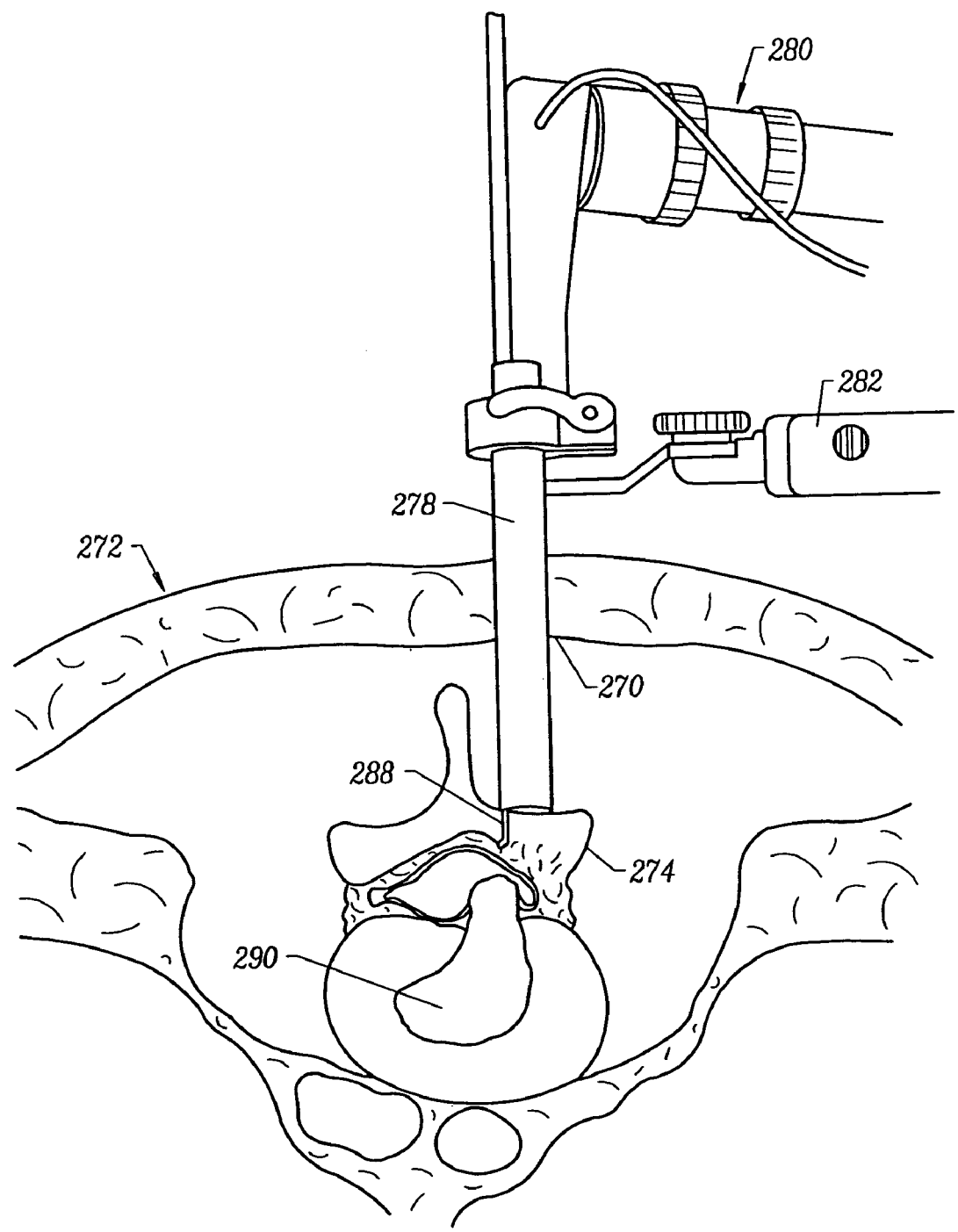
Figure 15:
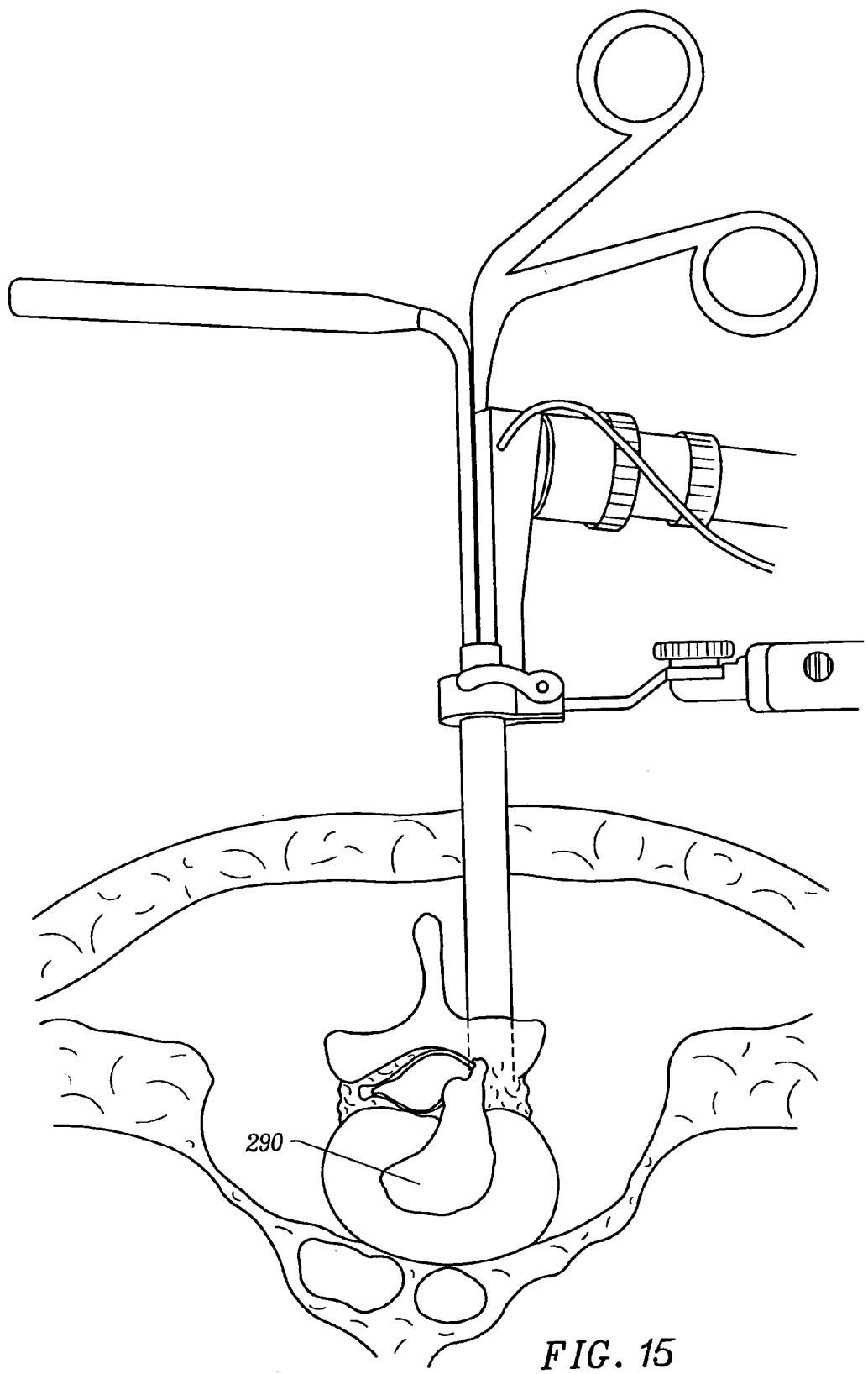

Referring now to FIGS. 14 and 15, once the operating corridor is sufficiently cleared, a laminotomy and medial facetectomy is accomplished either with conventional techniques (e.g., a Kerrison punch or a high speed drill) or with the electrosurgical probe 284 as discussed above. After the nerve root is identified, medical retraction can be achieved with a retractor 288, or the present invention can be used to ablate with precision the disc. If necessary, epidural veins are cauterized either automatically or with the coagulation mode of the present invention. If an annulotomy is necessary, it can be accomplished with a microknife or the ablation mechanism of the present invention while protecting the nerve root with the retractor 288. The herniated disc 290 is then removed with a pituitary rongeur in a standard fashion, or once again through ablation as described above.

In another embodiment, the electrosurgical probe of the present invention can be used to ablate and/or contract soft tissue within the disc 290 to allow the annulus 292 to repair itself to prevent reoccurrence of this procedure. For tissue contraction, a sufficient voltage difference is applied between the active electrodes 104 and the return electrode 112 to elevate the tissue temperature from normal body temperatures (e.g., 37° C.) to temperatures in the range of 45° C. to 90° C., preferably in the range from 60° C. to 70° C. This temperature elevation causes contraction of the collagen connective fibers within the disc tissue so that the nucleus pulposus 291 withdraws into the annulus fibrosus 292.

In one method of tissue contraction according to the present invention, an electrically conductive fluid is delivered to the target site as described above, and heated to a sufficient temperature to induce contraction or shrinkage of the collagen fibers in the target tissue. The electrically conductive fluid is heated to a temperature sufficient to substantially irreversibly contract the collagen fibers, which generally requires a tissue temperature in the range of about 45° C. to 90° C., usually about 60° C. to 70° C. The fluid is heated by applying high frequency electrical energy to the active electrode(s) in contact with the electrically conducting fluid. The current emanating from the active electrode(s)

104 heats the fluid and generates a jet or plume of heated fluid, which is directed towards the target tissue. The heated fluid elevates the temperature of the collagen sufficiently to cause hydrothermal shrinkage of the collagen fibers. The return electrode 112 draws the electric current away from the tissue site to limit the depth of penetration of the current into the tissue, thereby inhibiting molecular dissociation and breakdown of the collagen tissue and minimizing or completely avoiding damage to surrounding and underlying tissue structures beyond the target tissue site. In an exemplary embodiment, the active electrode(s) 104 are held away from the tissue a sufficient distance such that the RF current does not pass into the tissue at all, but rather passes through the electrically conductive fluid back to the return electrode. In this embodiment, the primary mechanism for imparting energy to the tissue is the heated fluid, rather than the electric current.

In an alternative embodiment, the active electrode(s) 104 are brought into contact with, or close proximity to, the target tissue so that the electric current passes directly into the tissue to a selected depth. In this embodiment, the return electrode draws the electric current away from the tissue site to limit its depth of penetration into the tissue. Applicant has discovered that the depth of current penetration can also be varied with the electrosurgical system of the present invention by changing the frequency of the voltage applied to the active electrode and the return electrode. This is because the electrical impedance of tissue is known to decrease with increasing frequency due to the electrical properties of cell membranes which surround electrically conductive cellular fluid. At lower frequencies (e.g., less than 350 kHz), the higher tissue impedance, the presence of the return electrode and the active electrode configuration of the present invention (discussed in detail below) cause the current flux lines to penetrate less deeply resulting in a smaller depth of tissue heating. In an exemplary embodiment, an operating frequency of about 100 to 200 kHz is applied to the active electrode(s) to obtain shallow depths of collagen shrinkage (e.g., usually less than 1.5 mm and preferably less than 0.5 mm).

In another aspect of the invention, the size (e.g., diameter or principal dimension) of the active electrodes employed for treating the tissue are selected according to the intended depth of tissue treatment. As described previously in copending patent application PCT International Application, U.S. National Phase Serial No. PCT/US94/05168, the depth of current penetration into tissue increases with increasing dimensions of an individual active electrode (assuming other factors remain constant, such as the frequency of the electric current, the return electrode configuration, etc.). The depth of current penetration (which refers to the depth at which the current density is sufficient to effect a change in the tissue, such as collagen shrinkage, irreversible necrosis, etc.) is on the order of the active electrode diameter for the bipolar configuration of the present invention and operating at a frequency of about 100 kHz to about 200 kHz. Accordingly, for applications requiring a smaller depth of current penetration, one or more active electrodes of smaller dimensions would be selected. Conversely, for applications requiring a greater depth of current penetration, one or more active electrodes of larger dimensions would be selected.

Figure 16:
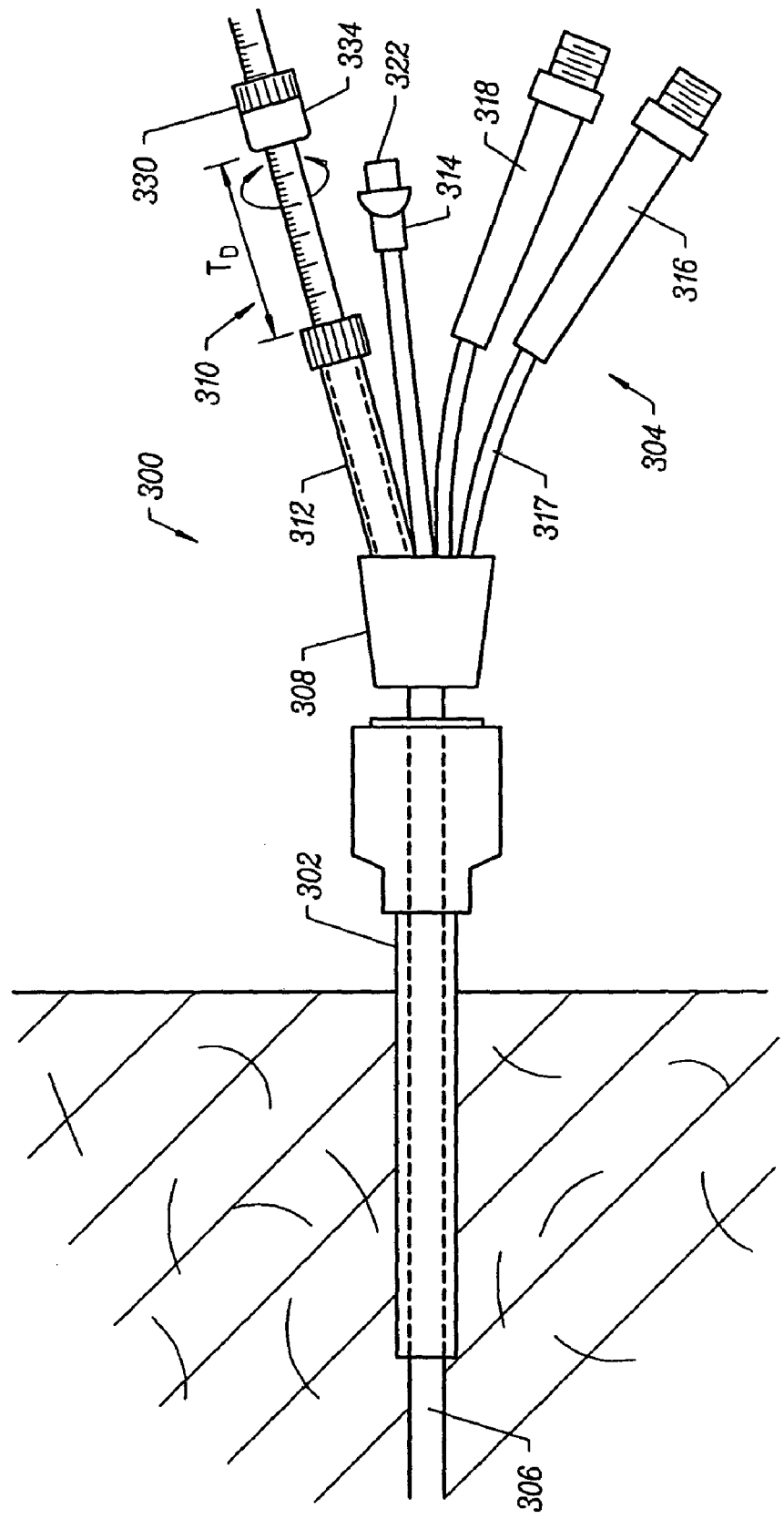
FIG. 16 is a schematic view of the proximal portion of another electrosurgical system for endoscopic spine surgery incorporating an electrosurgical instrument according to the present invention.
Figure 17:
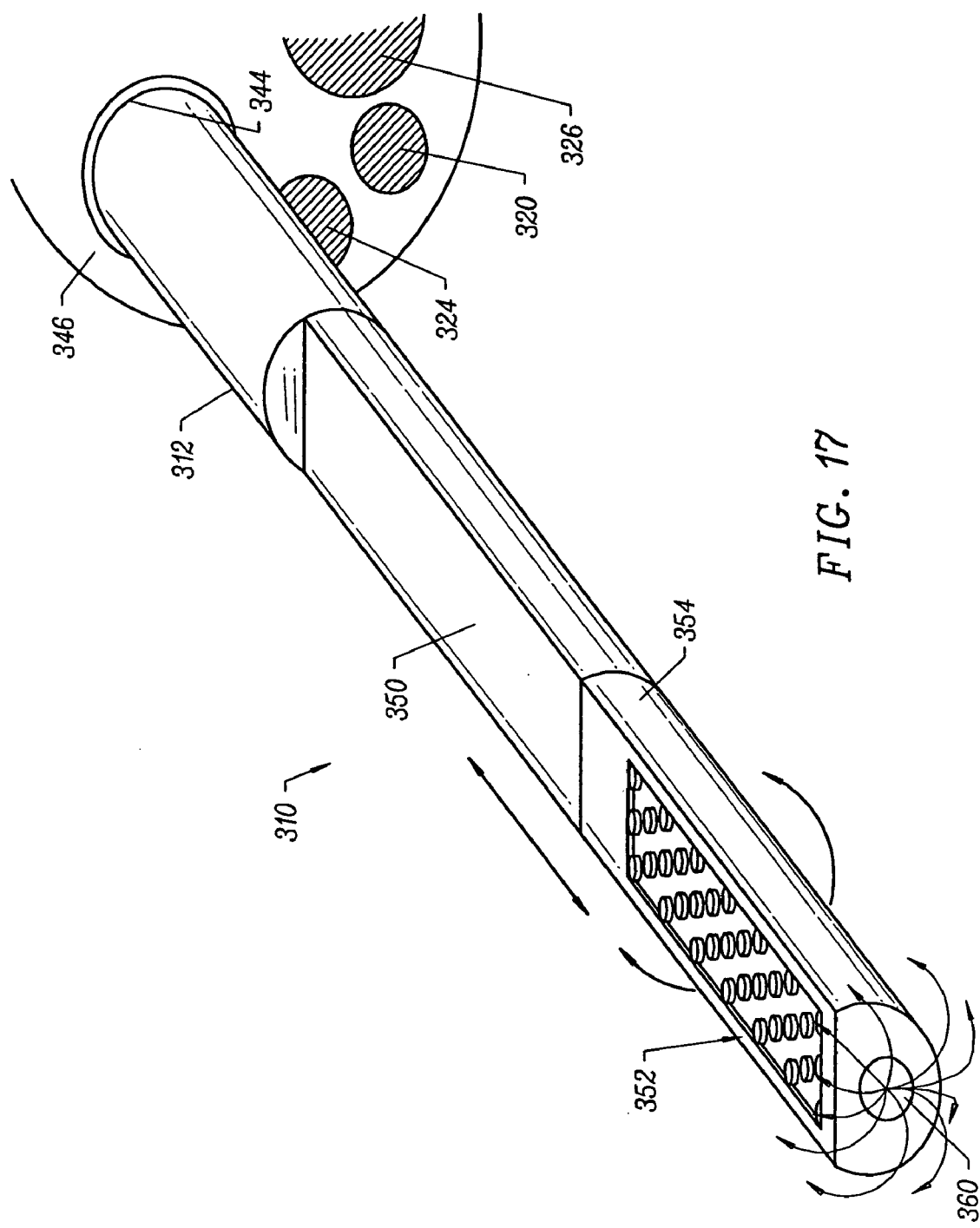
FIG. 17 is an enlarged view of a distal portion of the electrosurgical instrument of FIG. 16.
Figure 18:
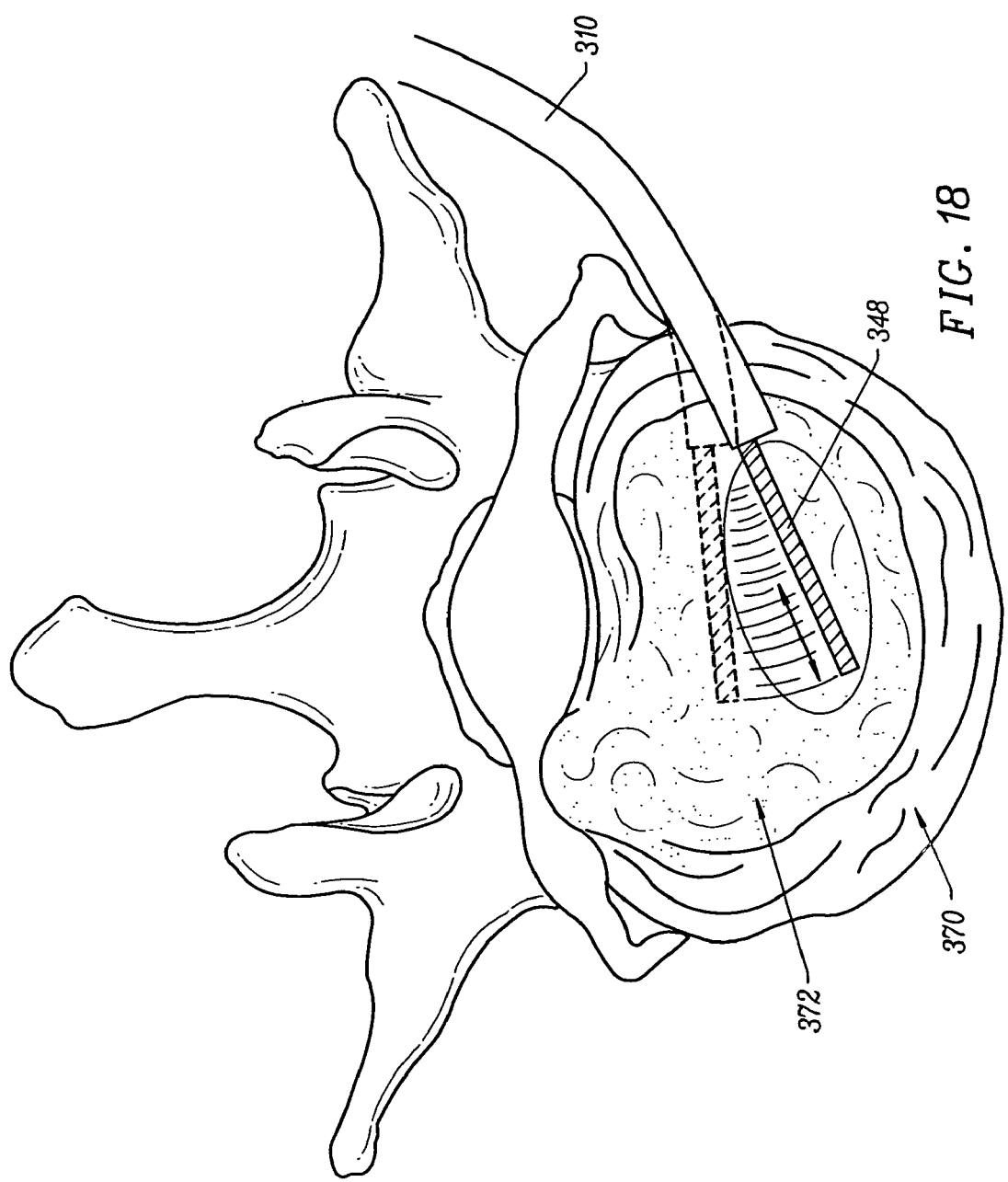
FIG. 18 illustrates a method of ablating a volume of tissue from the nucleus pulposus of a herniated disc with the electrosurgical system of FIG. 16.

FIGS. 16–18 illustrate an alternative electrosurgical system 300 specifically configured for endoscopic discectomy procedures, e.g., for treating extruded or non-extruded herniated discs. As shown in FIG. 16 system 300 includes a trocar cannula 302 for introducing a catheter assembly 304 through a percutaneous penetration in the patient to a target disc in the patient's spine. As discussed above, the catheter assembly 304 may be introduced through the thorax in a thoracoscopic procedure, through the abdomen in a laparascopic procedure, or directly through the patient's back. Catheter assembly 304 includes a catheter body 306 with a plurality of inner lumens (not shown) and a proximal hub 308 for receiving the various instruments that will pass through catheter body 306 to the target site. In this embodiment, assembly 304 includes an electrosurgical instrument 310 with a flexible shaft 312, an aspiration catheter 314, an endoscope 316 and an illumination fiber shaft 318 for viewing the target site. As shown in FIGS. 16 and 17, aspiration catheter 314 includes a distal port 320 and a proximal fitment 322 for attaching catheter 314 to a source of vacuum (not shown). Endoscope 316 will usually comprise a thin metal tube 317 with a lens 324 at the distal end, and an eyepiece (not shown) at the proximal end.

In the exemplary embodiment, electrosurgical instrument 310 includes a twist locking stop 330 at a proximal end of the shaft 312 for controlling the axial travel distance $T_D$ of the probe. As discussed in detail below, this configuration allows the surgeon to "set" the distance of ablation within the disc. In addition, instrument 310 includes a rotational indicator 334 for displaying the rotational position of the distal portion of instrument 310 to the surgeon. This rotational indicator 334 allows the surgeon to view this rotational position without relying on the endoscope 316 if visualization is difficult, or if an endoscope is not being used in the procedure.

Referring now to FIGS. 17 and 18, a distal portion 340 of electrosurgical instrument 310 and catheter body 306 will now be described. As shown, instrument 310 comprises a relatively stiff, but deflectable electrically insulating support cannula 312 and a working end portion 348 movably coupled to cannula 312 for rotational and translational movement of working end 348. Working end 348 of electrosurgical instrument 310 can be rotated and translated to ablate and remove a volume of nucleus pulposus within a disc. Support cannula 312 extends through an internal lumen 344 and beyond the distal end 346 of catheter body 306. Alternatively, support cannula 312 may be separate from instrument 310, or even an integral part of catheter body 306. The distal portion of working end 348 includes an exposed return electrode 350 separated from an active electrode array 352 by an insulating support member 354, such as ceramic. In the representative embodiment, electrode array 352 is disposed on only one side of ceramic support member 354 so that its other side is insulating and thus atraumatic to tissue. Instrument 310 will also include a fluid lumen (not shown) having a distal port 360 in working end 348 for delivering electrically conductive fluid to the target site.

In use, trocar cannula 302 is introduced into a percutaneous penetration suitable for endoscopic delivery to the target disc in the spine. A trephine (not shown) or other conventional instrument may be used to form a channel from the trocar cannula 302 through the annulus fibrosus 292 and into the nucleus pulposus. Alternatively, the probe 310 may be used for this purpose, as discussed above. The working end 348 of instrument 310 is then advanced through cannula 302 a short distance (e.g., about 7 to 10 mm) into the nucleus pulposus 291, as shown in FIG. 18. Once the electrode array 352 is in position, electrically conductive fluid is delivered through distal port 360 to immerse the active electrode array 352 in the fluid. The vacuum source may also be activated to ensure a flow of conductive fluid between electrode array 352 past return electrode 350 to suction port 320, if necessary. In some embodiments, the mechanical stop 330 may then be set at the proximal end of the instrument 310 to limit the axial travel distance of working end 348. Preferably, this distance will be set to minimize (or completely eliminate) ablation of the surrounding annulus.

The probe is then energized by applying high frequency voltage difference between the electrode array 352 and return electrode 350 so that electric current flows through the conductive fluid from the array 352 to the return electrode 350. The electric current causes vaporization of the fluid and ensuing molecular dissociation of the nucleus pulposus tissue as described in detail above. The instrument 310 may then be translated in an axial direction forwards and backwards to the preset limits. While still energized and translating, the working end 348 may also be rotated to ablate tissue surrounding the electrode array 352. In the representative embodiment, working end 348 will also include an inflatable gland 380 opposite electrode array 352 to allow deflection of working end 348 relative to support cannula 312. As shown in FIG. 18, working end 348 may be deflected to produce a large diameter bore within the nucleus pulposus, which assures close contact with tissue surfaces to be ablated. Alternatively, the entire catheter body 306, or the distal end of catheter body 306 may be deflected to increase the volume of nucleus pulposus removed.

After the desired volume of nucleus pulposus is removed (based on direct observation through port 324, or by kinesthetic feedback from movement of working end 348 of instrument 310), instrument 310 is withdrawn into catheter body 306 and the catheter body is removed from the patient. Typically, the preferred volume of removed tissue is about 0.2 cm$^3$ to 5.0 cm$^3$.

Figure 19:
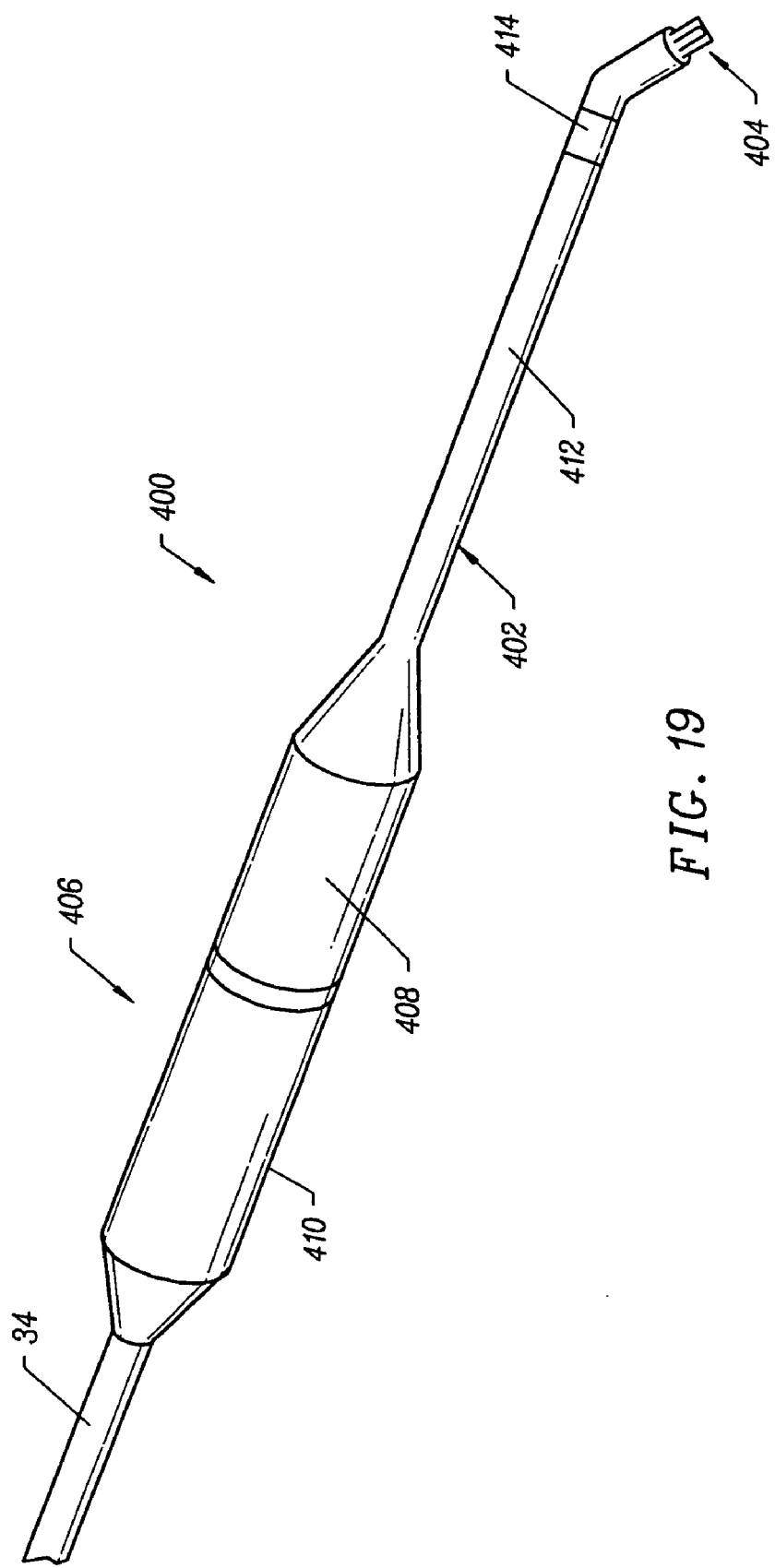
FIG. 19 illustrates a planar ablation probe for ablating tissue in confined spaces within a patient's body according to the present invention.

Referring now to FIGS. 19–28, alternative systems and methods for ablating tissue in confined (e.g., narrow) body spaces will now be described. FIG. 19 illustrates an exemplary planar ablation probe 400 according to the present invention. Similar to the instruments described above, probe 400 can be incorporated into electrosurgical system 11 (or other suitable systems) for operation in either the bipolar or monopolar modalities.

Probe 400 generally includes a support member 402, a distal working end 404 attached to the distal end of support member 402 and a proximal handle 406 attached to the proximal end of support member 402. As shown in FIG. 19, handle 406 includes a handpiece 408 and a power source connector 410 removably coupled to handpiece 408 for electrically connecting working end 404 with power supply 28 through cable 34 (see FIG. 1).

In the embodiment shown in FIG. 19, planar ablation probe 400 is configured to operate in the bipolar modality. Accordingly, support member 402 or a portion thereof functions as the return electrode and comprises an electrically conducting material, such as titanium, or alloys containing one or more of nickel, chromium, iron, cobalt, copper, aluminum, platinum, molybdenum, tungsten, tantalum or carbon. In the preferred embodiment, support member 402 is an austenitic stainless steel alloy, such as stainless steel Type 304 from MicroGroup, Inc., Medway, Mass. As shown in FIG. 19, support member 402 is substantially covered by an insulating layer 412 to prevent electric current from damaging surrounding tissue. An exposed portion 414 of support member 402 functions as the return electrode for probe 400. Exposed portion 414 is preferably spaced proximally from active electrodes 416 by a distance of about 1 mm to 20 mm.

Figure 20:
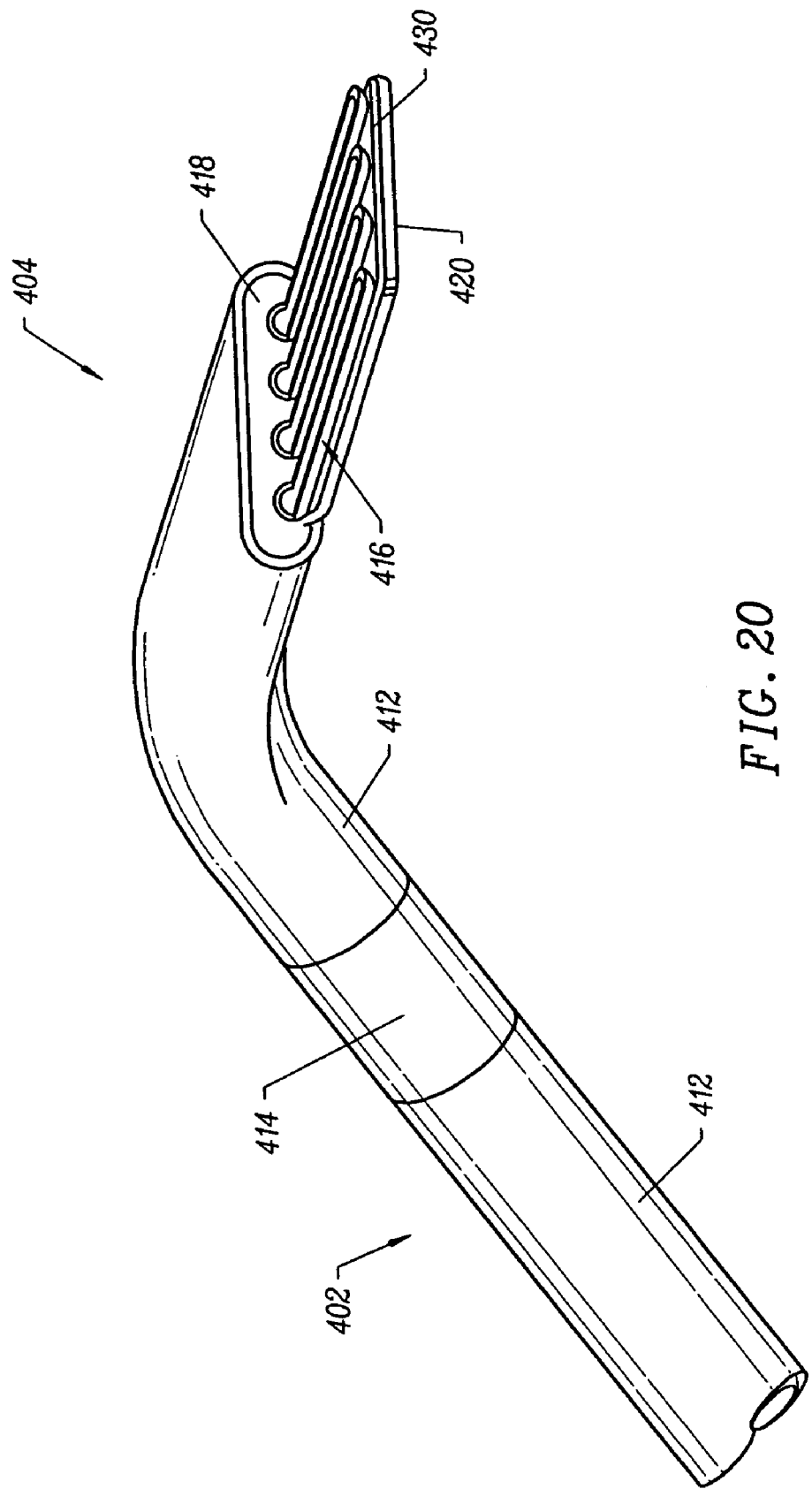
FIG. 20 illustrates a distal portion of the planar ablation probe of FIG. 19.

Referring to FIGS. 20 and 21, planar ablation probe 400 further comprises a plurality of active electrodes 416 extending from an electrically insulating spacer 418 at the distal end of support member 402. Of course, it will be recognized that probe 400 may include a single electrode depending on the size of the target tissue to be treated and the accessibility of the treatment site (see FIG. 26, for example). Insulating spacer 418 is preferably bonded to support member 402 with a suitable epoxy adhesive 419 to form a mechanical bond and a fluid-tight seal. Electrodes 416 usually extend about 2.0 mm to 20 mm from spacer 418, and preferably less than 10 mm. A support tongue 420 extends from the distal end of support member 402 to support active electrodes 416. Support tongue 420 and active electrodes 416 have a substantially low profile to facilitate accessing narrow spaces within the patient's body, such as the spaces between adjacent vertebrae and between articular cartilage and the meniscus in the patient's knee. Accordingly, tongue 420 and electrodes 416 have a substantially planar profile, usually having a combined height He of less than 4.0 mm, preferably less than 2.0 mm and more preferably less than 1.0 mm (see FIG. 25). In the case of ablation of meniscus near articular cartilage, the height He of both the tongue 420 and electrodes 416 is preferably between about 0.5 mm to 1.5 mm. The width of electrodes 416 and support tongue 420 will usually be less than 10.0 mm and preferably between about 2.0 mm to 4.0 mm.

Support tongue 420 includes a "non-active" surface 422 opposing active electrodes 416 covered with an electrically insulating layer (not shown) to minimize undesirable current flow into adjacent tissue or fluids. Non-active surface 422 is preferably atraumatic, i.e., having a smooth planar surface with rounded corners, to minimize unwanted injury to tissue or nerves in contact therewith, such as disc tissue or the nearby spinal nerves, as the working end of probe 400 is introduced into a narrow, confined body space. Non-active surface 422 of tongue 420 help to minimize iatrogenic injuries to tissue and nerves so that working end 404 of probe 400 can safely access confined spaces within the patient's body.

Figure 21A:
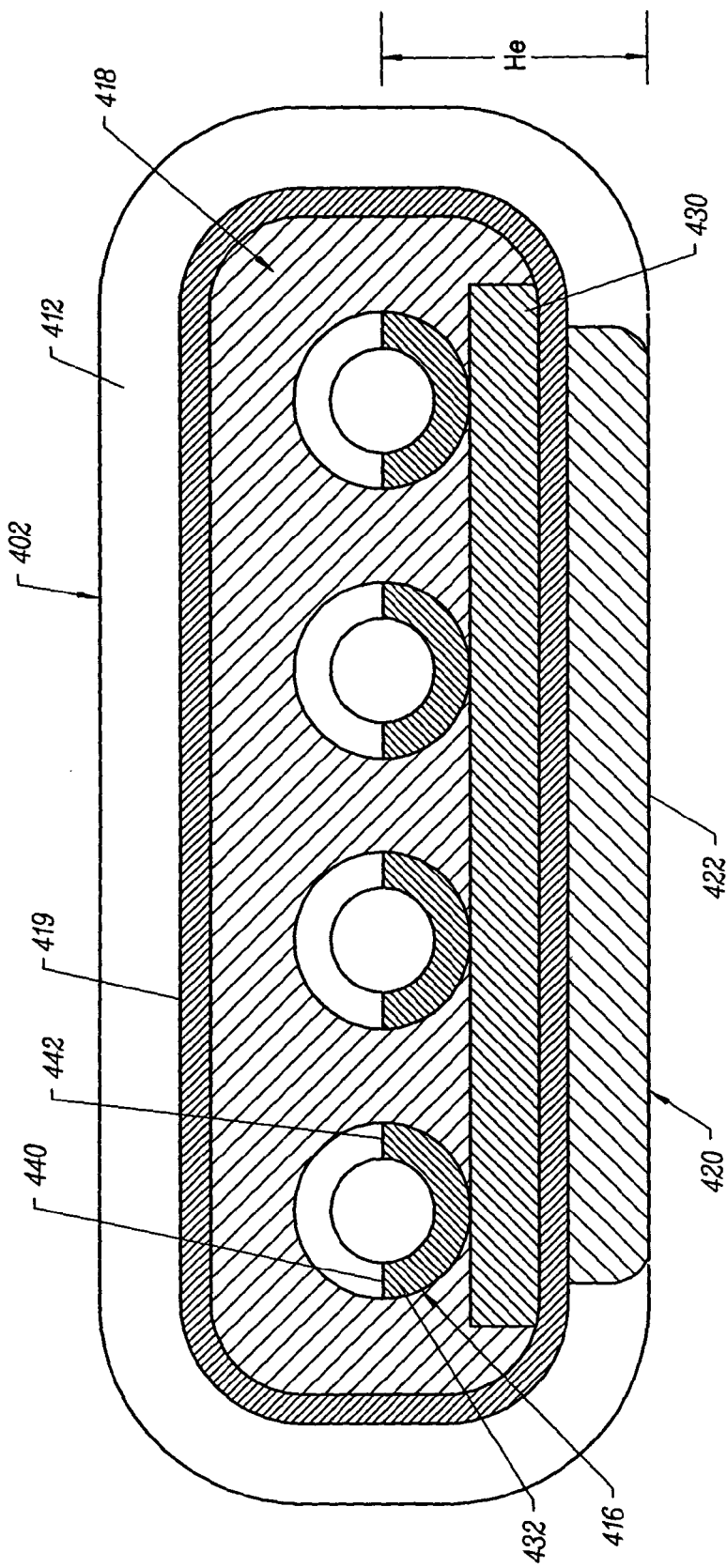
FIG. 21A is a front sectional view of the planar ablation probe, illustrating an array of semi-cylindrical active electrodes.
Figure 21B:
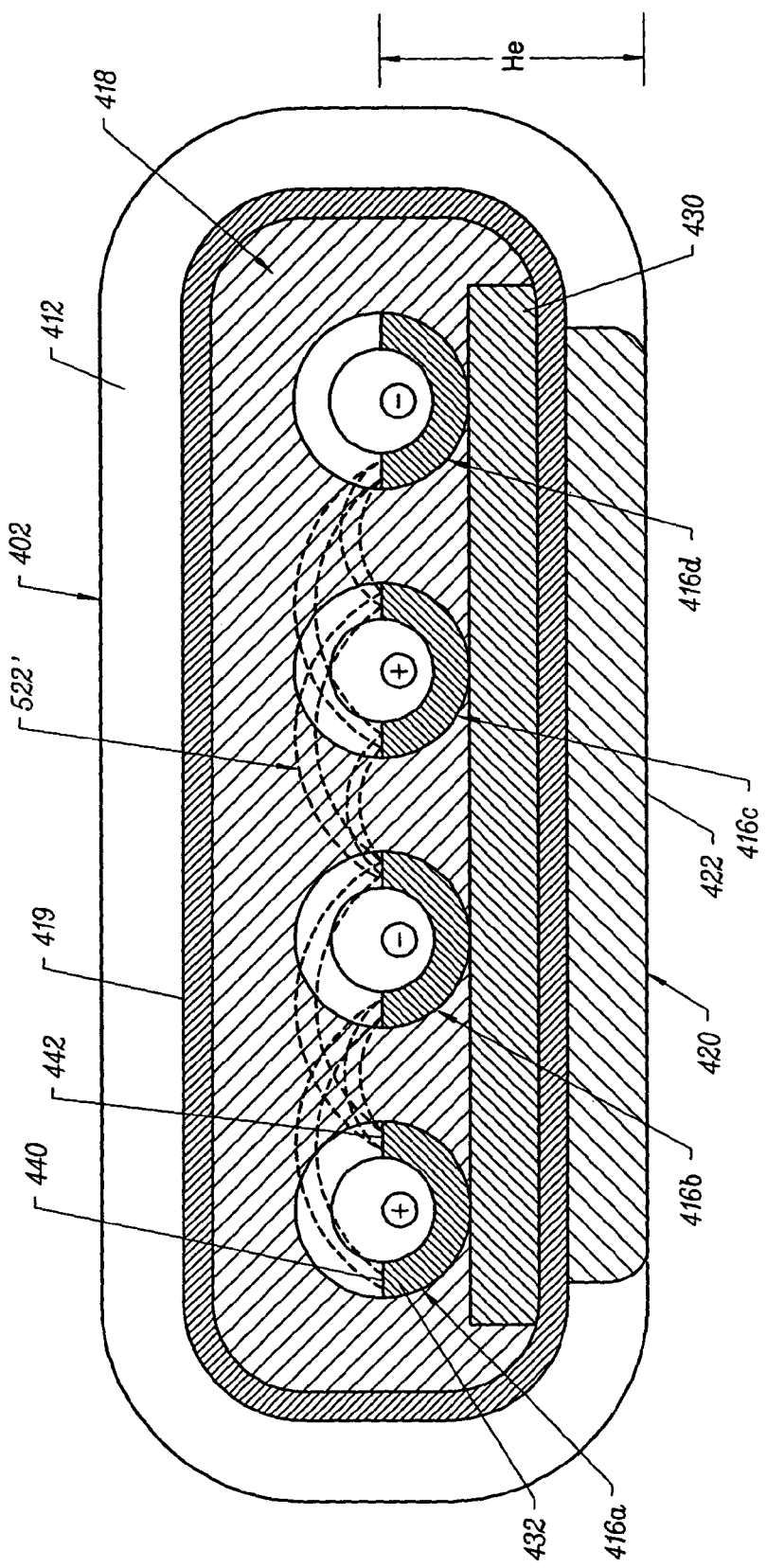
FIG. 21B is a front sectional view of an alternative planar ablation probe, illustrating an array of active electrodes having opposite polarities.
Figure 22:
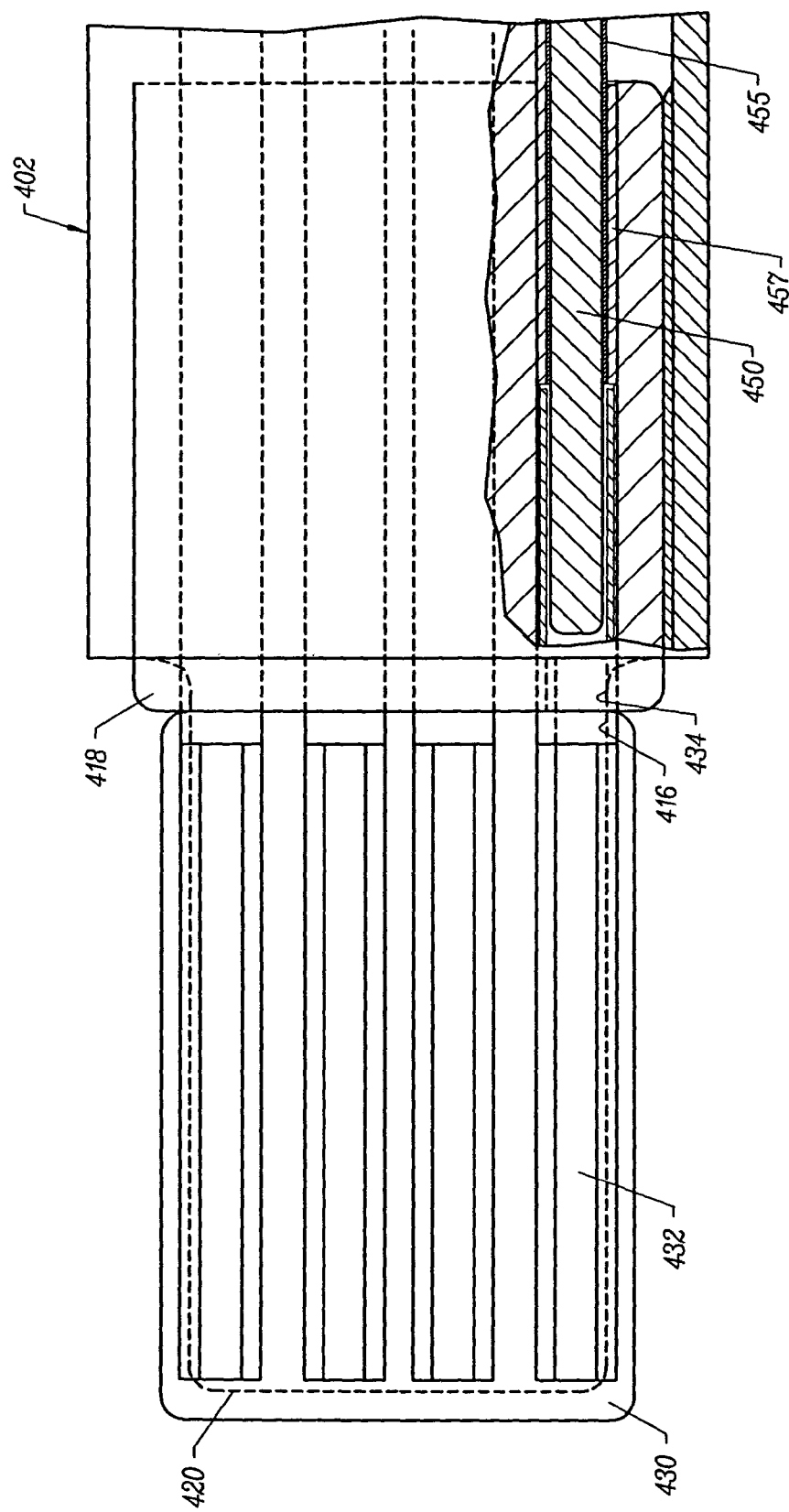
FIG. 22 is a top, partial sectional, view of the working end of the planar ablation probe of FIG. 19.
Figure 26:
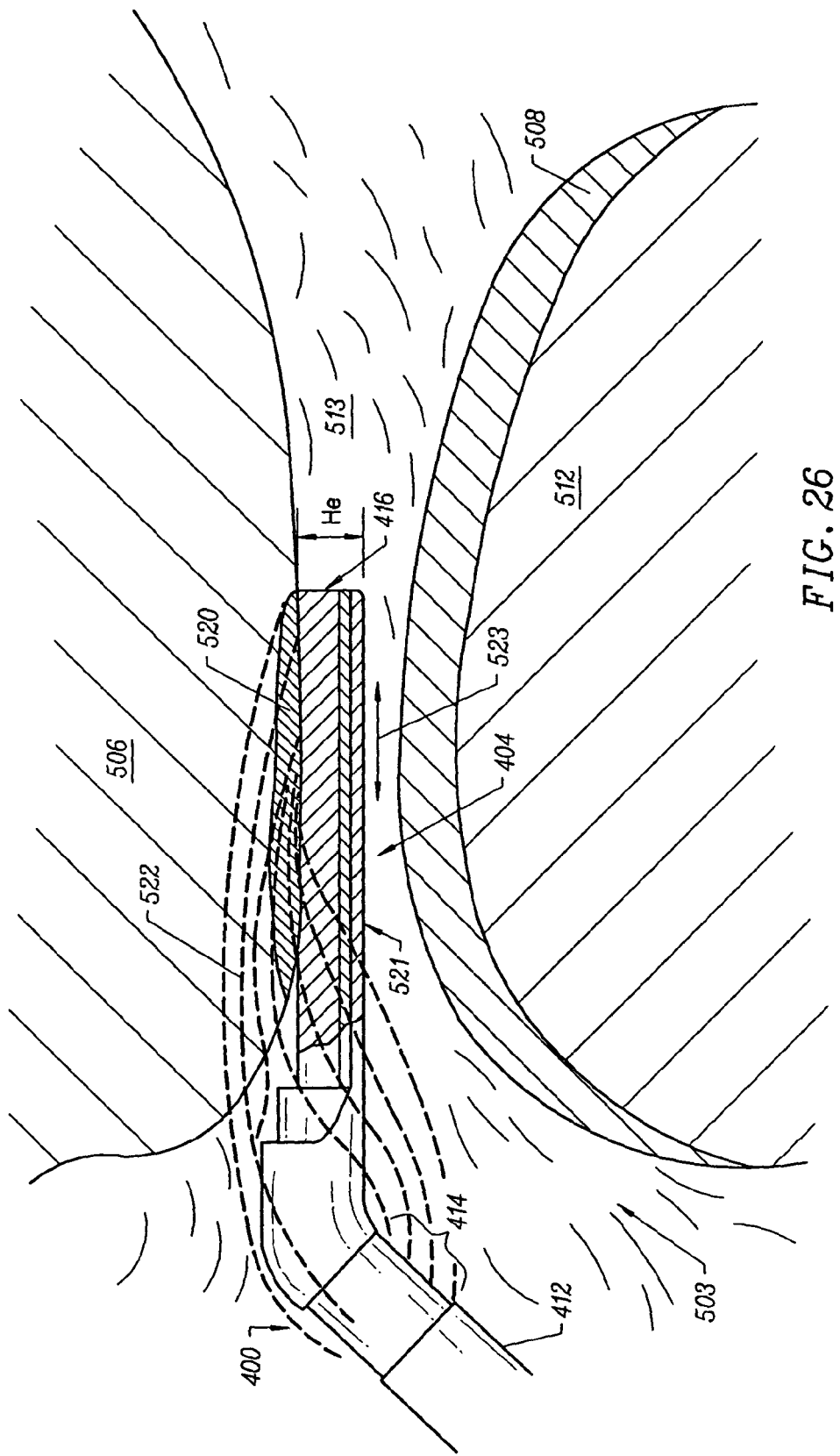
FIG. 26 is an enlarged view of the distal portion of the planar ablation probe, illustrating ablation or cutting of meniscus tissue.

Referring to FIGS. 21A–B and 22, an electrically insulating support member 430 is disposed between support tongue 420 and active electrodes 416 to inhibit or prevent electric current from flowing into tongue 420. Insulating member 430 and insulating layer 412 preferably comprise a ceramic, glass or glass ceramic material, such as alumina. Insulating member 430 is mechanically bonded to support tongue 420 with a suitable epoxy adhesive to electrically insulate active electrodes 416 from tongue 420. As shown in FIG. 26, insulating member 430 may overhang support tongue 420 to increase the electrical path length between the active electrodes 416 and the insulation covered support tongue 420.

As shown in FIGS. 21A–23, active electrodes 416 are preferably constructed from a hollow, round tube, with at least the distal portion 432 of electrodes 416 being filed off to form a semi-cylindrical tube with first and second ends 440, 442 facing away from support tongue 420. Preferably, the proximal portion 434 of electrodes 416 will remain cylindrical to facilitate the formation of a crimp-type electrical connection between active electrodes 416 and lead wires 450 (see FIG. 23). As shown in FIG. 26, cylindrical proximal portions 434 of electrodes 416 extend beyond spacer 418 by a slight distance of 0.1 mm to 0.4 mm. The semi-cylindrical configuration of distal electrode portion 432 increases the electric field intensity and associated current density around the edges of ends 440, 442, as discussed above. Alternatively, active electrodes 416 may have any of the shapes and configurations described above or other configurations, such as square wires, triangular shaped wires, U-shaped or channel shaped wires and the like. In addition, the surface of active electrodes 416 may be roughened, e.g., by grit blasting, chemical or electrochemical etching, to further increase the electric field intensity and associated current density around distal portions 432 of electrodes 416.

As shown in FIG. 24, each lead wire 450 terminates at a connector pin 452 contained in a pin insulator block 454 within handpiece 408. Lead wires 450 are covered with an insulation layer (not shown), e.g., Tefzel™, and sealed from the inner portion of support member 402 with an adhesive seal 457 (FIG. 22). In the preferred embodiment, each electrode 416 is coupled to a separate source of voltage within power supply 28. To that end, connector pins 452 are removably coupled to mating receptacles 456 within connector 410 to provide electrical communication with active electrodes 416 and power supply 28 (FIG. 1). Electrically insulated lead wires 458 connect receptacles 456 to the corresponding sources of voltage within power supply 28. The electrically conductive wall 414 of support member 402 serves as the return electrode, and is suitably coupled to one of the lead wires 450.

In an alternative embodiment, adjacent electrodes 416 may be connected to the opposite polarity of source 28 so that current flows between adjacent active electrodes 416 rather than between active electrodes 416 and return electrode 414. By way of example, FIG. 21B illustrates a distal portion of a planar ablation probe 400' in which electrodes 416*a* and 416*c* are at one voltage polarity (i.e., positive) and electrodes 416*b* and 416*d* are at the opposite voltage polarity (negative). When a high frequency voltage is applied between electrodes 416*a*, 416*c* and electrodes 416*b*, 416*d* in the presence of electrically conductive liquid, current flows between electrodes 416*a*, 416*c* and 416*b*, 416*d* as illustrated by current flux lines 522'. Similar to the above embodiments, the opposite surface 420 of working end 404' of probe 400' is generally atraumatic and electrically insulated from active electrodes 416*a*, 416*b*, 416*c* and 416*d* to minimize unwanted injury to tissue in contact therewith.

In an exemplary configuration, each source of voltage includes a current limiting element or circuitry (not shown) to provide independent current limiting based on the impedance between each individual electrode 416 and return electrode 414. The current limiting elements may be contained within the power supply 28, the lead wires 450, cable 34, handle 406, or within portions of the support member 402 distal to handle 406. By way of example, the current limiting elements may include resistors, capacitors, inductors, or a combination thereof. Alternatively, the current limiting function may be performed by (1) a current sensing circuit which causes the interruption of current flow if the current flow to the electrode exceeds a predetermined value and/or (2) an impedance sensing circuit which causes the interruption of current flow (or reduces the applied voltage to zero) if the measured impedance is below a predetermined value. In another embodiment, two or more of the electrodes 416 may be connected to a single lead wire 450 such that all of the electrodes 416 are always at the same applied voltage relative to return electrode 414. Accordingly, any current limiting elements or circuits will modulate the current supplied or the voltage applied to the array of electrodes 416, rather than limiting their current individually, as discussed in the previous embodiment.

Referring to FIGS. 25–28, methods for ablating tissue structures with planar ablation probe 400 according to the present invention will now be described. In particular, exemplary methods for treating a diseased meniscus within the knee (FIGS. 29–31) and for removing soft tissue between adjacent vertebrae in the spine (FIG. 32) will be described. In both procedures, at least the working end 404 of planar ablation probe 400 is introduced to a treatment site either by minimally invasive techniques or open surgery. Electrically conductive liquid is delivered to the treatment site, and voltage is applied from power supply 28 between active electrodes 416 and return electrode 414. The voltage is preferably sufficient to generate electric field intensities near active electrodes that form a vapor layer in the electrically conductive liquid, and induce the discharge of energy from the vapor layer to ablate tissue at the treatment site, as described in detail above.

Figure 25:
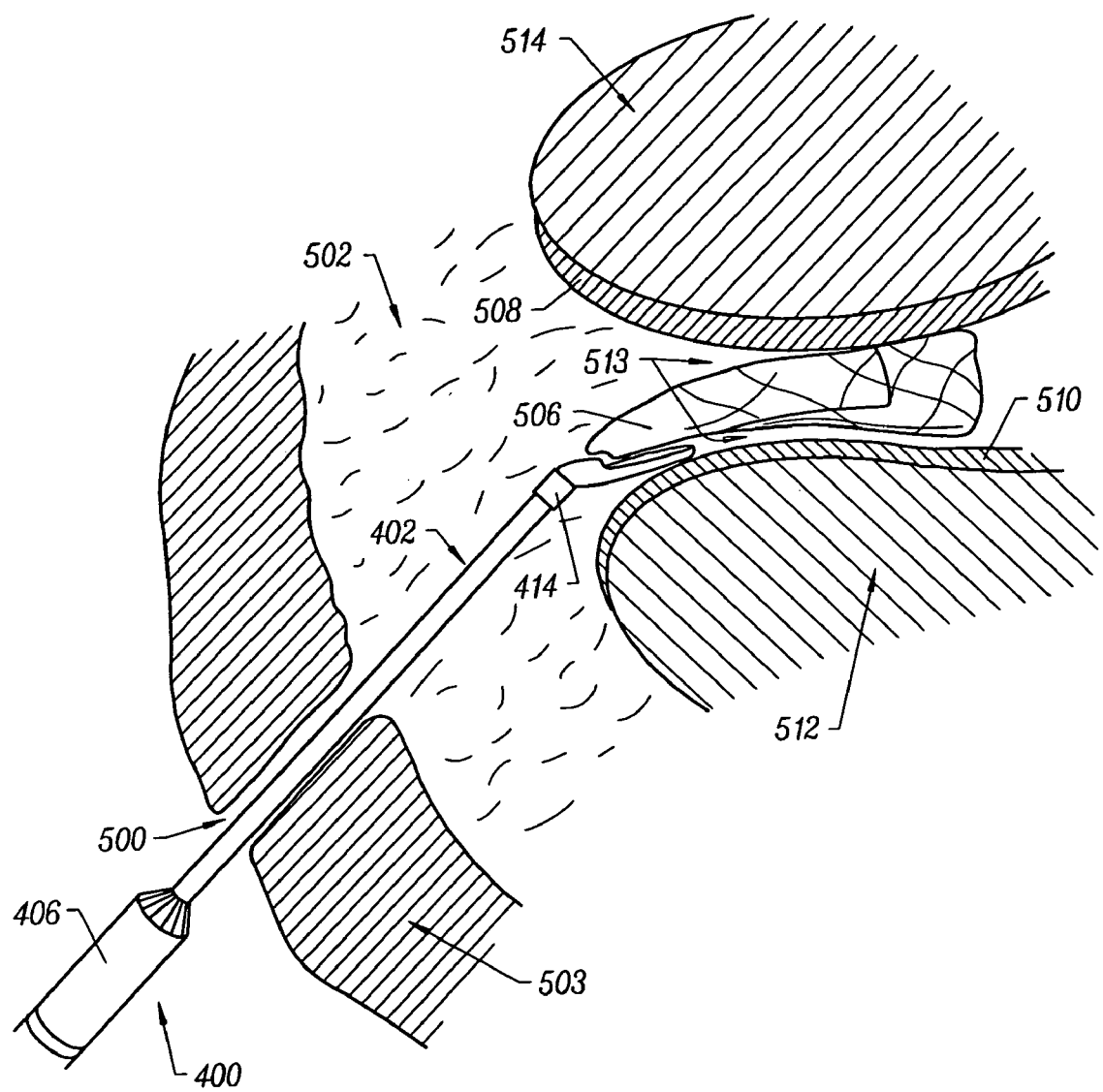
FIG. 25 is a schematic view illustrating the ablation of meniscus tissue located close to articular cartilage between the tibia and femur of a patient with the ablation probe of FIG. 19.

Referring to FIG. 25, working end 404 and at least the distal portion of support member 402 are introduced through a percutaneous penetration 500, such as a cannula, into the arthroscopic cavity 502. The insertion of probe 400 is usually guided by an arthroscope (not shown) which includes a light source and a video camera to allow the surgeon to selectively visualize a zone within the knee joint. To maintain a clear field of view and to facilitate the generation of a vapor layer, a transparent, electrically conductive irrigant 503, such as isotonic saline, is injected into the treatment site either through a liquid passage in support member 402 of probe 400, or through another instrument. Suitable methods for delivering irrigant to a treatment site are described in commonly assigned U.S. Pat. No. 5,697,281 filed on Jun. 7, 1995, the contents of which are incorporated herein by reference.

In the example shown in FIG. 25, the target tissue is a portion of the meniscus 506 adjacent to and in close proximity with the articular cartilage 510, 508 which normally covers the end surfaces of the tibia 512 and the femur 514, respectively. The articular cartilage 508, 510 is important to the normal functioning of joints, and once damaged, the body is generally not capable of regenerating this critical lining of the joints. Consequently, it is desirable that the surgeon exercise extreme care when treating the nearby meniscus 506 to avoid unwanted damage to the articular cartilage 508, 510. The confined spaces 513 between articular cartilage 508, 510 and meniscus 506 within the knee joint are relatively narrow, typically on the order of about 1.0 mm to 5.0 mm. Accordingly, the narrow, low profile working end 404 of ablation probe 400 is ideally suited for introduction into these confined spaces 513 to the treatment site. As mentioned previously, the substantially planar arrangement of electrodes 416 and support tongue 420 (typically having a combined height of about 0.5 to 1.5 mm) allows the surgeon to deliver working end 404 of probe 400 into the confined spaces 513, while minimizing contact with the articular cartilage 508, 510 (see FIG. 26).

As shown in FIG. 26, active electrodes 416 are disposed on one face of working end 404 of probe 400. Accordingly, a zone 520 of high electric field intensity is generated on each electrode 416 on one face of working end 404 while the opposite side 521 of working end 404 is atraumatic with respect to tissue. In addition, the opposite side 521 is insulated from electrodes 416 to minimize electric current from passing through this side 521 to the tissue (i.e., adjacent articular cartilage 508). As shown in FIGS. 26, the bipolar arrangement of active electrodes 416 and return electrode 414 causes electric current to flow along flux lines 522 predominantly through the electrically conducting irrigant 503, which envelops the tissue and working end 404 of ablation probe 400 and provides an electrically conducting path between electrodes 416 and return electrode 414. As electrodes 416 are engaged with, or positioned in close proximity to, the target meniscus 506, the high electric field present at the electrode edges cause controlled ablation of the tissue by forming a vapor layer and inducing the discharge of energy therefrom. In addition, the motion of electrodes 416 relative to the meniscus 506 (as shown by vector 523) causes tissue to be removed in a controlled manner. The presence of the irrigant also serves to minimize the increase in the temperature of the meniscus during the ablation process because the irrigant generally comes in contact with the treated tissue shortly after one of the electrodes 416 has been translated across the surface of the tissue.

Figure 28:
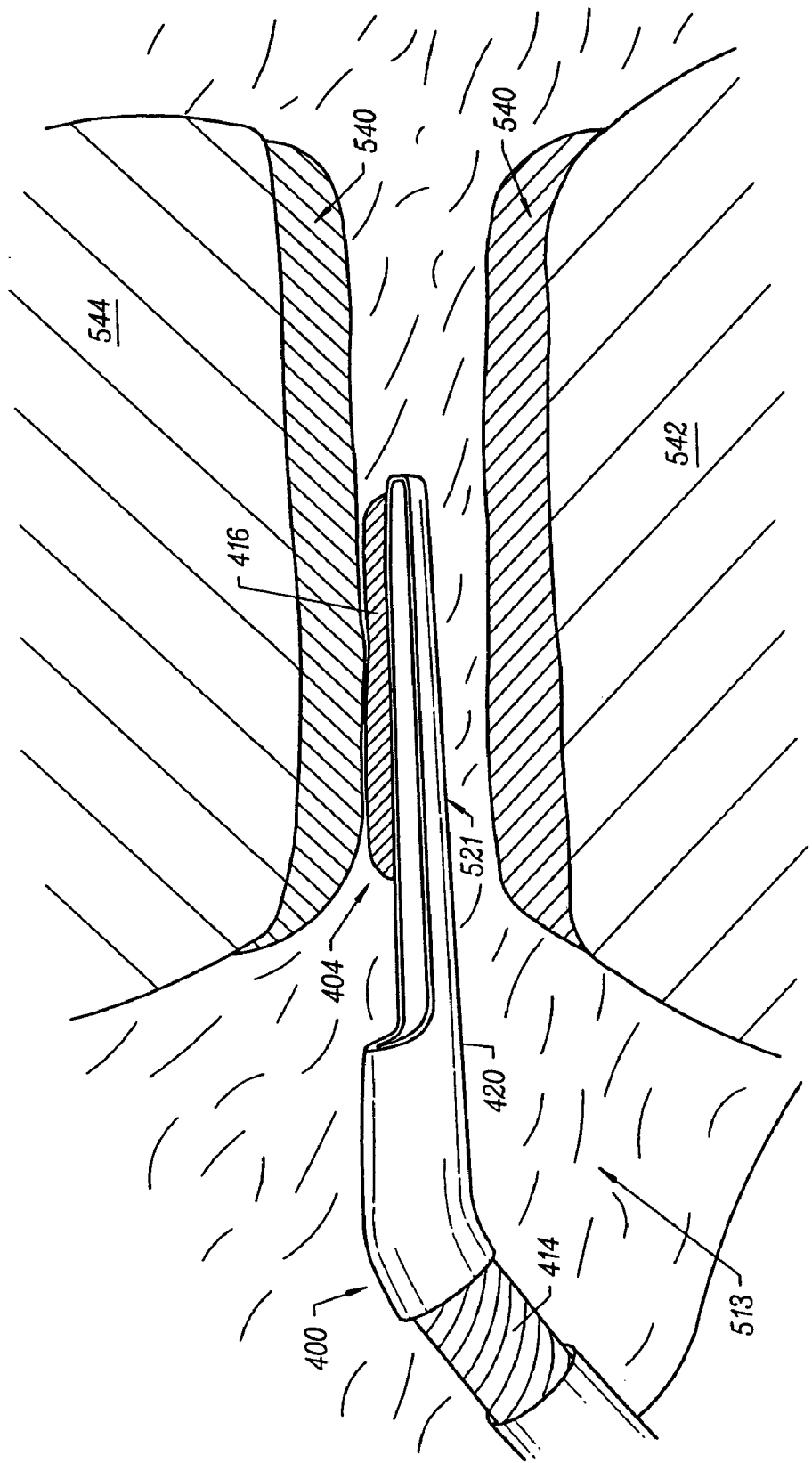
FIG. 28 is a schematic view illustrating the ablation of soft tissue from adjacent surfaces of the vertebrae with the planar ablation probe of the present invention.

Referring now to FIG. 28, an exemplary method for removing soft tissue 540 from the surfaces of adjacent vertebrae 542, 544 in the spine will now be described. Removal of this soft tissue 540 is often necessary, for example, in surgical procedures for fusing or joining adjacent vertebrae together. Following the removal of tissue 540, the adjacent vertebrae 542, 544 are stabilized to allow for subsequent fusion together to form a single monolithic vertebra. As shown, the low-profile of working end 404 of probe 400 (i.e., thickness values as low as 0.2 mm) allows access to and surface preparation of closely spaced vertebrae. In addition, the shaped electrodes 416 promote substantially high electric field intensities and associated current densities between active electrodes 416 and return electrode 414 to allow for the efficient removal of tissue attached to the surface of bone without significantly damaging the underlying bone. The "non-active" insulating side 521 of working end 404 also minimizes the generation of electric fields on this side 521 to reduce ablation of the adjacent vertebra 542.

The target tissue is generally not completely immersed in electrically conductive liquid during surgical procedures within the spine, such as the removal of soft tissue described above. Accordingly, electrically conductive liquid will preferably be delivered into the confined spaces 513 between adjacent vertebrae 542, 544 during this procedure. The fluid may be delivered through a liquid passage (not shown) within support member 402 of probe 400, or through another suitable liquid supply instrument.

Figure 27:
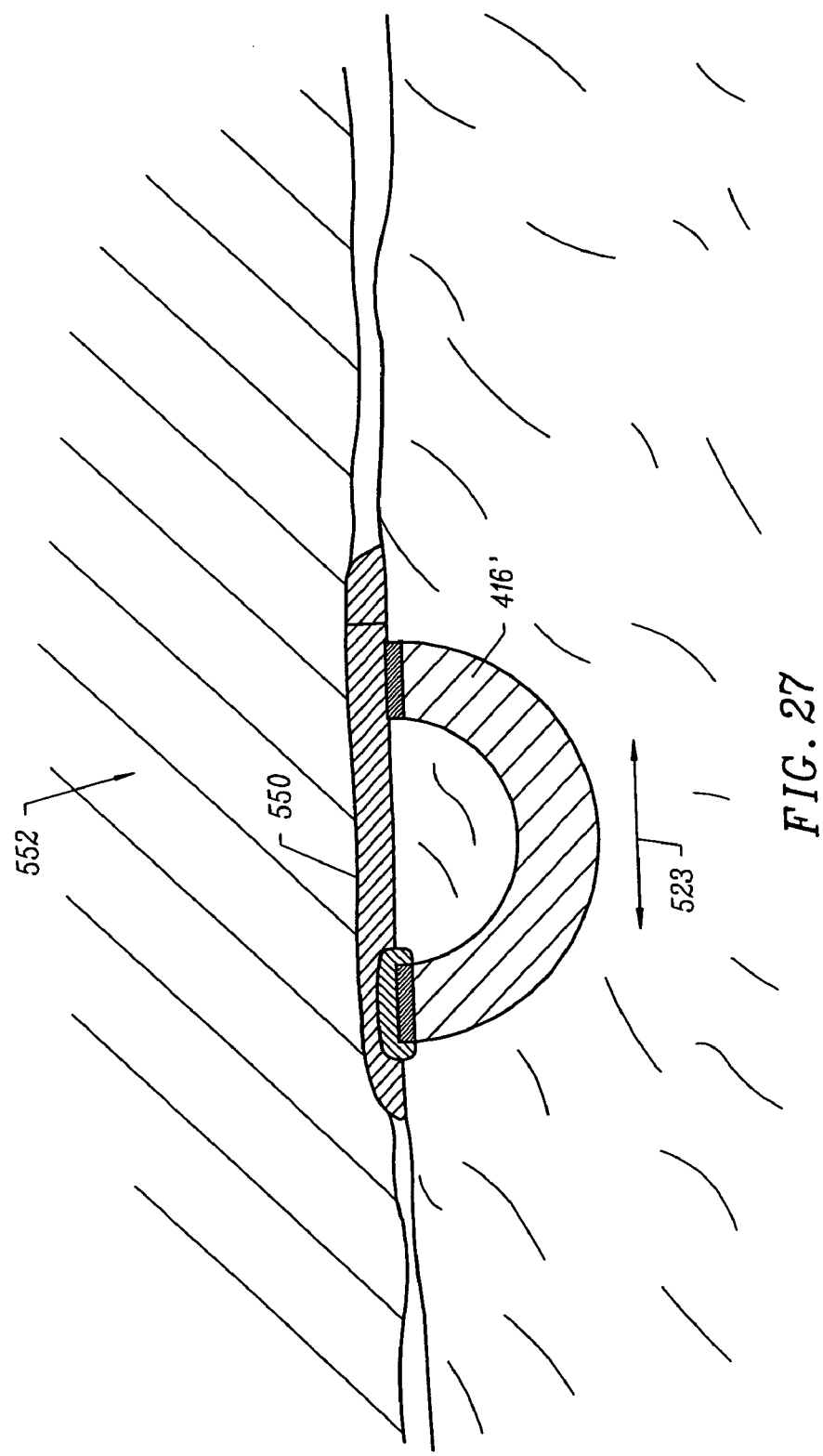
FIG. 27 illustrates a method of ablating tissue with a planar ablation probe incorporating a single active electrode.
Figure 31:
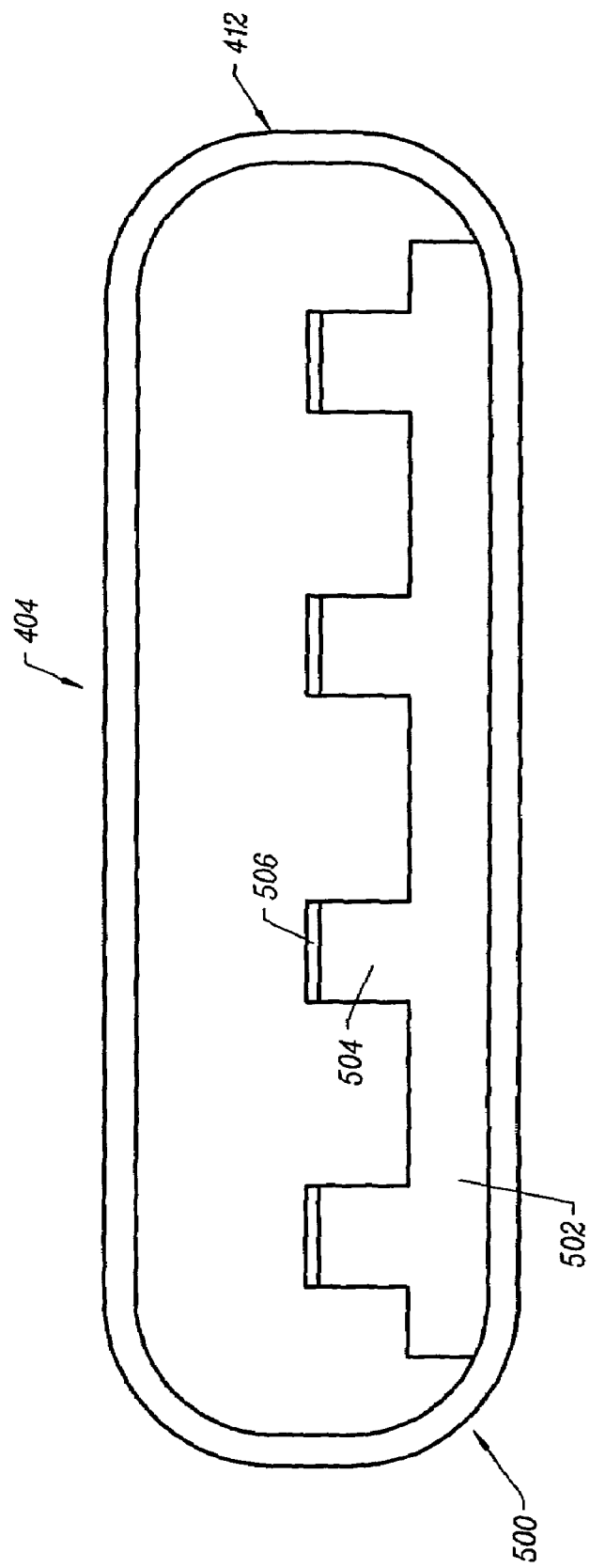
FIG. 31 is an end view of the probe of FIG. 30.

Other modifications and variations can be made to disclose embodiments without departing from the subject invention as defined in the following claims. For example, it should be clearly understood that the planar ablation probe 400 described above may incorporate a single active electrode, rather than a plurality of such active electrodes as described above in the exemplary embodiment. FIG. 27 illustrates a portion of a planar ablation probe according to the present invention that incorporates a single active electrode 416' for generating high electric field densities 550 to ablate a target tissue 552. Electrode 416' may extend directly from a proximal support member, as depicted in FIG. 31, or it may be supported on an underlying support tongue (not shown) as described in the previous embodiment. As shown, the representative single active electrode 416' has a semi-cylindrical cross-section, similar to the electrodes 416 described above. However, the single electrode 416' may also incorporate any of the above described configurations (e.g., square or star shaped solid wire) or other specialized configurations depending on the function of the device.

Figure 29:
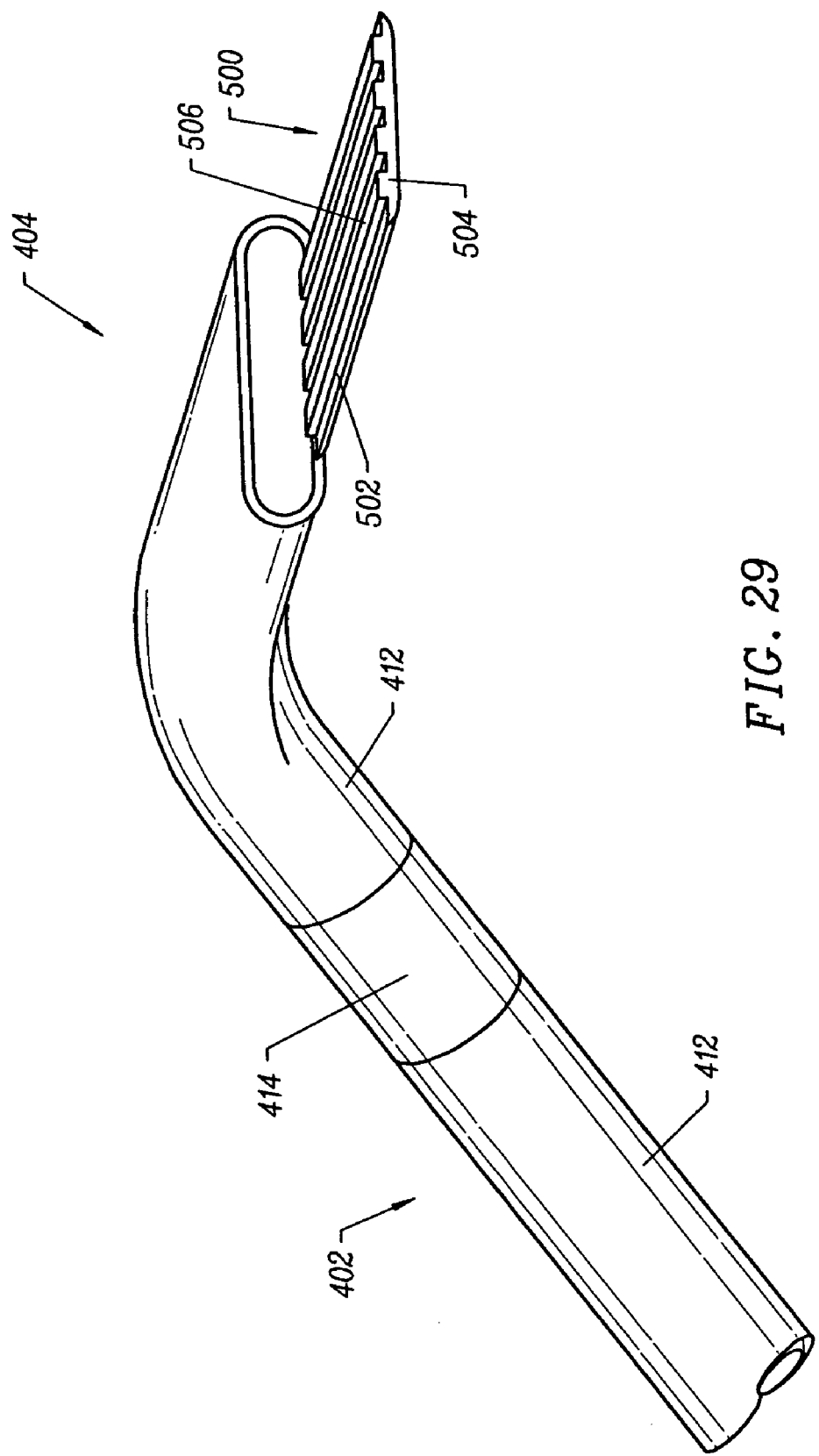
FIG. 29 is a perspective view of an alternative embodiment of the planar ablation probe incorporating a ceramic support structure with conductive strips printed thereon.
Figure 30:
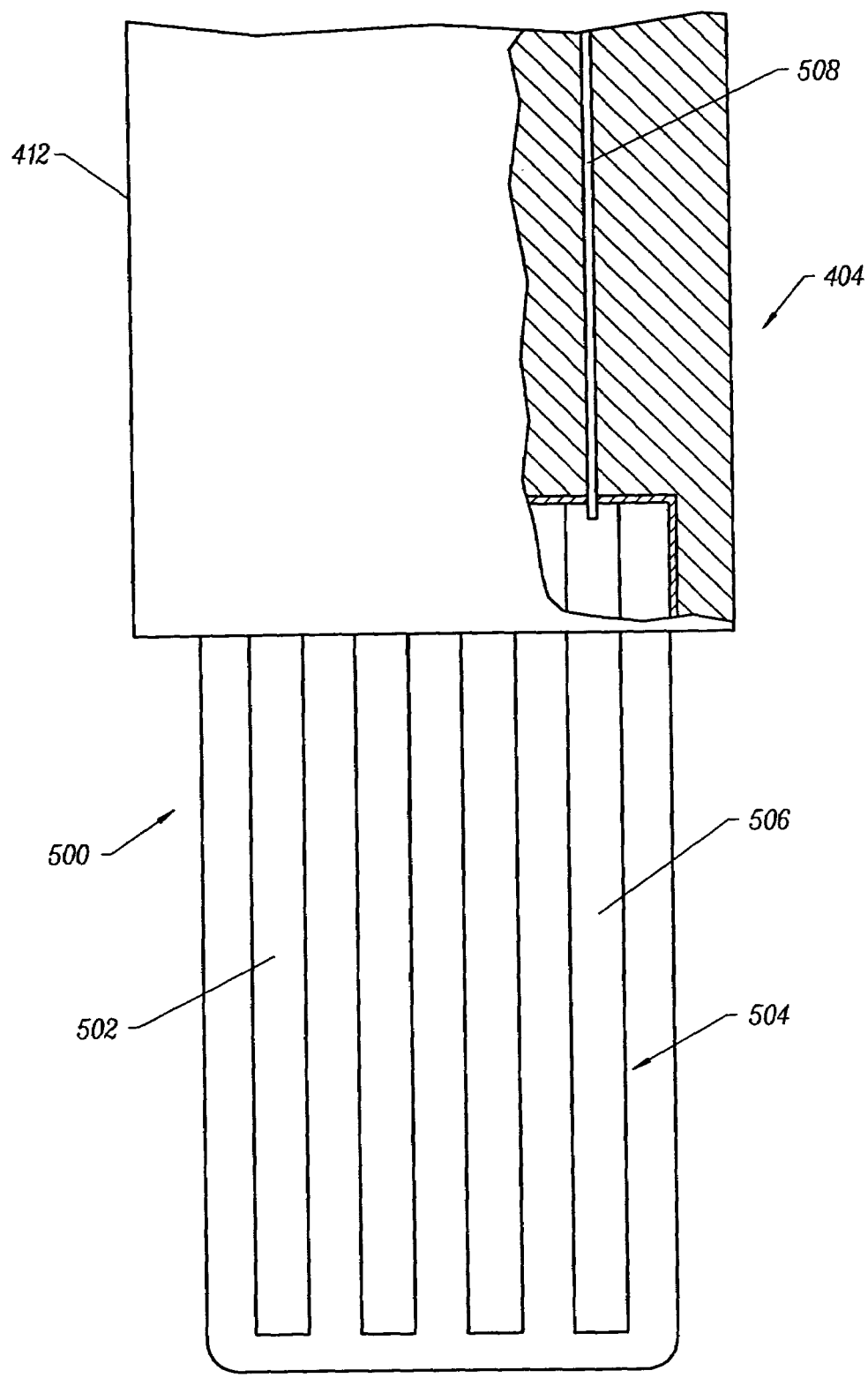
FIG. 30 is a top partial cross-sectional view of the planar ablation probe of FIG. 29.

Referring now to FIGS. 29–31 an alternative electrode support member 500 for a planar ablation probe 404 will be described in detail. As shown, electrode support member 500 preferably comprises a multilayer or single layer substrate 502 comprising a suitable high temperature, electrically insulating material, such as ceramic. The substrate 502 is a thin or thick film hybrid having conductive strips that are adhered to, e.g., plated onto, the ceramic wafer. The conductive strips typically comprise tungsten, gold, nickel or equivalent materials. In the exemplary embodiment, the conductive strips comprise tungsten, and they are co-fired together with the wafer layers to form an integral package. The conductive strips are coupled to external wire connectors by holes or vias that are drilled through the ceramic layers, and plated or otherwise covered with conductive material.

In the representative embodiment, support member 500 comprises a single ceramic wafer having a plurality of longitudinal ridges 504 formed on one side of the wafer 502. Typically, the wafer 502 is green pressed and fired to form the required topography (e.g., ridges 504). A conductive material is then adhered to the ridges 504 to form conductive strips 506 extending axially over wafer 502 and spaced from each other. As shown in FIG. 30, the conductive strips 506 are attached to lead wires 508 within shaft 412 of the probe 404 to electrically couple conductive strips 506 with the power supply 28 (FIG. 1). This embodiment provides a relatively low profile working end of probe 404 that has sufficient mechanical structure to withstand bending forces during a surgical procedure.

FIGS. 34–36 illustrate another system and method for treating swollen or herniated intervertebral discs according to the present invention. In this procedure, an electrosurgical probe 700 comprises a long, thin shaft 702 (e.g., on the order of about 1 mm or less in diameter) that can be percutaneously introduced posteriorly through the patient's back directly into the spine. The probe shaft 702 will include one or more active electrode(s) 704 for applying electrical energy to tissues within the spine. The probe 700 may include one or more return electrodes 706, or the return electrode may be positioned on the patient's back as a dispersive pad (not shown).

As shown in FIG. 34, the distal portion of shaft 702 is introduced posteriorly through a small percutaneous penetration into the annulus 292 of the target intervertebral disc 290. To facilitate this process, the distal end of shaft 702 may taper down to a sharper point (e.g., a needle), which can then be retracted to expose active electrode(s) 704. Alternatively, the active electrode(s) may be formed around the surface of the tapered distal portion of shaft 702 (not shown). In either embodiment, the distal end of shaft 702 is delivered through the annulus 292 to the target nucleus pulposus 291, which may be herniated, extruded, non-extruded, or simply swollen. As shown in FIG. 35, high frequency voltage is applied between active electrode(s) 704 and return electrode(s) 706 to heat the surrounding collagen to suitable temperatures for contraction (i.e., typically about 55° C. to about 70° C.). As discussed above, this procedure may be accomplished with a monopolar configuration, as well. However, applicant has found that the bipolar configuration shown in FIGS. 34–36 provides enhanced control of the high frequency current, which reduces the risk of spinal nerve damage.

As shown in FIGS. 35 and 36, once the nucleus pulposus 291 has been sufficiently contracted to retract from impingement on a nerve or nerve root, probe 700 is removed from the target site. In the representative embodiment, the high frequency voltage is applied between active and return electrode(s) 704, 706 as the probe is withdrawn through the annulus 292. This voltage is sufficient to cause contraction of the collagen fibers within the annulus 292, which allows the annulus 292 to contract around the hole formed by probe 700, thereby improving the healing of this hole. Thus, the probe 700 seals its own passage as it is withdrawn from the disc.

Figure 37A:
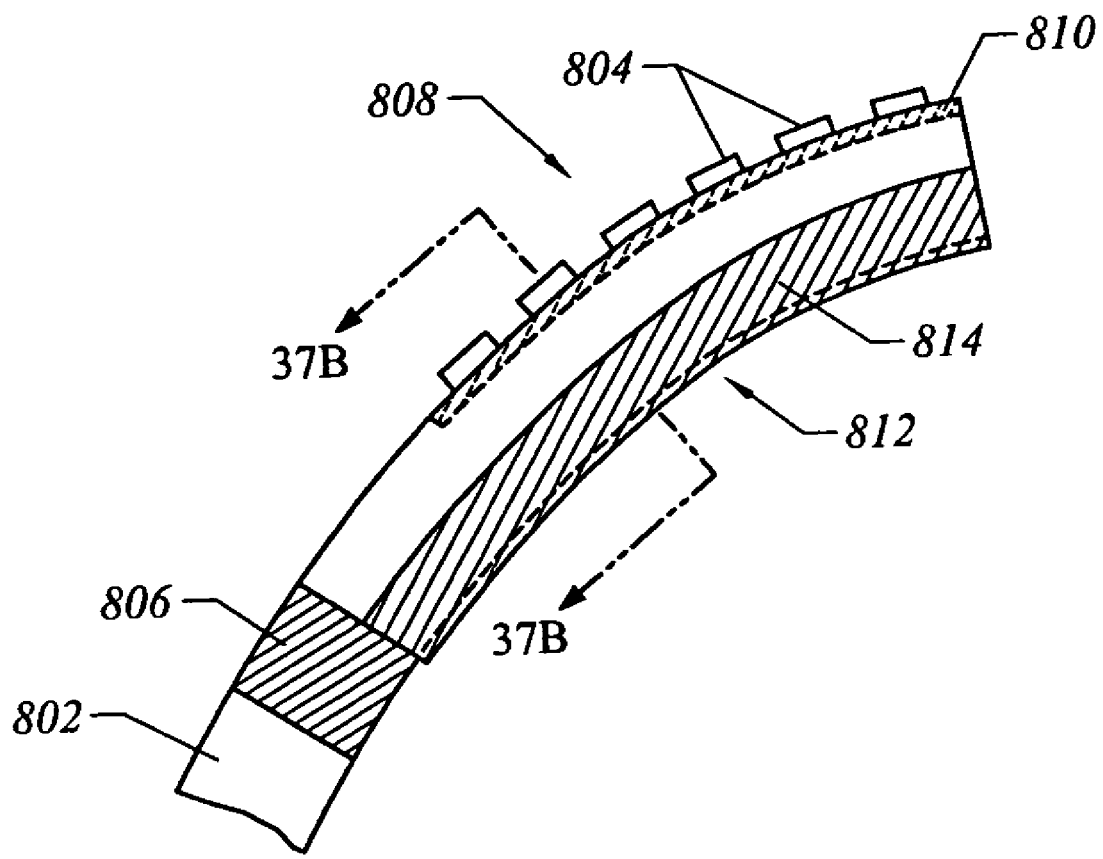
FIG. 37A illustrates a system having a curved distal tip and an insulator for protecting adjacent tissue.

FIGS. 37A to 39 illustrate systems and methods for treating and ablating intervertebral discs according to the present invention. Electrosurgical probe 800 generally comprises a shaft 802 that can be percutaneously introduced posteriorly (through the patient's back) into the spine. The shaft 802 will include one or more active electrode(s) 804 for applying electrical energy to the intervertebral disc. The system may include one or more return electrodes 806. The return electrode(s) 806 can be positioned proximal of the active electrode(s) 804 on the electrosurgical probe or on a separate instrument (not shown). The ablation probe 800 shown in FIG. 37A is configured to operate in the bipolar modality. In alternative embodiments, however, the return electrode 806 may be positioned on the patient's back as a dispersive pad (not shown) so as to operate in a monopolar modality.

Figure 37B:
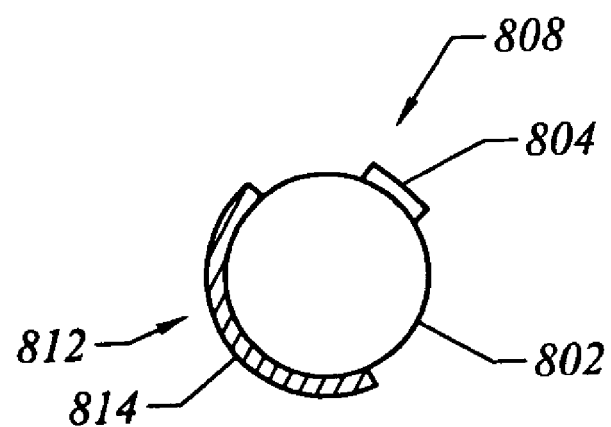
FIG. 37B is an end view of one embodiment of the system of FIG. 37A.

In the exemplary embodiment shown in FIGS. 37A and 37B, the distal end of the shaft 802 is curved or bent to improve access to the disk being treated. The treatment surface 808 of the electrosurgical probe is usually curved or bent to an angle of about 10 degrees to 90 degrees relative to the longitudinal axis of shaft 802, preferably about 15 degrees to 60 degrees and more preferably about 15 degrees. In alternative embodiments, the distal portion of shaft 802 comprises a flexible material which can be deflected relative to the longitudinal axis of the shaft. Such deflection may be selectively induced by mechanical tension of a pull wire, for example, or by a shape memory wire that expands or contracts by externally applied temperature changes. A more complete description of this embodiment can be found in U.S. Pat. No. 5,697,909, the complete disclosure of which is incorporated herein by reference. Alternatively, the shaft 802 of the present invention may be bent by the physician to the appropriate angle using a conventional bending tool or the like.

The active electrode(s) 804 typically extend from an active tissue treatment surface of an electrode support member 810 of the probe shaft 802. Opposite of the active electrodes 802 is a non-active insulating side 812, which has an insulator 814 that is configured to protect the dura mater 816 and other non-target tissue, e.g., spinal cord 818. The insulator 814 minimizes the generation of electric fields on the non-active side and reduces the electrical damage to the dura mater 816 and spinal cord 818 during disc ablation. While the insulator 814 is shown opposite the active electrode array 804, it will be appreciated that the insulator 814 can be positioned completely around the probe, be positioned around only portions of the probe, be along the sides of the active electrode array, and the like.

The tissue treatment surface 808 and individual active electrodes 804 will usually have dimensions within the ranges set forth above. In some embodiments, the active electrodes 804 can be disposed within or on an insulating support member 810, as described above. In the representative embodiment, the surface of the active electrodes 804 has a circular cross-sectional shape with a diameter in the range of about 1 mm to 30 mm, usually about 2 mm to 20 mm. The individual active electrodes 802 preferably extend outward from tissue treatment surface 808 by a distance of about 0.1 mm to 8 mm, usually about 0.2 mm to 4 mm. Applicant has found that this configuration increases the electric field intensities and associated current densities around active electrodes 804 to facilitate the ablation of tissue as described in detail above. Of course, it will be recognized that the active electrodes may have a variety of different configurations. For example, instead of an array of active electrodes, a single active electrode may be used.

An exemplary method for ablating and removing at least a portion of the target intervertebral disc 290 will now be described. Removal of a degenerative or damaged disc is necessary, for example, in surgical procedures during placement of a cage, or the fusing or joining of adjacent vertebrae together. Following the removal of the disc 290, the adjacent vertebrae 824 are stabilized to allow for subsequent fusion together to form a single monolithic vertebra. During such procedures it would be preferable to protect the dura mater 816 and spinal cord 818 from damage from the electrosurgical probe 800.

Figure 38:
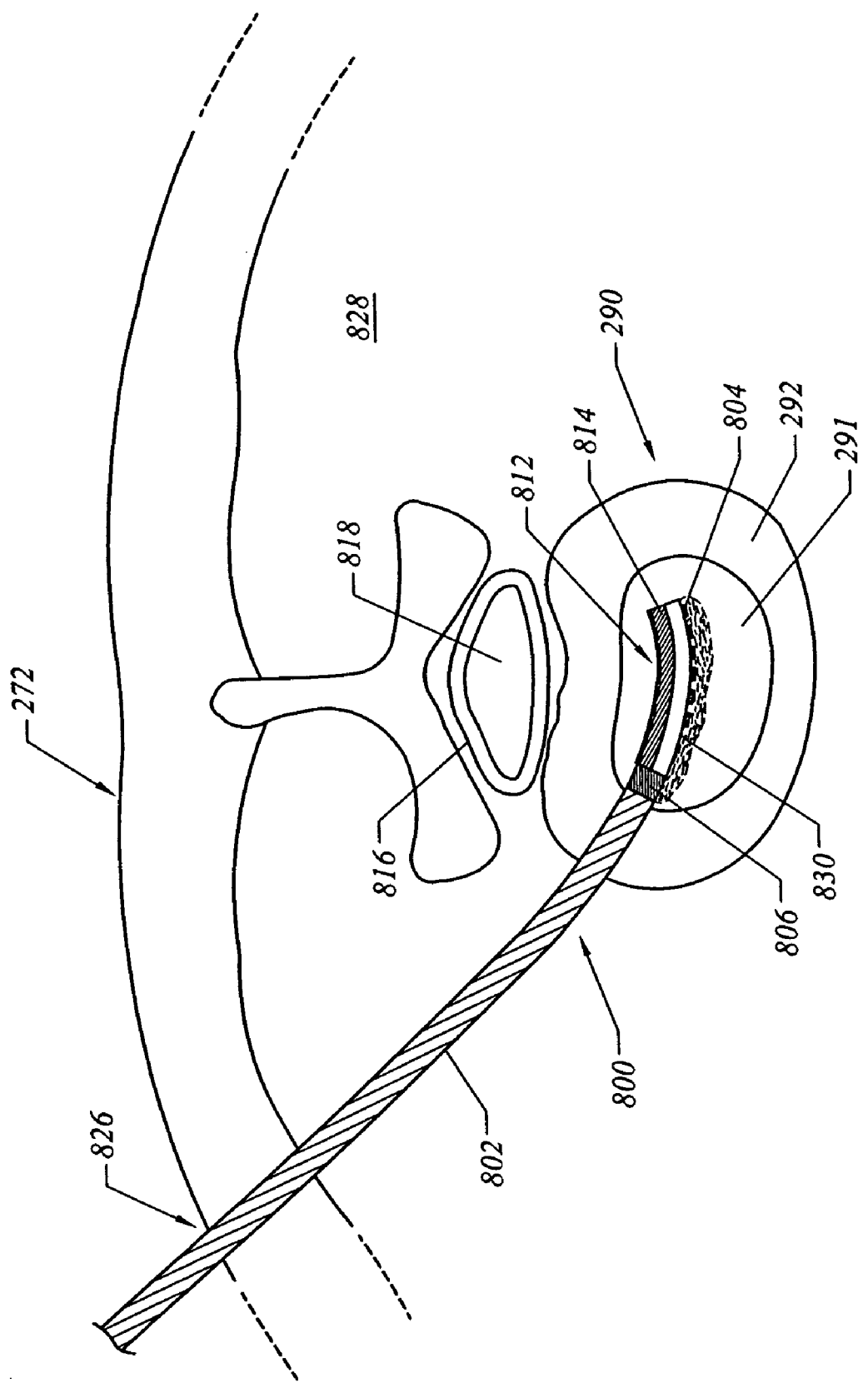
FIG. 38 illustrates the probe of FIG. 37A being percutaneously introduced into a target intervertebral disc.
Figure 39:
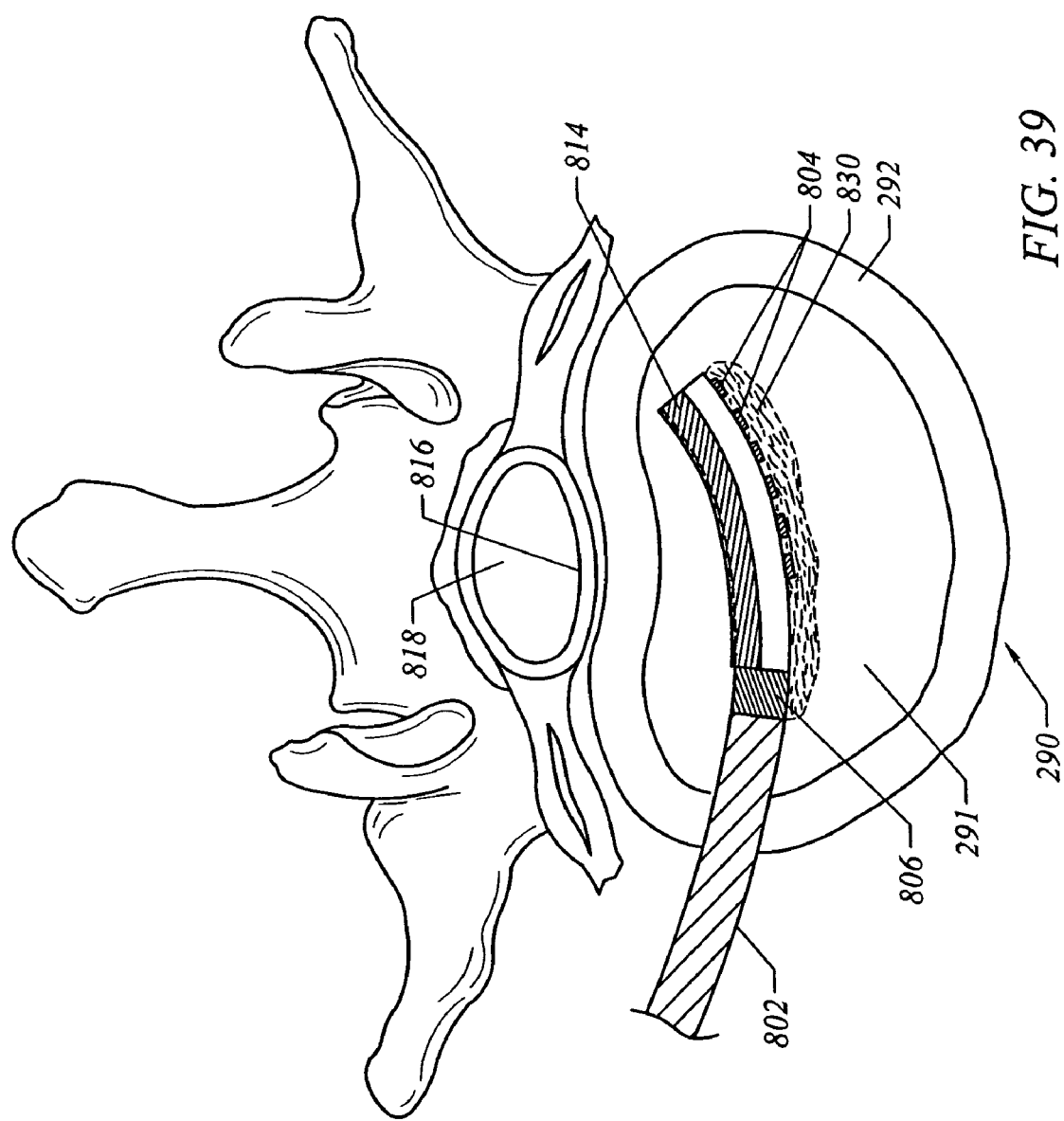
FIG. 39 shows the shaft distal end of the system of FIG. 37A with the shaft distal end located within an intervertebral disc.

In use, the distal end of probe 800 is introduced into a treatment site either by minimally invasive techniques or open surgery. The distal portion of electrosurgical probe 800 can be introduced through a percutaneous penetration 826 e.g., via a camiula, into the body cavity 828. The insertion of probe 800 is usually guided by an endoscope (not shown) which can include a light source and a video camera to allow the surgeon to selectively visualize a zone within the vertebral column. The distal portion of shaft 802 can be introduced posteriorly through a small percutaneous penetration into the annulus fibrosus 292 of the target intervertebral disc 290 (FIGS. 38 and 39).

To maintain a clear field of view and to facilitate the generation of a vapor layer, a transparent, electrically conductive irrigant (not shown), such as isotonic saline, can be injected into the treatment site either through a liquid passage in probe 800, or through another instrument. Suitable methods for delivering irrigant to a treatment site are described in commonly assigned, U.S. Pat. No. 5,697,281 filed on Jun. 7, 1995, the contents of which are incorporated herein by reference.

After (or during) introduction of the electrosurgical probe 800 into the intervertebral disc 290, an electrically conductive liquid 830 can be delivered to the treatment site, and voltage can be applied from power supply 28 between active electrodes 804 and return electrode 806 through the conductive fluid. The voltage is preferably sufficient to generate electric field intensities near active electrodes 804 that form a vapor layer in the electrically conductive liquid so as to induce a discharge of energy from the vapor layer to ablate tissue at the treatment site, as described in detail above. As shaft 802 is moved through the spinal disc 290, the insulator 814 can be positioned to engage the dura mater 816 and protect the dura mater 816 (and spinal cord 818) from damaging electrical current flow.

Figure 40:
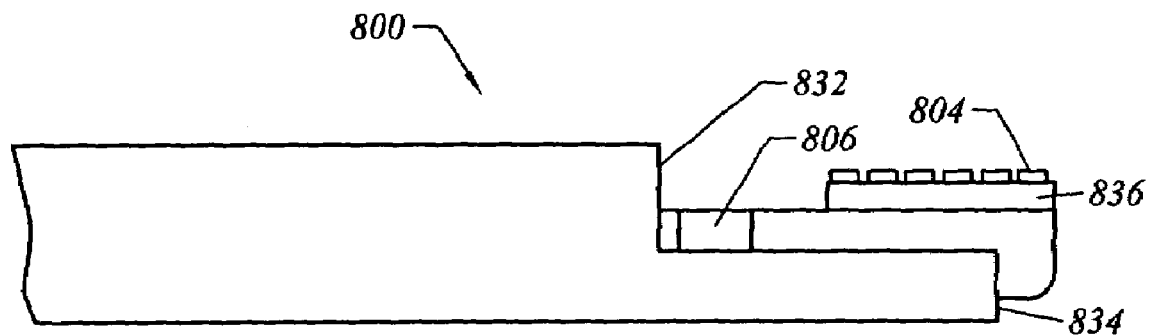
FIG. 40 is an electrosurgical probe having a fluid delivery lumen and an aspiration lumen.
Figure 41:
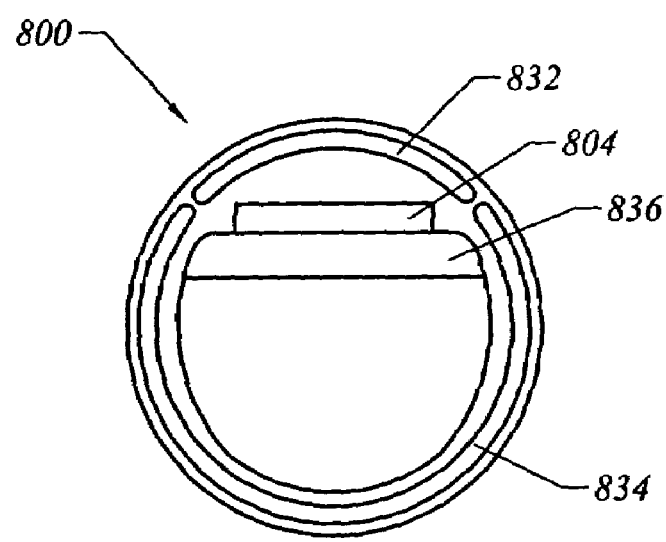
FIG. 41 is an end view of the electrosurgical probe of FIG. 40.

FIGS. 40 to 41 show yet another embodiment of the present invention. The electrosurgical probe 800 includes an aspiration lumen 832 for aspirating the target area and a fluid delivery lumen 834 for directing an electrically conductive fluid 830 to the target area. In some implementations, the aspiration lumen 832 and the fluid delivery lumen 834 are coupled together in an annular pattern along the exterior of the electrosurgical probe. A distal end of the aspiration lumen 832 typically ends proximal of the return electrode 806 while the distal end of the fluid delivery lumen 834 extends to a point adjacent the distal end of the electrosurgical probe 800. As shown in FIG. 41, the fluid delivery lumen 834 preferably occupies a larger portion of the annular region. In one specific embodiment, the fluid delivery lumen 834 occupies approximately two-thirds of the annular region.

The electrosurgical probe may have a single active electrode 804 or an electrode array distributed over a contact surface of a probe. In the latter embodiment, the electrode array usually includes a plurality of independently current-limited and/or power-controlled active electrodes to apply electrical energy selectively to the target tissue while limiting the unwanted application of electrical energy to the surrounding tissue and environment. In one specific configuration the electrosurgical probe comprises 23 active electrodes. Of course, it will be appreciated that the number, size, and configuration of the active electrodes may vary depending on the specific use of the electrosurgical probe (e.g. tissue contraction, tissue ablation, or the like).

The shaft 802 will usually house a plurality of wires or other conductive elements axially therethrough to permit connection of active electrodes or electrode array 804 to a connector at the proximal end of the shaft (not shown). Each active electrode of an active electrode array may be connected to a separate power source that is isolated from the other active electrodes. Alternatively, active electrodes 804 may be connected to each other at either the proximal or distal ends of the probe to form a single wire that couples to a power source.

The active electrode(s) 804 are typically supported by an electrically insulating electrode support member 836 that extends from the electrosurgical probe 800. Electrode support member 836 typically extends from the distal end of shaft 802 about 1 mm to 20 mm. Electrode support member 836 typically comprises an insulating material (e.g., a silicone, ceramic, or glass material, such as alumina, zirconia and the like) which could be formed at the time of manufacture in a flat, hemispherical or other shape according to the requirements of a particular procedure.

Figure 42:
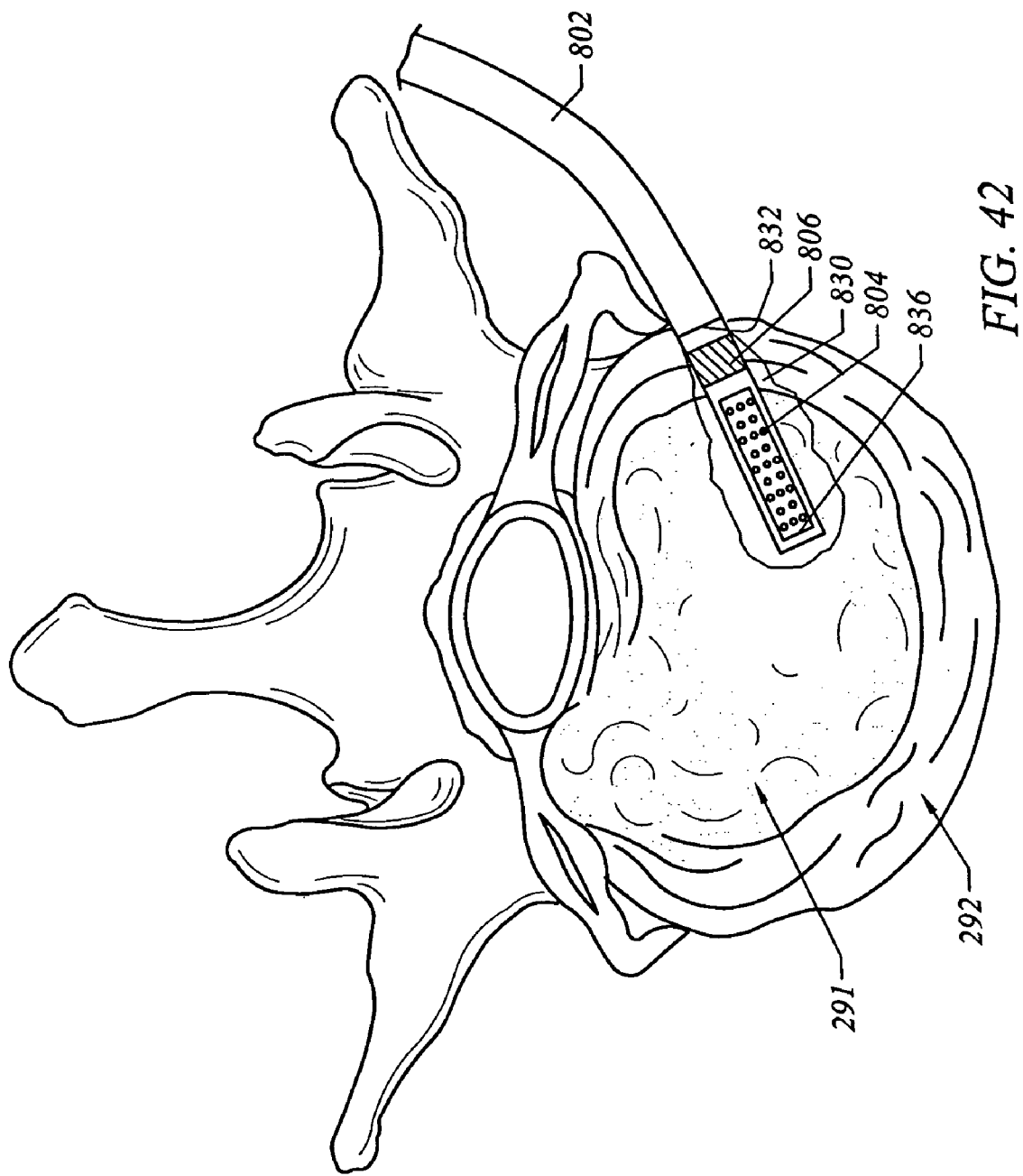
FIG. 42 illustrates a system having an aspiration lumen and a fluid delivery lumen.

In use, the electrosurgical probe 800 can be positioned adjacent the target tissue, as described above. When treating an intervertebral disc, the distal end of shaft 802 is typically delivered through the annulus to the nucleus pulposus 291, which may be herniated, extruded, non-extruded, or simply swollen. As shown in FIG. 42, high frequency voltage is applied between active electrode(s) 804 and return electrode(s) 806 to heat the surrounding collagen to suitable temperatures for contraction (i.e., typically about 55° C. to about 70° C.) or ablation (i.e. typically less than 150° C.). As discussed above, this procedure may also be performed with a monopolar configuration. However, applicant has found that the bipolar configuration provides enhanced control of the high frequency current, which reduces the risk of spinal nerve damage.

In the exemplary embodiments, an electrically conductive fluid 830 is delivered through fluid delivery lumen 834 to the target site. In these embodiments, the high frequency voltage applied to the active electrode(s) is sufficient to vaporize the electrically conductive fluid (e.g., gel or saline) between the active electrode(s) and the tissue. Within the vaporized fluid, an ionized plasma is formed and charged particles (e.g., electrons) are accelerated towards the tissue to cause the molecular breakdown or disintegration of several cell layers of the tissue. This molecular dissociation is accompanied by the volumetric removal of the tissue. Because the aspiration lumen 832 is placed proximal of the return electrode (and typically outside of the intervertebral disc 290), the aspiration lumen 832 typically removes the air bubbles from the spinal disc and leaves the disc tissue relatively intact. Moreover, because the aspiration lumen 834 is spaced from the target area, the conductive fluid 830 is allowed to stay in the target area longer and the plasma can be created more aggressively.

Figure 43A:
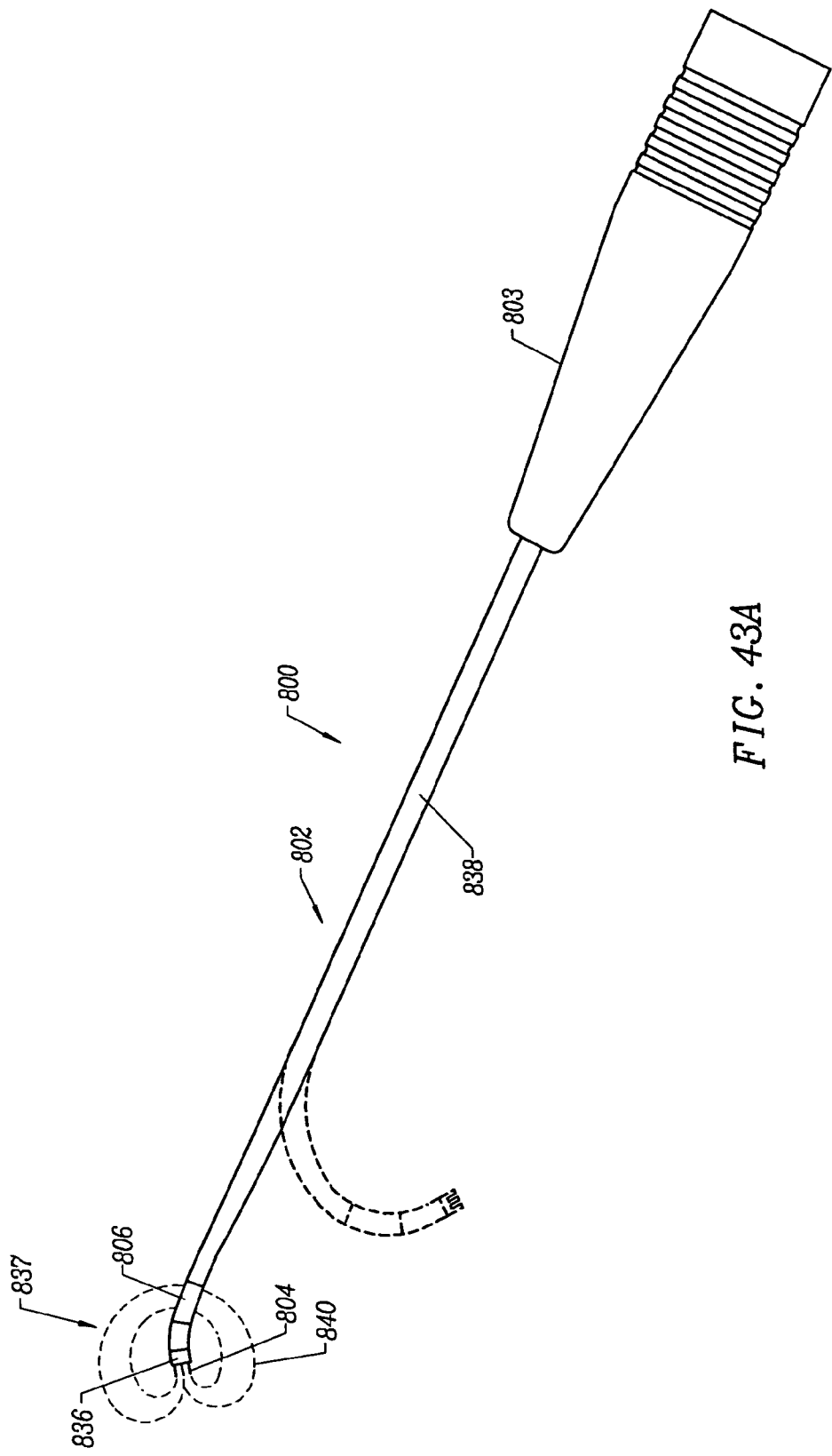
FIGS. 43A–43D illustrate four embodiments of electrosurgical probes specifically designed for treating spinal defects.

FIGS. 43A to 43D show embodiments of the electrosurgical probe of the present invention which have a curved or steerable distal tip for improving navigation of the electrosurgical probe 800 within the disc. Referring now to FIG. 43A, probe 800 comprises an electrically conductive shaft 802, a handle 803 coupled to the proximal end of shaft 802 and an electrically insulating support member 836 at the distal end of shaft 802. Probe 800 further includes an insulating sleeve 838 over shaft 802, and an exposed portion of shaft 802 that functions as the return electrode 806. In the representative embodiment, probe 800 comprises a plurality of active electrodes 804 extending from the distal end of support member 836. As shown, return electrode 806 is spaced a further distance from active electrodes 804 than in the embodiments described above. In this embodiment, the return electrode 806 is spaced a distance of about 2.0 mm to 50 mm, preferably about 5 mm to 25 mm. In addition, return electrode 806 has a larger exposed surface area than in previous embodiments, having a length in the range of about 2.0 mm to 40 mm, preferably about 5 mm to 20 mm. Accordingly, electric current passing from active electrodes 804 to return electrode 806 will follow a current flow path 840 that is further away from shaft 802 than in the previous embodiments. In some applications, this current flow path 840 results in a deeper current penetration into the surrounding tissue with the same voltage level, and thus increased thermal heating of the tissue. As discussed above, this increased thermal heating may have advantages in some applications of treating disc or other spinal defects. Typically, it is desired to achieve a tissue temperature in the range of about 60° C. to 100° C. to a depth of about 0.2 mm to 5 mm, usually about 1 mm to 2 mm. The voltage required for this thermal treatment will depend in part on the electrode configuration, the conductivity of the tissue and of the milieu immediately surrounding the electrodes, and the time period during which the voltage is applied. With the electrode configuration described in FIGS. 43A–43D, the voltage level for thermal heating will usually be in the range of about 20 volts rms to 300 volts rms, preferably about 60 volts rms to 200 volts rms. The peak-to-peak voltages for thermal heating with a square wave form having a crest factor of about 2 are typically in the range of about 40 to 600 volts peak-to-peak, preferably about 120 to 400 volts peak-to-peak. The higher the voltage is within this range, the less time required for a given effect. If the voltage is too high, however, the surface tissue may be vaporized, debulked or ablated, which is often undesirable.

Figure 46A:
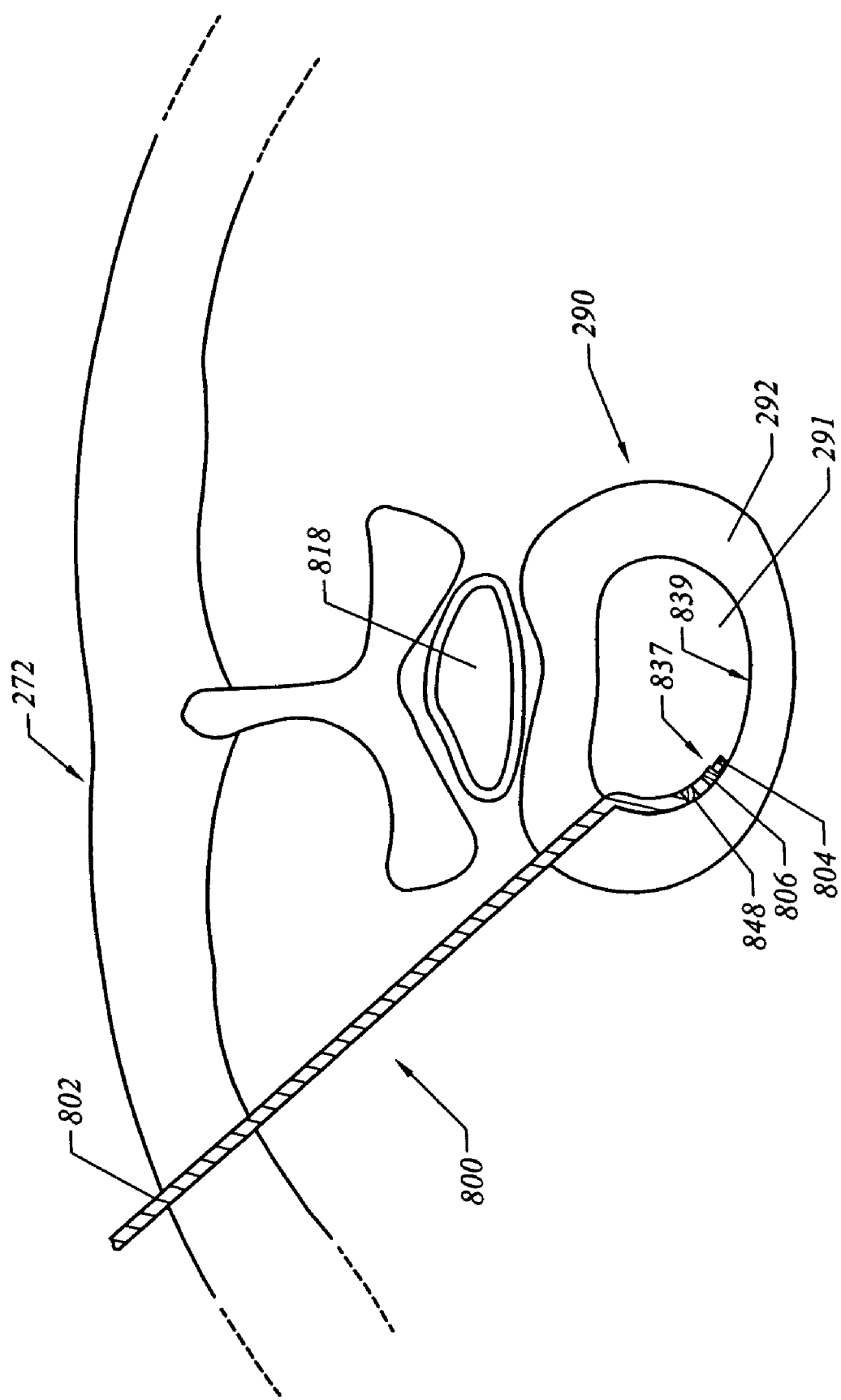
FIGS. 46A and 46B illustrate the distal tip of the electrosurgical probe moving along an inner surface of the annulus fibrosus.
Figure 46B:
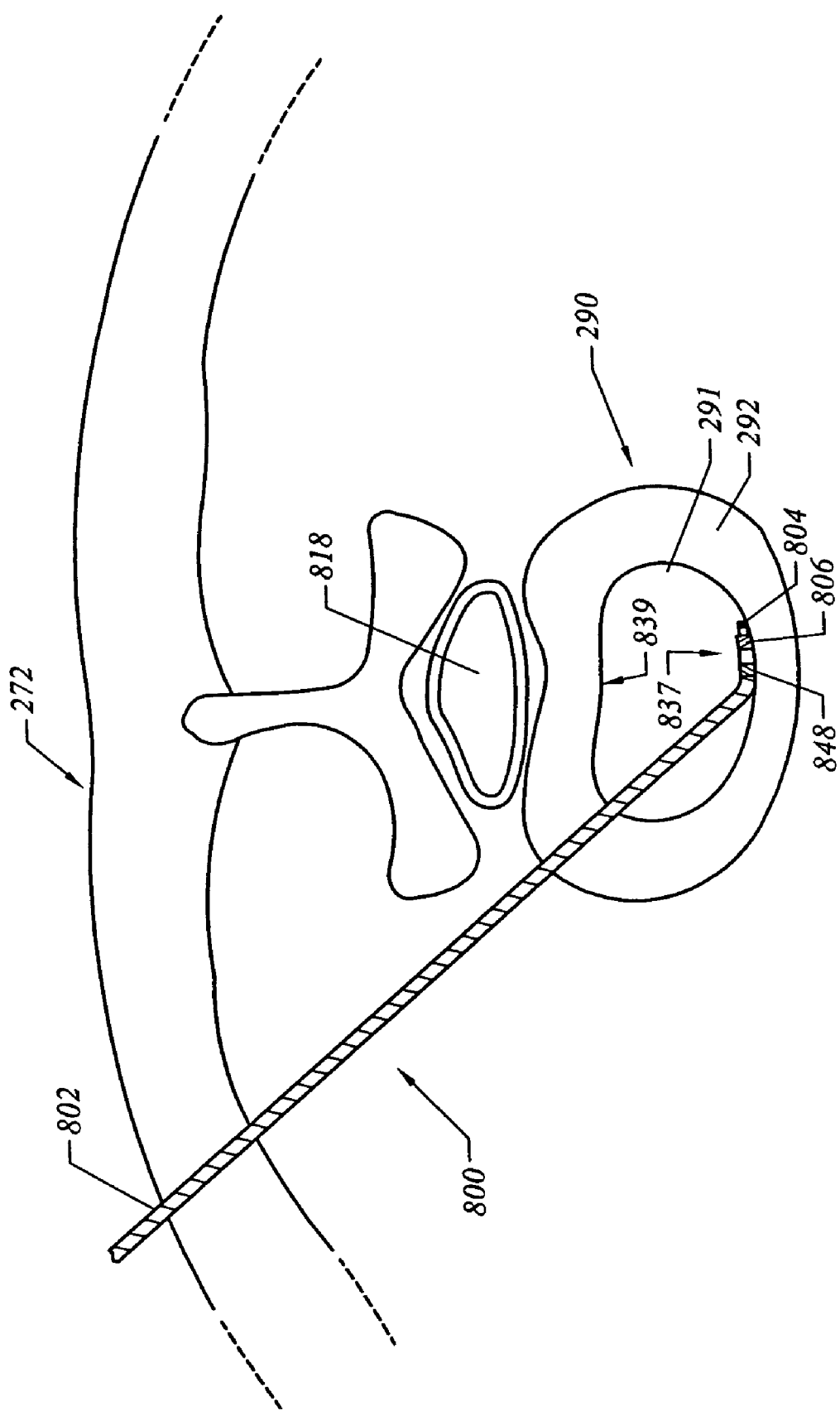

As shown by the dotted lines in FIGS. 43A–43D, the distal tip 837 of the electrosurgical probe 800 can have a pre-formed curvature or can be steered to a curved configuration so as to approximate the curvature of the inner surface 839 of the annulus (FIGS. 46A–B). In some embodiments, distal tip 837 is made of a shape memory material that can be shaped to approximate the inside curvature of the annulus. In other embodiments, distal tip 837 of the electrosurgical probe 800 is steerable or deflectable by the user. The flexible shaft and steerable distal tip may be combined with pull wires, shape memory actuators, heat actuated materials, or other conventional or proprietary mechanisms for effecting selective deflection of the distal tip of the shaft to facilitate positioning of the electrode array relative to a target tissue. A user can track the position of the steerable distal tip using fluoroscopy, optical fibers, transducers positioned on the probe, or the like.

Figure 44:
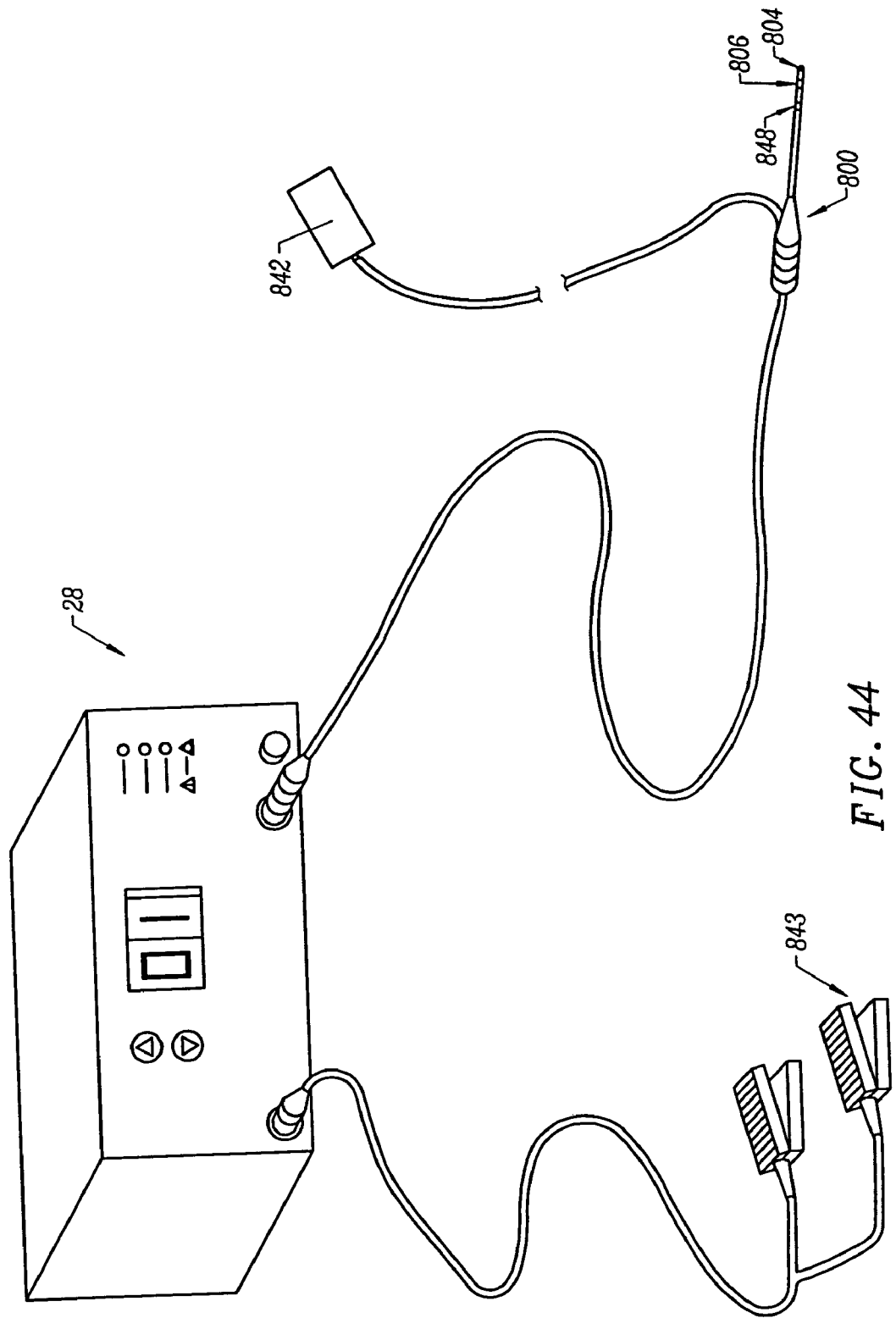
FIG. 44 illustrates an electrosurgical system having a dispersive return pad for monopolar and/or bipolar operations.

In some embodiments, the electrosurgical probe 800 may include a dispersive return electrode 842 (FIG. 44) for operating the apparatus in monopolar mode. In this embodiment, the power supply 28 will typically include a switch, e.g., a foot pedal 843, for switching between the monopolar and bipolar modes. The system will switch between an ablation mode, where the dispersive pad 842 is deactivated and voltage is applied between active and return electrodes 804, 806, and a subablation or thermal heating mode, where the active electrode(s) 804 are deactivated and voltage is applied between the dispersive pad 842 and the return electrode 806. In the subablation mode, a lower voltage is typically applied and the return electrode 806 functions as the active electrode to provide thermal heating and/or coagulation of tissue surrounding return electrode 806. A more complete description of the use of the dispersive return electrode is described in co-pending U.S. patent application Ser. No. 09/316,472, filed May 21, 1999, the complete disclosure of which is incorporated herein by reference.

Figure 43B:
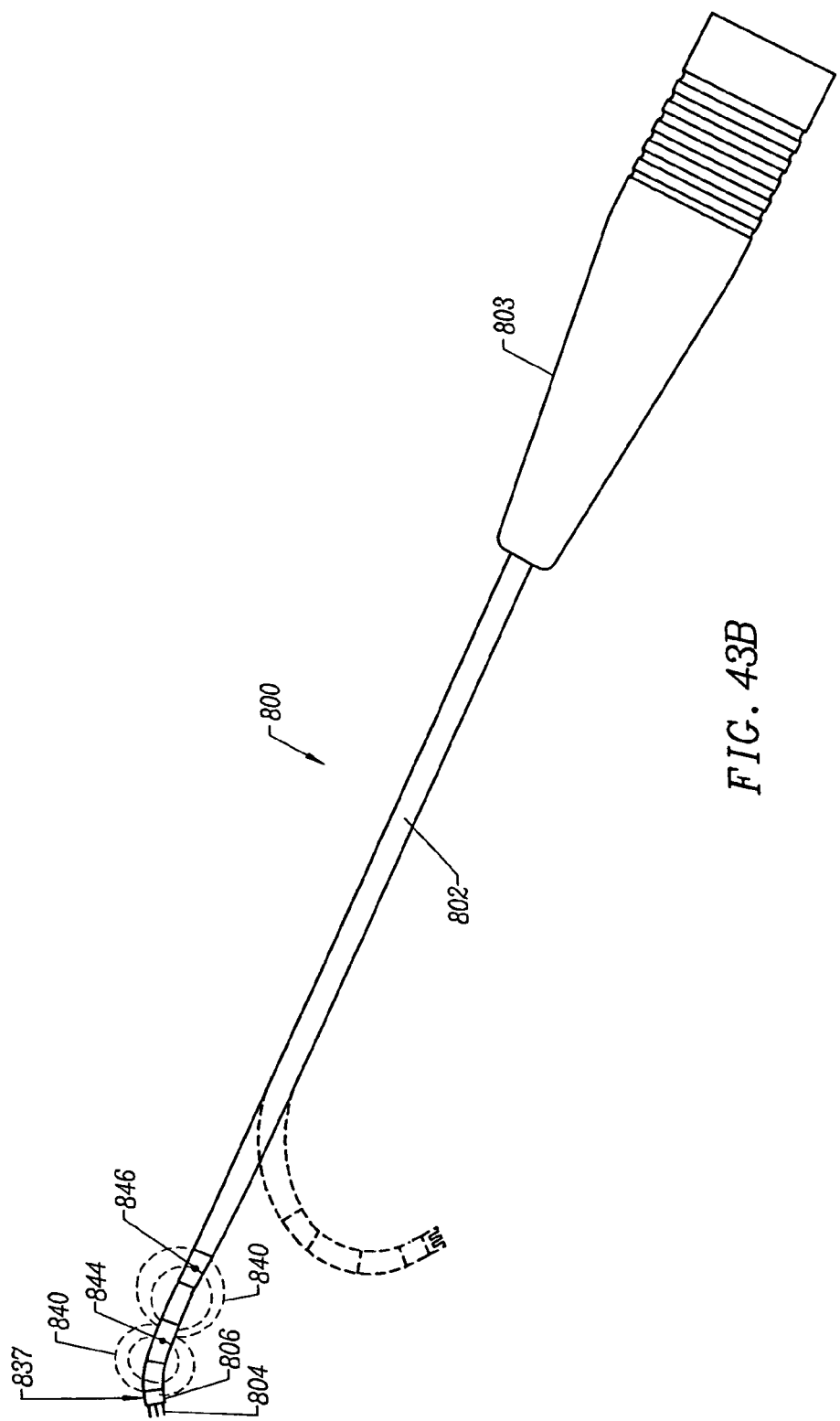

FIG. 43B illustrates yet another embodiment of the present invention. As shown, electrosurgical probe 800 comprises an electrode assembly having one or more active electrode(s) 804 and a proximally spaced return electrode 806 as in previous embodiments. Return electrode 806 is typically spaced about 0.5 mm to 25 mm, preferably 1.0 mm to 5.0 mm from the active electrode(s) 804, and has an exposed length of about 1 mm to 20 mm. In addition, the electrode assembly can include two additional electrodes 844, 846 spaced axially on either side of return electrode 806. Electrodes 844, 846 are typically spaced about 0.5 mm to 25 mm, preferably about 1 mm to 5 mm from return electrode 806. In the representative embodiment, the additional electrodes 844, 846 are exposed portions of shaft 802, and the return electrode 806 is electrically insulated from shaft 802 such that a voltage difference may be applied between electrodes 844, 846 and electrode 806. In this embodiment, probe 800 may be used in at least two different modes, an ablation mode and a subablation or thermal heating mode. In the ablation mode, voltage is applied between active electrode(s) 804 and return electrode 806 in the presence of electrically conductive fluid, as described above. In the ablation mode, electrodes 844, 846 are deactivated. In the thermal heating or coagulation mode, active electrode(s) 804 are deactivated and a voltage difference is applied between electrodes 844, 846 and electrode 806 such that a high frequency current 840 flows therebetween, as shown in FIG. 43B. In the thermal heating mode, a lower voltage is typically applied such that the voltage is below the threshold for plasma formation and ablation, but sufficient to cause some thermal damage to the tissue immediately surrounding the electrodes without vaporizing or otherwise debulking this tissue so that the current 840 provides thermal heating and/or coagulation of tissue surrounding the electrodes 804, 844, 846.

Figure 43C:
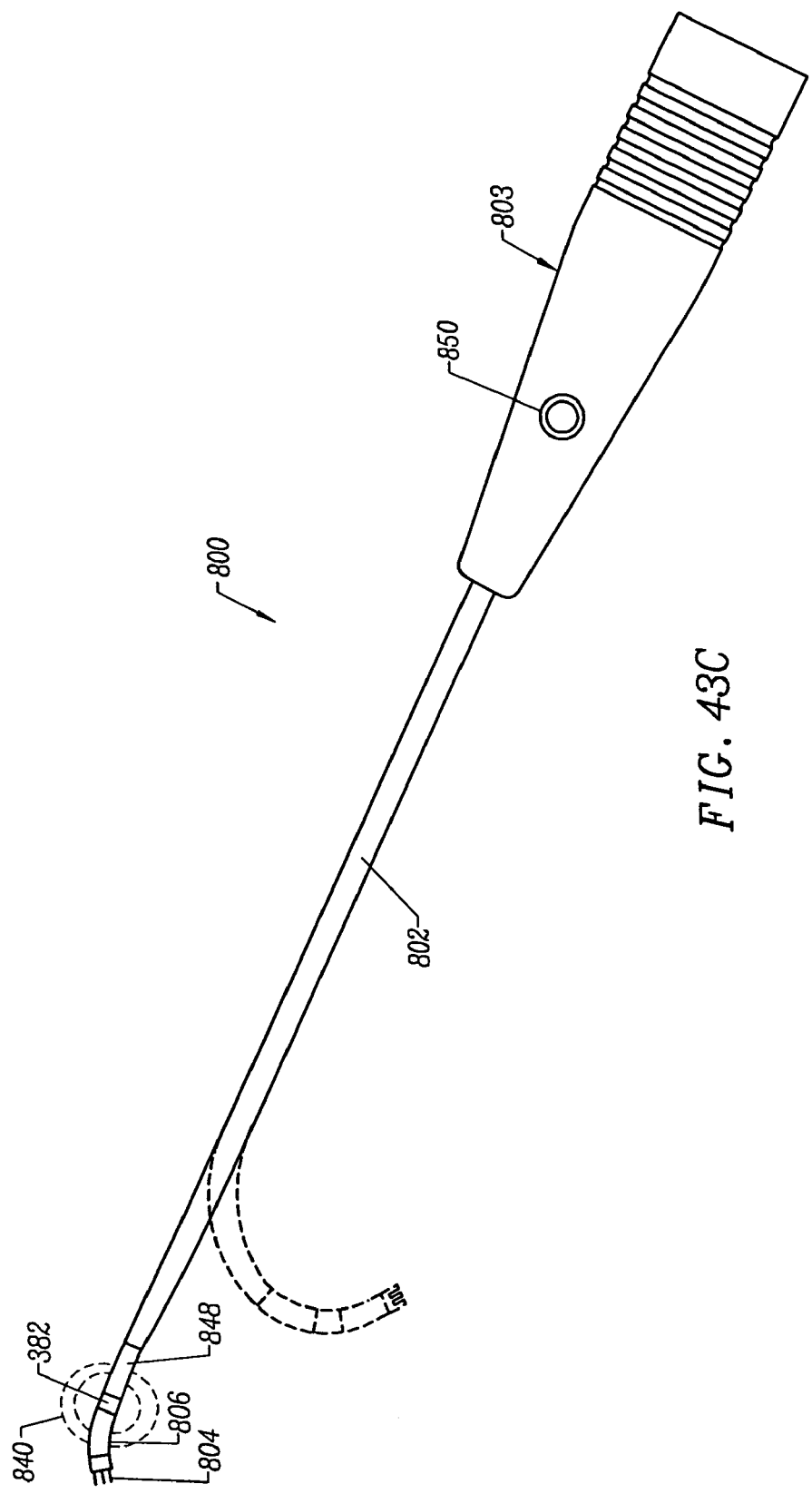

FIG. 43C illustrates another embodiment of probe 800 incorporating an electrode assembly having one or more active electrode(s) 804 and a proximally spaced return electrode 806 as in previous embodiments. Return electrode 806 is typically spaced about 0.5 mm to 25 mm, preferably 1.0 mm to 5.0 mm from the active electrode(s) 804, and has an exposed length of about 1 mm to 20 mm. In addition, the electrode assembly includes a second active electrode 848 separated from return electrode 806 by an electrically insulating spacer 382. In this embodiment, handle 803 includes a switch 850 for toggling probe 800 between at least two different modes, an ablation mode and a subablation or thermal heating mode. In the ablation mode, voltage is applied between active electrode(s) 804 and return electrode 806 in the presence of electrically conductive fluid, as described above. In the ablation mode, electrode 848 is deactivated. In the thermal heating or coagulation mode, active electrode(s) 804 may be deactivated and a voltage difference is applied between electrode 848 and electrode 806 such that a high frequency current 840 flows therebetween. Alternatively, active electrode(s) 804 may not be deactivated as the higher resistance of the smaller electrodes (active electrodes 804) may automatically send the electric current to electrode 848 without having to physically decouple electrode(s) 804 from the circuit. In the thermal heating mode, a lower voltage is typically applied, i.e. a voltage below the threshold for plasma formation and ablation, but sufficient to cause some thermal damage to the tissue immediately surrounding the electrodes without vaporizing or otherwise debulking this tissue so that the current 840 provides thermal heating and/or coagulation of tissue surrounding electrodes 804, 848.

Figure 43D:
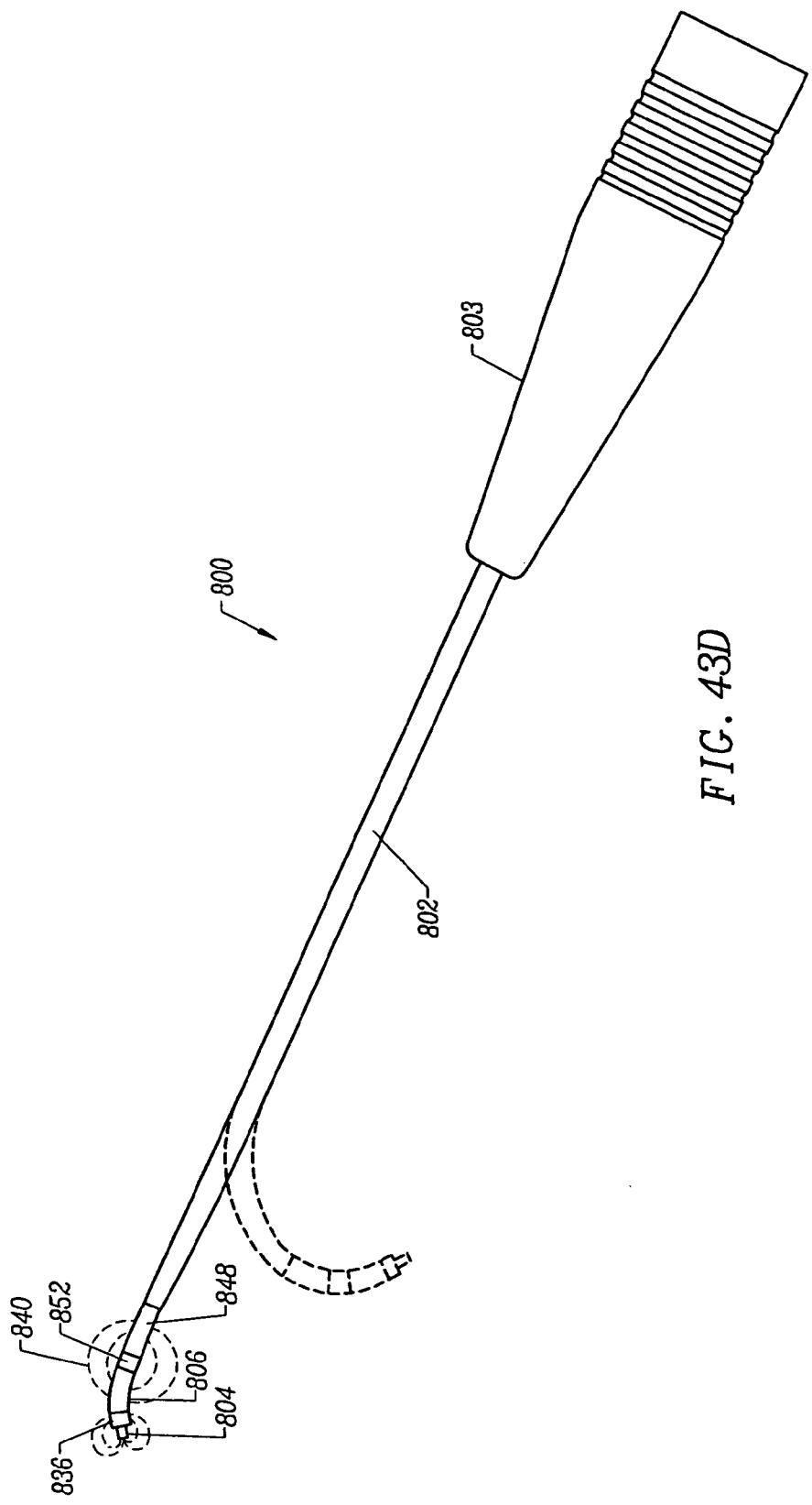

FIG. 43D illustrates yet another embodiment of the invention designed for channeling through tissue and creating lesions therein to treat the interior tissue of intervertebral discs. As shown, probe 800 is similar to the probe in FIG. 43C having a return electrode 806 and a third, coagulation electrode 848 spaced proximally from the return electrode 806. In this embodiment, active electrode 804 comprises a single electrode wire extending distally from insulating support member 836. Of course, the active electrode 804 may have a variety of configurations to increase the current densities on its surfaces, e.g., a conical shape tapering to a distal point, a hollow cylinder, loop electrode and the like. This embodiment includes a proximal support member 852. In the representative embodiment, support members 836 and 852 are constructed of inorganic material, such as a ceramic, a glass, a silicone, and the like. The proximal support member 852 may also comprise a more conventional organic material as this support member 852 will generally not be in the presence of a plasma that would otherwise etch or wear away an organic material.

The probe 800 in FIG. 43D does not include a switching element. In this embodiment, all three electrodes are activated when the power supply is activated. The return electrode 806 has an opposite polarity from the active and coagulation electrodes 804, 848 such that current 840 flows from the latter electrodes to the return electrode 806 as shown. In the preferred embodiment, the electrosurgical system includes a voltage reduction element or a voltage reduction circuit for reducing the voltage applied between the coagulation electrode 848 and return electrode 806. The voltage reduction element allows the power supply 28 (FIG. 1) to, in effect, apply two different voltages simultaneously to two different electrodes. Thus, for channeling through tissue, the operator may apply a voltage sufficient to provide ablation of the tissue at the tip of the probe (i.e., tissue adjacent to the active electrode 804). At the same time, the voltage applied to the coagulation electrode 848 will be insufficient to ablate tissue. For thermal heating or coagulation of tissue, for example, the voltage reduction element will serve to reduce a voltage from about 100 to 300 volts rms down to about 45 to 90 volts rms, wherein the latter range provides a suitable voltage for coagulation of tissue without ablation (e.g., without molecular dissociation) of the tissue.

In the representative embodiment, the voltage reduction element is a capacitor (not shown) coupled to the power supply and coagulation electrode 848. The capacitor usually has a capacitance of about 200 pF to 500 pF (at 500 volts) and preferably about 300 pF to 350 pF (at 500 volts). Of course, the capacitor may be located in other places within the system, such as in, or distributed along the length of, the cable, the generator, the connector, etc. In addition, it will be recognized that other voltage reduction elements, such as diodes, transistors, inductors, resistors, capacitors or combinations thereof, may be used in conjunction with the present invention. For example, the probe 800 may include a coded resistor (not shown) that is constructed to lower the voltage applied between the return and coagulation electrodes 806, 848. In addition, electrical circuits may be employed for this purpose.

Of course, for some procedures, the probe will typically not require a voltage reduction element. Alternatively, the probe may include a voltage increasing element or circuit, if desired. Alternatively or additionally, cable 22 (FIG. 1) that couples power supply 28 to probe 800 may be used as a voltage reduction element. The cable has an inherent capacitance that can be used to reduce the power supply voltage if the cable is placed into the electrical circuit between the power supply, the active electrodes and the return electrode. In this embodiment, the cable 22 may be used alone, or in combination with one of the voltage reduction elements discussed above, e.g., a capacitor. Further, it should be noted that the present invention can be used with a power supply that is adapted to apply two different voltages within the selected range for treatment of tissue. In this embodiment, a voltage reduction element or circuitry may not be desired.

In use, the electrosurgical instruments of FIGS. 43A–43D can be used to treat the tissue within the disc 290. In particular, the electrosurgical instrument 800 can be used to treat damaged discs (e.g., herniated, bulging, fissured, protruding, or the like), denervate selected nerves embedded in the annulus, cauterize granulation tissue that is ingrown into the annulus, seal fissures along the inner surface of the annulus, and the like. Preferably, the electrosurgical probe 800 can achieve these results in a minimally destructive manner so as to maintain the water content and tissue mass within the disc. Of course, the present invention can also be adapted to ablate tissue, to shrink tissue, to decrease the mass of tissue, or to reduce the water content of the disc.

In preferred embodiments, the electrosurgical probe 800 minimizes ablation of the nucleus pulposus 291 by moving along an inner surface of the annulus 292. Accordingly, after the distal tip of the electrosurgical probe is inserted into the disc 290 (FIG. 45), the distal tip 837 can be steered along the interface between the annulus 292 and nucleus pulposus 291.

Figure 45:
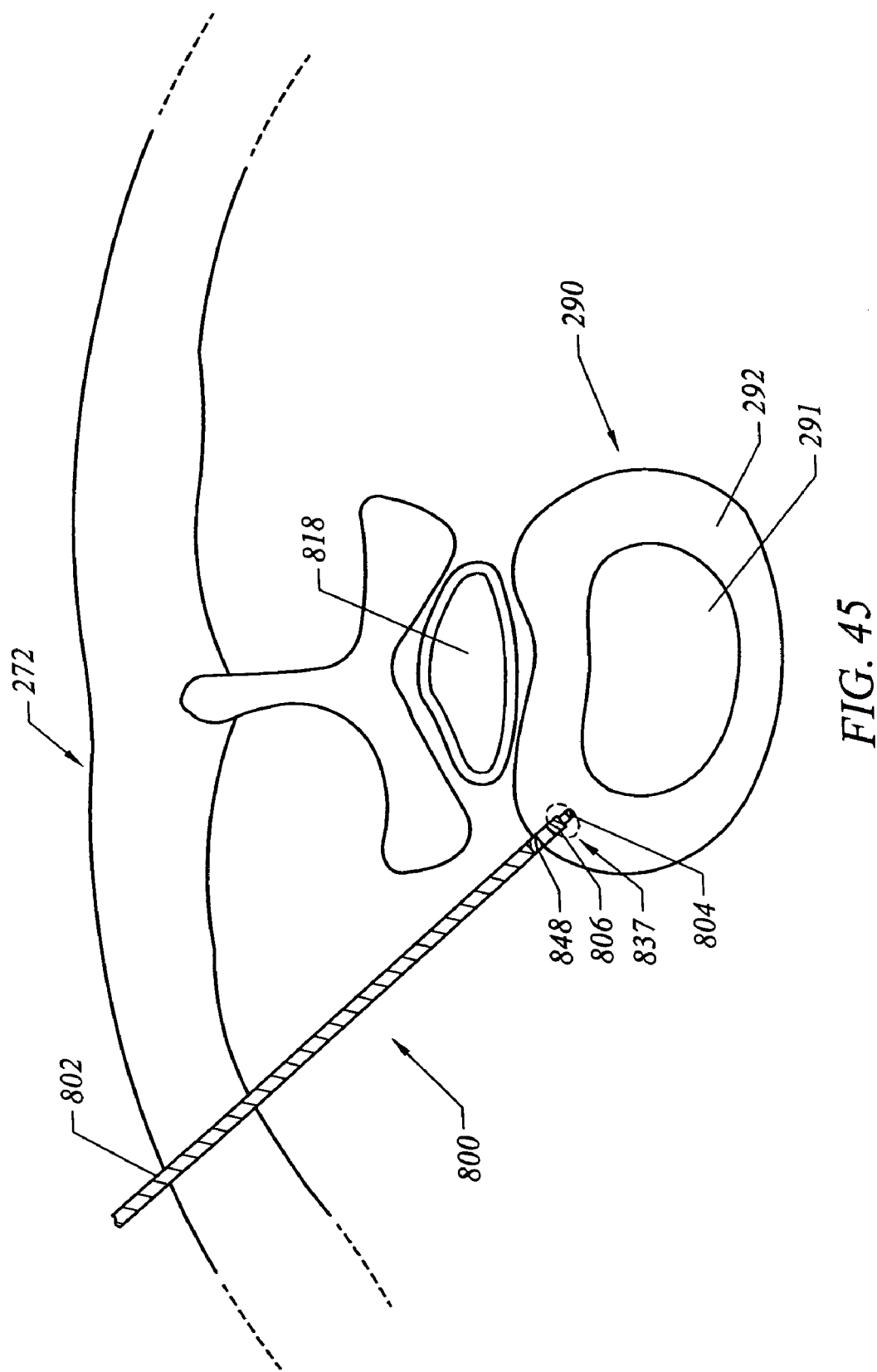
FIG. 45 illustrates an electrosurgical probe being inserted into an intervertebral disc.

Referring now to FIG. 45, in some methods the physician positions active electrode 804 adjacent to the tissue surface to be treated (e.g., an intervertebral disc). The power supply is activated to provide an ablation voltage between active and return electrodes 804, 806 and a coagulation or thermal heating voltage between coagulation and return electrodes 806, 848. An electrically conductive fluid can then be provided around active electrode 804, and in the junction between the active and return electrodes 804, 806 to provide a current flow path therebetween. This may be accomplished in a variety of manners, as discussed above. The active electrode 804 is then advanced through the space left by the ablated tissue to form a channel in the disc. During ablation, the electric current between the coagulation and return electrode is typically insufficient to cause any damage to the surface of the tissue as these electrodes pass through the tissue surface into the channel created by active electrode 804. Once the physician has formed the channel to the appropriate depth, he or she will cease advancement of the active electrode, and will either hold the instrument in place for approximately 5 seconds to 30 seconds, or can immediately remove the distal tip of the instrument from the channel (see detailed discussion of this below). In either event, when the active electrode is no longer advancing, it will eventually stop ablating tissue.

Prior to entering the channel formed by the active electrode 804, an open circuit exists between return and coagulation electrodes 806, 848. Once coagulation electrode 848 enters this channel, electric current will flow from coagulation electrode 848, through the tissue surrounding the channel, to return electrode 806. This electric current will heat the tissue immediately surrounding the channel to coagulate any severed vessels at the surface of the channel. If the physician desires, the instrument may be held within the channel for a period of time to create a lesion around the channel.

In an exemplary embodiment, once the distal tip 837 of the electrosurgical probe 800 has channeled through the annulus fibrosus 292, the distal tip 837 can be steered or deflected so as to move along the inner surface of the annulus fibrosus 292. As shown in FIGS. 46A and 46B, the electrosurgical device is advanced into an intervertebral disc 290, and the physician can simultaneously steer the distal tip 237 from the proximal end of the electrosurgical device (not shown). As noted above, the distal end of the electrosurgical device preferably is steered or deflected around the inner surface 839 of the annulus fibrosus 292. The physician can use fluoroscopy to monitor the position and movement of the distal end of the probe. Alternatively, the surgeon may insert an imaging device or transducer directly into the disc to monitor the position of electrodes 804, 806, and 848. The imaging device (not shown) can be positioned on the electrosurgical probe or it can be on a separate instrument.

In other embodiments, instead of a steerable distal tip 837, the distal tip of the electrosurgical probe 800 can be composed of a shape-memory material that can be pre-shaped to have the approximate curve of the inner surface of the annulus 292. The shape-memory tip can be biased to a pre-bent curved configuration, such that in the absence of a straightening force (e.g., within the annulus, within a tube, or the like) the distal tip will bias to the curved configuration. For example, after an operating corridor has been created to the target site, electrosurgical probe 800 can be moved adjacent the outer surface of the annulus fibrosus 292 (FIGS. 12–15). The active electrode 804 can channel through the tough annulus fibrosus 292, as described above. Once the distal tip 837 enters the nucleus pulposus 291, the distal tip will no longer be constrained in the substantially straight configuration by the tough, annulus fibrosus 292 and the distal tip will bias to its pre-bent curved configuration. As the electrosurgical device is advanced into the disc 290, the biased distal tip encourages the electrosurgical instrument to follow the curved inner surface 839 of the annulus fibrosus 292.

As described in detail above, once electrosurgical probe 800 has been steered to the target position, the high frequency voltage can be delivered between the active electrode(s) and return electrode(s) in a bipolar mode or monopolar mode to treat inner surface 839 of annulus fibrosus 292. In some embodiments, an electrically conductive fluid, such as isotonic saline, can be delivered to the active electrode. As noted above, in procedures requiring ablation of tissue, the tissue is removed by molecular dissociation or disintegration processes. In these embodiments, the high frequency voltage applied to the active electrode(s) is sufficient to vaporize the electrically conductive fluid between the active electrode(s) and the tissue. Within the vaporized fluid, an ionized plasma is formed and charged particles (e.g., electrons) cause the molecular breakdown or disintegration of the tissue to a depth of perhaps several cell layers. This molecular dissociation is accompanied by the volumetric removal of the tissue. The molecular dissociation process can be precisely controlled to target specific tissue structures or layers, thereby minimizing damage and necrosis to non-target tissue. In monopolar embodiments, the conductive fluid need only be sufficient to surround the active electrode and to provide a layer of fluid between the active electrode and the tissue. In bipolar embodiments, the conductive fluid preferably generates a current flow path between the active electrode(s) and the return electrode(s).

Depending on the procedure, the inner surface 839 of annulus 292 can be ablated, contracted, coagulated, sealed, or the like. For example, the high frequency voltage can be used to denervate the pain receptors in a fissure in the annulus fibrosus, deactivate the neurotransmitters, deactivate heat-sensitive enzymes, denervate nerves embedded in the wall of the annulus fibrosus, ablate granulation tissue in the annulus fibrosus, shrink collagen in the annulus fibrosus, or the like.

Other modifications and variations can be made to disclose embodiments without departing from the subject invention as defined in the following claims. For example, it should be noted that the invention is not limited to an electrode array comprising a plurality of active electrodes. Certain embodiments of the invention could utilize a plurality of return electrodes, e.g., in a bipolar array or the like. In addition, depending on other conditions, such as the peak-to-peak voltage, electrode diameter, etc., a single active electrode may be sufficient to contract collagen tissue, ablate tissue, or the like.

In addition, the active and return electrodes may both be located on a distal tissue treatment surface adjacent to each other. The active and return electrodes may be located in active/return electrode pairs, or one or more return electrodes may be located on the distal tip together with a plurality of electrically isolated active electrodes. The proximal return electrode may or may not be employed in these embodiments. For example, if it is desired to maintain the current flux lines around the distal tip of the probe, the proximal return electrode will not be desired.

There now follows a description, with reference to FIGS. 47A–50B, of an electrosurgical probe having a curved shaft, according to additional embodiments of the invention. FIG. 47A is a side view of an electrosurgical probe 900, including a shaft 902 having a distal end portion 902a and a proximal end portion 902b. An active electrode 910 is disposed on distal end portion 902a. Although only one active electrode is shown in FIG. 26A, embodiments having a plurality of active electrodes are also within the scope of the invention. Probe 900 further includes a handle 904 which houses a connection block 906 for coupling electrodes, e.g. active electrode 910, thereto. Connection block 906 includes a plurality of pins 908 adapted for coupling probe 900 to a power supply unit, e.g. power supply 28 (FIG. 1). FIG. 47A also shows a first curve 924 and a second curve 926 located at shaft distal end portion 902a, wherein second curve 926 is proximal to first curve 924. First curve 924 and second curve 926 may be separated by a linear (i.e. straight, or non-curved), or substantially linear, inter-curve portion 925 of shaft 902.

FIG. 47B is a side view of shaft distal end portion 902a within a representative introducer device or needle 928 having an inner diameter D. Shaft distal end portion 902a includes first curve 924 and second curve 926 separated by inter-curve portion 925. In one embodiment, shaft distal end portion 902a includes a linear or substantially linear proximal portion 901 extending from proximal end portion 902b to second curve 926, a linear or substantially linear inter-curve portion 925 between first and second curves 924, 926, and a linear or substantially linear distal portion 909 between first curve 924 and the distal tip of shaft 902 (the distal tip is represented in FIG. 47B as an electrode head 911). When shaft distal end portion 902a is located within introducer needle 928, first curve 924 subtends a first angle ∀ to the inner surface of needle 928, and second curve 926 subtends a second angle ∃ to inner surface 932 of needle 928. (In the situation shown in FIG. 47B, needle inner surface 932 is essentially parallel to the longitudinal axis of shaft proximal end portion 902b (FIG. 47A).) In one embodiment, shaft distal end portion 902a is designed such that the shaft distal tip occupies a substantially central transverse location within the lumen of introducer needle 928 when shaft distal end portion 902a is translated axially with respect to introducer needle 928. Thus, as shaft distal end portion 902a is advanced through the distal opening of needle 928 (FIGS. 30B, 31B), and then retracted back into the distal opening, the shaft distal tip will always occupy a transverse location towards the center of introducer needle 928 (even though the tip may be curved or biased away from the longitudinal axis of shaft 902 and needle 928 upon its advancement past the distal opening of introducer needle 928). In one embodiment, shaft distal end portion 902a is flexible and has a configuration which requires shaft distal end portion 902a be distorted in the region of at least second curve 926 by application of a lateral force imposed by inner wall 932 of introducer needle 928 as shaft distal end portion 902a is introduced or retracted into needle 928. In one embodiment, first curve 924 and second curve 926 are in the same plane relative to the longitudinal axis of shaft 902, and first and second curves 924, 926 are in opposite directions.

Figure 47C:
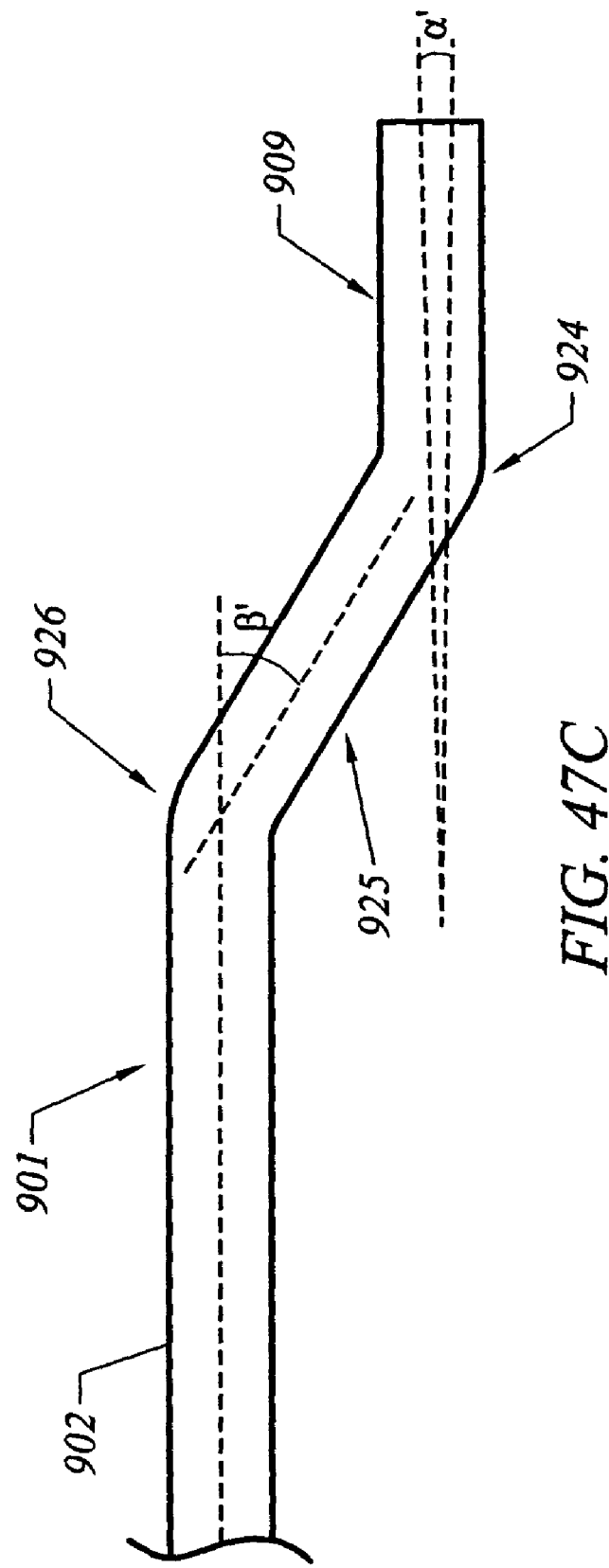
FIG. 47C is a side view of the distal end portion of the curved shaft of FIG. 47B in the absence of the introducer device.

The "S-curve" configuration of shaft 902 shown in FIGS. 47A–C allows the distal end or tip of a device to be advanced or retracted through needle distal end 928a and within the lumen of needle 928 without the distal end or tip contacting introducer needle 928. Accordingly, this design allows a sensitive or delicate component to be located at the distal tip of a device, wherein the distal end or tip is advanced or retracted through a lumen of an introducer instrument comprising a relatively hard material (e.g., an introducer needle comprising stainless steel). This design also allows a component located at a distal end or tip of a device to be constructed from a relatively soft material, and for the component located at the distal end or tip to be passed through an introducer instrument comprising a hard material without risking damage to the component comprising a relatively soft material.

The "S-curve" design of shaft distal end portion 902a allows the distal tip (e.g., electrode head 911) to be advanced and retracted through the distal opening of needle 928 while avoiding contact between the distal tip and the edges of the distal opening of needle 928. (If, for example, shaft distal end portion 902a included only a single curve, the distal tip would ordinarily come into contact with needle distal end 928a as shaft 902 is retracted into the lumen of needle 928.) In preferred embodiments, the length L2 of distal portion 909 and the angle ∀ between distal portion 909 and needle inner surface 932 928, when shaft distal end portion 902a is compressed within needle 928, are selected such that the distal tip is substantially in the center of the lumen of needle 928, as shown in FIG. 47B. Thus, as the length L2 increases, the angle ∀ will decrease, and vice versa. The exact values of length L2 and angle ∀ will depend on the inner diameter, D of needle 928, the inner diameter, d of shaft distal end portion 902*a*, and the size of the shaft distal tip.

The presence of first and second curves, 924, 926 provides a pre-defined bias in shaft 902. In addition, in one embodiment shaft distal end portion 902*a* is designed such that at least one of first and second curves 924, 926 are compressed to some extent as shaft distal end portion 902*a* is retracted into the lumen of needle 928. Accordingly, the angle of at least one of curves 924, 926 may be changed when distal end portion 902*a* is advanced out through the distal opening of introducer needle 928, as compared with the corresponding angle when shaft distal end portion is completely retracted within introducer needle 928. For example, FIG. 47C shows shaft 902 of FIG. 47B free from introducer needle 928, wherein first and second curves 924, 926 are allowed to adopt their natural or uncompressed angles ∀' and ∃', respectively, wherein ∃' is typically equal to or greater than ∃. Angle ∀' may be greater than, equal to, or less than angle ∀. Angle ∃' is subtended by inter-curve portion 925 and proximal portion 901. When shaft distal end portion 902*a* is unrestrained by introducer needle 928, proximal portion 901 approximates the longitudinal axis of shaft 902. Angle ∀' is subtended between linear distal portion 909 and a line drawn parallel to proximal portion 901. Electrode head 911 is omitted from FIG. 47C for the sake of clarity.

The principle described above with reference to shaft 902 and introducer needle 928 may equally apply to a range of other medical devices. That is to say, the "S-curve" configuration of the invention may be included as a feature of any medical system or apparatus in which a medical instrument may be axially translated or passed within an introducer device. In particular, the principle of the "S-curve" configuration of the invention may be applied to any apparatus wherein it is desired that the distal end of the medical instrument does not contact or impinge upon the introducer device as the medical instrument is advanced from or retracted into the introducer device. The introducer device may be any apparatus through which a medical instrument is passed. Such medical systems may include, for example, a catheter, a cannula, an endoscope, and the like.

When shaft 902 is advanced distally through the needle lumen to a point where second curve 926 is located distal to needle distal end 928*a*, the shaft distal tip is deflected from the longitudinal axis of needle 928. The amount of this deflection is determined by the relative size of angles ∃' and ∀', and the relative lengths of L1 and L2. The amount of this deflection will in turn determine the size of a channel or lesion (depending on the application) formed in a tissue treated by electrode head 911 when shaft 902 is rotated circumferentially with respect to the longitudinal axis of probe 900.

As a result of the pre-defined bias in shaft 902, shaft distal end portion 902a will contact a larger volume of tissue than a linear shaft having the same dimensions. In addition, in one embodiment the pre-defined bias of shaft 902 allows the physician to guide or steer the distal tip of shaft 902 by a combination of axial movement of needle distal end 928*a* and the inherent curvature at shaft distal end portion 902*a* of probe 900.

Shaft 902 preferably has a length in the range of from about 4 to 30 cm. In one aspect of the invention, probe 900 is manufactured in a range of sizes having different lengths and/or diameters of shaft 902. A shaft of appropriate size can then be selected by the surgeon according to the body structure or tissue to be treated and the age or size of the patient. In this way, patients varying in size from small children to large adults can be accommodated. Similarly, for a patient of a given size, a shaft of appropriate size can be selected by the surgeon depending on the organ or tissue to be treated, for example, whether an intervertebral disc to be treated is in the lumbar spine or the cervical spine. For example, a shaft suitable for treatment of a disc of the cervical spine may be substantially smaller than a shaft for treatment of a lumbar disc. For treatment of a lumbar disc in an adult, shaft 902 is preferably in the range of from about 15 to 20 cm. For treatment of a cervical disc, shaft 902 is preferably in the range of from about 4 to about 15 cm.

The diameter of shaft 902 is preferably in the range of from about 0.5 to about 2.5 mm, and more preferably from about 1 to 1.5 mm. First curve 924 is characterized by a length L1, while second curve 926 is characterized by a length L2 (FIG. 47B). Inter-curve portion 925 is characterized by a length L3, while shaft 902 extends distally from first curve 924 a length L4. In one embodiment, L2 is greater than L1. Length L1 may be in the range of from about 0.5 to about 5 mm, while L2 may be in the range of from about 1 to about 10 mm. Preferably, L3 and L4 are each in the range of from about 1 to 6 mm.

Figure 48A:
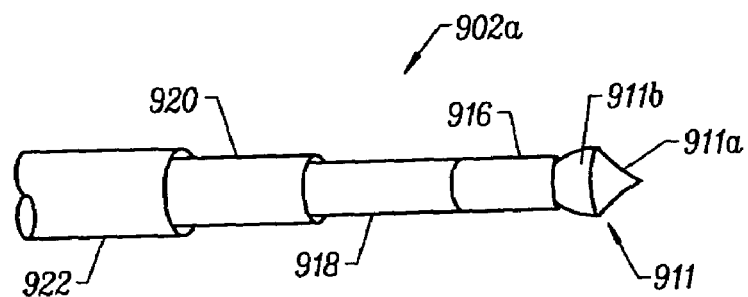
FIG. 48A is a side view of the distal end portion of an electrosurgical probe showing an active electrode having an apical spike and an equatorial cusp.
Figure 50A:
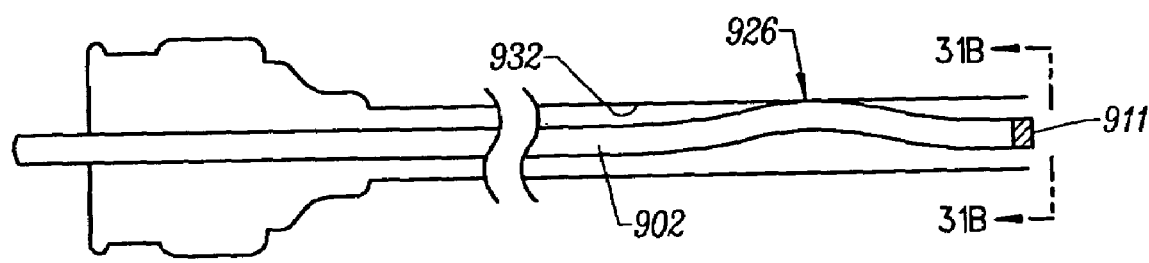
FIGS. 50A, 50B show a side view and an end view, respectively, of a curved shaft of an electrosurgical probe, in relation to an introducer needle.

FIG. 48A is a side view of electrosurgical probe 900 showing details of shaft distal end portion 902*a* including an active electrode head 911 of active electrode 910 (the latter not shown in FIG. 48A), according to one embodiment of the invention. Distal end portion 902*a* includes an insulating collar or spacer 916 proximal to active electrode head 911, and a return electrode 918 proximal to collar 916. A first insulating sleeve (FIG. 48B) may be located beneath return electrode 918. A second insulating jacket or sleeve 920 may extend proximally from return electrode 918. Second insulating sleeve 920 serves as an electrical insulator to inhibit current flow into non-target tissue. In a currently preferred embodiment, probe 900 further includes a shield 922 extending proximally from second insulating sleeve 920. Shield 922 may be formed from a conductive metal such as stainless steel, and the like. Shield 922 functions to decrease the amount of leakage current passing from probe 900 to a patient or a user (e.g., surgeon). In particular, shield 922 decreases the amount of capacitive coupling between return electrode 918 and an introducer needle 928 (FIG. 50A).

In this embodiment, electrode head 911 includes an apical spike 911*a* and an equatorial cusp 911*b*. Electrode head 911 exhibits a number of advantages as compared with, for example, an electrosurgical probe having a blunt, globular, or substantially spherical active electrode. In particular, electrode head 911 provides a high current density at apical spike 911*a* and cusp 911*b*. In turn, high current density in the vicinity of an active electrode is advantageous in the generation of a plasma; and, as is described fully hereinabove, generation of a plasma in the vicinity of an active electrode is fundamental to ablation of tissue with minimal collateral thermal damage according to certain embodiments of the instant invention. Electrode head 911 provides an additional advantage, in that the sharp edges of cusp 911*b*, and more particularly of apical spike 911*a*, facilitate movement and guiding of head 911 into fresh tissue during surgical procedures, as described fully hereinbelow. In contrast, an electrosurgical probe having a blunt or rounded apical electrode is more likely to follow a path of least resistance, such as a channel which was previously ablated within nucleus pulposus tissue. Although certain embodiments of the invention depict head 911 as having a single apical spike, other shapes for the apical portion of active electrode 910 are also within the scope of the invention.

Figure 48B:
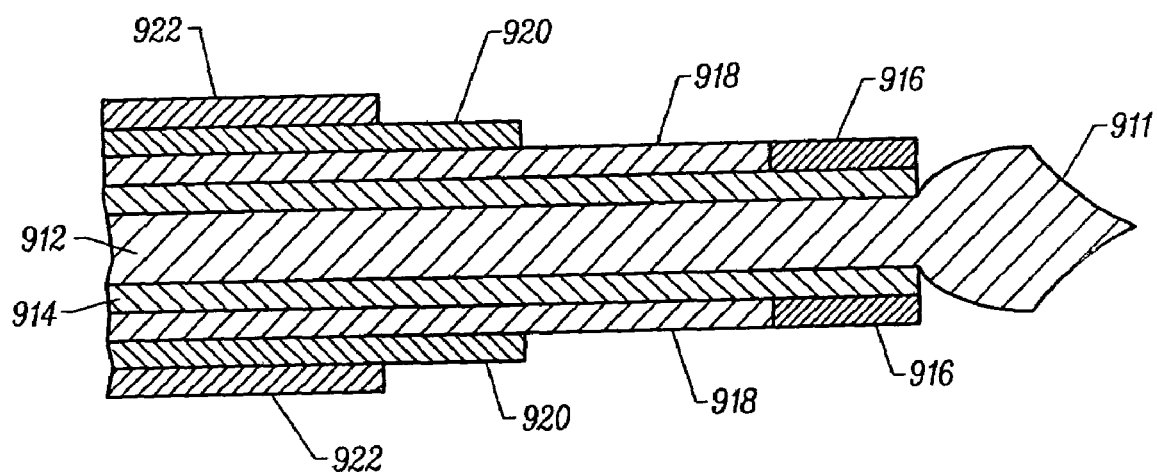
FIG. 48B is a cross-sectional view of the distal end portion of the electrosurgical probe of FIG. 48A.

FIG. 48B is a longitudinal cross-sectional view of distal end portion 902a of shaft 902. Apical electrode head 911 is in communication with a filament 912. Filament 912 typically comprises an electrically conductive wire encased within a first insulating sleeve 914. First insulating sleeve 914 comprises an insulator, such as various synthetic polymeric materials. An exemplary material from which first insulating sleeve 914 may be constructed is a polyimide. First insulating sleeve 914 may extend the entire length of shaft 902 proximal to head 911. An insulating collar or spacer 916 is disposed on the distal end of first insulating sleeve 914, adjacent to electrode head 911. Collar 916 preferably comprises a material such as a glass, a ceramic, or silicone. The exposed portion of first insulating sleeve 914 (i.e., the portion proximal to collar 916) is encased within a cylindrical return electrode 918. Return electrode 918 may extend proximally the entire length of shaft 902. Return electrode 918 may comprise an electrically conductive material such as stainless steel, tungsten, platinum or its alloys, titanium or its alloys, molybdenum or its alloys, nickel or its alloys, and the like. A proximal portion of return electrode 918 is encased within a second insulating sleeve 920, so as to provide an exposed band of return electrode 918 located distal to second sleeve 920 and proximal to collar 916. Second sleeve 920 provides an insulated portion of shaft 920 which facilitates handling of probe 900 by the surgeon during a surgical procedure. A proximal portion of second sleeve 920 is encased within an electrically conductive shield 922. Second sleeve 920 and shield 922 may also extend proximally for the entire length of shaft 902.

Figure 49A:
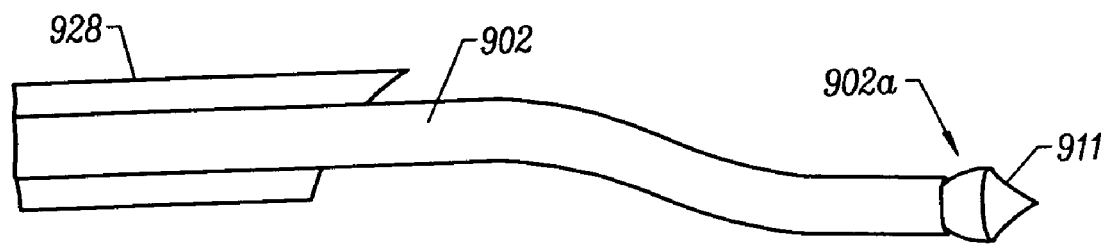
FIG. 49A shows the distal end portion of the shaft of an electrosurgical probe extended distally from an introducer needle.
Figure 49B:
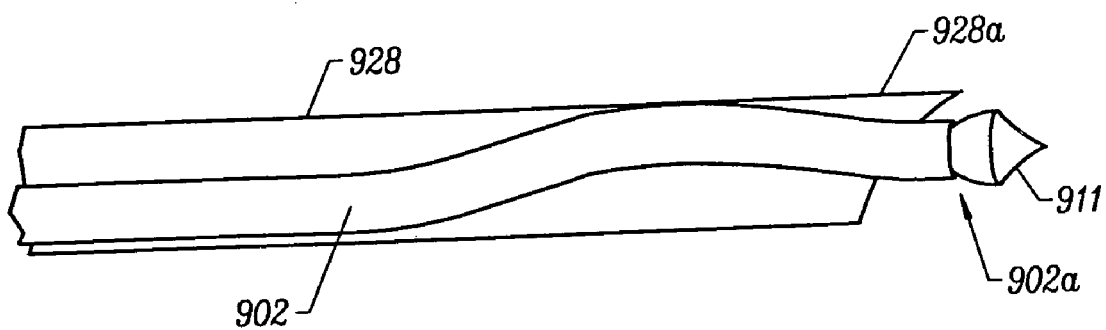
FIG. 49B illustrates the position of the active electrode in relation to the inner wall of the introducer needle upon retraction of the active electrode within the introducer needle.

FIG. 49A shows distal end portion 902a of shaft 902 extended distally from an introducer needle 928, according to one embodiment of the invention. Introducer needle 928 may be used to conveniently introduce shaft 902 into tissue, such as the nucleus pulposus of an intervertebral disc. In this embodiment, due to the curvature of shaft distal end 902a, when shaft 902 is extended distally beyond introducer needle 928, head 911 is displaced laterally from the longitudinal axis of introducer needle 928. However, as shown in FIG. 49B, as shaft 902 is retracted into introducer needle 928, head 911 assumes a substantially central transverse location within lumen 930 (see also FIG. 50B) of introducer 928. Such re-alignment of head 911 with the longitudinal axis of introducer 928 is achieved by specific design of the curvature of shaft distal end 902a, as accomplished by the instant inventors. In this manner, contact of various components of shaft distal end 902a (e.g., electrode head 911, collar 916, return electrode 918) is prevented, thereby not only facilitating extension and retraction of shaft 902 within introducer 928, but also avoiding a potential source of damage to sensitive components of shaft 902.

Figure 50B:
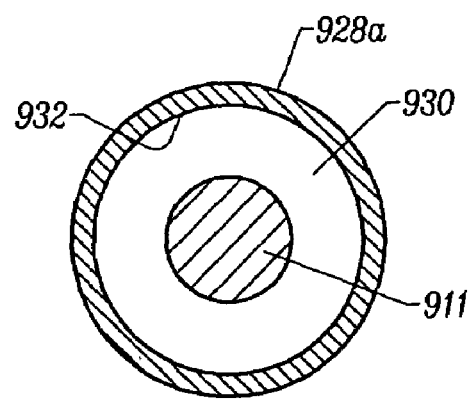

FIG. 50A shows a side view of shaft 902 in relation to an inner wall 932 of introducer needle 928 upon extension or retraction of electrode head 911 from, or within, introducer needle 928. Shaft 902 is located within introducer 928 with head 911 adjacent to introducer distal end 928a (FIG. 50B). Under these circumstances, curvature of shaft 902 may cause shaft distal end 902a to be forced into contact with introducer inner wall 932, e.g., at a location of second curve 926. Nevertheless, due to the overall curvature of shaft 902, and in particular the nature and position of first curve 924 (FIGS. 47A–B), head 911 does not contact introducer distal end 928a.

FIG. 50B shows an end view of electrode head 911 in relation to introducer needle 928 at a point during extension or retraction of shaft 902, wherein head 911 is adjacent to introducer distal end 928a (FIGS. 49B, 50B). In this situation, head 911 occupies a substantially central transverse location within lumen 930 of introducer 928. Therefore, contact between head 911 and introducer 928 is avoided, allowing shaft distal end 902a to be extended and retracted repeatedly without sustaining any damage to shaft 902.

Figure 51A:
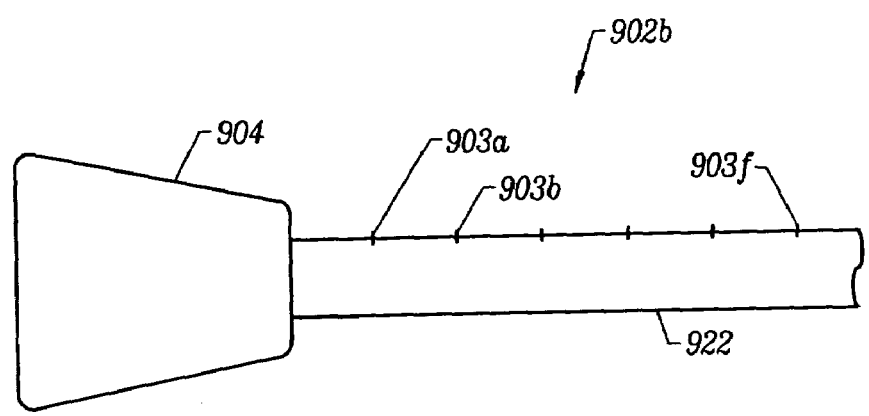
FIG. 51A shows the proximal end portion of the shaft of an electrosurgical probe, wherein the shaft includes a plurality of depth markings.

FIG. 51A shows shaft proximal end portion 902b of electrosurgical probe 900, wherein shaft 902 includes a plurality of depth markings 903 (shown as 903a–f in FIG. 51A). In other embodiments, other numbers and arrangements of depth markings 903 may be included on shaft 902. For example, in certain embodiments, depth markings may be present along the entire length of shield 922, or a single depth marking 903 may be present at shaft proximal end portion 902b. Depth markings serve to indicate to the surgeon the depth of penetration of shaft 902 into a patient's tissue, organ, or body, during a surgical procedure. Depth markings 903 may be formed directly in or on shield 922, and may comprise the same material as shield 922. Alternatively, depth markings 903 may be formed from a material other than that of shield 922. For example, depth markings may be formed from materials which have a different color and/or a different level of radiopacity, as compared with material of shield 922. For example, depth markings may comprise a metal, such as tungsten, gold, or platinum oxide (black), having a level of radiopacity different from that of shield 922. Such depth markings may be visualized by the surgeon during a procedure performed under fluoroscopy. In one embodiment, the length of introducer needle 928 and shaft 902 are selected to limit the range of shaft distal end 902a beyond the distal tip of introducer needle 928.

Figure 51B:
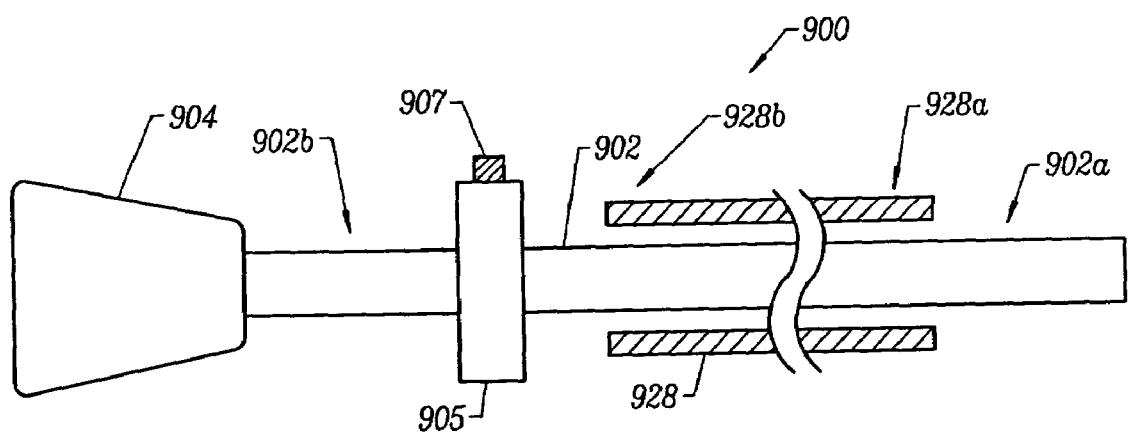
FIG. 51B shows the proximal end portion of the shaft of an electrosurgical probe, wherein the shaft includes a mechanical stop.

FIG. 51B shows a probe 900, wherein shaft 902 includes a mechanical stop 905. Preferably, mechanical stop 905 is located at shaft proximal end portion 902b. Mechanical stop 905 limits the distance to which shaft distal end 902a can be advanced through introducer 928 by making mechanical contact with a proximal end 928b of introducer 928. Mechanical stop 905 may be a rigid material or structure affixed to, or integral with, shaft 902. Mechanical stop 905 also serves to monitor the depth or distance of advancement of shaft distal end 902a through introducer 928, and the degree of penetration of distal end 902a into a patient's tissue, organ, or body. In one embodiment, mechanical stop 905 is movable on shaft 902, and stop 905 includes a stop adjustment unit 907 for adjusting the position of stop 905 and for locking stop 905 at a selected location on shaft 902.

Figure 52A:
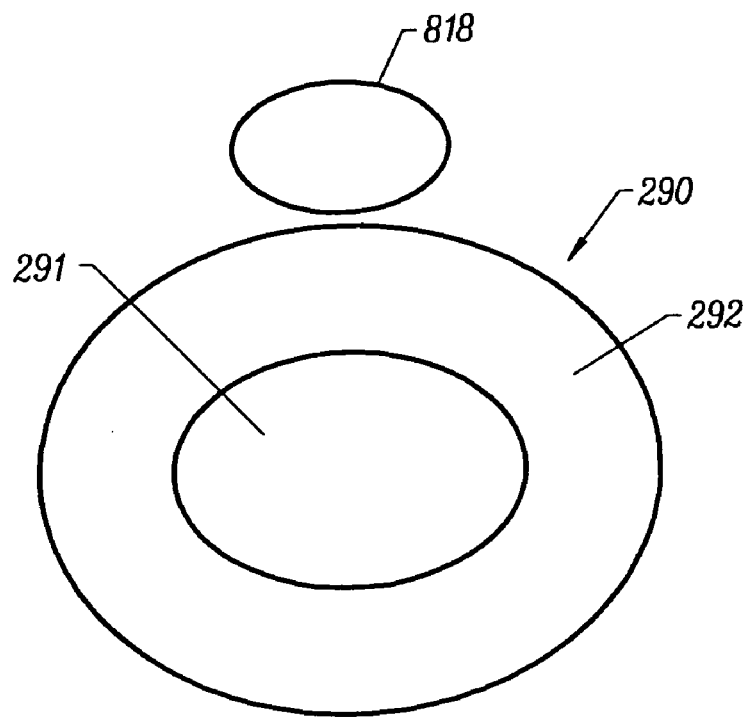
FIG. 52A schematically represents a normal intervertebral disc in relation to the spinal cord.
Figure 52B:
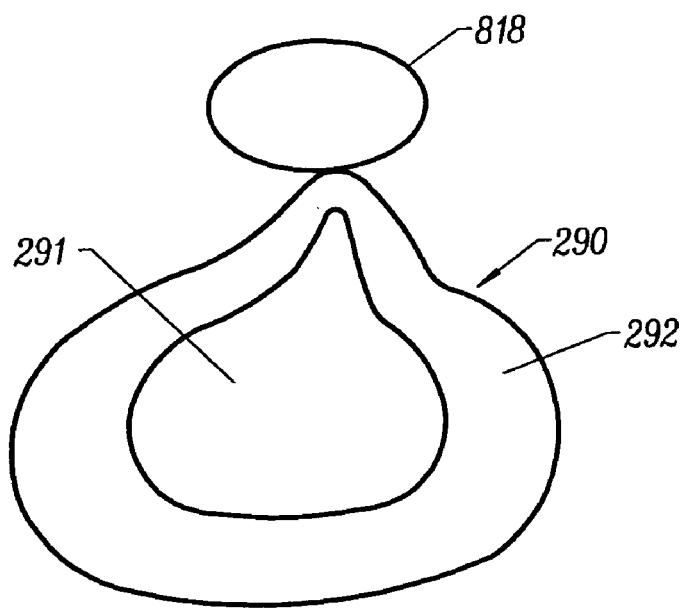
FIG. 52B schematically represents an intervertebral disc exhibiting a protrusion of the nucleus pulposus and a concomitant distortion of the annulus fibrosus.
Figure 52C:
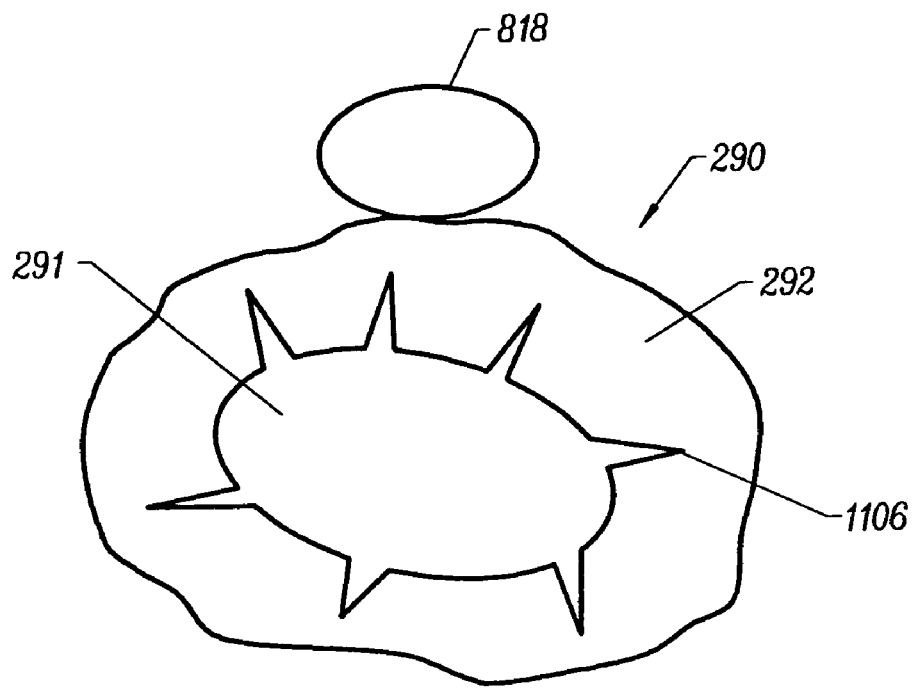
FIG. 52C schematically represents an intervertebral disc exhibiting a plurality of fissures within the annulus fibrosus and a concomitant distortion of the annulus fibrosus.
Figure 52D:
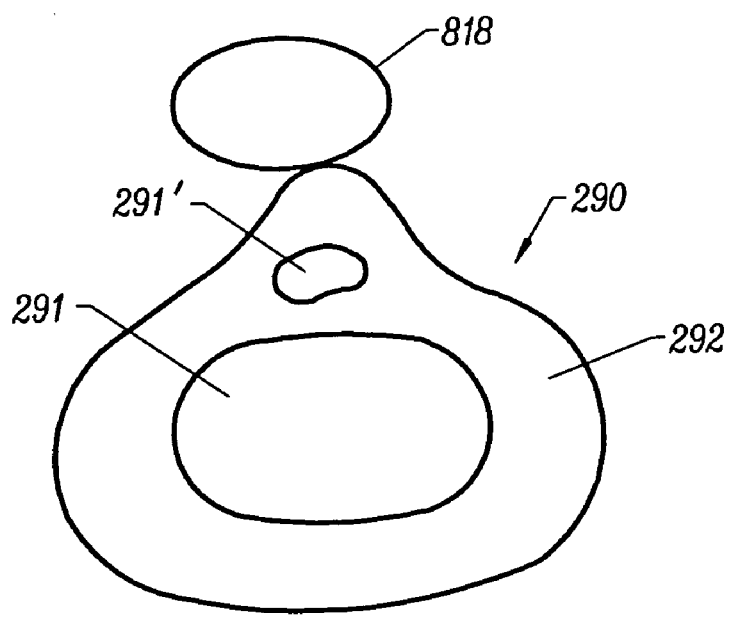
FIG. 52D schematically represents an intervertebral disc exhibiting fragmentation of the nucleus pulposus and a concomitant distortion of the annulus fibrosus.

FIG. 52A schematically represents a normal intervertebral disc 290 in relation to the spinal cord 818, the intervertebral disc having an outer annulus fibrosus 292 enclosing an inner nucleus pulposus 291. The nucleus pulposus is a relatively soft tissue comprising proteins and having a relatively high water content, as compared with the harder, more fibrous annulus fibrosus. FIGS. 52B–D each schematically represent an intervertebral disc having a disorder which can lead to discogenic pain, for example due to compression of a nerve root by a distorted annulus fibrosus. Thus, FIG. 52B schematically represents an intervertebral disc exhibiting a bulge or protrusion of the nucleus pulposus and a concomitant distortion of the annulus fibrosus. The condition depicted in FIG. 52B clearly represents a contained herniation, which can result in severe and often debilitating pain. FIG. 52C schematically represents an intervertebral disc exhibiting a plurality of fissures 1106 within the annulus fibrosus, again with concomitant distortion of the annulus fibrosus. Such annular fissures may be caused by excessive pressure exerted by the nucleus pulposus on the annulus fibrosus. Excessive pressure within the nucleus pulposus tends to intensify disc disorders associated with the presence of such fissures. FIG. 52D schematically represents an intervertebral disc exhibiting fragmentation of the nucleus pulposus and a concomitant distortion of the annulus fibrosus. In this situation, over time, errant fragment 291' of the nucleus pulposus tends to dehydrate and to diminish in size, often leading to a decrease in discogenic pain over an extended period of time (e.g., several months). For the sake of clarity, each FIGS. 52B, 52C, 52D shows a single disorder. However, in practice more than one of the depicted disorders may occur in the same disc.

Many patients suffer from discogenic pain resulting, for example, from conditions of the type depicted in FIGS. 52B–D. However, only a small percentage of such patients undergo laminotomy or discectomy. Presently, there is a need for interventional treatment for the large group of patients who ultimately do not undergo major spinal surgery, but who sustain significant disability due to various disorders or defects of an intervertebral disc. A common disorder of intervertebral discs is a contained herniation in which the nucleus pulposus does not breach the annulus fibrosus, but a protrusion of the disc causes compression of the exiting nerve root, leading to radicular pain. Typical symptoms are leg pain compatible with sciatica. Such radicular pain may be considered as a particular form of discogenic pain. Most commonly, contained herniations leading to radicular pain are associated with the lumbar spine, and in particular with intervertebral discs at either L4-5 or L5-S1. Various disc defects are also encountered in the cervical spine. Methods and apparatus of the invention are applicable to all segments of the spine, including the cervical spine and the lumbar spine.

Figure 53:
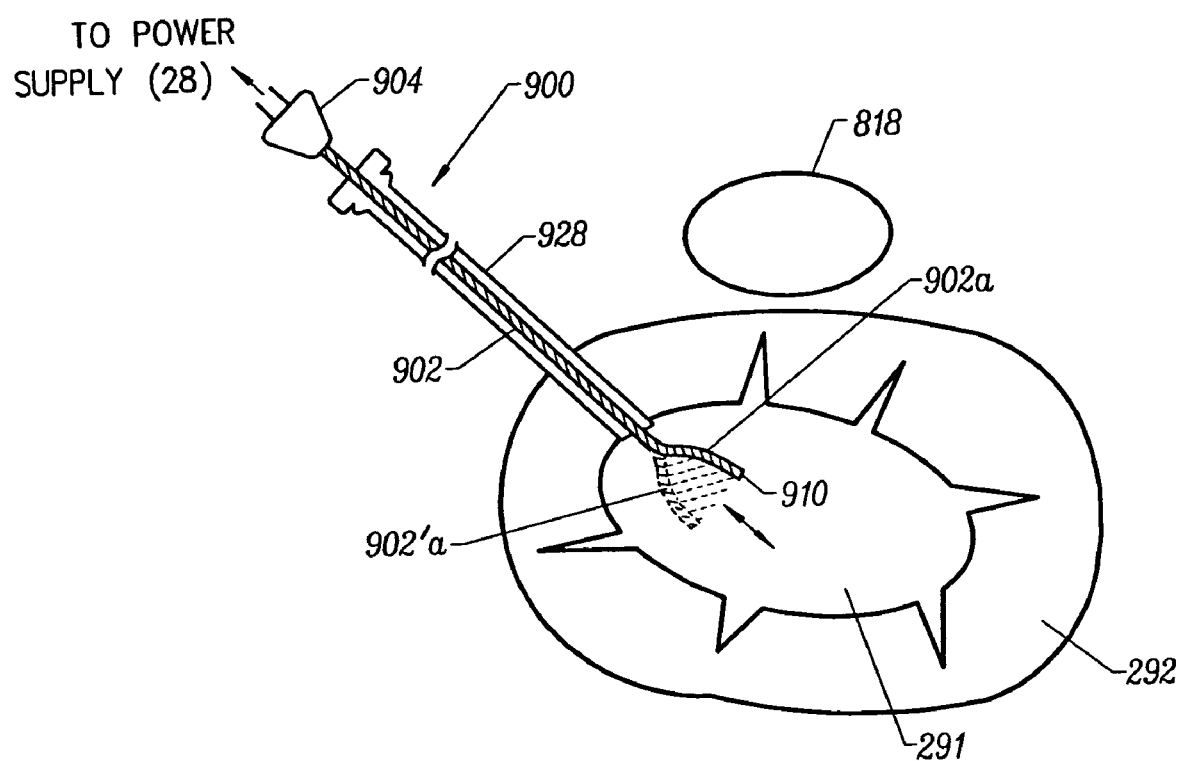
FIG. 53 schematically represents translation of a curved shaft of an electrosurgical probe within the nucleus pulposus for treatment of an intervertebral disc.

FIG. 53 schematically represents shaft 902 of probe 900 inserted within a nucleus pulposus of a disc having at least one fissure in the annulus. Shaft 902 may be conveniently inserted within the nucleus pulposus via introducer needle 928 in a minimally invasive percutaneous procedure. In a preferred embodiment, a disc in the lumbar spine may be accessed via a posterior lateral approach, although other approaches are possible and are within the scope of the invention. The preferred length and diameter of shaft 902 and introducer needle 928 to be used in a procedure will depend on a number of factors, including the region of the spine (e.g., lumbar, cervical) or other body region to be treated, and the size of the patient. Preferred ranges for shaft 902 are given elsewhere herein. In one embodiment for treatment of a lumbar disc, introducer needle 928 preferably has a diameter in the range of from about 50% to 150% the internal diameter of a 17 Gauge needle. In an embodiment for treatment of a cervical disc, introducer needle 928 preferably has a diameter in the range of from about 50% to 150% the internal diameter of a 20 Gauge needle.

Shaft 902 includes an active electrode 910, as described hereinabove. Shaft 902 features curvature at distal end 902a/902'a, for example, as described with reference to FIGS. 47A–B. By rotating shaft 902 through approximately 180°, shaft distal end 902a can be moved to a position indicated by the dashed lines and labeled as 902'a. Thereafter, rotation of shaft 902 through an additional 180° defines a substantially cylindrical three-dimensional space with a proximal frusto-conical region, the latter represented as a hatched area (shown between 902a and 902'a). The bi-directional arrow distal to active electrode 910 indicates translation of shaft 902 substantially along the longitudinal axis of shaft 902. By a combination of axial and rotational movement of shaft 902, a much larger volume of the nucleus pulposus can be contacted by electrode 910, as compared with a corresponding probe having a linear (non-curved) shaft. Furthermore, the curved nature of shaft 902 allows the surgeon to change the direction of advancement of shaft 902 by appropriate rotation thereof, and to guide shaft distal end 902a to a particular target site within the nucleus pulposus. In addition, further control may be exerted over which sites or regions within the disc can be accessed by shaft distal end 902a by advancing or retracting introducer needle 928 to change the initiation point from which shaft distal end 902a may be guided or steered. Alternatively, selection of an appropriate position from which shaft distal end 902a may be advanced, guided, or steered to a target location may make use of an introducer extension tube (FIG. 61A) which acts as an extension of introducer needle 928. By changing the location of the introducer needle or the introducer extension tube relative to the disc, different regions of the disc can be accessed by shaft distal end 902a.

It is to be understood that according to certain embodiments of the invention, the curvature of shaft 902 is the same, or substantially the same, both prior to it being used in a surgical procedure and while it is performing ablation during a procedure, e.g., within an intervertebral disc. (One apparent exception to this statement, relates to the stage in a procedure wherein shaft 902 may be transiently "molded" into a somewhat more linear configuration by the constraints of introducer inner wall 932 during housing, or passing, of shaft 902 within introducer 928.) In contrast, certain prior art devices, and embodiments of the invention to be described hereinbelow (e.g., with reference to FIGS. 59A, 59B), may be linear or lacking a naturally defined configuration prior to use, and then be steered into a selected configuration during a surgical procedure.

While shaft distal end 902a is at or adjacent to a target site within the nucleus pulposus, probe 900 may be used to ablate tissue by application of a first high frequency voltage between active electrode 910 and return electrode 918 (e.g., FIG. 26B), wherein the volume of the nucleus pulposus is decreased, the pressure exerted by the nucleus pulposus on the annulus fibrosus is decreased, and at least one nerve or nerve root is decompressed. Accordingly, discogenic pain experienced by the patient may be alleviated. Preferably, application of the first high frequency voltage results in formation of a plasma in the vicinity of active electrode 910, and the plasma causes ablation by breaking down high molecular weight disc tissue components (e.g., proteins) into low molecular weight gaseous materials. Such low molecular weight gaseous materials may be at least partially vented or exhausted from the disc, e.g., by piston action, upon removal of shaft 902 and introducer 928 from the disc and the clearance between introducer needle 928 and shaft 902. In addition, by-products of tissue ablation may be removed by an aspiration device (not shown in FIG. 53), as is well known in the art. In this manner, the volume and/or mass of the nucleus pulposus may be decreased.

Figure 57:
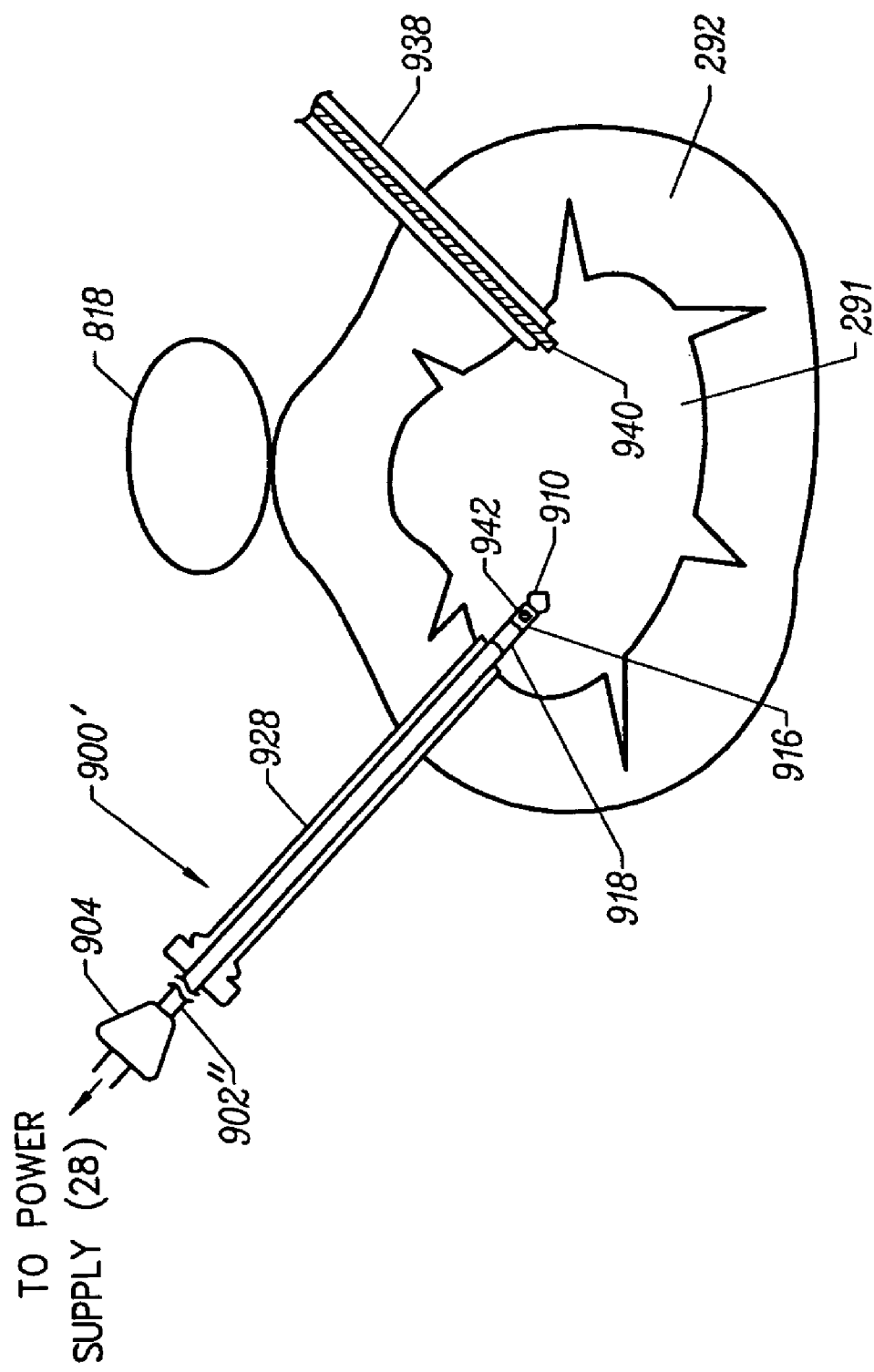
FIG. 57 shows treatment of an intervertebral disc using an electrosurgical probe and a separately introduced ancillary device, according to another embodiment of the invention.

In order to initiate and/or maintain a plasma in the vicinity of active electrode 910, a quantity of an electrically conductive fluid may be applied to shaft 902 and/or the tissue to ablated. The electrically conductive fluid may be applied to shaft 902 and/or to the tissue to be ablated, either before or during application of the first high frequency voltage. Examples of electrically conductive fluids are saline (e.g., isotonic saline), and an electrically conductive gel. An electrically conductive fluid may be applied to the tissue to be ablated before or during ablation. A fluid delivery unit or device may be a component of the electrosurgical probe itself, or may comprise a separate device, e.g., ancillary device 940 (FIG. 57). Alternatively, many body fluids and/or tissues (e.g., the nucleus pulposus, blood) at the site to be ablated are electrically conductive and can participate in initiation or maintenance of a plasma in the vicinity of the active electrode.

In one embodiment, after ablation of nucleus pulposus tissue by the application of the first high frequency voltage and formation of a cavity or channel within the nucleus pulposus, a second high frequency voltage may be applied between active electrode 910 and return electrode 918, wherein application of the second high frequency voltage causes coagulation of nucleus pulposus tissue adjacent to the cavity or channel. Such coagulation of nucleus pulposus tissue may lead to increased stiffness, strength, and/or rigidity within certain regions of the nucleus pulposus, concomitant with an alleviation of discogenic pain. Furthermore, coagulation of tissues may lead to necrotic tissue which is subsequently broken down as part of a natural bodily process and expelled from the body, thereby resulting in de-bulking of the disc. Although FIG. 53 depicts a disc having fissures within the annulus fibrosus, it is to be understood that apparatus and methods of the invention discussed with reference to FIG. 53 are also applicable to treating other types of disc disorders, including those described with reference to FIGS. 52B, 52D.

Figure 54:
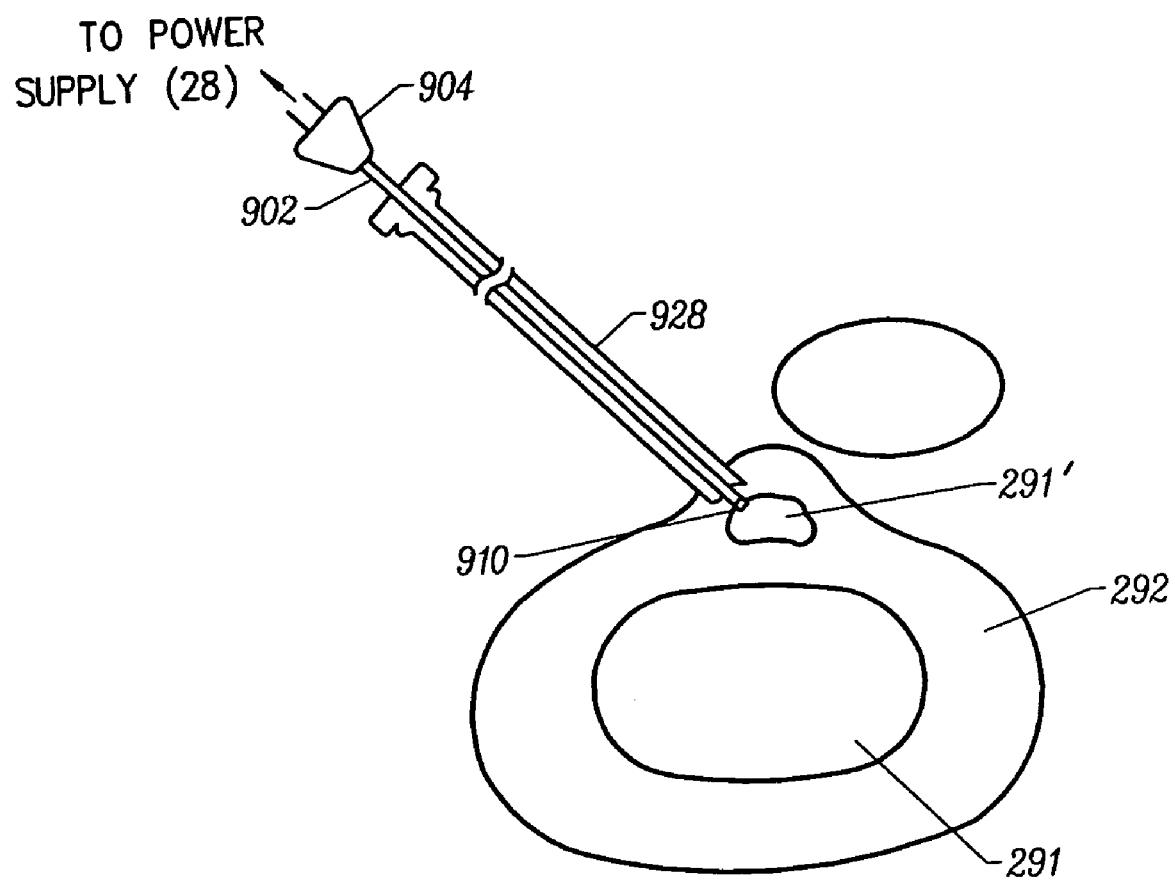
FIG. 54 shows a shaft of an electrosurgical probe within an intervertebral disc, wherein the shaft distal end is targeted to a specific site within the disc.

FIG. 54 shows shaft 902 of electrosurgical probe 900 within an intervertebral disc, wherein shaft distal end 902*a* is targeted to a specific site within the disc. In the situation depicted in FIG. 54, the target site is occupied by an errant fragment 291' of nucleus pulposus tissue. Shaft distal end 902 may be guided or directed, at least in part, by appropriate placement of introducer 928, such that active electrode 910 is in the vicinity of fragment 291'. Preferably, active electrode 910 is adjacent to, or in contact with, fragment 291'. Although FIG. 54 depicts a disc in which a fragment of nucleus pulposus is targeted by shaft 902, the invention described with reference to FIG. 54 may also be used for targeting other aberrant structures within an intervertebral disc, including annular fissures and contained herniations. In a currently preferred embodiment, shaft 902 includes at least one curve (not shown in FIG. 54), and other features described herein with reference to FIGS. 26A–35, wherein shaft distal end 902*a* may be precisely guided by an appropriate combination of axial and rotational movement of shaft 902. The procedure illustrated in FIG. 54 may be performed generally according to the description presented with reference to FIG. 53. That is, shaft 902 is introduced into the disc via introducer 928 in a percutaneous procedure. After shaft distal end 902*a* has been guided to a target site, tissue at or adjacent to that site is ablated by application of a first high frequency voltage. Thereafter, depending on the particular condition of the disc being treated, a second high frequency voltage may optionally be applied in order to locally coagulate tissue within the disc.

Figure 55:
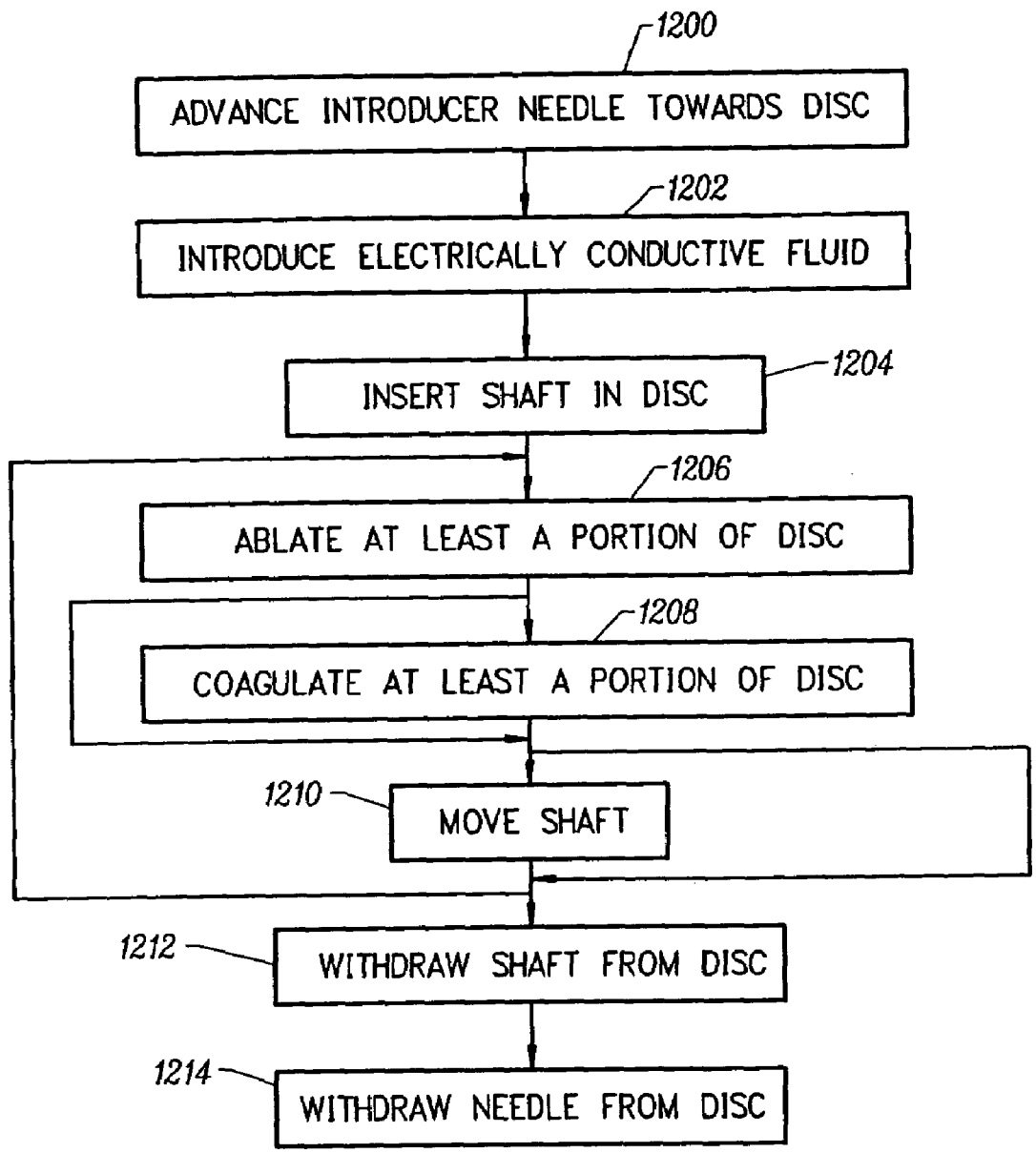
FIG. 55 schematically represents a series of steps involved in a method of ablating disc tissue according to the present invention.

FIG. 55 schematically represents a series of steps involved in a method of ablating disc tissue according to the present invention; wherein step 1200 involves advancing an introducer needle towards an intervertebral disc to be treated. The introducer needle has a lumen having a diameter greater than the diameter of the shaft distal end, thereby allowing free passage of the shaft distal end through the lumen of the introducer needle. In one embodiment, the introducer needle preferably has a length in the range of from about 3 cm to about 25 cm, and the lumen of the introducer needle preferably has a diameter in the range of from about 0.5 cm to about 2.5 mm. Preferably, the diameter of the shaft distal end is from about 30% to about 95% of the diameter of the lumen. The introducer needle may be inserted in the intervertebral disc percutaneously, e.g. via a posterior lateral approach. In one embodiment, the introducer needle may have dimensions similar to those of an epidural needle, the latter well known in the art.

Optional step 1202 involves introducing an electrically conductive fluid, such as saline, into the disc. In one embodiment, in lieu of step 1202, the ablation procedure may rely on the electrical conductivity of the nucleus pulposus itself. Step 1204 involves inserting the shaft of the electrosurgical probe into the disc, e.g., via the introducer needle, wherein the distal end portion of the shaft bears an active electrode and a return electrode. In one embodiment, the shaft includes an outer shield, first and second curves at the distal end portion of the shaft, and an electrode head having an apical spike, generally as described with reference to FIGS. 26A–32.

Step 1206 involves ablating at least a portion of disc tissue by application of a first high frequency voltage between the active electrode and the return electrode. In particular, ablation of nucleus pulposus tissue according to methods of the invention serves to decrease the volume of the nucleus pulposus, thereby relieving pressure exerted on the annulus fibrosus, with concomitant decompression of a previously compressed nerve root, and alleviation of discogenic pain.

In one embodiment, the introducer needle is advanced towards the intervertebral disc until it penetrates the annulus fibrosus and enters the nucleus pulposus. The shaft distal end in introduced into the nucleus pulposus, and a portion of the nucleus pulposus is ablated. These and other stages of the procedure may be performed under fluoroscopy to allow visualization of the relative location of the introducer needle and shaft relative to the nucleus pulposus of the disc. Additionally or alternatively, the surgeon may introduce the introducer needle into the nucleus pulposus from a first side of the disc, then advance the shaft distal end through the nucleus pulposus until resistance to axial translation of the electrosurgical probe is encountered by the surgeon. Such resistance may be interpreted by the surgeon as the shaft distal end having contacted the annulus fibrosus at the opposite side of the disc. Then, by use of depth markings on the shaft (FIG. 51A), the surgeon can retract the shaft a defined distance in order to position the shaft distal end at a desired location relative to the nucleus pulposus. Once the shaft distal end is suitably positioned, high frequency voltage may be applied to the probe via the power supply unit.

After step 1206, optional step 1208 involves coagulating at least a portion of the disc tissue. In one embodiment, step 1206 results in the formation of a channel or cavity within the nucleus pulposus. Thereafter, tissue at the surface of the channel may be coagulated during step 1208. Coagulation of disc tissue may be performed by application of a second high frequency voltage, as described hereinabove. After step 1206 or step 1208, the shaft may be moved (step 1210) such that the shaft distal end contacts fresh tissue of the nucleus pulposus. The shaft may be axially translated (i.e. moved in the direction of its longitudinal axis), may be rotated about its longitudinal axis, or may be moved by a combination of axial and rotational movement. In the latter case, a substantially spiral path is defined by the shaft distal end. After step 1210, steps 1206 and 1208 may be repeated with respect to the fresh tissue of the nucleus pulposus contacted by the shaft distal end. Alternatively, after step 1206 or step 1208, the shaft may be withdrawn from the disc (step 1212). Step 1214 involves withdrawing the introducer needle from the disc. In one embodiment, the shaft and the needle may be withdrawn from the disc concurrently. Withdrawal of the shaft from the disc may facilitate exhaustion of ablation by-products from the disc. Such ablation by-products include low molecular weight gaseous compounds derived from molecular dissociation of disc tissue components, as described hereinabove.

The above method may be used to treat any disc disorder in which Coblation® and or coagulation of disc tissue is indicated, including contained herniations. In one embodiment, an introducer needle may be introduced generally as described for step 1200, and a fluoroscopic fluid may be introduced through the lumen of the introducer needle for the purpose of visualizing and diagnosing a disc defect or disorder. Thereafter, depending on the diagnosis, a treatment procedure may be performed, e.g., according to steps 1202 through 1214, using the same introducer needle as access. In one embodiment, a distal portion, or the entire length, of the introducer needle may have an insulating coating on its external surface. Such an insulating coating on the introducer needle may prevent interference between the electrically conductive introducer needle and electrode(s) on the probe.

The size of the cavity or channel formed in a tissue by a single straight pass of the shaft through the tissue to be ablated is a function of the diameter of the shaft (e.g., the diameter of the shaft distal end and active electrode) and the amount of axial translation of the shaft. (By a "single straight pass" of the shaft is meant one axial translation of the shaft in a distal direction through the tissue, in the absence of rotation of the shaft about the longitudinal axis of the shaft, with the power from the power supply turned on.) In the case of a curved shaft, according to various embodiments of the instant invention, a larger channel can be formed by rotating the shaft as it is advanced through the tissue. The size of a channel formed in a tissue by a single rotational pass of the shaft through the tissue to be ablated is a function of the deflection of the shaft, and the amount of rotation of the shaft about its longitudinal axis, as well as the diameter of the shaft (e.g., the diameter of the shaft distal end and active electrode) and the amount of axial translation of the shaft. (By a "single rotational pass" of the shaft is meant one axial translation of the shaft in a distal direction through the tissue, in the presence of rotation of the shaft about the longitudinal axis of the shaft, with the power from the power supply turned on.) To a large extent, the diameter of a channel formed during a rotational pass of the shaft through tissue can be controlled by the amount of rotation of the shaft, wherein the "amount of rotation" encompasses both the rate of rotation (e.g., the angular velocity of the shaft), and the number of degrees through which the shaft is rotated (e.g. the number of turns) per unit length of axial movement. Typically, according to the invention, the amount of axial translation per pass (for either a straight pass or a rotational pass) is not limited by the length of the shaft. Instead, the amount of axial translation per single pass is preferably determined by the size of the tissue to be ablated. Depending on the size of the disc or other tissue to be treated, and the nature of the treatment, etc., a channel formed by a probe of the instant invention may preferably have a length in the range of from about 2 mm to about 50 mm, and a diameter in the range of from about 0.5 mm to about 7.5 mm. In comparison, a channel formed by a shaft of the instant invention during a single rotational pass may preferably have a diameter in the range of from about 1.5 mm to about 25 mm.

A channel formed by a shaft of the instant invention during a single straight pass may preferably have a volume in the range of from about 1 $mm^3$, or less, to about 2,500 $mm^3$. More preferably, a channel formed by a straight pass of a shaft of the instant invention has a volume in the range of from about 10 $mm^3$ to about 2,500 $mm^3$, and more preferably in the range of from about 50 $mm^3$ to about 2,500 $mm^3$. In comparison, a channel formed by a shaft of the instant invention during a single rotational pass typically has a volume from about twice to about 15 times the volume of a channel of the same length formed during a single rotational pass, i.e., in the range of from about 2 $mm^3$ to about 4,000 $mm^3$, more preferably in the range of from about 50 $mm^3$ to about 2,000 $mm^3$. While not being bound by theory, the reduction in volume of a disc having one or more channels therein is a function of the total volume of the one or more channels.

Figure 56:
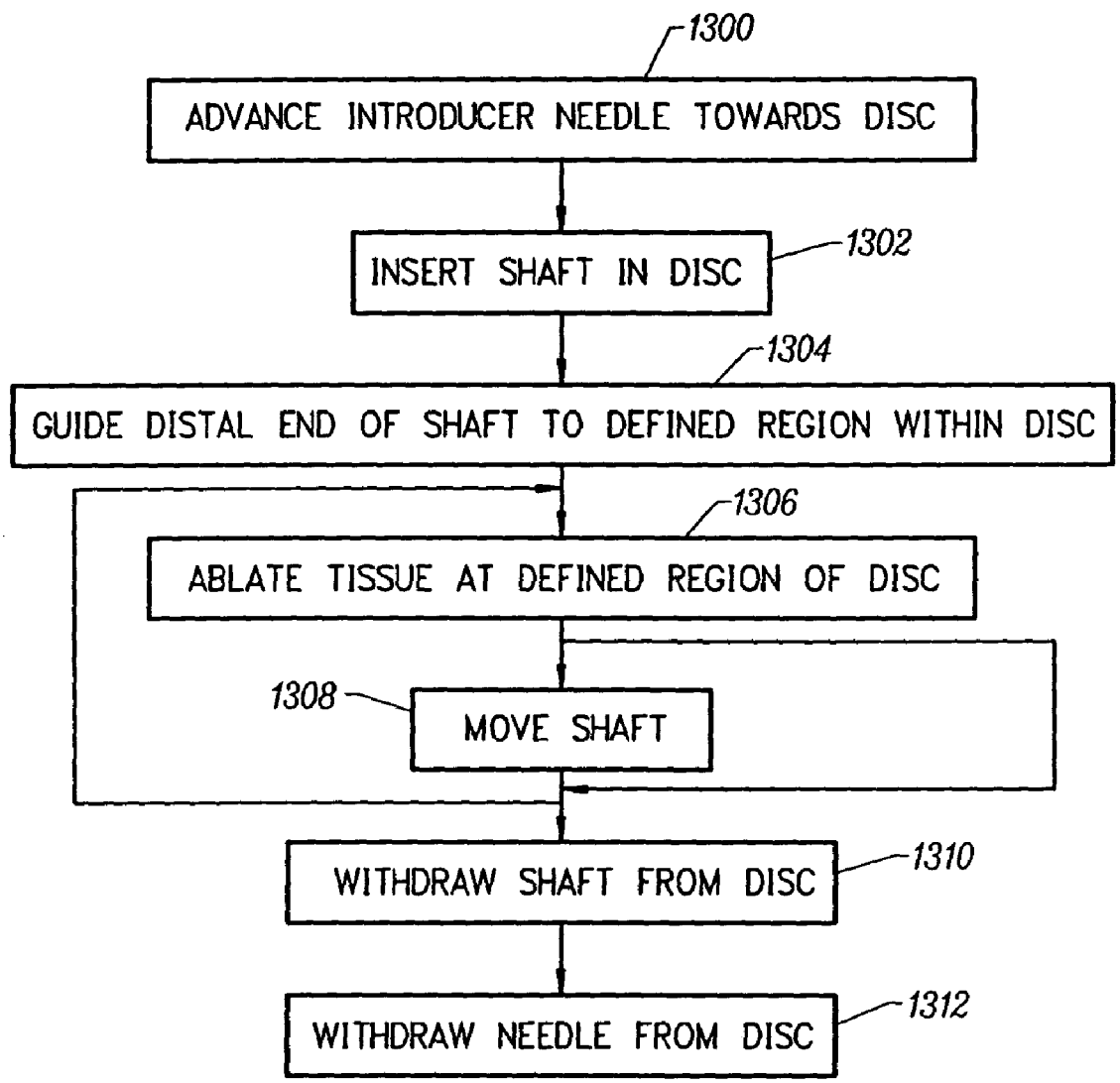
FIG. 56 schematically represents a series of steps involved in a method of guiding an electrosurgical probe to a target site within an intervertebral disc for ablation of targeted disc tissue, according to another embodiment of the invention.
Figure 62A:
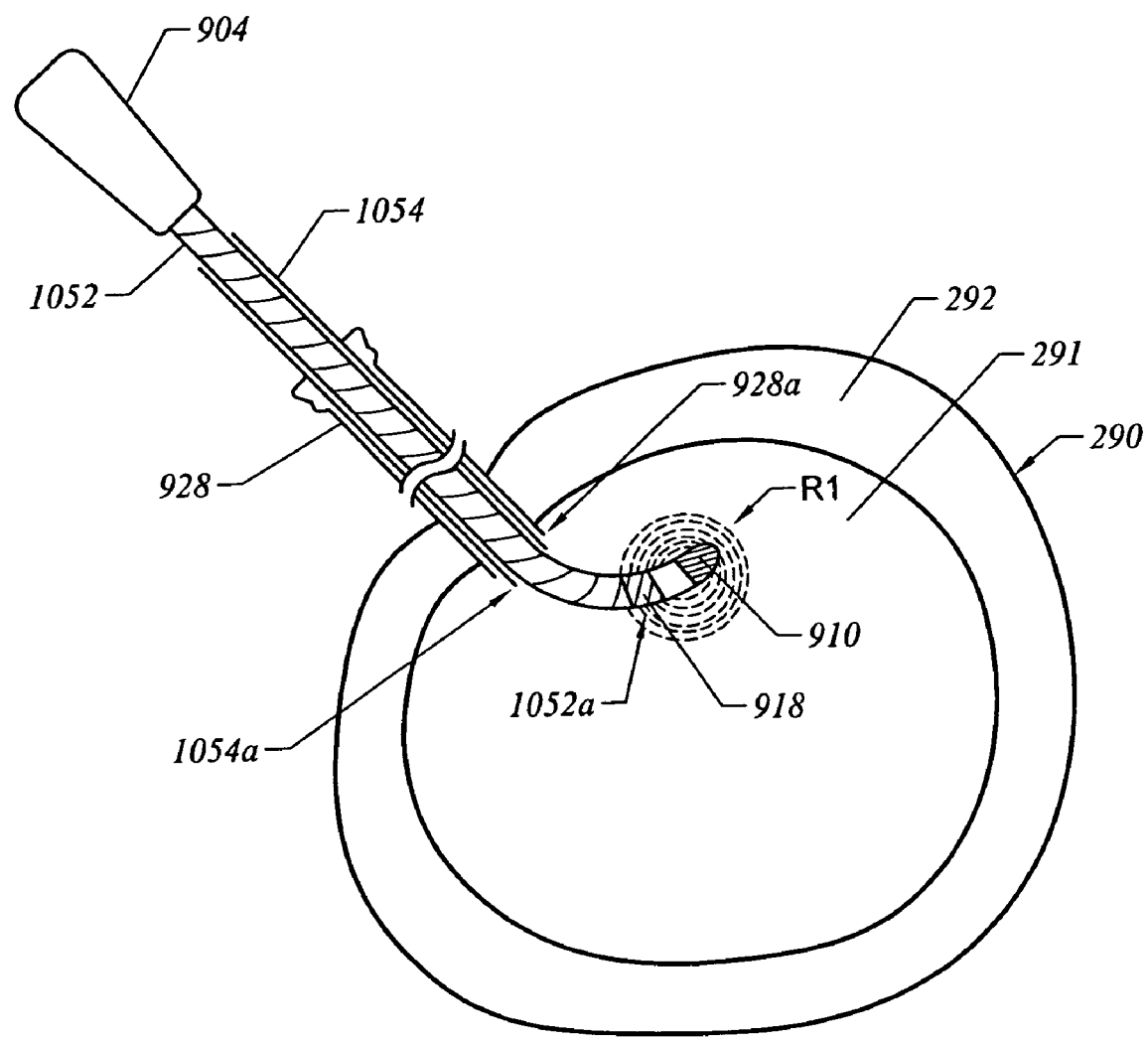
FIG. 62A shows the distal end of an introducer extension tube advanced to a first position within an intervertebral disc with the shaft distal end accessing a first region of disc tissue.
Figure 62B:
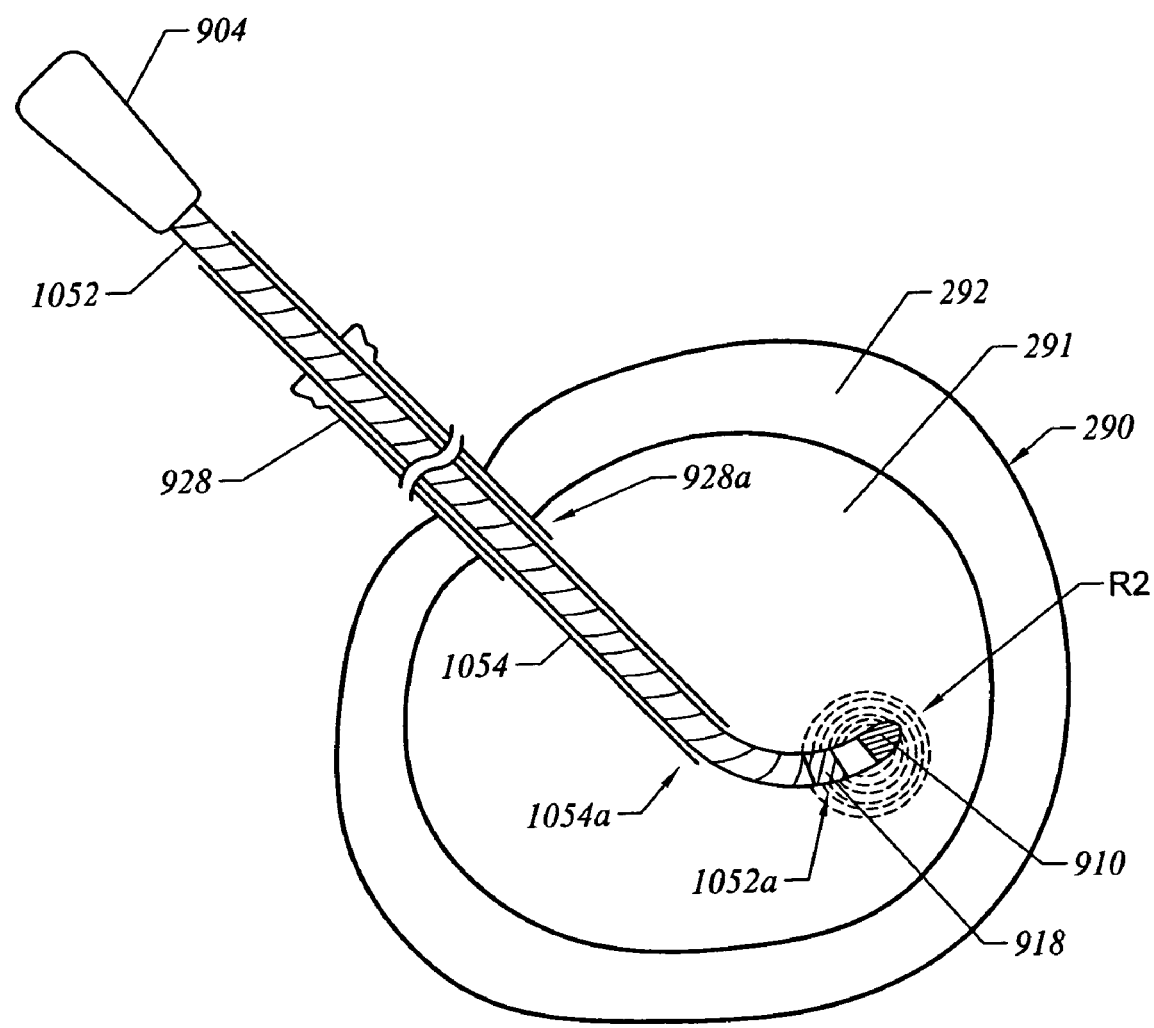
FIG. 62B shows the distal end of the introducer extension tube advanced to a second position within an intervertebral disc with the shaft distal end accessing a second region of disc tissue.

FIG. 56 schematically represents a series of steps involved in a method of guiding the distal end of a shaft of an electrosurgical probe to a target site within an intervertebral disc for ablation of specifically targeted disc tissue, wherein steps 1300 and 1302 are analogous to steps 1200 and 1204 of FIG. 55. Thereafter step 1304 involves guiding the shaft distal end to a defined region within the disc. The specific target site may be pre-defined as a result of a previous procedure to visualize the disc and its defect, e.g., via X-ray examination, endoscopically, or fluoroscopically. As an example, a defined target site within a disc may comprise a fragment of the nucleus pulposus that has migrated within the annulus fibrosus (see, e.g., FIG. 52D) resulting in discogenic pain. However, guiding the shaft to defined sites associated with other types of disc disorders are also possible and is within the scope of the invention. In one embodiment, as a prelude to guiding the shaft distal end to a target site, the shaft distal end may first be introduced into the disc at a selected location within the disc. Such a selected location defines a space within the disc from where the shaft distal end may be advanced in order to reach or access the target site. Preferably, the selected location defines a space in the general vicinity of the target site from where the shaft distal end may readily access the target site. The shaft distal end may be introduced at the selected location within the disc by advancing or retracting the introducer needle within the disc until the introducer needle distal end reaches the selected location. In another embodiment, the shaft distal end may be introduced at the selected location within the disc by advancing or retracting an introducer extension tube within the lumen of the introducer needle until the distal end of the introducer extension tube reaches the selected location (FIGS. 62A–B).

Guiding the shaft distal end to the defined target site may be performed by axial and/or rotational movement of a curved shaft, as described hereinabove. Or the shaft may be steerable, for example, by means of a guide wire, as is well known in the art. Guiding the shaft distal end may be performed during visualization of the location of the shaft relative to the disc, wherein the visualization may be performed endoscopically or via fluoroscopy. Endoscopic examination may employ a fiber optic cable (not shown). The fiber optic cable may be integral with the electrosurgical probe, or be part of a separate instrument (endoscope). Step 1306 involves ablating disc tissue, and is analogous to step 1206 (FIG. 55). Before or during step 1306, an electrically conductive fluid may be applied to the disc tissue and/or the shaft in order to provide a path for current flow between active and return electrodes on the shaft, and to facilitate and/or maintain a plasma in the vicinity of the distal end portion of the shaft. After the shaft distal end has been guided to a target site and tissue at that site has been ablated, the shaft may be moved locally, e.g., within the same region of the nucleus pulposus, or to a second defined target site within the same disc. The shaft distal end may be moved as described herein (e.g., with reference to step 1210, FIG. 55). Or, according to an alternative embodiment, the shaft may be steerable, e.g., by techniques well known in the art. Steps 1310 and 1312 are analogous to steps 1212 and 1214, respectively (described with reference to FIG. 55).

It is known in the art that epidural steroid injections can transiently diminish perineural inflammation of an affected nerve root, leading to alleviation of discogenic pain. In one embodiment of the invention, methods for ablation of disc tissue described hereinabove may be conveniently performed in conjunction with an epidural steroid injection. For example, ablation of disc tissue and epidural injection could be carried out as part of a single procedure, by the same surgeon, using equipment common to both procedures (e.g. visualization equipment). Combining Coblation® and epidural injection in a single procedure may provide substantial cost-savings to the healthcare industry, as well as a significant improvement in patient care.

As alluded to hereinabove, methods and apparatus of the present invention can be used to accelerate the healing process of intervertebral discs having fissures and/or contained herniations. In one method, the present invention is useful in microendoscopic discectomy procedures, e.g., for decompressing a nerve root with a lumbar discectomy. For example, as described above in relation to FIGS. 18–20, a percutaneous penetration can be made in the patient's back so that the superior lamina can be accessed. Typically, a small needle is used initially to localize the disc space level, and a guide wire is inserted and advanced under lateral fluoroscopy to the inferior edge of the lamina. Sequential cannulated dilators can be inserted over the guide wire and each other to provide a hole from the incision to the lamina. The first dilator may be used to "palpate" the lamina, assuring proper location of its tip between the spinous process and facet complex just above the inferior edge of the lamina. A tubular retractor can then be passed over the largest dilator down to the lamina. The dilators can then be removed, so as to establish an operating corridor within the tubular retractor. It should be appreciated however, that other conventional or proprietary methods can be used to access the target intervertebral disc. Once the target intervertebral disc has been accessed, an introducer device may be inserted into the intervertebral disc.

With reference to FIG. 57, in one embodiment, both introducer needle 928 and a second or ancillary introducer 938 may be inserted into the same disc, to allow introduction of an ancillary device 940 into the target disc via ancillary introducer 938. Ancillary device 940 may comprise, for example, a fluid delivery device, a return electrode, an aspiration lumen, a second electrosurgical probe, or an endoscope having an optical fiber component. Each of introducer needle 928 and ancillary introducer 938 may be advanced through the annulus fibrosus until at least the distal end portion of each introducer 928 and 938, is positioned within the nucleus pulposus. Thereafter, shaft 902" of electrosurgical probe 900' may be inserted through at least one of introducers 928, 938, to treat the intervertebral disc. Typically, shaft 902" of probe 900' has an outer diameter no larger than about 7 French (1 Fr: 0.33 mm), and preferably between about 6 French and 7 French.

Prior to inserting electrosurgical probe 900 into the intervertebral disc, an electrically conductive fluid can be delivered into the disk via a fluid delivery assembly (e.g., ancillary device 940) in order to facilitate or promote the Coblation® mechanism within the disc following the application of a high frequency voltage via probe 900'. By providing a separate device (940) for fluid delivery, the dimensions of electrosurgical probe 900' can be kept to a minimum. Furthermore, when the fluid delivery assembly is positioned within ancillary introducer 938, electrically conductive fluid can be conveniently replenished to the interior of the disc at any given time during the procedure. Nevertheless, in other embodiments, the fluid delivery assembly can be physically coupled to electrosurgical probe 900'.

In some methods, a radiopaque contrast solution (not shown) may be delivered through a fluid delivery assembly so as to allow the surgeon to visualize the intervertebral disc under fluoroscopy. In some configurations, a tracking device 942 can be positioned on shaft distal end portion 902"*a*. Additionally or alternatively, shaft 902" can be marked incrementally, e.g., with depth markings 903, to indicate to the surgeon how far the active electrode is advanced into the intervertebral disc. In one embodiment, tracking device 942 includes a radiopaque material that can be visualized under fluoroscopy. Such a tracking device 942 and depth markings 903 provide the surgeon with means to track the position of the active electrode 910 relative to a specific target site within the disc to which active electrode 910 is to be guided. Such specific target sites may include, for example, an annular fissure, a contained herniation, or a fragment of nucleus pulposus. The surgeon can determine the position of the active electrode 910 by observing the depth markings 903, or by comparing tracking device output, and a fluoroscopic image of the intervertebral disc to a pre-operative fluoroscopic image of the target intervertebral disc.

In other embodiments, an optical fiber (not shown) can be introduced into the disc. The optical fiber may be either integral with probe 900' or may be introduced as part of an ancillary device 940 via ancillary introducer 938. In this manner, the surgeon can visually monitor the interior of the intervertebral disc and the position of active electrode 910.

In addition to monitoring the position of the distal portion of electrosurgical probe 900', the surgeon can also monitor whether the probe is in Coblation® mode. In most embodiments, power supply 28 (e.g., FIG. 1) includes a controller having an indicator, such as a light, an audible sound, or a liquid crystal display (LCD), to indicate whether probe 900' is generating a plasma within the disc. If it is determined that the Coblation® mechanism is not occurring, (e.g., due to an insufficiency of electrically conductive fluid within the disc), the surgeon can then replenish the supply of the electrically conductive fluid to the disc.

Figure 58:
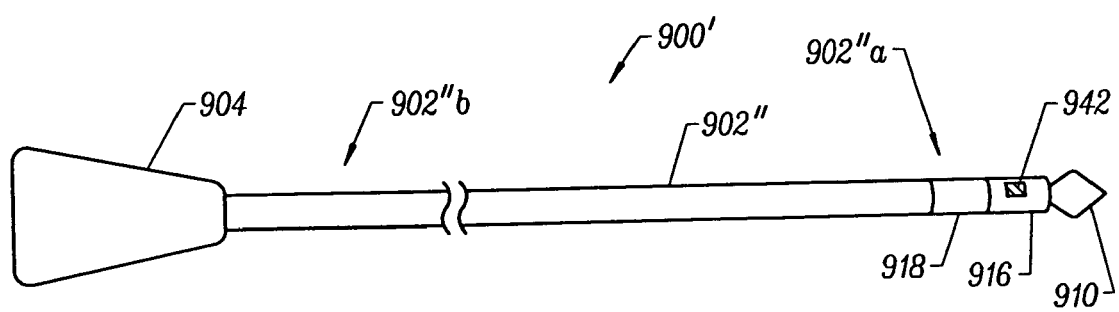
FIG. 58 is a side view of an electrosurgical probe having a tracking device.

FIG. 58 is a side view of an electrosurgical probe 900' including shaft 902' having tracking device 942 located at distal end portion 902"*a*. Tracking device 942 may serve as a radiopaque marker adapted for guiding distal end portion 902"*a* within a disc. Shaft 902" also includes at least one active electrode 910 disposed on the distal end portion 902"*a*. Preferably, electrically insulating support member or collar 916 is positioned proximal of active electrode 910 to insulate active electrode 910 from at least one return electrode 918. In most embodiments, the return electrode 918 is positioned on the distal end portion of the shaft 902" and proximal of the active electrode 910. In other embodiments, however, return electrode 918 can be omitted from shaft 902", in which case at least one return electrode may be provided on ancillary device 940, or the return electrode may be positioned on the patient's body, as a dispersive pad (not shown).

Although active electrode 910 is shown in FIG. 58 as comprising a single apical electrode, other numbers, arrangements, and shapes for active electrode 910 are within the scope of the invention. For example, active electrode 910 can include a plurality of isolated electrodes in a variety of shapes. Active electrode 910 will usually have a smaller exposed surface area than return electrode 918, such that the current density is much higher at active electrode 910 than at return electrode 918. Preferably, return electrode 918 has a relatively large, smooth surfaces extending around shaft 902" in order to reduce current densities in the vicinity of return electrode 918, thereby minimizing damage to non-target tissue.

While bipolar delivery of a high frequency energy is the preferred method of debulking the nucleus pulposus, it should be appreciated that other energy sources (i.e., resistive, or the like) can be used, and the energy can be delivered with other methods (i.e., monopolar, conductive, or the like) to debulk the nucleus.

Figure 59A:
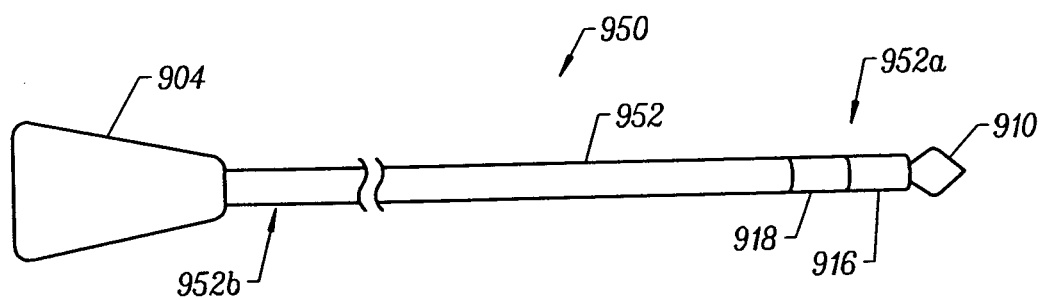
FIG. 59A shows a steerable electrosurgical probe wherein the shaft of the probe assumes a substantially linear configuration.
Figure 59B:
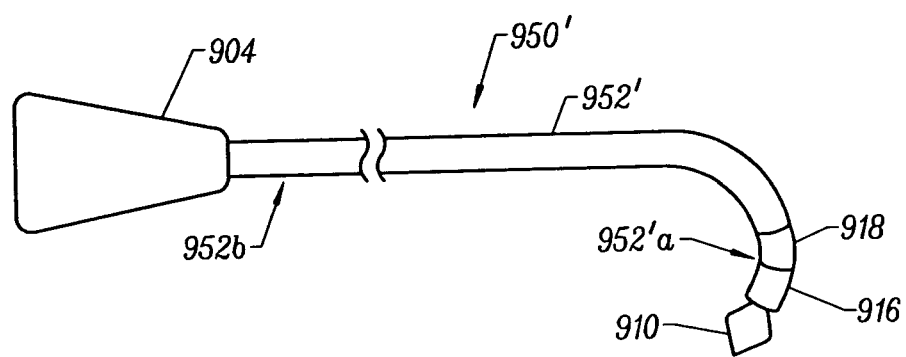
FIG. 59B shows the steerable electrosurgical probe of FIG. 59A, wherein the shaft distal end of the probe adopts a bent configuration.

FIG. 59A shows a steerable electrosurgical probe 950 including a shaft 952, according to another embodiment of the invention. Preferably, shaft 952 is flexible and may assume a substantially linear configuration as shown. Probe 950 includes handle 904, shaft distal end 952*a*, active electrode 910, insulating collar 916, and return electrode 918. As can be seen in FIG. 59B, under certain circumstances, e.g., upon application of a force to shaft 952 during guiding or steering probe 950 during a procedure, shaft distal end 952*a* can adopt a non-linear configuration, designated 952'*a*. The deformable nature of shaft distal end 952'*a* allows active electrode 910 to be guided to a specific target site within a disc.

Figure 60:
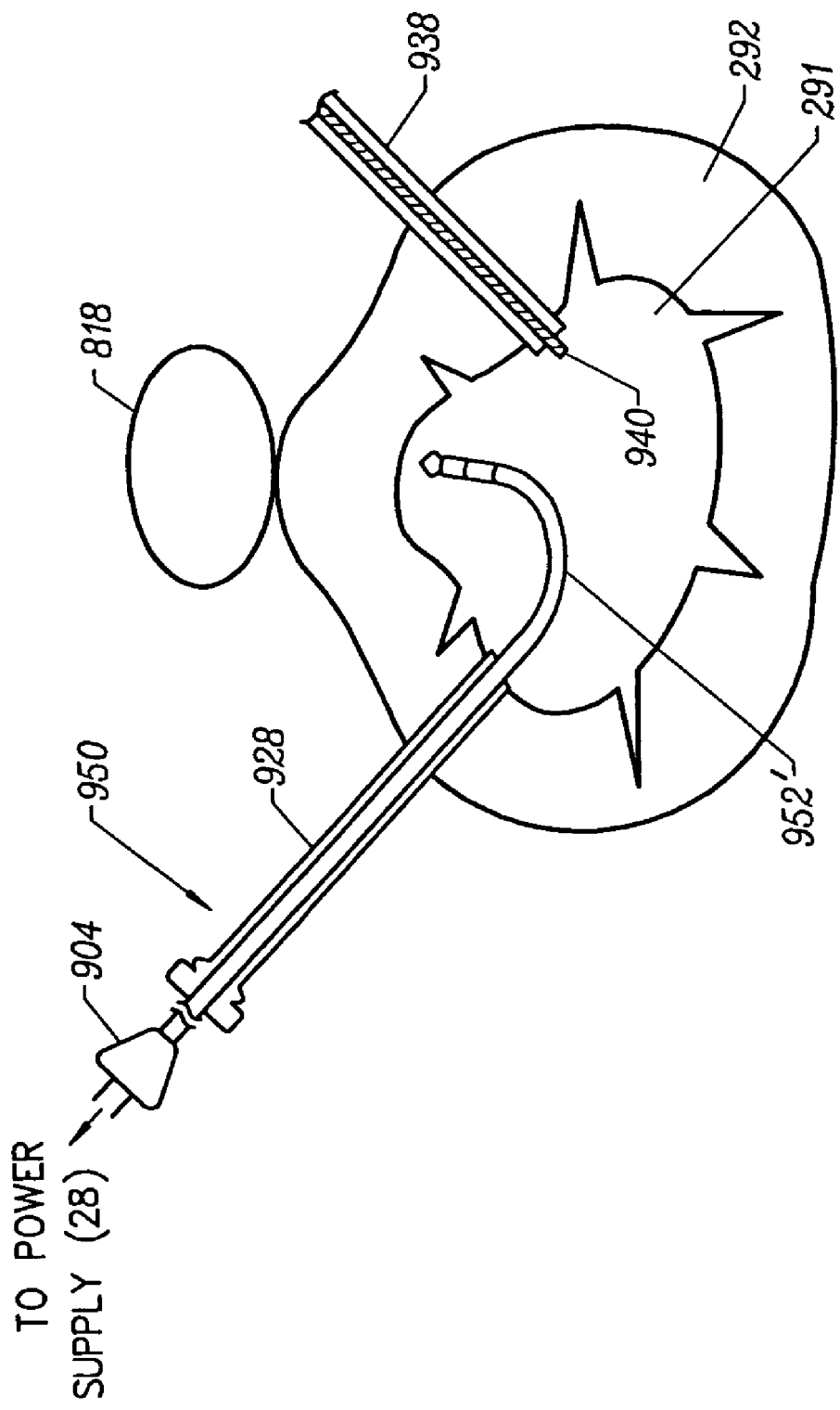
FIG. 60 shows a steerable electrosurgical probe and an ancillary device inserted within the nucleus pulposus of an intervertebral disc.

FIG. 60 shows steerable electrosurgical probe 950 inserted within the nucleus pulposus of an intervertebral disc. An ancillary device 940 and ancillary introducer 928 may also be inserted within the nucleus pulposus of the same disc. To facilitate the debulking of the nucleus pulposus adjacent to a contained herniation, shaft 952 (FIG. 59A) can be manipulated to a non-linear configuration, represented as 952'. Preferably, shaft 952/952' is flexible over at least shaft distal end 952*a* so as to allow steering of active electrode 910 to a position adjacent to the targeted disc defect. The flexible shaft may be combined with a sliding outer shield, a sliding outer introducer needle, pull wires, shape memory actuators, and other known mechanisms (not shown) for effecting selective deflection of distal end 952*a* to facilitate positioning of active electrode 910 within a disc. Thus, it can be seen that the embodiment of FIG. 60 may be used for the targeted treatment of annular fissures, or any other disc defect for which Coblation® is indicated.

In one embodiment shaft 952 has a suitable diameter and length to allow the surgeon to reach the target disc or vertebra by introducing the shaft through the thoracic cavity, the abdomen or the like. Thus, shaft 952 may have a length in the range of from about 5.0 cm to 30.0 cm, and a diameter in the range of about 0.2 mm to about 20 mm. Alternatively, shaft 952 may be delivered percutaneously in a posterior lateral approach. Regardless of the approach, shaft 952 may be introduced via a rigid or flexible endoscope. In addition, it should be noted that the methods described with reference to FIGS. 57 and 60 may also be performed in the absence of ancillary introducer 938 and ancillary device 940.

Figure 61A:
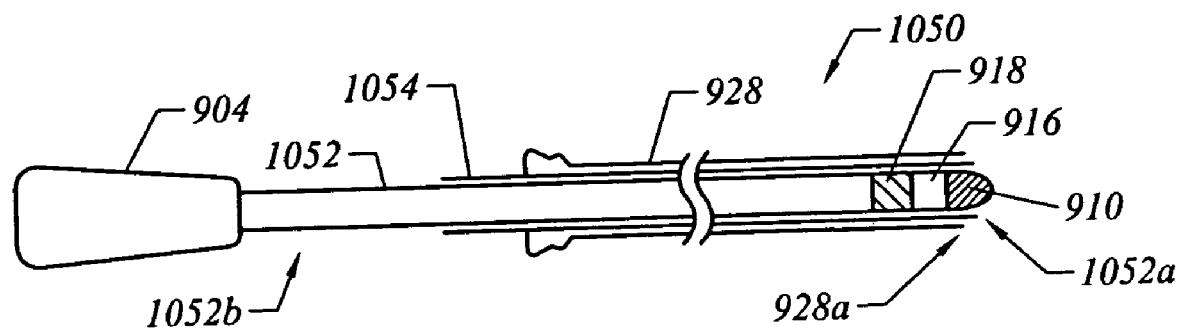
FIG. 61A shows the shaft distal end of an electrosurgical probe positioned within an introducer extension tube and within an introducer needle.

FIG. 61A shows an electrosurgical apparatus or system including a probe 1050 in combination with an introducer extension tube 1054, according to another aspect of the invention. Probe 1050 generally includes at least one active electrode 910 disposed at a shaft distal end 1502*a*, an electrically insulating spacer or support 916 proximal to active electrode 910, and a return electrode 918 proximal to support 916. FIG. 61A shows shaft distal end 1502*a* positioned within introducer extension tube 1054, which is in turn positioned within introducer needle 928. Introducer extension tube 1054 is adapted for passing shaft 1052 therethrough, and for being passed within introducer needle 928. Introducer extension tube 1054 may be advanced distally from introducer distal end 928*a* to a site targeted for treatment, e.g., to a selected location within an intervertebral disc. In this way, extension tube distal end 1054*a* (FIG. 61B) may define a starting point for advancement of shaft distal end 1052*a* into the disc tissue, and in some embodiments extension tube distal end 1054*a* may define a starting point from which guiding or steering of shaft distal end 1052*a* is initiated. By selecting a starting point within the disc from which guiding or steering of shaft distal end 1052*a* is initiated, much greater control can be exerted over accessing a given target site, and in addition a much greater range of regions within the disc can be accessed with a given probe (e.g., with a probe having a shaft of a given length and curvature).

Figure 61B:
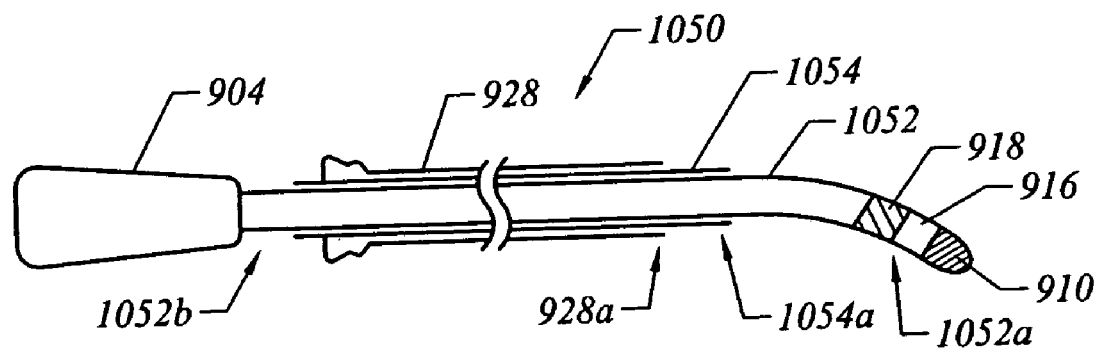
FIG. 61B shows the shaft distal end of the probe of FIG. 61A extending beyond the distal end of both the introducer extension tube and the introducer needle, with the shaft distal end adopting a curved configuration.

FIG. 61B shows shaft distal end 1052*a* of the probe of FIG. 61A extending beyond the distal end of both introducer extension tube 1054 and introducer needle 928, with shaft distal end 1052*a* adopting a curved configuration. Such a curved configuration allows access to a much greater number of regions, or to a much larger volume of tissue, within an intervertebral disc, for example, by rotating shaft 1052. Such a curved configuration may be due to a pre-defined bend or curve in shaft 1052 (e.g., FIGS. 47A–C), or may be the result of a steering mechanism, the latter well known in the art. In the former situation, a pre-defined curvature in shaft 1052 may be restrained or compressed while shaft 1052 is within introducer extension tube 1054 or introducer needle 928. Introducer extension tube 1054 may be rigid or somewhat flexible. Introducer extension tube 1054 may be constructed from an electrically conductive material such as stainless steel, and the like. Alternatively, introducer extension tube 1054 may be constructed from an electrically insulating material, such as various plastics, and the like.

FIG. 62A shows distal end 1054*a* of introducer extension tube 1054 advanced to a first position within an intervertebral disc 290. Shaft 1052 lies within introducer extension tube 1054, which in turn lies within introducer needle 928. Needle distal end 928*a* is introduced within disc 290, while extension tube distal end 1054*a* is advanced slightly distal to needle distal end 928*a*. Shaft distal end 1052*a* extends beyond extension tube distal end 1054*a* and adopts a curved configuration to access a first region, R1, of nucleus pulposus 291. Curvature of shaft distal end 1052*a* may result from a predefined bias or curve in shaft 1052, or shaft distal end 1052*a* may be steerable. Certain other regions of disc 290 may be accessed by shaft distal end 1052*a* by circumferentially rotating shaft 1052 about its longitudinal axis prior to shaft distal end 1052*a* being advanced distally beyond extension tube distal end 1054*a* (i.e., by rotating shaft 1052 while shaft 1052 lies within introducer extension tube 1054).

FIG. 62B schematically represents a situation wherein extension tube distal end 1054*a* is advanced to a second position within intervertebral disc 290. Much greater control can be exerted over the range of regions within disc 290 that can be accessed by shaft distal end 1052*a* when the location of introducer extension tube 1054 is selected prior to advancing shaft distal end 1052*a* into the disc tissue. For example, as represented in FIG. 62B, by advancing introducer extension tube 1054 distally within introducer needle 928 prior to advancing shaft distal end 1052*a* from introducer extension tube 1054, shaft distal end 1052*a* can readily access a second region R2, wherein R2 may be located remote from first region R1 (FIG. 62A). In contrast it is more problematic, if not impossible, for shaft distal end 1052a to access region R2 while introducer extension tube 1054 is positioned in relation to the disc as shown in FIG. 62A. Similarly, without the use of introducer extension tube 1054 (i.e., using an introducer needle 928 alone to advance shaft 1052 into the disc) it is problematic, if not impossible, for shaft distal end 1052a to access region R2. The inclusion of an extension device such as introducer extension tube 1054 as a component of the instant invention provides major advantages in accessing a target site within an intervertebral disc or other tissues.

Although certain embodiments of the invention have been described primarily with respect to treatment of intervertebral discs, it is to be understood that these methods and apparatus of the invention are also applicable to the treatment of other tissues, organs, and bodily structures. While the exemplary embodiments of the present invention have been described in detail, by way of example and for clarity of understanding, a variety of changes, adaptations, and modifications will be obvious to those of skill in the art. Therefore, the scope of the present invention is limited solely by the appended claims.

What is claimed is:

1. A method of treating an intervertebral disc having a nucleus pulposus and an annulus fibrosus, the method comprising:
   advancing a distal end of an electrosurgical instrument into the annulus fibrosus, wherein ar active electrode and a return electrode are positioned on the distal end of the electrosurgical instrument;
   moving the distal end of the electrosurgical instrument to a curved configuration that approximates a curvature of an inner surface of the annulus fibrosus; and
   delivering a high frequency voltage between the active electrode and the return electrode to treat the inner surface of the annulus fibrosus with a plasma in the vicinity of said active electrode, and wherein said active electrode having a shape and size different than said return electrode so as to create a higher current density at said active electrode than at said return electrode.

2. The method of claim 1, wherein advancing comprises channeling through the annulus fibrosus by delivering a high frequency voltage between the active electrode and the return electrode.

3. The method of claim 1 wherein moving comprises biasing the distal end.

4. The method of claim 1 wherein moving comprises steering the distal end.

5. The method of claim 4 wherein steering comprises actuating an actuator positioned at the proximal portion of the electrosurgical instrument.

6. The method of claim 1 further comprising tracking the movement or location of the distal end of the electrosurgical instrument.

7. The method of claim 6 wherein tracking comprises visualizing the distal end fluoroscopically.

8. The method of claim 1 wherein advancing comprises positioning the active electrode and return electrode within the nucleus pulposus.

9. The method of claim 1 wherein at least some tissue in contact with said plasma is ablated.

10. The method of claim 9 wherein said tissue ablated comprises at least a portion of annulus fibrosis.

11. The method of claim 9 wherein said tissue ablated comprises at least a portion of nucleus pulposus.

12. The method of claim 1 further comprising providing an electrically conductive fluid from outside the body in the vicinity of said distal end to facilitate the format on of said plasma.

13. A method of treating an intervertebral disc, the method comprising:
   positioning a distal end of an electrosurgical probe within close proximity of an outer surface of the intervertebral disc, the distal end of the electrosurgical probe comprising at least one active electrode;
   delivering a high frequency voltage between the at least one active electrode and a return electrode, the high frequency voltage being sufficient to create a channel in the disc tissue;
   advancing the active electrode through the channel created in the intervertebral disc;
   conforming the distal end of the electrosurgical probe to a curved configuration that approximates a curvature of an inner surface of an annulus fibrosus; and
   delivering a high frequency voltage between the active electrode and the return electrode to treat the inner surface of the annulus fibrosus.

14. The method of claim 13 further comprising delivering a heating voltage between a coagulation electrode and the return electrode to heat at least a portion of the intervertebral disc, wherein the heating voltage is sufficient to coagulate a severed blood vessel, and the heating voltage is insufficient to induce molecular dissociation of disc tissue components ablate the intervertebral disc tissue.

15. The method of claim 13 wherein conforming comprises biasing the distal end or steering the distal end.

16. An apparatus for treating intervertebral discs, the apparatus comprising:
   a steerable shaft defining a shaft distal end portion, wherein the shaft distal end portion is moveable to a curved configuration that approximates the curvature of the inner surface of an annulus fibrosus;
   at least one active electrode positioned on the distal end portion of the shaft;
   a return electrode positioned proximal of the at least one active electrode;
   a high frequency energy source configured to create a voltage difference between the active electrode and the return electrode; and
   a coagulation electrode associated with the distal end portion and electrically coupled to said high frequency energy source.

17. The apparatus of claim 16 further comprising a fluid delivery lumen configured to deliver a conductive fluid to the at least one active electrode.

18. The apparatus of claim 17 further comprising an aspiration lumen adapted to aspirate the conductive fluid to a location adjacent the active electrode.

19. The apparatus of claim 16, wherein the high frequency energy voltage source is configured to deliver a high frequency voltage to the coagulation electrode, wherein the high frequency voltage is insufficient for the coagulation electrode to produce an effect selected from the group consisting of: generating a plasma in the presence of an electrically conductive fluid, ablating tissue in a temperature range of 45° to 90° C., and causing molecular dissociation of tissue components.

* * * * *